(12) United States Patent
Ronsick et al.

(10) Patent No.: US 11,850,584 B2
(45) Date of Patent: Dec. 26, 2023

(54) ISOLATION TUBE

(71) Applicants: bioMerieux, Inc., Durham, NC (US); BioFire Defense, LLC, Salt Lake City, UT (US)

(72) Inventors: Christopher S. Ronsick, Durham, NC (US); Kirk Ririe, Salt Lake City, UT (US); Mark S. Wilson, Hillsborough, NC (US); John D. Walsh, Bahama, NC (US); Ryan T. Hill, Durham, NC (US)

(73) Assignees: bioMerieux, Inc., Durham, NC (US); BioFire Defense, LLC, Salt Lake City, UT (US)

( * ) Notice: Subject to any disclaimer, the term of this patent is extended or adjusted under 35 U.S.C. 154(b) by 220 days.

(21) Appl. No.: 17/356,052

(22) Filed: Jun. 23, 2021

(65) Prior Publication Data

US 2021/0370284 A1    Dec. 2, 2021

Related U.S. Application Data

(63) Continuation of application No. 16/046,275, filed on Jul. 26, 2018, now Pat. No. 11,090,646.
(Continued)

(51) Int. Cl.
*B01L 3/00* (2006.01)
*G01N 1/40* (2006.01)
(Continued)

(52) U.S. Cl.
CPC ......... *B01L 3/50215* (2013.01); *B01L 3/0296* (2013.01); *B01L 3/5021* (2013.01);
(Continued)

(58) Field of Classification Search
CPC ........ B01L 3/50; B01L 3/5021; B01L 3/0296; B01L 3/5082; B01L 3/50825; B04B 5/0414; C12M 45/05
See application file for complete search history.

(56) References Cited

U.S. PATENT DOCUMENTS 1,742,605 A    1/1930    Marie-Louise
1,806,256 A    5/1931    Montalvo
(Continued)

FOREIGN PATENT DOCUMENTS

AU    2003265160 B2    11/2003
AU    2008 328202 B2    5/2009
(Continued)

OTHER PUBLICATIONS

Extended European Search Report for Application No. 20162708.0 dated Oct. 6, 2020.
(Continued)

*Primary Examiner* — Brian J. Sines
(74) *Attorney, Agent, or Firm* — bioMerieux, Inc.

(57) ABSTRACT

A separation container for extracting a portion of a sample for use or testing and method for preparing samples for downstream use or testing are provided. The separation container may include a body defining an internal chamber. The body may define an opening, and the body may be configured to receive the sample within the internal chamber. The separation container may further include a seal disposed across the opening, such that the seal may be configured to seal the opening of the body, and a plunger movably disposed at least partially inside the internal chamber. The plunger may be configured to be actuated to open the seal and express the portion of the sample.

15 Claims, 136 Drawing Sheets

Related U.S. Application Data

(60) Provisional application No. 62/643,918, filed on Mar. 16, 2018, provisional application No. 62/537,731, filed on Jul. 27, 2017.

(51) Int. Cl.
| | |
|---|---|
| *C12M 1/00* | (2006.01) |
| *B04B 5/04* | (2006.01) |
| *C12Q 1/24* | (2006.01) |
| *B01L 3/02* | (2006.01) |
| *G01N 1/20* | (2006.01) |
| *B04B 11/04* | (2006.01) |

(52) U.S. Cl.
CPC ......... *B01L 3/5082* (2013.01); *B01L 3/50825* (2013.01); *B04B 5/0414* (2013.01); *C12M 45/05* (2013.01); *C12Q 1/24* (2013.01); *G01N 1/2035* (2013.01); *G01N 1/4077* (2013.01); *B01L 2200/02* (2013.01); *B01L 2200/0652* (2013.01); *B01L 2200/0684* (2013.01); *B01L 2200/0689* (2013.01); *B01L 2300/042* (2013.01); *B01L 2300/044* (2013.01); *B01L 2300/0672* (2013.01); *B01L 2300/0681* (2013.01); *B01L 2300/0832* (2013.01); *B01L 2300/0848* (2013.01); *B01L 2300/123* (2013.01); *B01L 2400/0409* (2013.01); *B01L 2400/0478* (2013.01); *B01L 2400/0633* (2013.01); *B01L 2400/0683* (2013.01); *B04B 2005/0435* (2013.01); *B04B 2011/046* (2013.01); *G01N 2001/4083* (2013.01)

(56) References Cited

U.S. PATENT DOCUMENTS

| | | |
|---|---|---|
| 1,865,764 A | 7/1932 | Keenan |
| 1,925,466 A | 9/1933 | Simpson |
| 1,929,247 A | 10/1933 | Hein |
| 2,035,278 A | 3/1936 | Sager |
| 2,114,583 A | 4/1938 | Adams |
| 2,189,116 A | 2/1940 | Niemiec |
| 2,281,051 A | 4/1942 | Roger |
| 2,364,126 A | 12/1944 | Abraham et al. |
| 2,419,401 A | 4/1947 | Hinds |
| 2,483,656 A | 10/1949 | Marschalk |
| 2,534,310 A | 12/1950 | Silverman |
| 2,683,566 A | 7/1954 | Bentley |
| 2,698,015 A | 12/1954 | Brown |
| 2,706,702 A | 4/1955 | Carski |
| 2,787,249 A | 4/1957 | Barlow |
| 2,832,513 A | 4/1958 | Tubin |
| 2,847,996 A | 8/1958 | Cohen et al. |
| 2,941,712 A | 6/1960 | Cook |
| 3,081,029 A | 3/1963 | Gauslaa |
| 3,107,805 A | 10/1963 | Asher |
| 3,120,318 A | 2/1964 | Rigor |
| 3,152,727 A | 10/1964 | Evans |
| 3,154,116 A | 10/1964 | Mitchell |
| 3,199,957 A | 8/1965 | Vivion |
| 3,235,117 A | 2/1966 | Mason |
| 3,434,615 A | 3/1969 | Barletta |
| 3,521,745 A | 7/1970 | Schwartzman |
| 3,539,300 A | 11/1970 | Stone |
| 3,548,562 A | 12/1970 | Schwartzman |
| 3,590,889 A | 7/1971 | Vannus |
| 3,593,909 A | 7/1971 | Bergmann |
| 3,682,596 A | 8/1972 | Stone |
| 3,692,487 A | 9/1972 | Sanz |
| 3,706,305 A | 12/1972 | Berger et al. |
| 3,749,646 A | 7/1973 | Pirt |
| 3,770,155 A | 11/1973 | Novitch |
| 3,773,468 A | 11/1973 | Hubbard et al. |
| 3,810,545 A | 5/1974 | Filz |
| 3,850,174 A | 11/1974 | Ayres |
| 3,871,545 A | 3/1975 | Bereziat |
| 3,875,012 A | 4/1975 | Dorn et al. |
| 3,897,902 A | 8/1975 | Yanez, Jr. |
| 3,928,139 A | 12/1975 | Dorn |
| 3,932,222 A | 1/1976 | Dorn |
| 3,940,003 A | 2/1976 | Larson |
| 3,969,250 A | 7/1976 | Farr |
| 3,977,555 A | 8/1976 | Larson |
| 4,012,325 A | 3/1977 | Columbus |
| 4,017,007 A | 4/1977 | Riccio |
| 4,040,959 A | 8/1977 | Berman |
| 4,066,407 A | 1/1978 | Lupica |
| 4,080,175 A | 3/1978 | Chulay et al. |
| 4,109,530 A | 8/1978 | Kim |
| 4,154,690 A | 5/1979 | Ballies |
| 4,308,347 A | 12/1981 | Forrer et al. |
| 4,358,425 A | 11/1982 | Finney et al. |
| 4,396,655 A | 8/1983 | Graham et al. |
| 4,412,623 A | 11/1983 | Schmidt |
| 4,435,507 A | 3/1984 | Stenkvist |
| 4,465,200 A | 8/1984 | Percarpio |
| 4,542,833 A | 9/1985 | DeVaughn |
| 4,545,497 A | 10/1985 | Martha, Jr. et al. |
| 4,552,278 A | 11/1985 | Romanauskas |
| 4,559,052 A | 12/1985 | Babson |
| 4,562,844 A | 1/1986 | Carpenter et al. |
| 4,580,682 A | 4/1986 | Gorski et al. |
| 4,582,207 A | 4/1986 | Howard et al. |
| 4,591,486 A | 5/1986 | Eberle |
| 4,697,717 A | 10/1987 | Grippi |
| 4,713,974 A | 12/1987 | Stone |
| 4,722,459 A | 2/1988 | Goncalves |
| 4,764,342 A | 8/1988 | Kelln et al. |
| 4,828,716 A | 5/1989 | McEwen et al. |
| 4,952,498 A | 8/1990 | Waters |
| 5,061,263 A | 10/1991 | Yamazaki et al. |
| 5,070,884 A | 12/1991 | Columbus et al. |
| 5,143,236 A | 9/1992 | Gueret |
| 5,154,702 A | 10/1992 | Foyil |
| 5,230,427 A | 7/1993 | Betts et al. |
| 5,271,513 A | 12/1993 | Crosnier et al. |
| 5,275,731 A | 1/1994 | Jahn |
| 5,306,270 A | 4/1994 | Macartney et al. |
| 5,344,036 A | 9/1994 | Stanescu et al. |
| 5,499,751 A | 3/1996 | Meyer |
| 5,613,957 A | 3/1997 | Py |
| 5,641,010 A | 6/1997 | Maier |
| 5,713,843 A | 2/1998 | Vangsness |
| 5,733,446 A | 3/1998 | Holm |
| 5,817,082 A | 10/1998 | Niedospial et al. |
| 5,823,373 A | 10/1998 | Sudo et al. |
| 5,846,233 A | 12/1998 | Lilley et al. |
| 5,860,937 A | 1/1999 | Cohen |
| 5,866,071 A | 2/1999 | Leu |
| 5,902,298 A | 5/1999 | Niedospial et al. |
| 6,045,755 A | 4/2000 | Lebl et al. |
| RE37,047 E | 2/2001 | Py |
| 6,254,834 B1 | 7/2001 | Anderson et al. |
| 6,277,331 B1 | 8/2001 | Konrad |
| 6,308,867 B1 | 10/2001 | Wolter |
| 6,479,239 B1 | 11/2002 | Anderson et al. |
| 6,479,298 B1 | 11/2002 | Miller et al. |
| 6,582,665 B2 | 6/2003 | Faulkner |
| 6,803,022 B2 | 10/2004 | DiCesare et al. |
| 6,905,612 B2 | 6/2005 | Dorian et al. |
| 6,911,312 B2 | 6/2005 | Anderson et al. |
| 7,179,391 B2 | 2/2007 | Leach et al. |
| 7,258,840 B2 | 8/2007 | van der Maas et al. |
| 7,374,678 B2 | 5/2008 | Leach et al. |
| 7,470,371 B2 | 12/2008 | Dorian et al. |
| 7,553,413 B2 | 6/2009 | Dorian et al. |
| 7,736,593 B2 | 6/2010 | Dastane et al. |
| 7,771,590 B2 | 8/2010 | Leach et al. |
| 7,832,566 B2 | 11/2010 | Leach et al. |
| 7,845,517 B2 | 12/2010 | Py et al. |
| 7,947,236 B2 | 5/2011 | Losada et al. |
| 7,992,725 B2 | 8/2011 | Leach et al. |
| 8,048,297 B2 | 11/2011 | Leach et al. |

(56) References Cited

U.S. PATENT DOCUMENTS

| | | | |
|---|---|---|---|
| 8,048,320 B2 | 11/2011 | Leach et al. |
| 8,119,082 B2 | 2/2012 | Chiarin et al. |
| 8,122,922 B2 | 2/2012 | Baker |
| 8,236,258 B2 | 8/2012 | Leach et al. |
| 8,278,118 B2 | 10/2012 | Horn et al. |
| 8,313,954 B2 | 11/2012 | Leach et al. |
| 8,322,539 B1 | 12/2012 | Ellis et al. |
| 8,328,024 B2 | 12/2012 | Leach et al. |
| 8,450,081 B2 | 5/2013 | Weller |
| 8,512,575 B2 | 8/2013 | Leach et al. |
| 8,524,171 B2 | 9/2013 | Losada et al. |
| 8,569,010 B2 | 10/2013 | Maier |
| 8,609,330 B2 | 12/2013 | Rajagopal |
| 8,609,364 B2 | 12/2013 | Walsh et al. |
| 8,632,740 B2 | 1/2014 | Dastane et al. |
| 8,652,800 B2 | 2/2014 | Walsh et al. |
| 8,748,122 B2 | 6/2014 | Hyman et al. |
| 8,877,459 B2 | 11/2014 | Weller |
| 8,975,060 B2 | 3/2015 | Talebpour et al. |
| 8,992,862 B2 | 3/2015 | Leach et al. |
| 9,039,999 B2 | 5/2015 | Campton et al. |
| 9,095,849 B2 | 8/2015 | Losada et al. |
| 9,128,058 B2 | 9/2015 | Walsh et al. |
| 9,175,329 B2 | 11/2015 | Walsh et al. |
| 9,199,250 B2 | 12/2015 | Sharon et al. |
| 9,217,697 B2 | 12/2015 | U'Ren et al. |
| 9,452,427 B2 | 9/2016 | Felix et al. |
| 9,492,819 B2 | 11/2016 | Campton et al. |
| 9,513,291 B2 | 12/2016 | Campton et al. |
| 9,539,570 B2 | 1/2017 | U'Ren et al. |
| 9,541,481 B2 | 1/2017 | Campton et al. |
| 9,649,579 B2 | 5/2017 | Leach et al. |
| 9,682,373 B2 | 6/2017 | Losada et al. |
| 10,006,076 B2 | 6/2018 | Franzen et al. |
| 11,090,646 B2 * | 8/2021 | Ronsick | B01L 3/50825 |
| 2001/0034502 A1 | 10/2001 | Moberg et al. |
| 2002/0066712 A1 | 6/2002 | Brockwell |
| 2002/0079284 A1 | 6/2002 | Carano |
| 2002/0094305 A1 | 7/2002 | Dicesare et al. |
| 2002/0127546 A1 | 9/2002 | Anderson et al. |
| 2003/0012667 A1 | 1/2003 | Maruyama |
| 2003/0013205 A1 | 1/2003 | Konrad |
| 2003/0129738 A1 | 7/2003 | Sorenson et al. |
| 2005/0014273 A1 | 1/2005 | Dahm et al. |
| 2005/0059163 A1 | 3/2005 | Dastane et al. |
| 2005/0065454 A1 | 3/2005 | Manoussakis |
| 2005/0150903 A1 | 7/2005 | Py et al. |
| 2005/0186120 A1 | 8/2005 | Dorian et al. |
| 2006/0057033 A1 | 3/2006 | Goldenberg |
| 2006/0213964 A1 | 9/2006 | Excoffler et al. |
| 2006/0216196 A1 | 9/2006 | Satoh et al. |
| 2007/0066935 A1 | 3/2007 | Morishita et al. |
| 2007/0075016 A1 | 4/2007 | Leach |
| 2007/0163366 A1 | 7/2007 | Jeong et al. |
| 2007/0194054 A1 | 8/2007 | Ganzeboom et al. |
| 2007/0272612 A1 | 11/2007 | Horn et al. |
| 2008/0260581 A1 | 10/2008 | Rosman et al. |
| 2010/0024914 A1 | 2/2010 | Baker |
| 2010/0113976 A1 | 5/2010 | Wahl et al. |
| 2010/0120085 A1 | 5/2010 | Hyman et al. |
| 2010/0120133 A1 | 5/2010 | Walsh et al. |
| 2010/0120596 A1 | 5/2010 | Froman et al. |
| 2010/0124763 A1 | 5/2010 | Walsh et al. |
| 2010/0129857 A1 | 5/2010 | Walsh et al. |
| 2010/0255527 A1 | 10/2010 | Weller |
| 2010/0256595 A1 | 10/2010 | Leach et al. |
| 2010/0285447 A1 | 11/2010 | Walsh et al. |
| 2010/0288060 A1 | 11/2010 | Ronsick et al. |
| 2010/0291615 A1 | 11/2010 | Ronsick et al. |
| 2010/0291618 A1 | 11/2010 | Robinson et al. |
| 2010/0291619 A1 | 11/2010 | Robinson et al. |
| 2010/0291669 A1 | 11/2010 | Robinson et al. |
| 2011/0087173 A1 | 4/2011 | Sibbitt et al. |
| 2011/0124106 A1 | 5/2011 | Froman et al. |
| 2011/0130263 A1 | 6/2011 | Del Vecchio |
| 2012/0115182 A1 | 5/2012 | Maier |
| 2012/0115705 A1 | 5/2012 | Sharon et al. |
| 2012/0126024 A1 | 5/2012 | Boyd et al. |
| 2012/0288897 A1 | 11/2012 | Ching et al. |
| 2013/0017620 A1 | 1/2013 | Scott et al. |
| 2013/0029324 A1 | 1/2013 | Rajagopal et al. |
| 2013/0030322 A1 | 1/2013 | Levine et al. |
| 2013/0078735 A1 | 3/2013 | Sandra et al. |
| 2013/0228534 A1 | 9/2013 | Ellis et al. |
| 2013/0241099 A1 | 9/2013 | Losada et al. |
| 2013/0270173 A1 | 10/2013 | Tortorella et al. |
| 2013/0284680 A1 | 10/2013 | Tortorella et al. |
| 2013/0330250 A1 | 12/2013 | Koeda |
| 2014/0042768 A1 | 2/2014 | Watanabe et al. |
| 2014/0051117 A1 | 2/2014 | Maier |
| 2014/0154687 A1 | 6/2014 | Talebpour et al. |
| 2014/0161688 A1 | 6/2014 | Campton et al. |
| 2014/0260118 A1 | 9/2014 | Knight |
| 2014/0330217 A1 | 11/2014 | Thorley et al. |
| 2014/0349828 A1 | 11/2014 | U'Ren et al. |
| 2015/0025454 A1 | 1/2015 | Wetzel et al. |
| 2015/0129592 A1 | 5/2015 | Staples et al. |
| 2015/0192506 A1 | 7/2015 | U'Ren et al. |
| 2015/0224497 A1 | 8/2015 | Furrer et al. |
| 2015/0231626 A1 | 8/2015 | Shi et al. |
| 2015/0337358 A1 | 11/2015 | Driscoll |
| 2016/0053295 A1 | 2/2016 | Walsh et al. |
| 2016/0068897 A1 | 3/2016 | Talebpour et al. |
| 2016/0130631 A1 | 5/2016 | Maier |
| 2016/0136658 A1 | 5/2016 | Sharon et al. |
| 2016/0138072 A1 | 5/2016 | Talebpour et al. |
| 2016/0251694 A1 | 9/2016 | Franzen et al. |
| 2016/0279320 A1 | 9/2016 | Zanin et al. |
| 2016/0341641 A1 | 11/2016 | Williams et al. |
| 2017/0074759 A1 | 3/2017 | Campton et al. |
| 2017/0080422 A1 | 3/2017 | Maaskant et al. |
| 2017/0297016 A1 | 10/2017 | Janas et al. |
| 2018/0055999 A1 | 3/2018 | Bare et al. |
| 2018/0136194 A1 | 5/2018 | Blandy et al. |
| 2019/0030527 A1 | 1/2019 | Walsh et al. |
| 2019/0046971 A1 | 2/2019 | Ririe et al. |
| 2019/0046975 A1 | 2/2019 | Ronsick et al. |
| 2019/0046976 A1 | 2/2019 | Ronsick et al. |
| 2019/0046977 A1 | 2/2019 | Ronsick et al. |

FOREIGN PATENT DOCUMENTS

| | | |
|---|---|---|
| AU | 2009 320330 B2 | 6/2010 |
| AU | 2009 320332 B2 | 6/2010 |
| AU | 2010 245860 B2 | 11/2010 |
| AU | 2014 202752 A | 6/2014 |
| BR | 112016010203 A2 | 8/2017 |
| CA | 2 705 930 A1 | 5/2009 |
| CA | 2 892 813 A1 | 6/2014 |
| CA | 2 893 131 A1 | 6/2014 |
| CA | 2 922 511 A1 | 6/2015 |
| CA | 2 949 151 A1 | 11/2015 |
| CN | 102149472 A | 8/2011 |
| CN | 104655840 B | 3/2018 |
| DE | 10 2010 033 105 B4 | 5/2016 |
| DE | 10 2007 058 516 B4 | 8/2017 |
| EP | 1 006 360 A2 | 6/2000 |
| EP | 2 892 648 B1 | 7/2015 |
| JP | S55-152435 A | 11/1980 |
| JP | H 08-201380 A | 8/1996 |
| JP | 2005 279507 A | 10/2005 |
| JP | 2012-513773 A | 6/2012 |
| WO | WO 96/24058 A1 | 8/1996 |
| WO | WO 2009/016431 | 2/2009 |
| WO | WO 2012/085006 A1 | 6/2012 |
| WO | WO 2014/007846 A1 | 1/2014 |
| WO | WO 2015/101925 A1 | 7/2015 |
| WO | WO 2015/172255 A1 | 11/2015 |
| WO | WO 2016 059141 A1 | 4/2016 |
| WO | WO 2017/019598 A1 | 2/2017 |
| WO | WO 2017 046736 A1 | 3/2017 |

OTHER PUBLICATIONS

(56) References Cited

OTHER PUBLICATIONS

Non-Final Office Action for U.S. Appl. No. 16/046,293 dated Aug. 25, 2021, 15 pages.
International Search Report and Written Opinion for Application No. PCT/US2018/043870 dated Oct. 23, 2018.
Partial European Search Report for European Application No. 20162078.0 dated Jun. 29, 2020.

\* cited by examiner

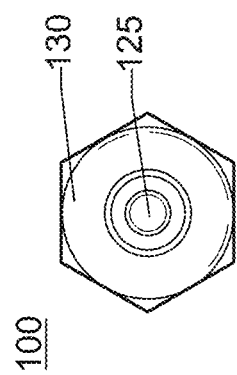
FIG. 4
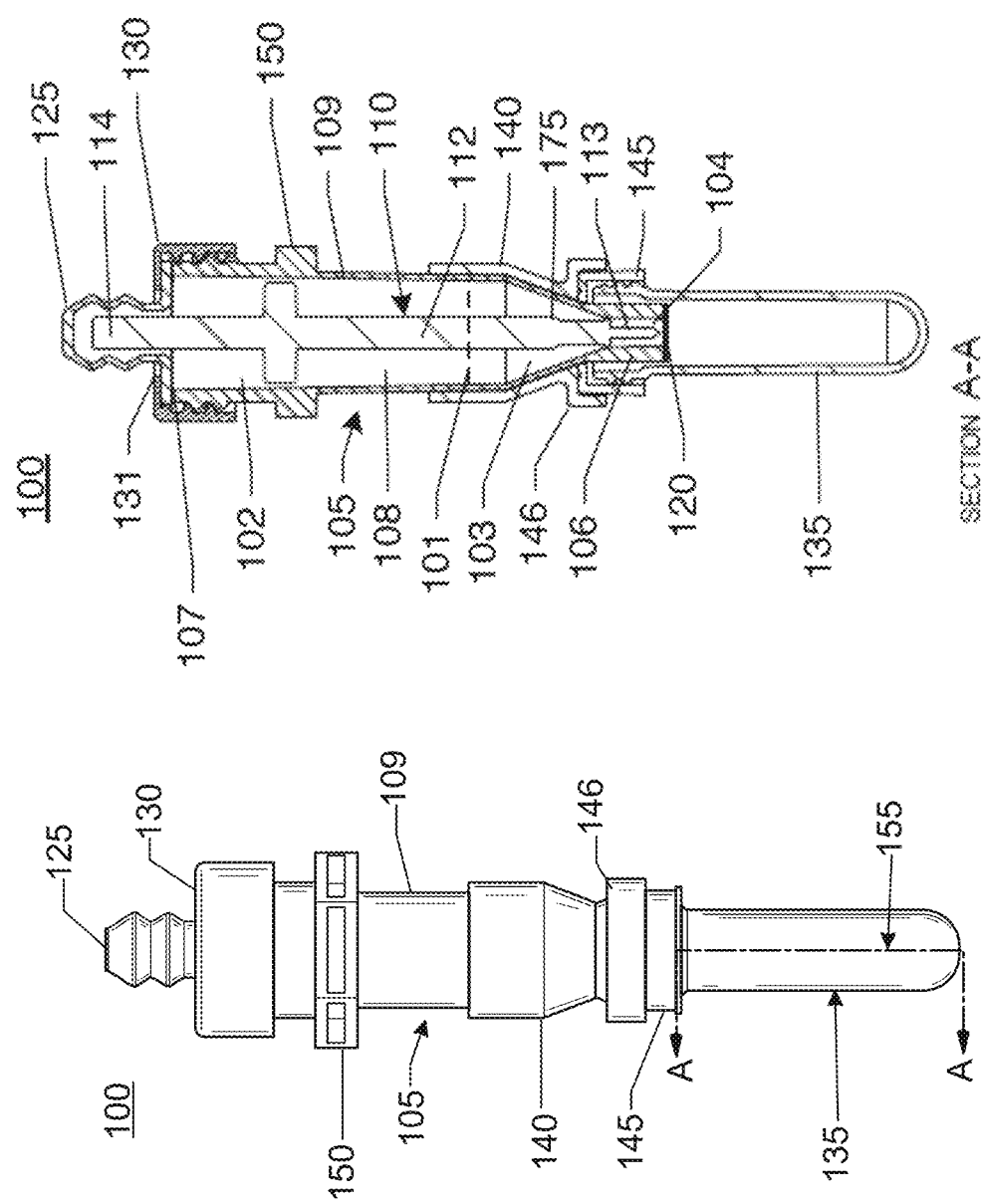
FIG. 3
FIG. 2

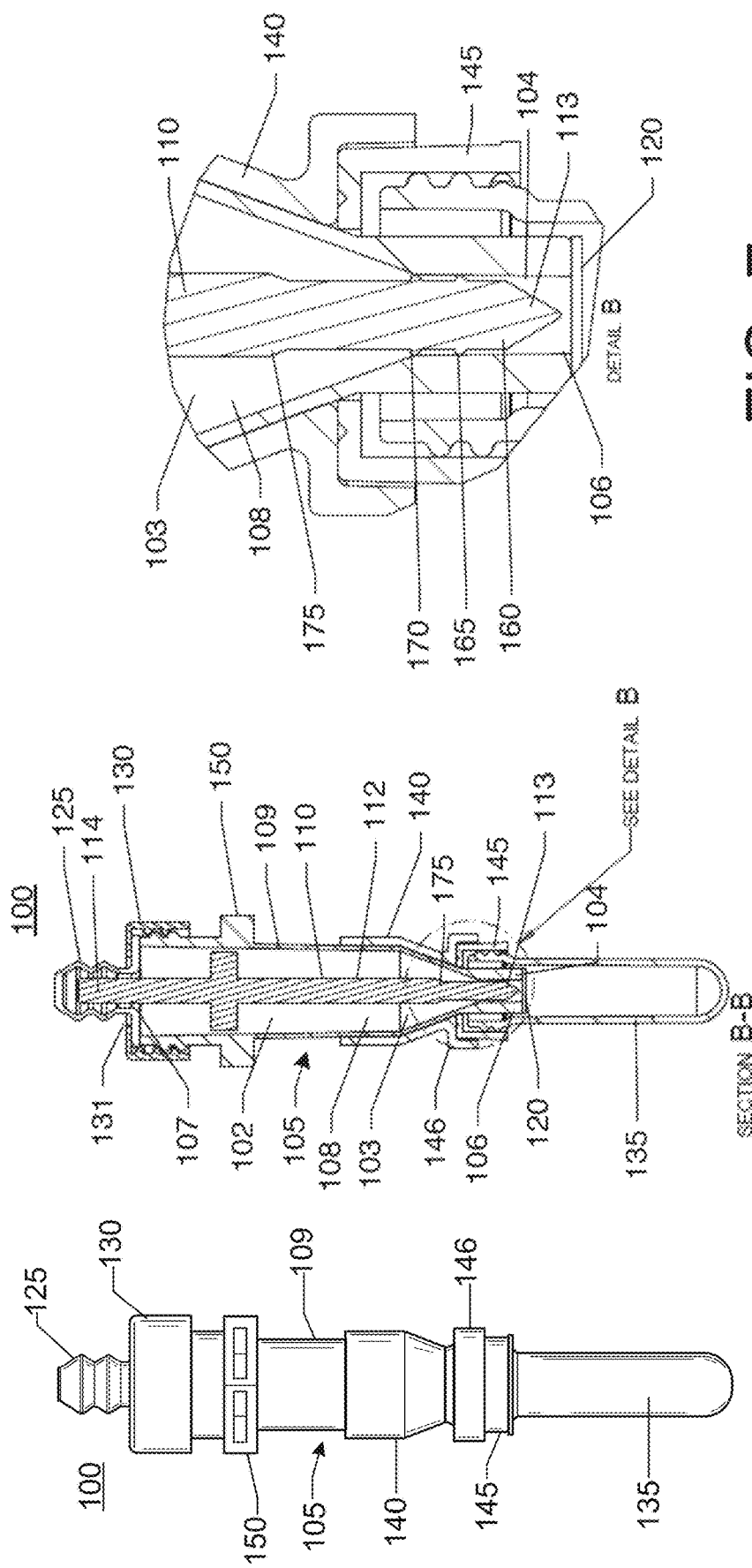

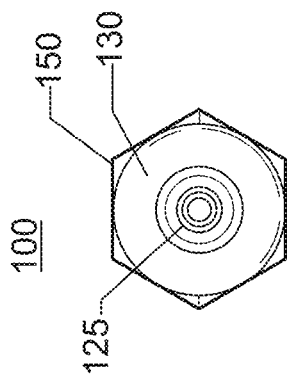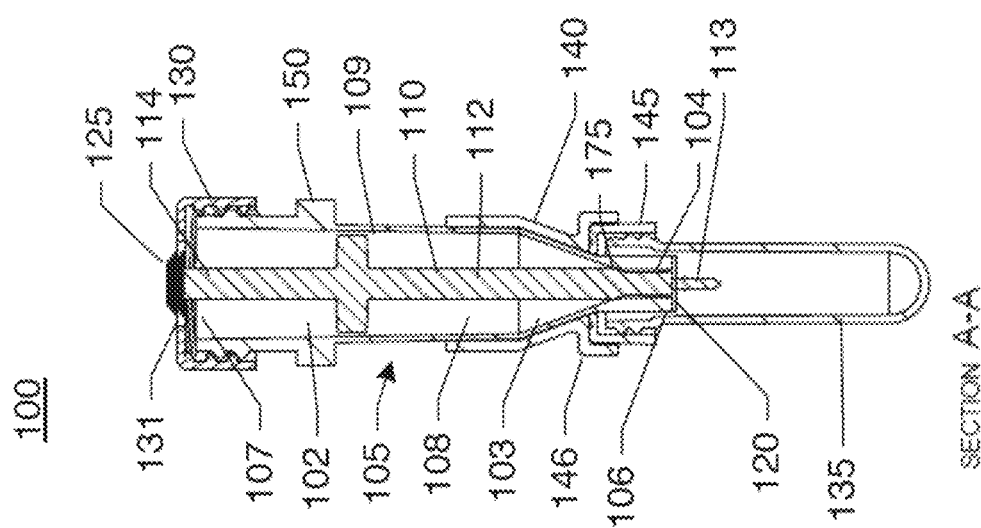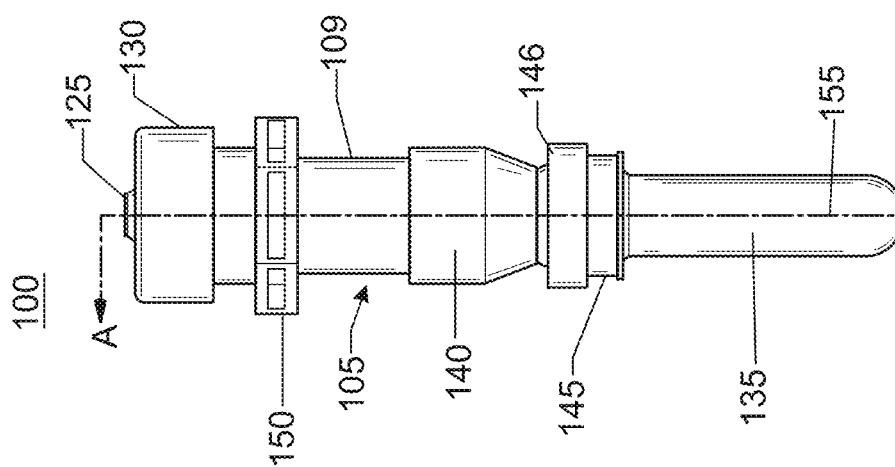

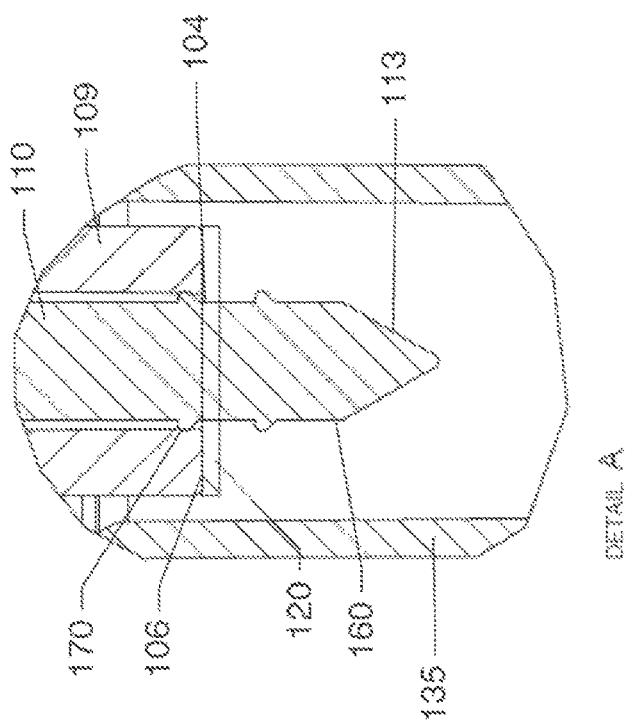
FIG. 13
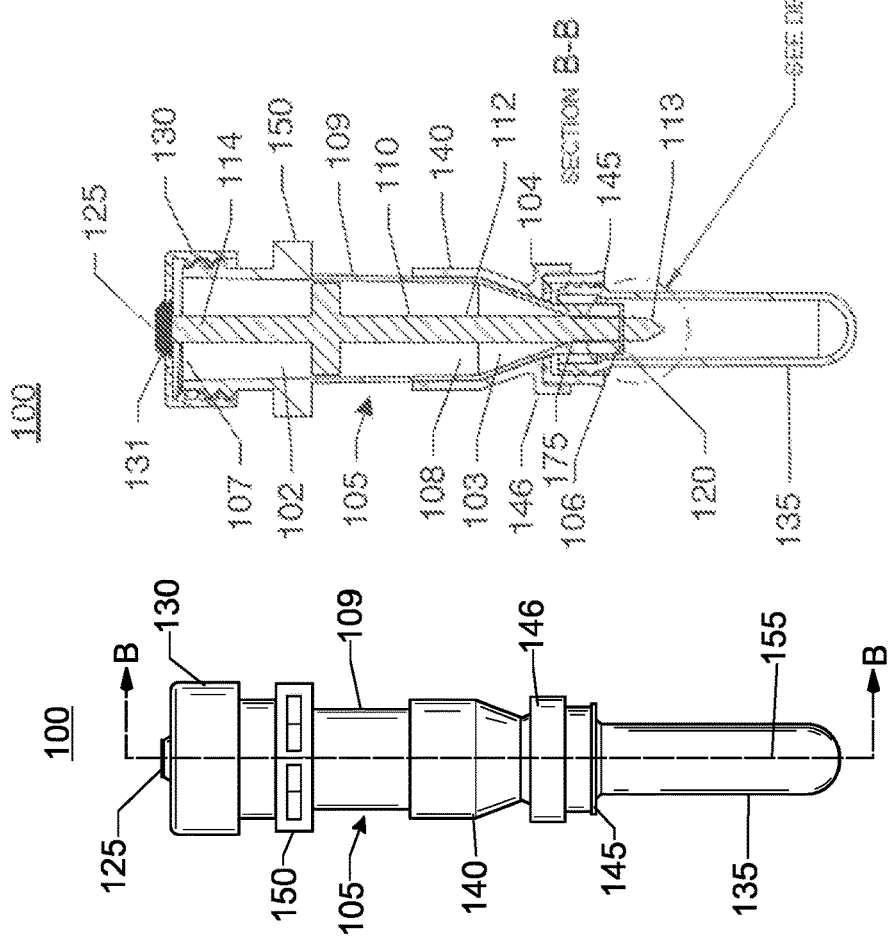
FIG. 12
FIG. 11

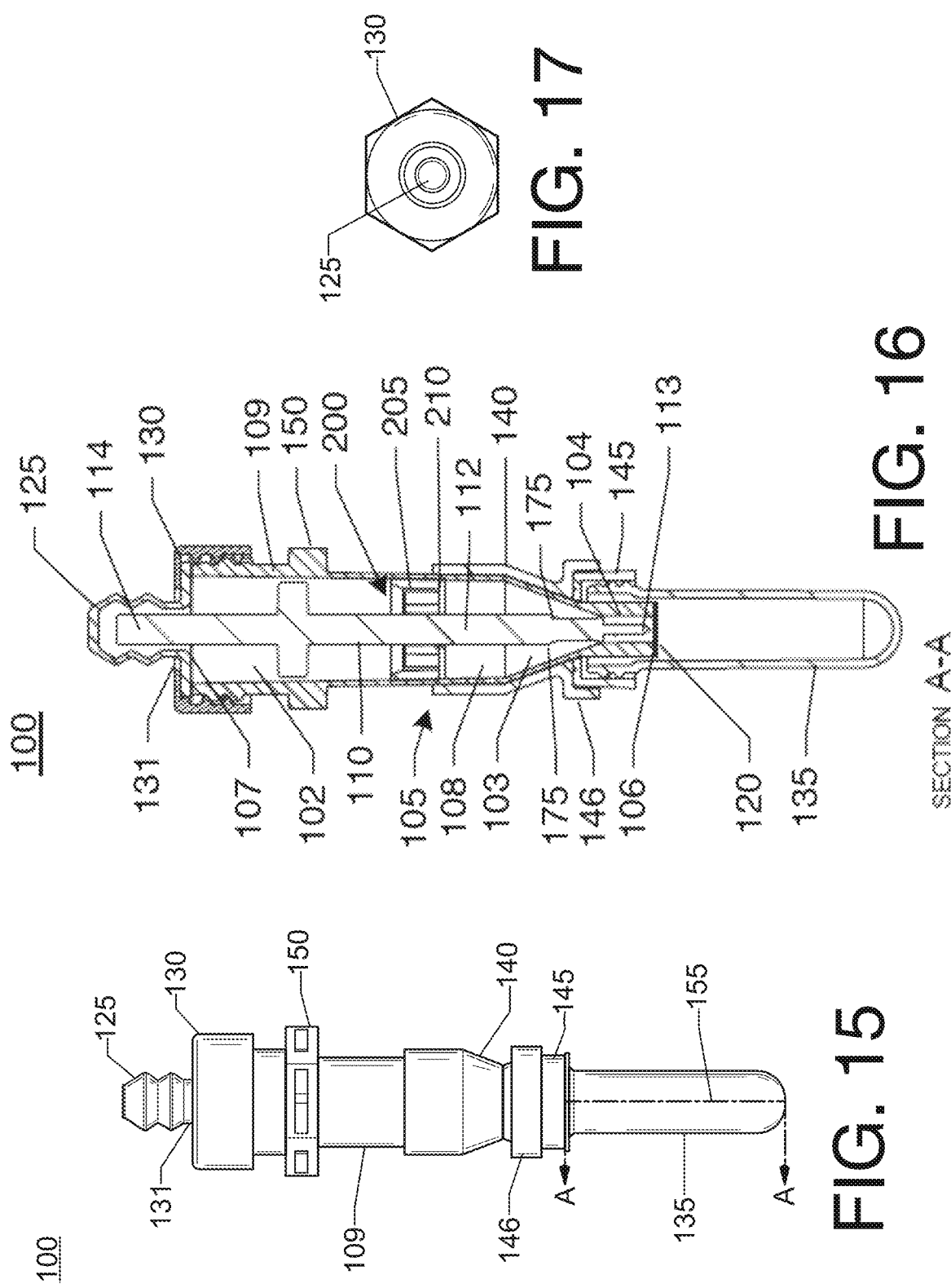

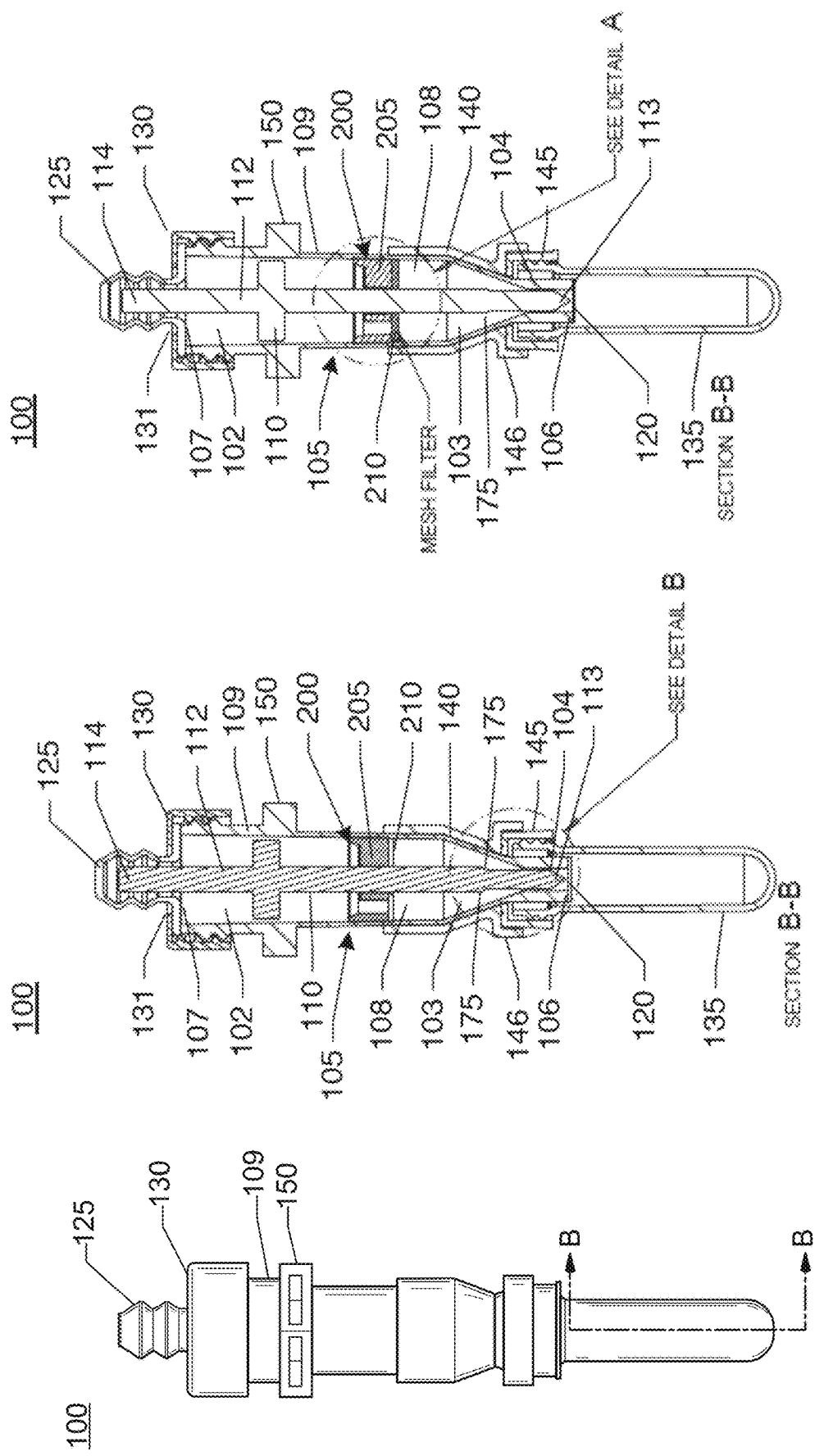

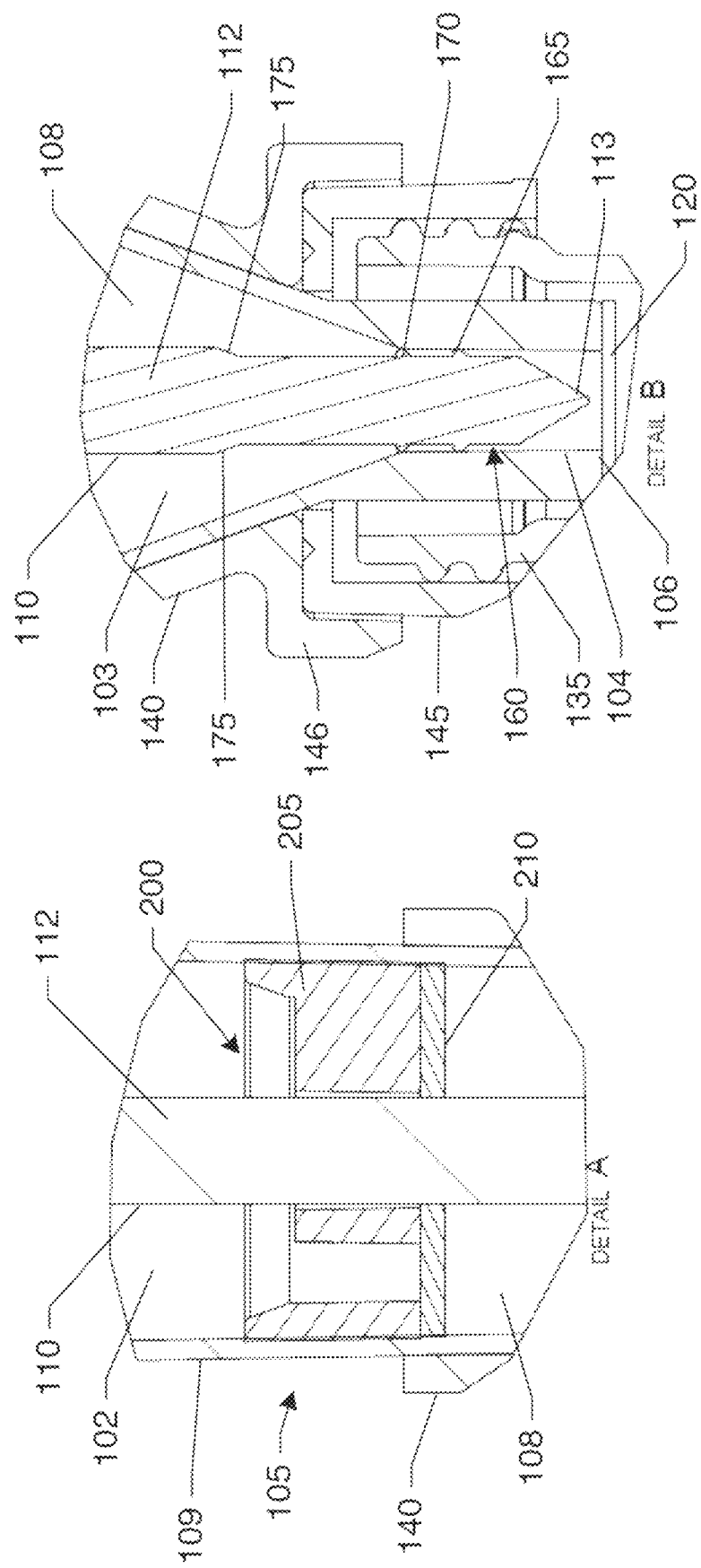

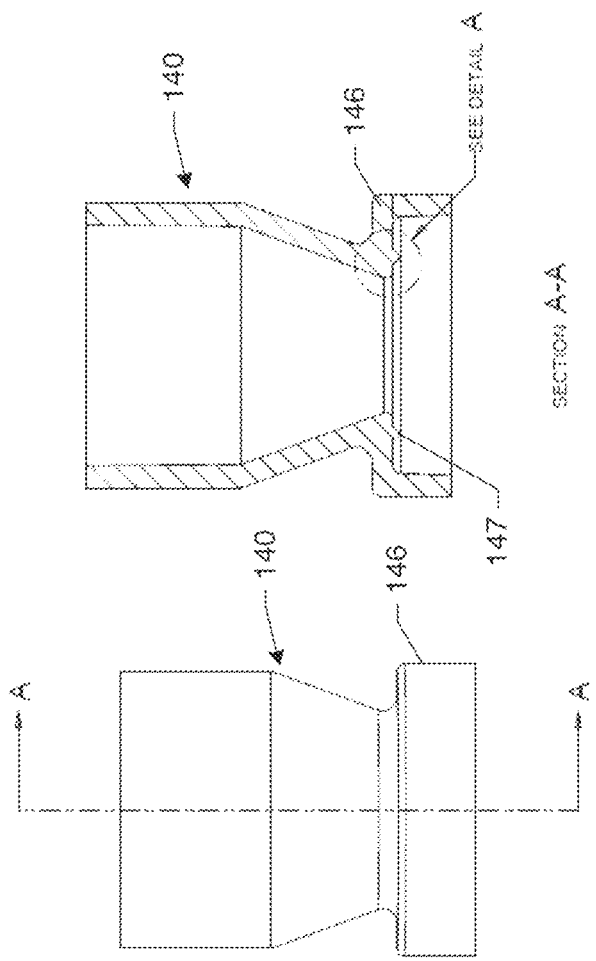
FIG. 28
FIG. 29
FIG. 31
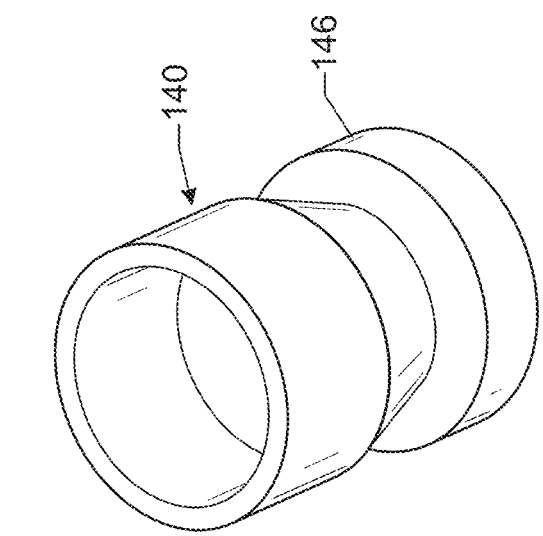
FIG. 27
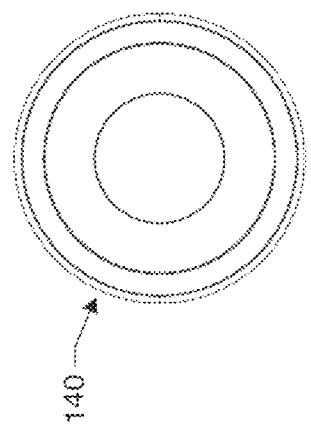
FIG. 30

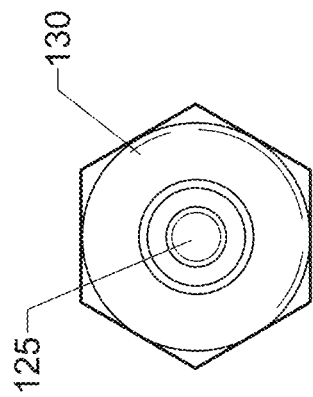
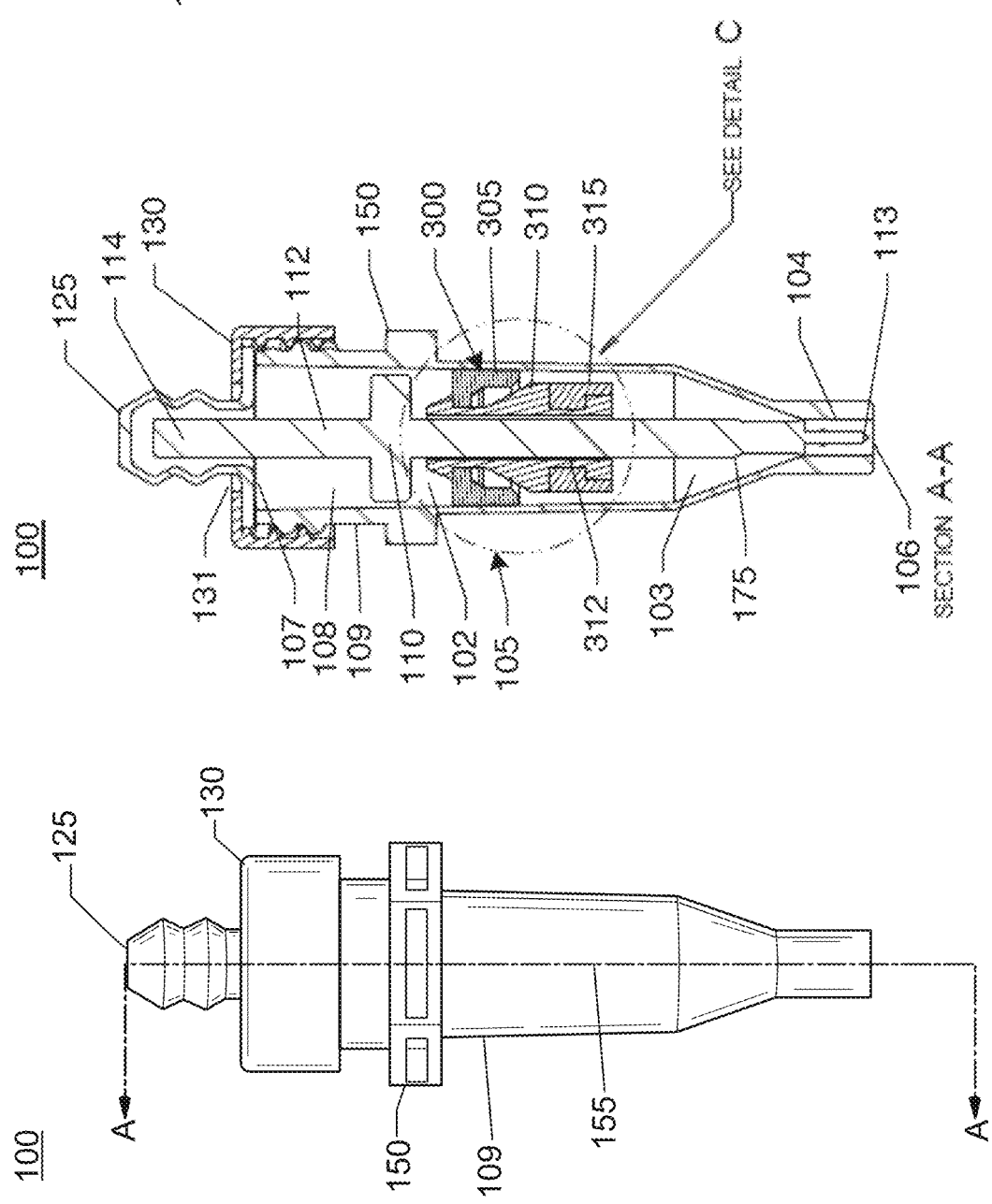
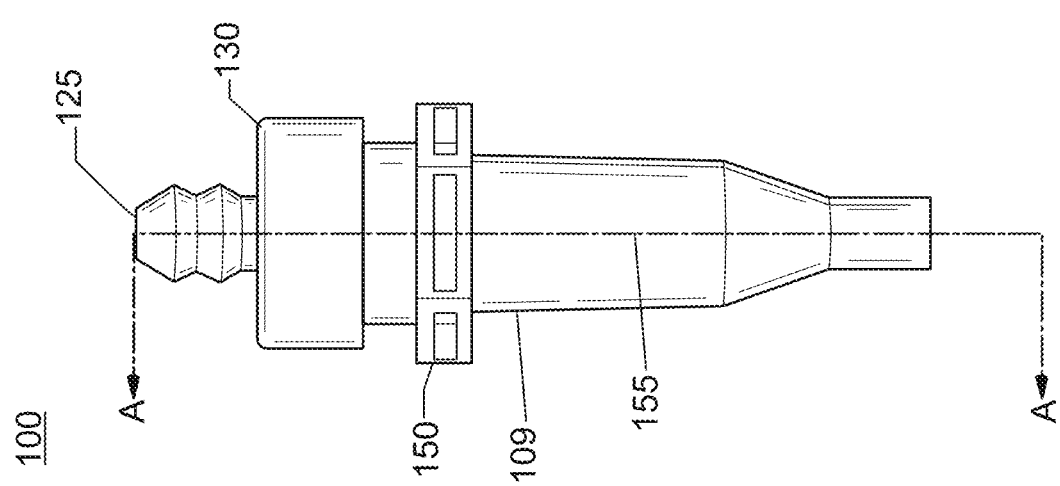

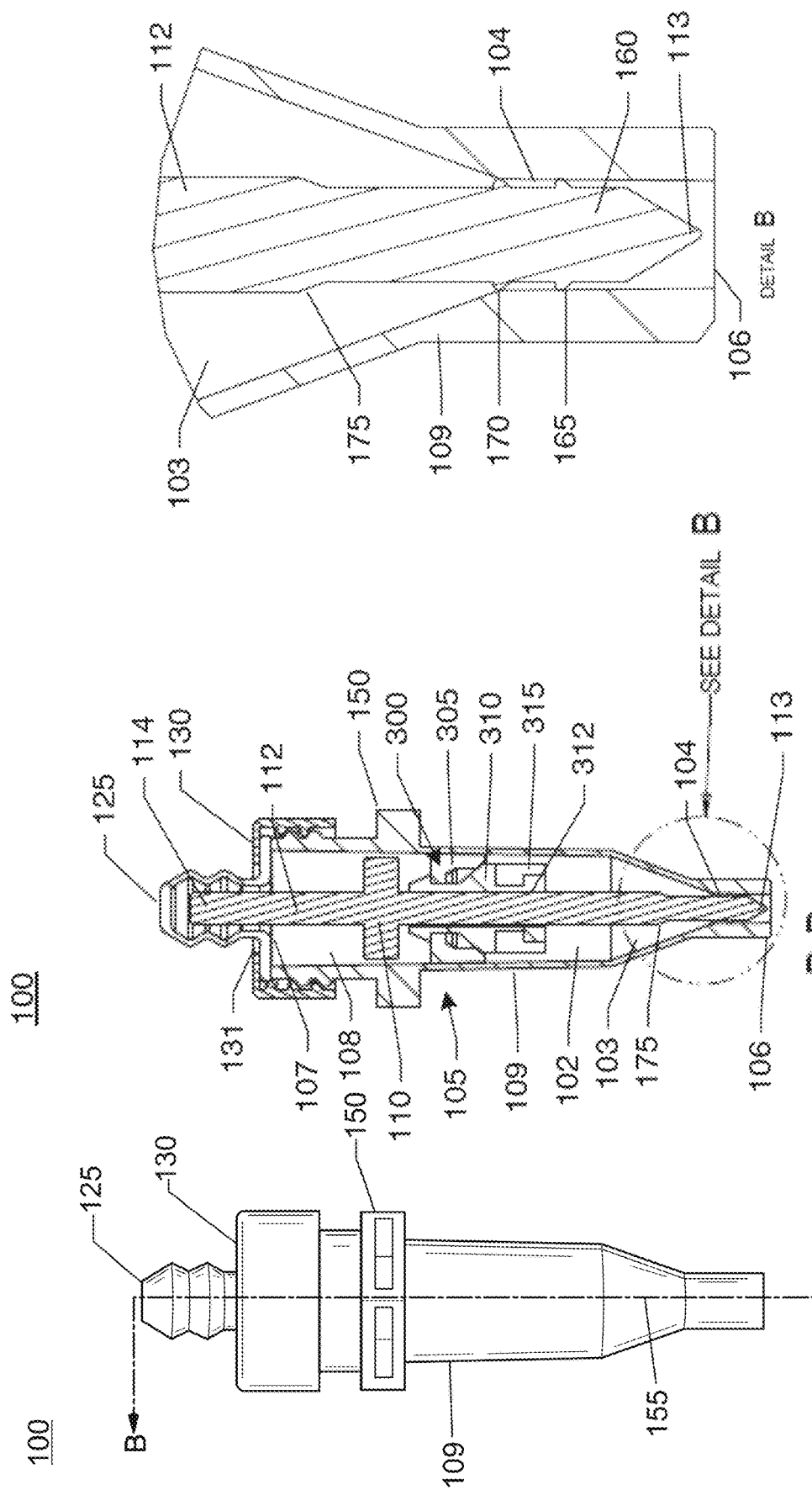

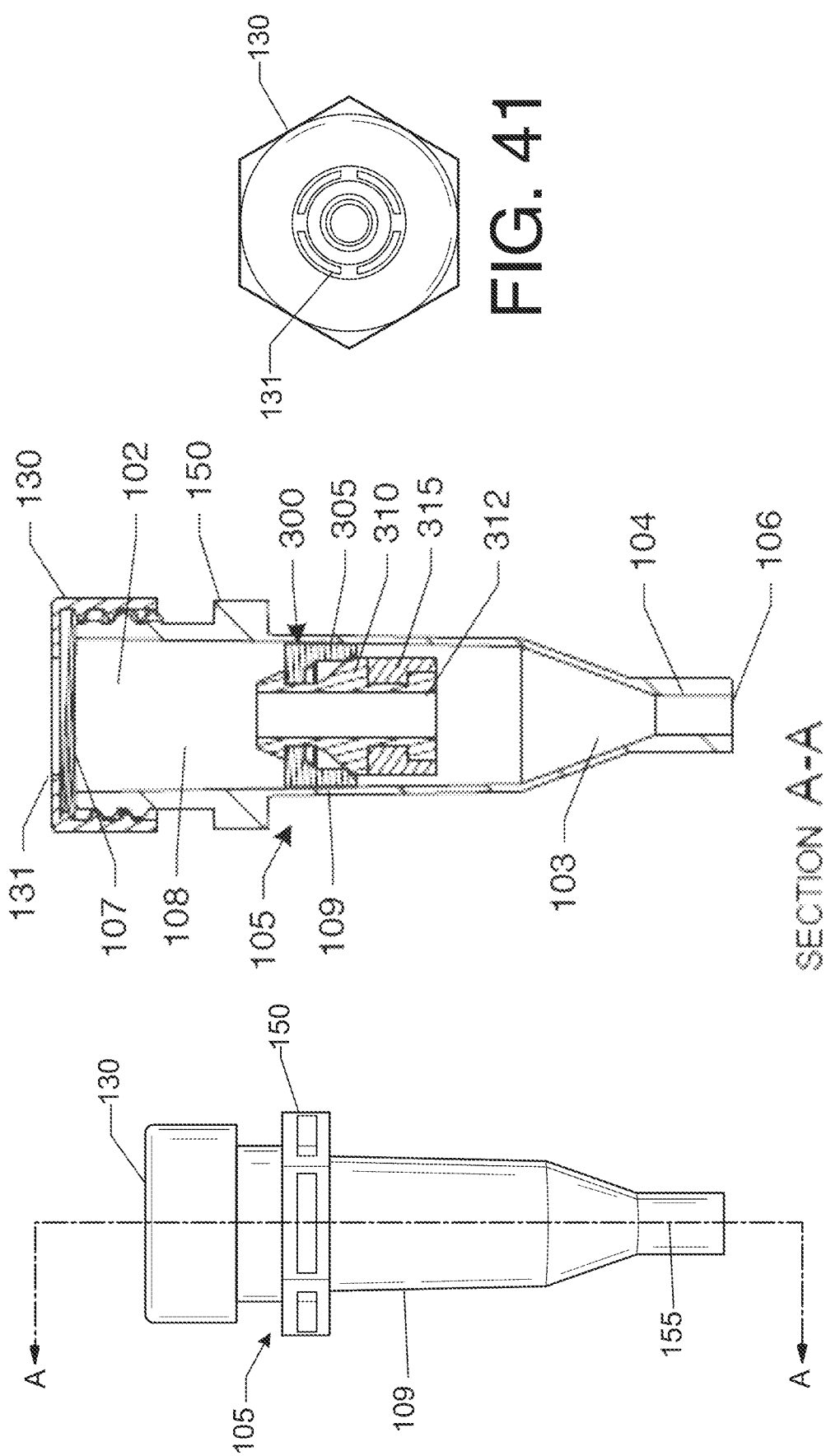

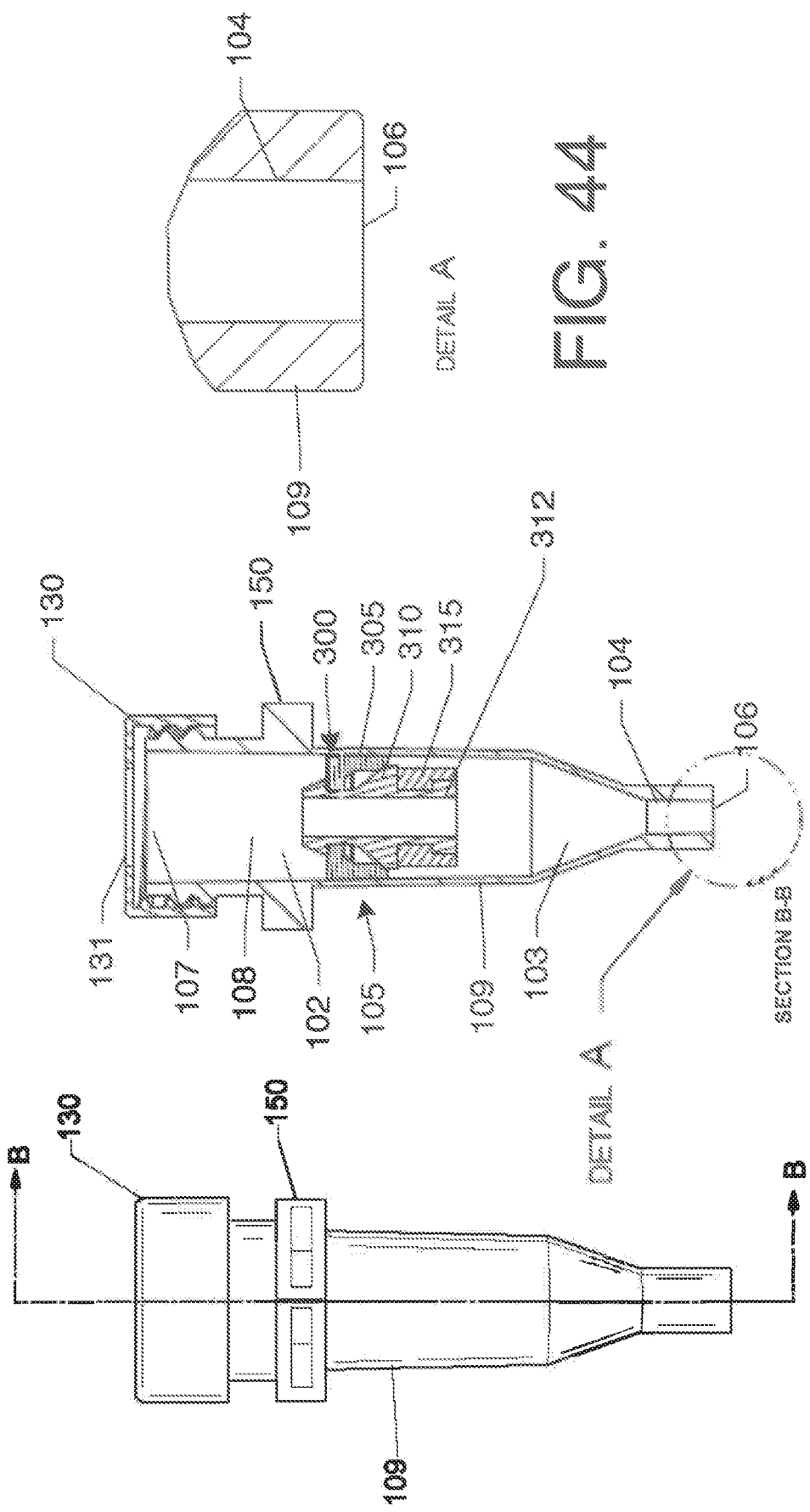

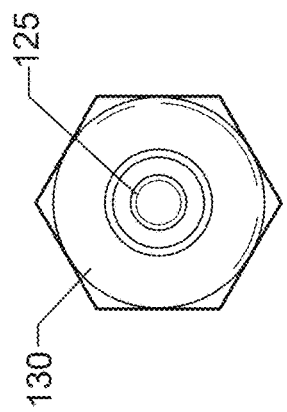
FIG. 53
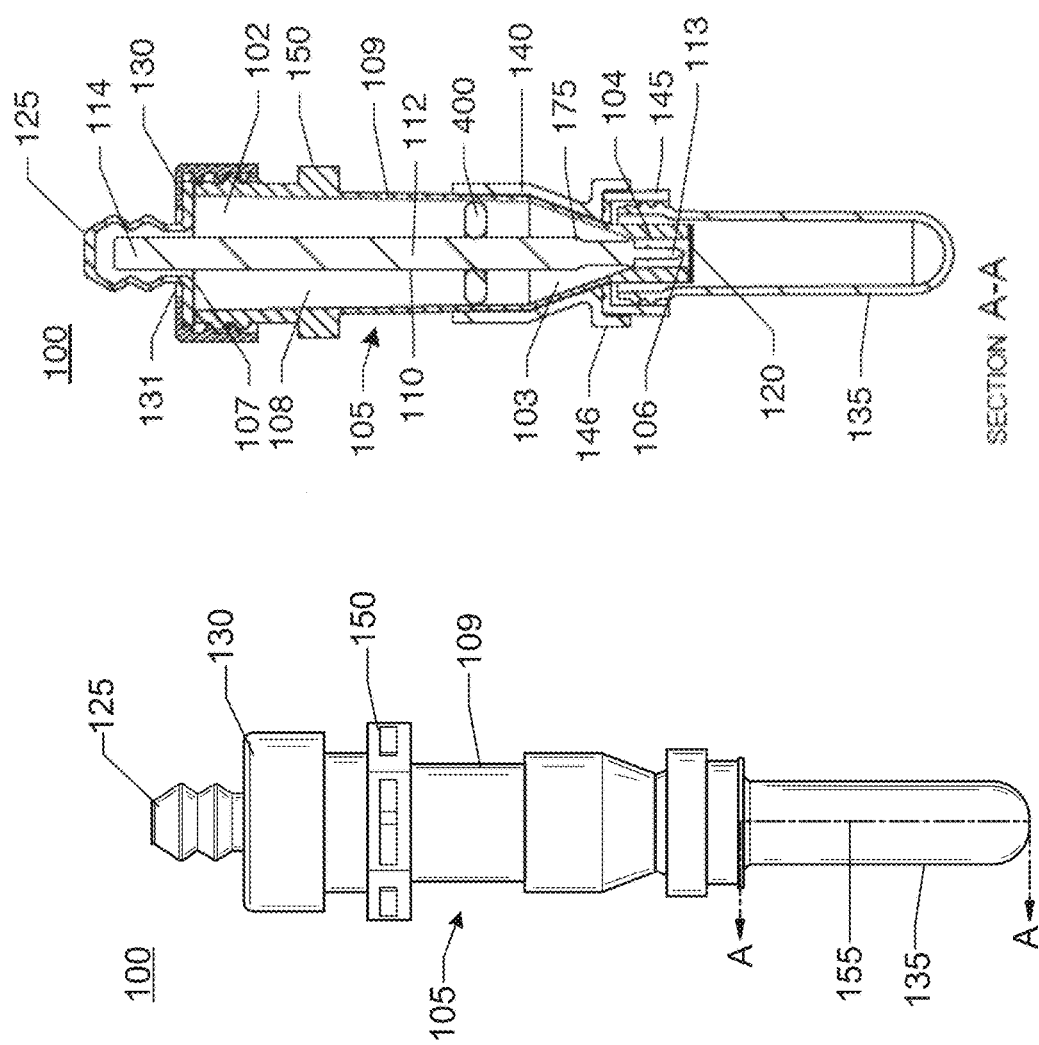
FIG. 52
FIG. 51

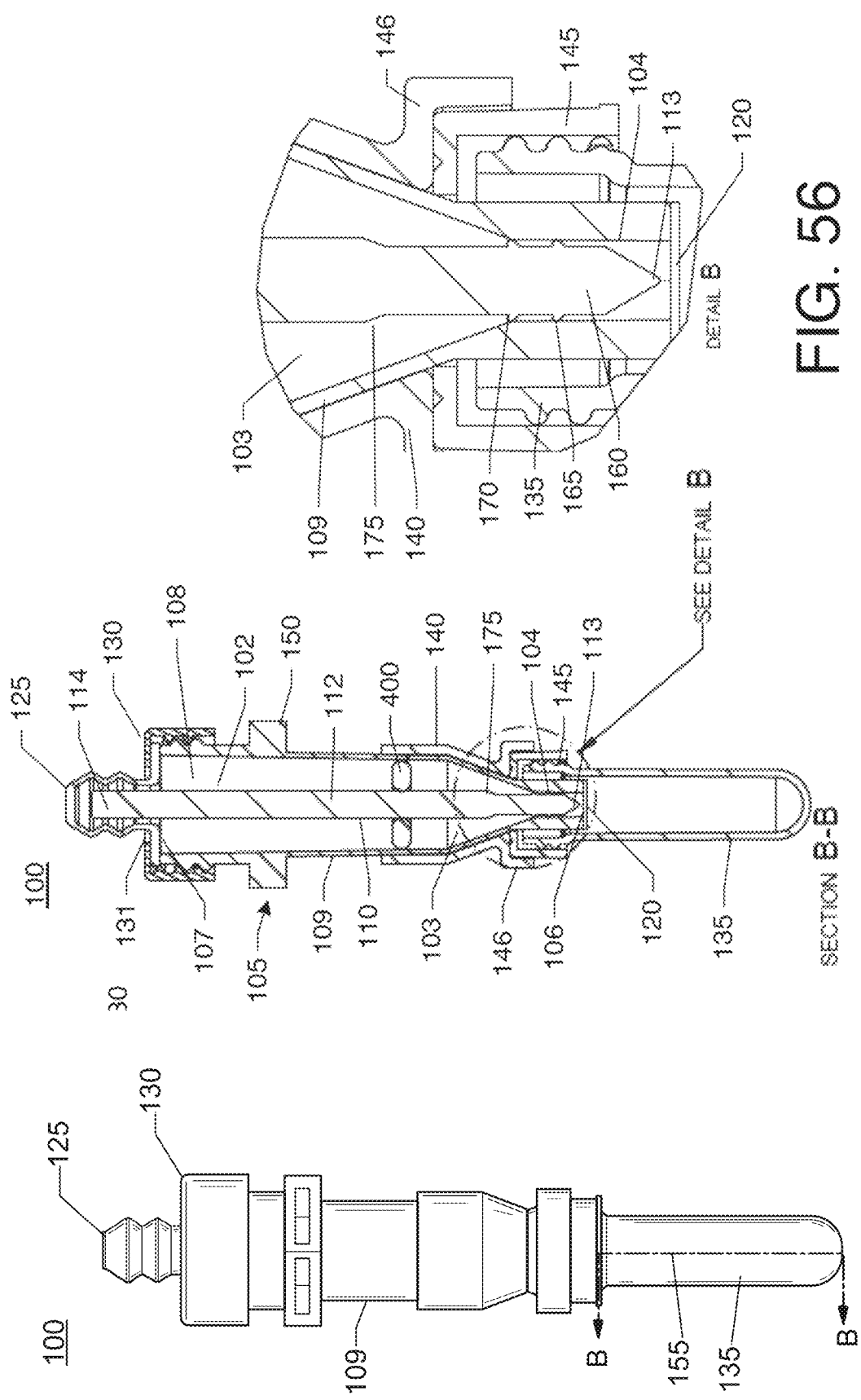

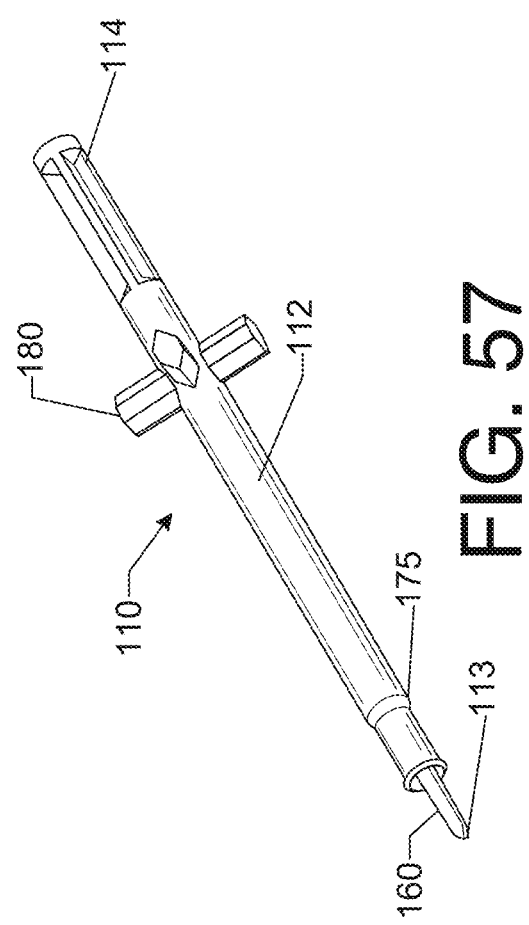
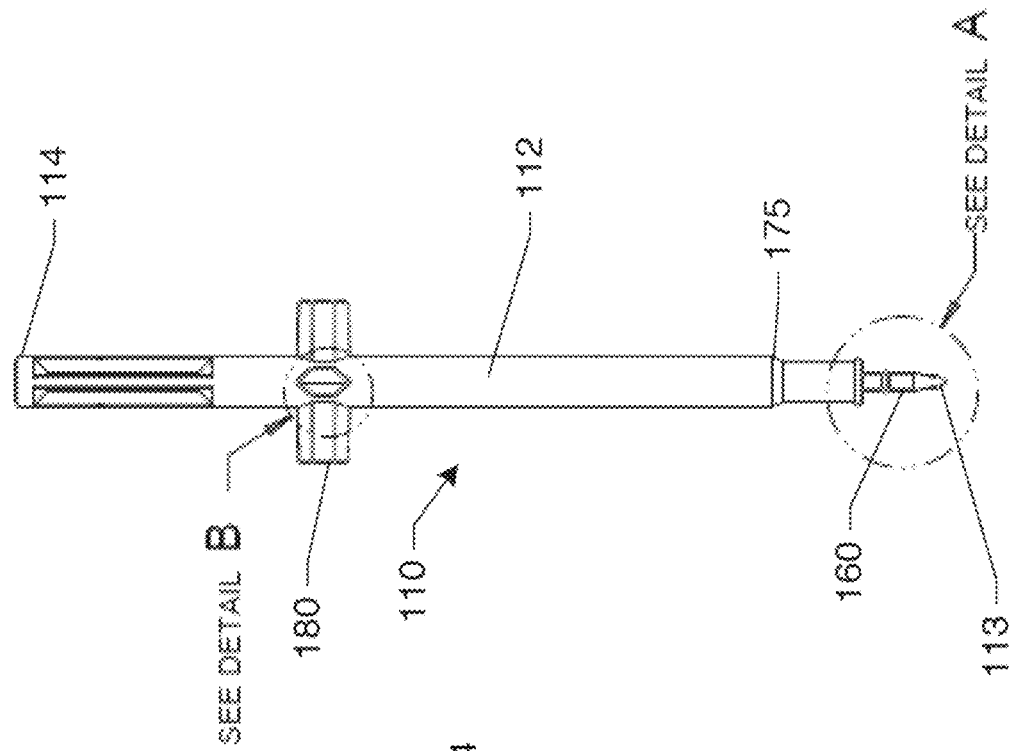
FIG. 57
FIG. 58

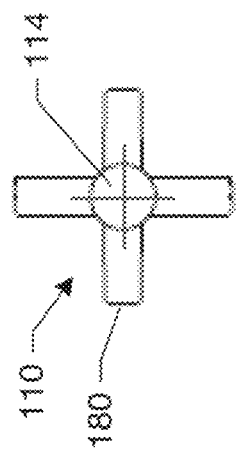
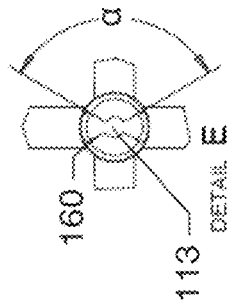
FIG. 61
FIG. 63
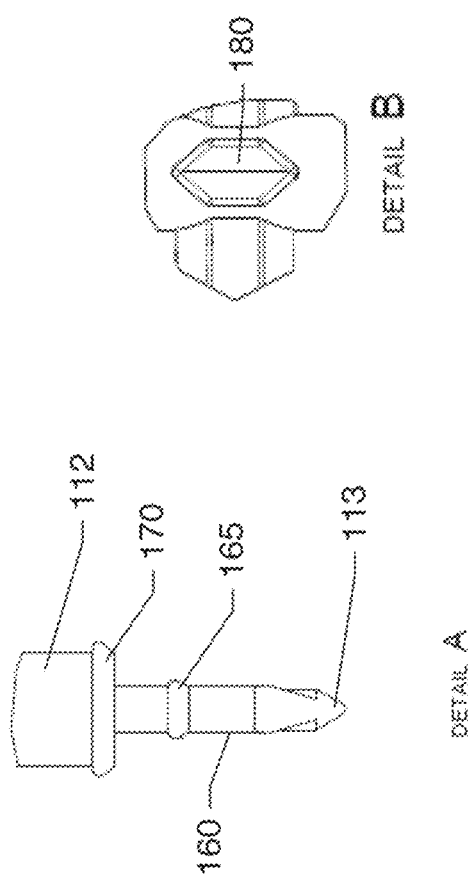
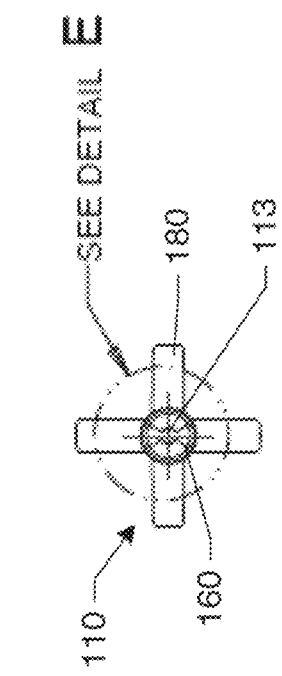
FIG. 59
FIG. 60
FIG. 62

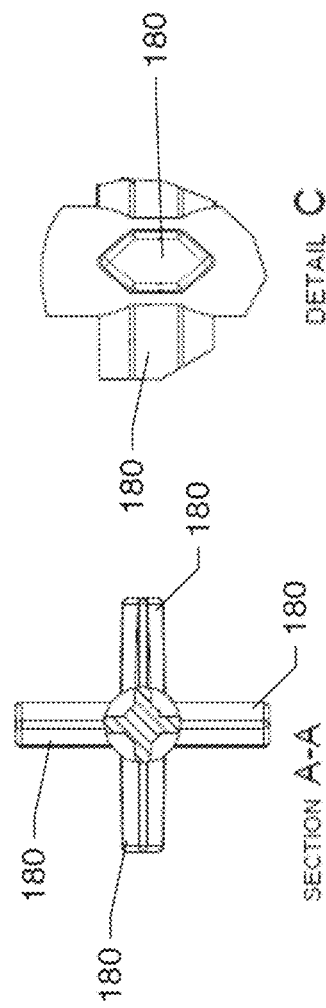
FIG. 65
FIG. 66
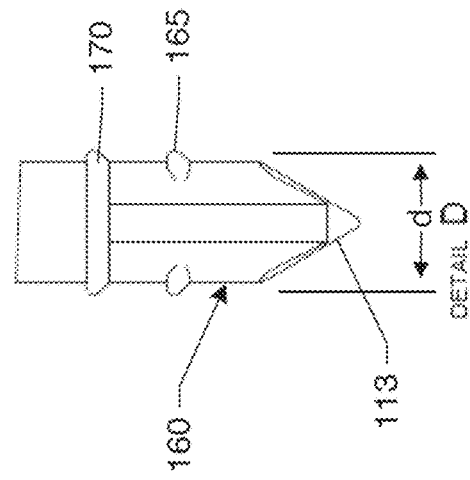
FIG. 67
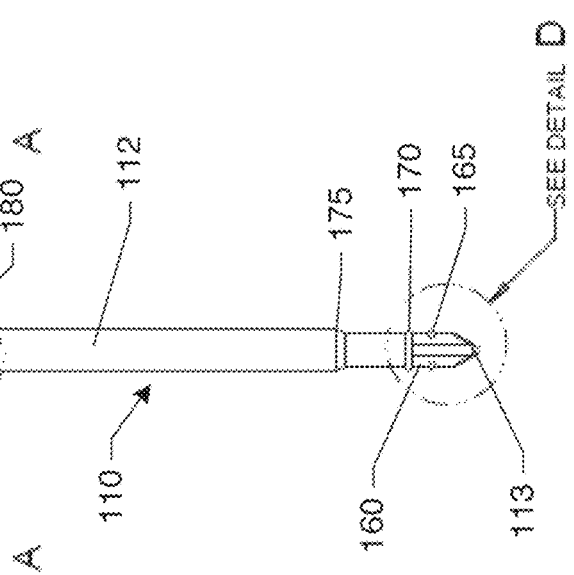
FIG. 64

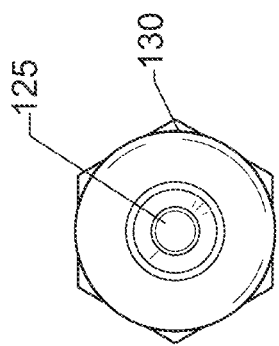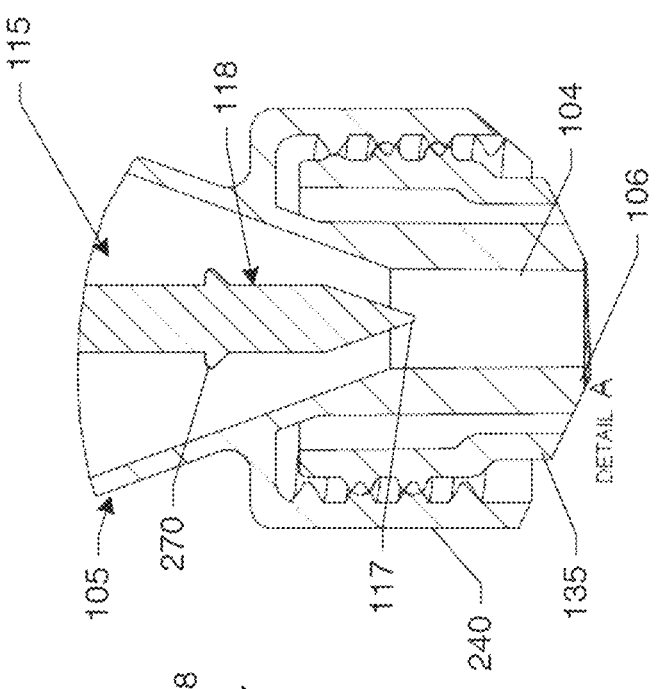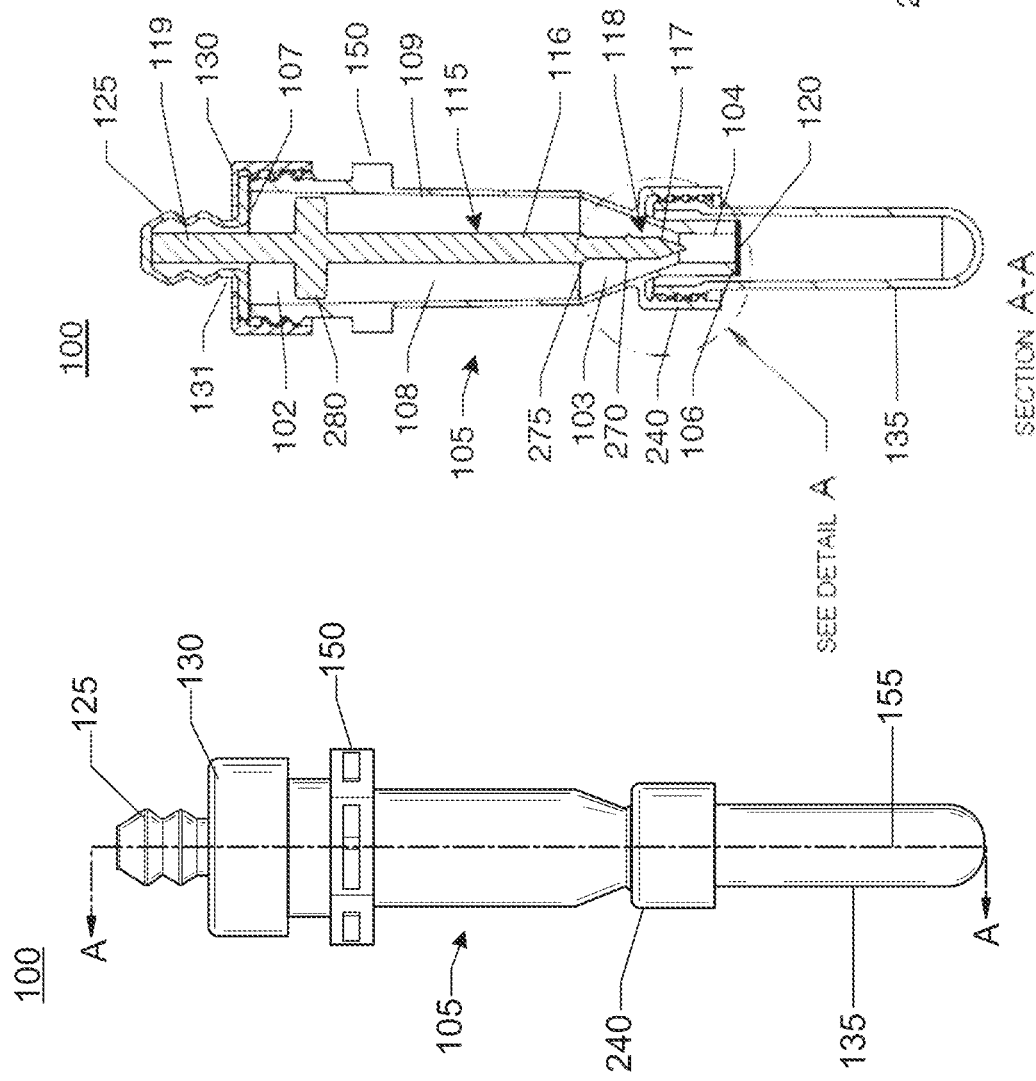

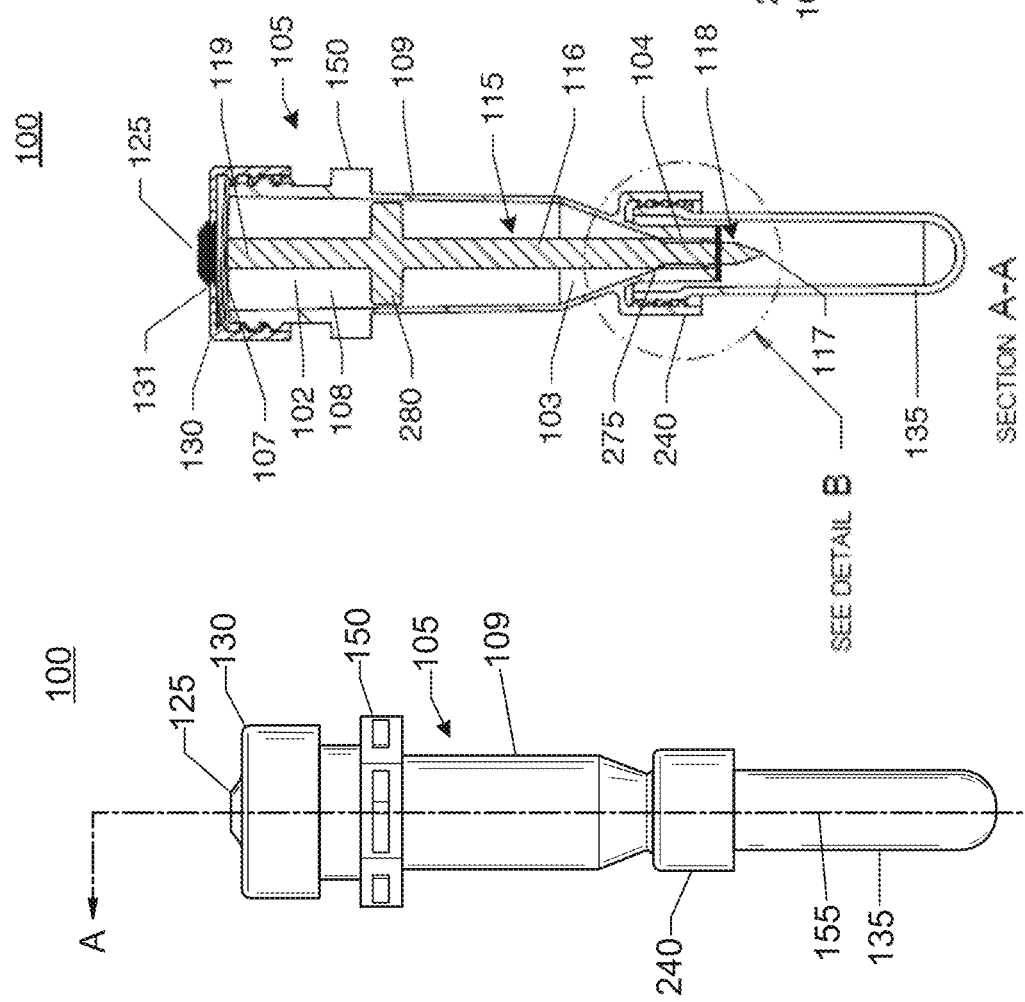

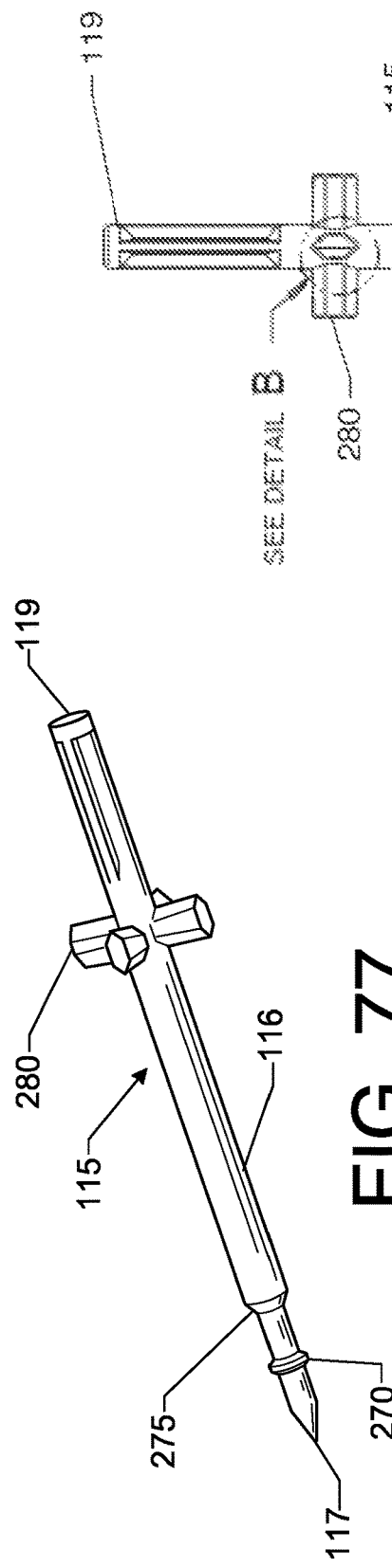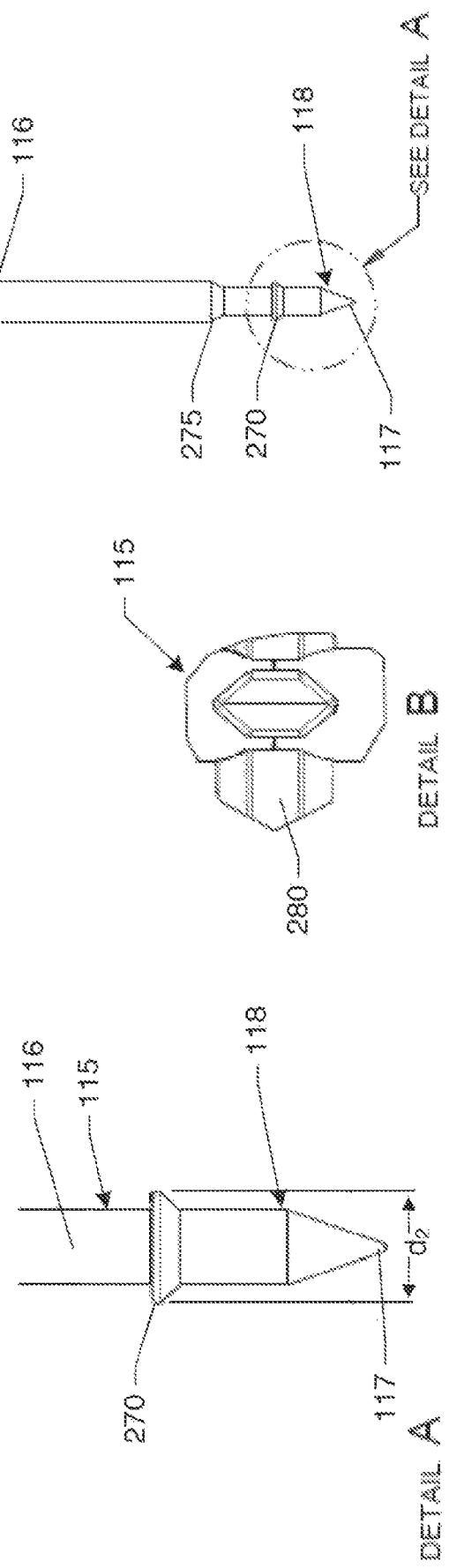

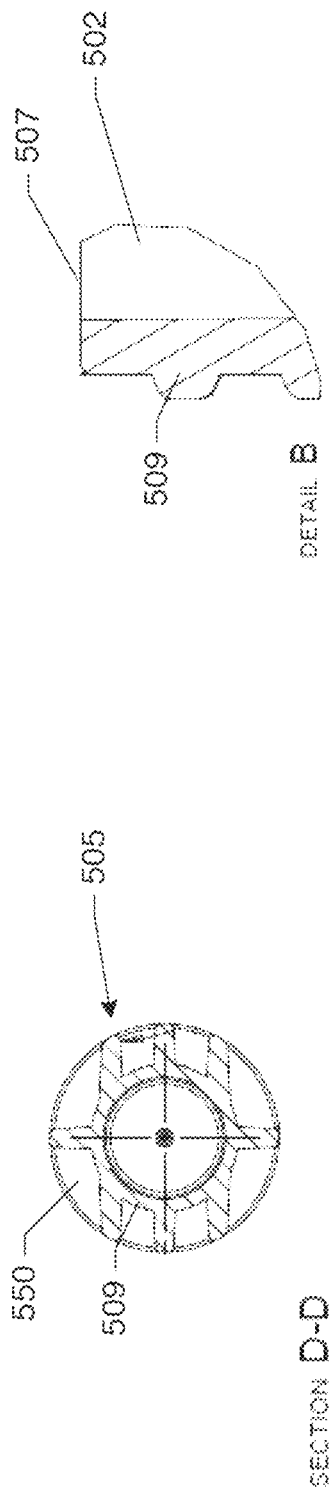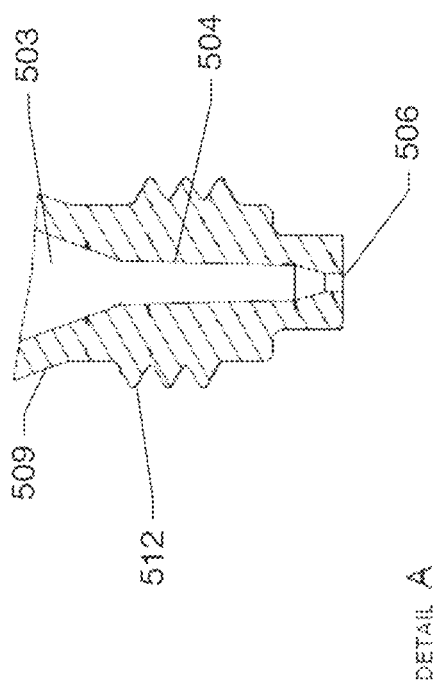

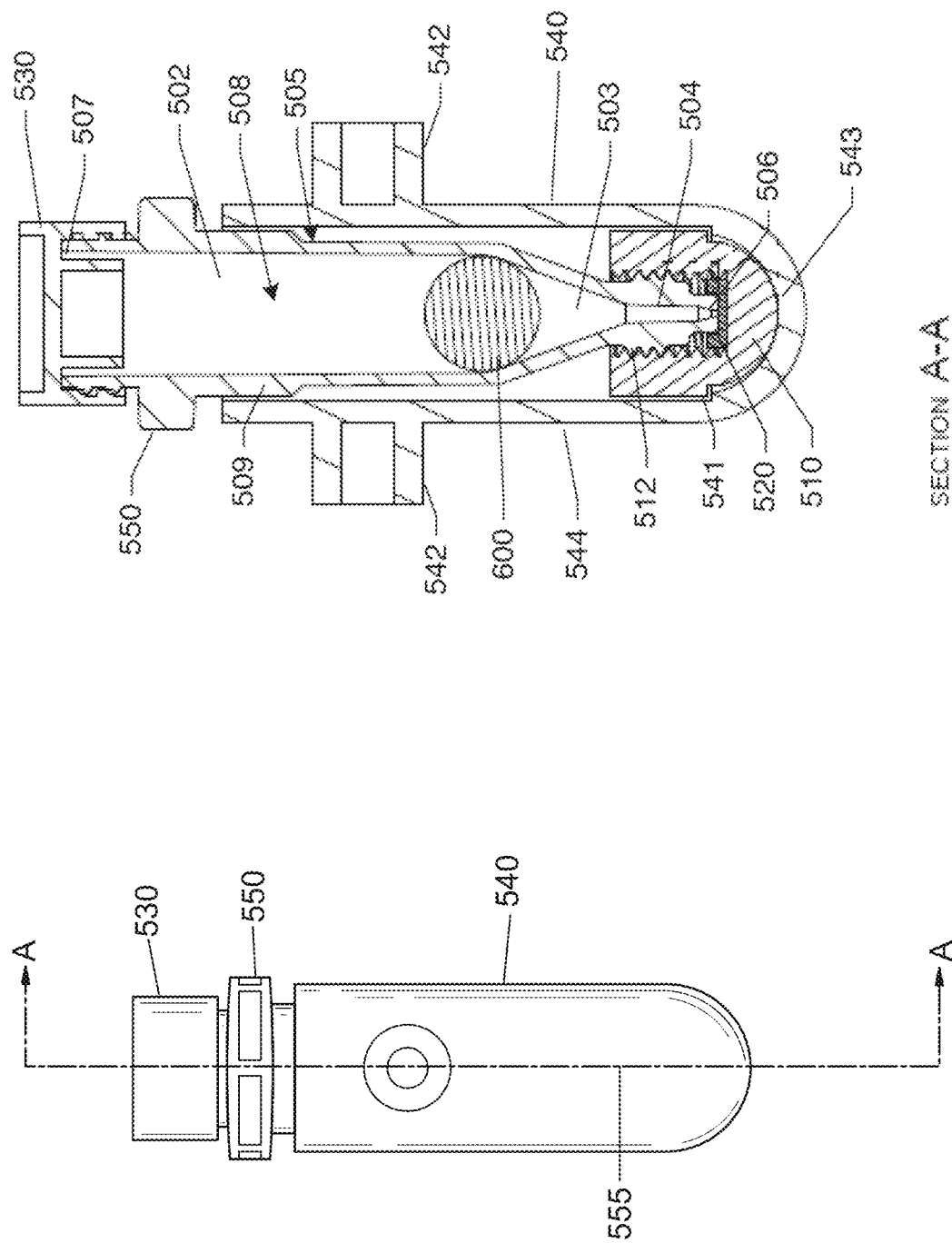

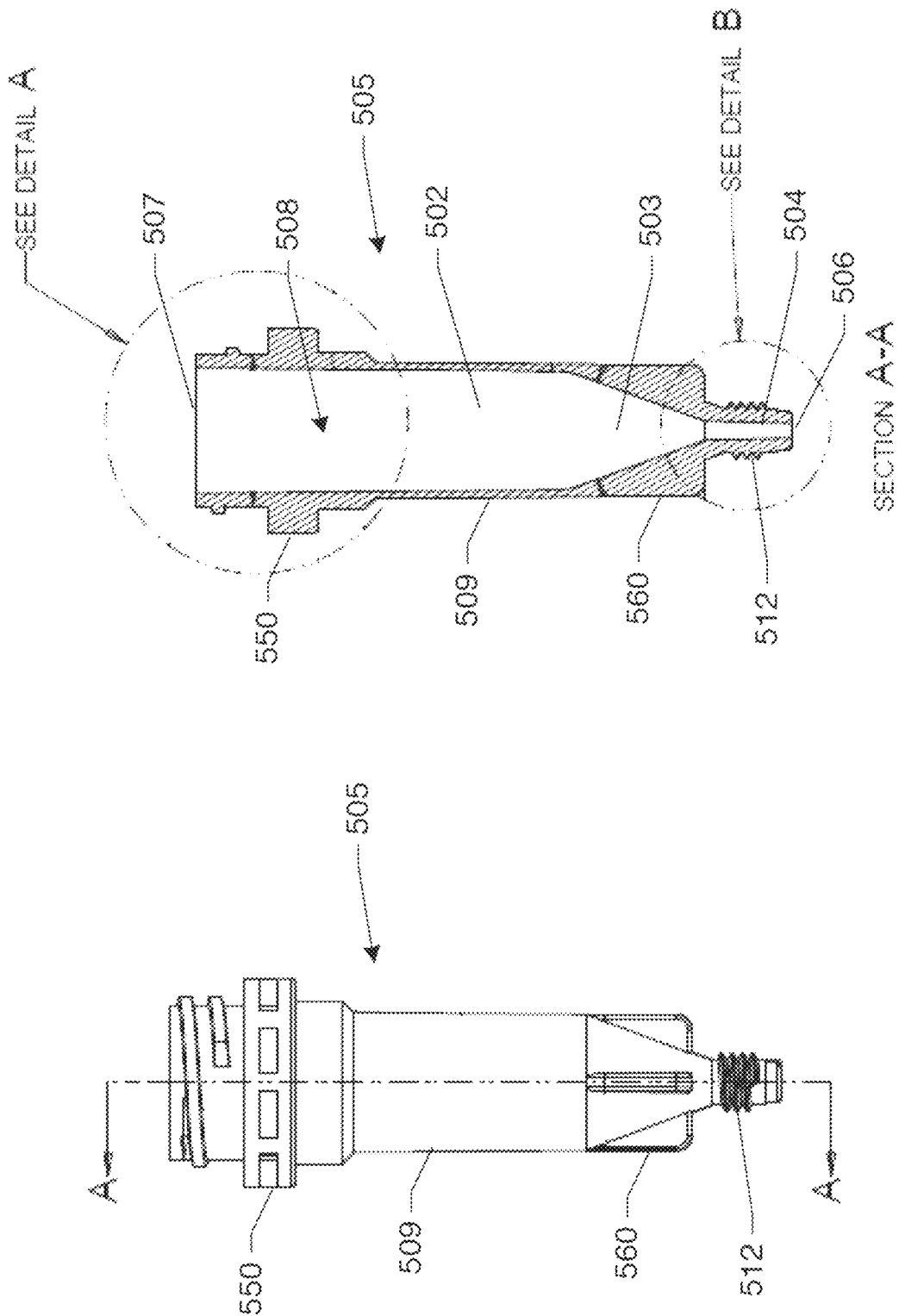

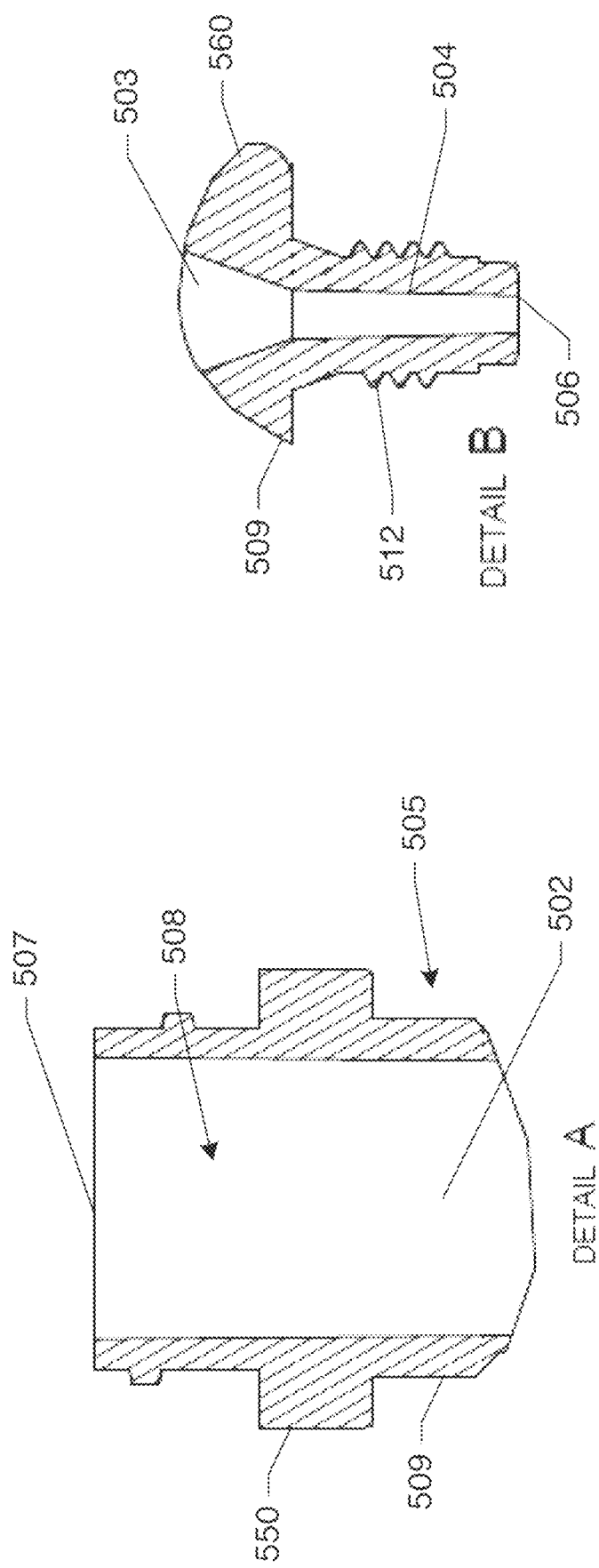

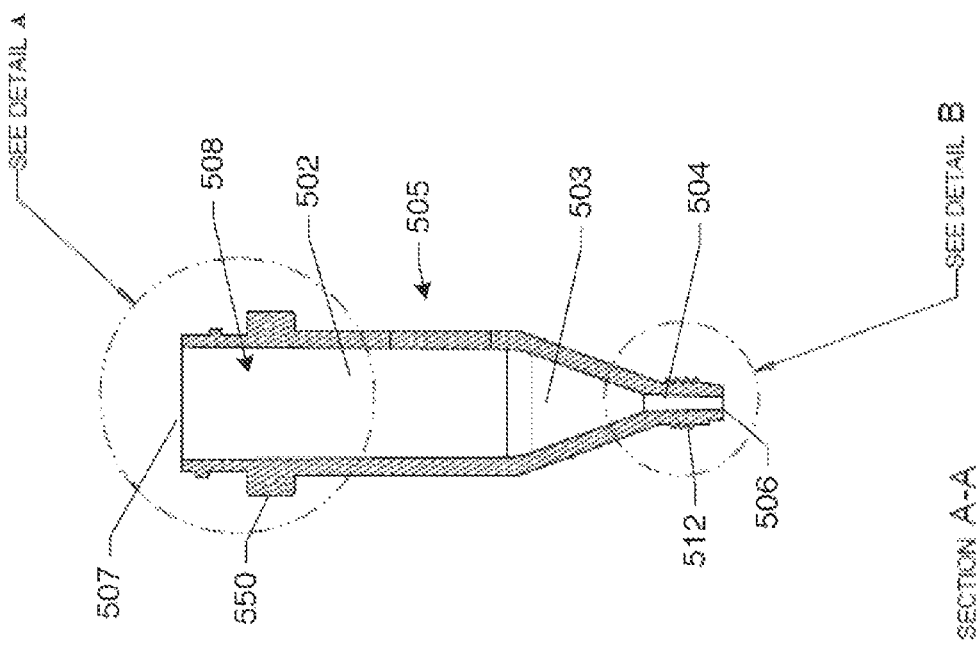
FIG. 125
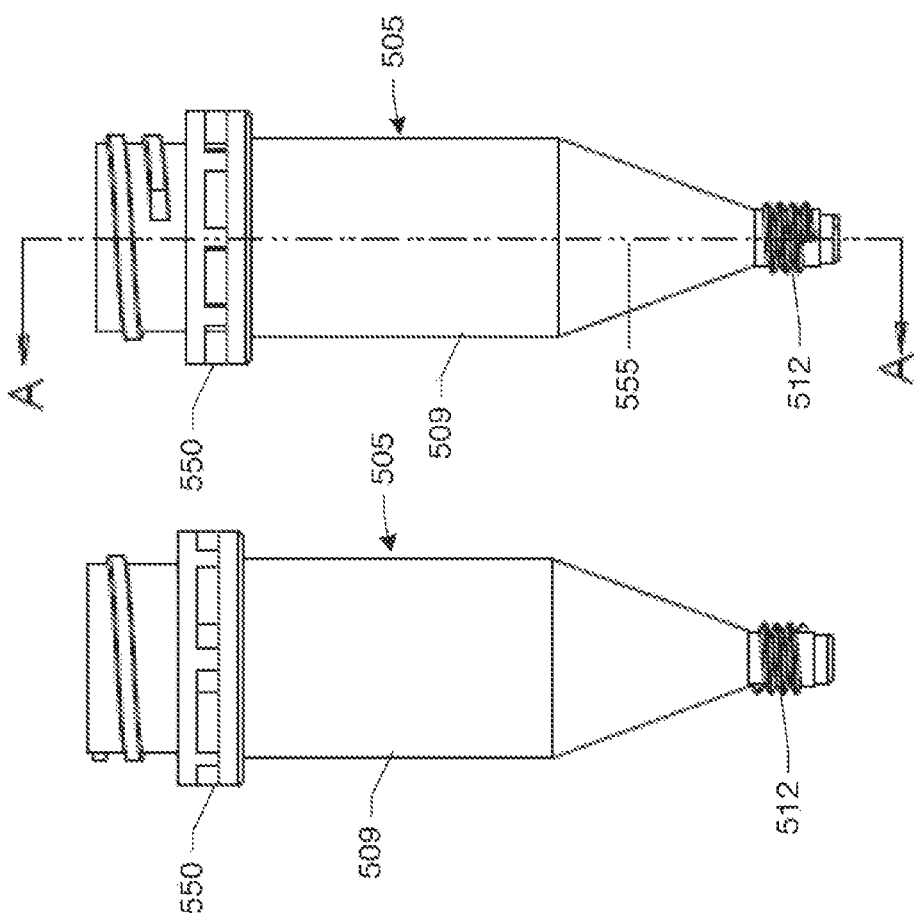
FIG. 124
FIG. 123

MALDI-TOF ID Results for Recovered Suspensions

| Species | Strain | McF | Volume | FA | Species ID | Probability | Score | Av. Score |
|---|---|---|---|---|---|---|---|---|
| P. aeruginosa | 1935 | 0.96 | 2 uL | 0 | Ps.aeruginosa | 100.00 | 1.17 | |
| | | (initial) | 2 uL | 0 | Ps.aeruginosa | 100.00 | 1.46 | 1.32 |
| | | | 2 uL | 0.5 uL | Ps.aeruginosa | 100.00 | 0.73 | |
| | | | 2 uL | 0.5 uL | Ps.aeruginosa | 99.99 | 0.10 | 0.41 |
| | | 0.55 | 5 uL | 0 | Ps.aeruginosa | 100.00 | 0.83 | |
| | | (diluted) | 5 uL | 0 | Ps.aeruginosa | 100.00 | 0.86 | 0.84 |
| | | | 5 uL | 0.5 uL | Ps.aeruginosa | 100.00 | 0.77 | |
| | | | 5 uL | 0.5 uL | Ps.aeruginosa | 99.99 | 0.29 | 0.53 |
| K. pneumoniae | 79382 | 1.75 | 2 uL | 0 | K.pneumoniae | 99.99 | 0.41 | |
| | | (initial) | 2 uL | 0 | K.pneumoniae | 99.99 | 0.33 | 0.37 |
| | | | 2 uL | 0.5 uL | K.pneumoniae | 94.90 | -0.06 | |
| | | | 2 uL | 0.5 uL | K.pneumoniae | 91.72 | -0.09 | -0.07 |
| | | 0.57 | 5 uL | 0 | K.pneumoniae | 99.87 | 0.11 | |
| | | (diluted) | 5 uL | 0 | K.pneumoniae | 86.59 | -0.11 | 0.00 |
| | | | 5 uL | 0.5 uL | K.pneumoniae | 69.74 | -0.16 | |
| | | | 5 uL | 0.5 uL | K.pneumoniae | 91.00 | -0.09 | -0.13 |
| E. faecium | 50215 | 5.1 | 2 uL | 0 | Entero.faecium | 99.99 | 0.29 | |
| | | (initial) | 2 uL | 0 | Entero.faecium | 99.99 | 0.33 | 0.31 |
| | | | 2 uL | 0.5 uL | Entero.faecium | 99.99 | 0.30 | |
| | | | 2 uL | 0.5 uL | Entero.faecium | 99.99 | 0.22 | 0.26 |
| | | 0.59 | 5 uL | 0 | Entero.faecium | 100.00 | 0.77 | |
| | | (diluted) | 5 uL | 0 | Entero.faecium | 100.00 | 0.59 | 0.68 |
| | | | 5 uL | 0.5 uL | Entero.faecium | 100.00 | 0.57 | |
| | | | 5 uL | 0.5 uL | Entero.faecium | 99.99 | 0.36 | 0.47 |
| S. aureus | 60570 | 0.63 | 2 uL | 0 | Staph.aureus | 99.99 | 0.16 | |
| | | (initial) | 2 uL | 0 | Staph.aureus | 99.90 | 0.00 | 0.08 |
| | | | 2 uL | 0.5 uL | Staph.aureus | 99.86 | -0.02 | |
| | | | 2 uL | 0.5 uL | Staph.aureus | 99.99 | 0.13 | 0.06 |
| | | 0.63 | 5 uL | 0 | Staph.aureus | 99.99 | 0.46 | |
| | | (diluted) | 5 uL | 0 | Staph.aureus | 99.99 | 0.47 | 0.47 |
| | | | 5 uL | 0.5 uL | Staph.aureus | 99.99 | 0.28 | |
| | | | 5 uL | 0.5 uL | Staph.aureus | 97.80 | -0.14 | 0.07 |

FIG. 158

| Microorganism | P. aeruginosa 1935 | | | | | | | | K. pneumoniae 79382 | | | | | | | |
|---|---|---|---|---|---|---|---|---|---|---|---|---|---|---|---|---|
| Sample Type | Large Tube Suspension | | | | Historical Colony Control | | | | Large Tube Suspension | | | | Historical Colony Control | | | |
| ESBL | NEG | - | NEG | - | NEG | - | NEG | - | POS | + | POS | + | POS | + | POS | + |
| Ampicillin | >=32 | R | >=32 | R | >=32 | R | >=32 | R | >=32 | R | >=32 | R | >=32 | R | >=32 | R |
| Amoxicillin/Clavulanic Acid | >=32 | R | >=32 | R | >=32 | R | >=32 | R | 4 | S | 4 | S | 8 | S | 8 | S |
| Ampicillin/Sulbactam | >=32 | R | >=32 | R | >=32 | R | >=32 | R | 16 | - | 16 | - | >=32 | R | >=32 | R |
| Piperacillin/Tazobactam | <=4 | S | <=4 | S | <=4 | S | <=4 | S | 16 | S | 16 | S | 32 | - | 32 | - |
| Cefazolin | >=64 | R | >=64 | R | >=64 | R | >=64 | R | >=64 | R | >=64 | R | >=64 | R | >=64 | R |
| Ceftazidime | <=1 | S | <=1 | S | 2 | S | 2 | S | 16 | *R | 16 | *R | 16 | *R | 16 | *R |
| Ceftriaxone | 8 | *R | 8 | *R | 16 | R | 16 | R | 8 | *R | 8 | *R | 8 | *R | 8 | *R |
| Cefepime | <=1 | S | <=1 | S | <=1 | S | <=1 | S | 4 | S | 4 | S | <=1 | S | <=1 | S |
| Ertapenem | 2 | S | 2 | S | 2 | S | 2 | S | <=0.5 | S | <=0.5 | S | <=0.5 | S | <=0.5 | S |
| Imipenem | <=1 | S | <=1 | S | <=1 | S | <=1 | S | <=0.25 | - | <=0.25 | - | 0.5 | - | 0.5 | - |
| Gentamicin | <=1 | S | <=1 | S | <=1 | S | <=1 | S | 8 | S | 8 | S | >=16 | R | >=16 | R |
| Tobramycin | <=1 | S | <=1 | S | <=1 | S | <=1 | S | 8 | S | 8 | S | 8 | S | 8 | S |
| Ciprofloxacin | <=0.25 | S | <=0.25 | S | <=0.25 | S | <=0.25 | S | <=0.25 | S | <=0.25 | S | 0.5 | S | 0.5 | S |
| Levofloxacin | 1 | S | 1 | S | 1 | S | 1 | S | 1 | S | 1 | S | 1 | - | 1 | - |
| Nitrofurantoin | >=512 | R | >=512 | R | >=512 | R | >=512 | R | 32 | S | 32 | S | 128 | R | 128 | R |
| Trimeth/Sulfamethoxazole | >=320 | R | >=320 | R | >=320 | R | >=320 | R | <=20 | S | <=20 | S | <=20 | S | <=20 | S |

FIG. 159

| Microorganism | E. faecium 50215 | | | | S. aureus 60570 | | | |
|---|---|---|---|---|---|---|---|---|
| Sample Type | Large Tube Suspension | | Historical Colony Control | | Large Tube Suspension | | Historical Colony Control | |
| Beta Lactamase | NEG | - | NEG | - | POS | + | POS | + |
| Cefoxitin Screen | | | | | POS | + | POS | + |
| Benzylpenicillin | 16 | R | 16 | R | >=0.5 | R | >=0.5 | R |
| Ampicillin | 4* | *R | 4* | *R | | | | |
| Oxacillin | | | | | 0.5* | *R | >=4 | R |
| Gentamycin HL syn | SYN-S | S | SYN-S | S | | | | |
| Streptomycin HL syn | SYN-R | R | SYN-R | R | | | | |
| Gentamycin | 2 | 1 | 2 | 1 | >=16 | R | >=16 | R |
| Ciprofloxacin | | | | | <=0.5 | S | <=0.5 | S |
| Levofloxacin | 4 | 1 | 4 | 1 | <=0.12 | S | <=0.12 | S |
| Moxifloxacin | | | | | <=0.25 | S | <=0.25 | S |
| Inducible Clind R | | | | | NEG | - | NEG | - |
| Erythromycin | >=8 | R | >=8 | R | >=8 | R | >=8 | R |
| Clindamycin | | | | | >=8 | R | >=8 | R |
| Quinupristin/Dalfopristin | 0.5 | S | 0.5 | S | <=0.25 | S | <=0.25 | S |
| Linezolid | 2 | S | 2 | S | 1 | S | 2 | S |
| Vancomycin | 1 | S | 1 | S | 1 | S | 1 | S |
| Tetracycline | >=16 | R | >=16 | R | <=1 | S | <=1 | S |
| Tigecycline | <=0.12 | S | <=0.12 | S | <=0.12 | S | <=0.12 | S |
| Nitrofurantoin | 256 | R | 128 | R | <=16 | S | <=16 | S |
| Rifampicin | | | | | <=0.5 | S | <=0.5 | S |
| Trimeth/Sulfamethox | | | | | <=10 | S | <=10 | S |

FIG. 160

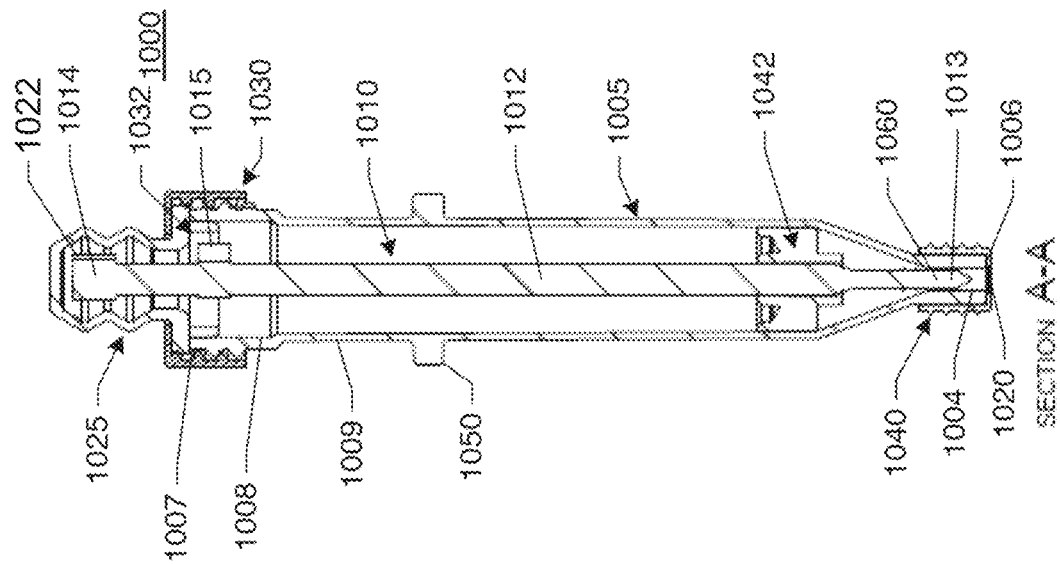
FIG. 163
FIG. 162
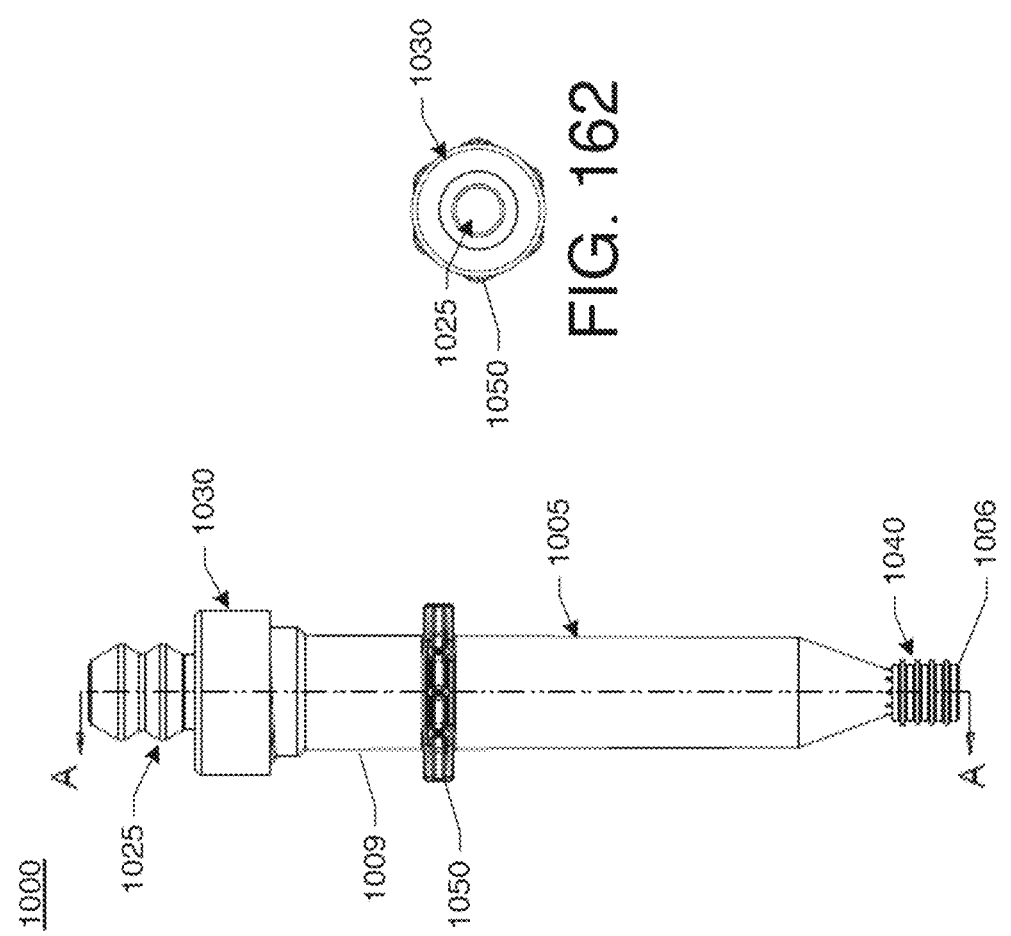
FIG. 161

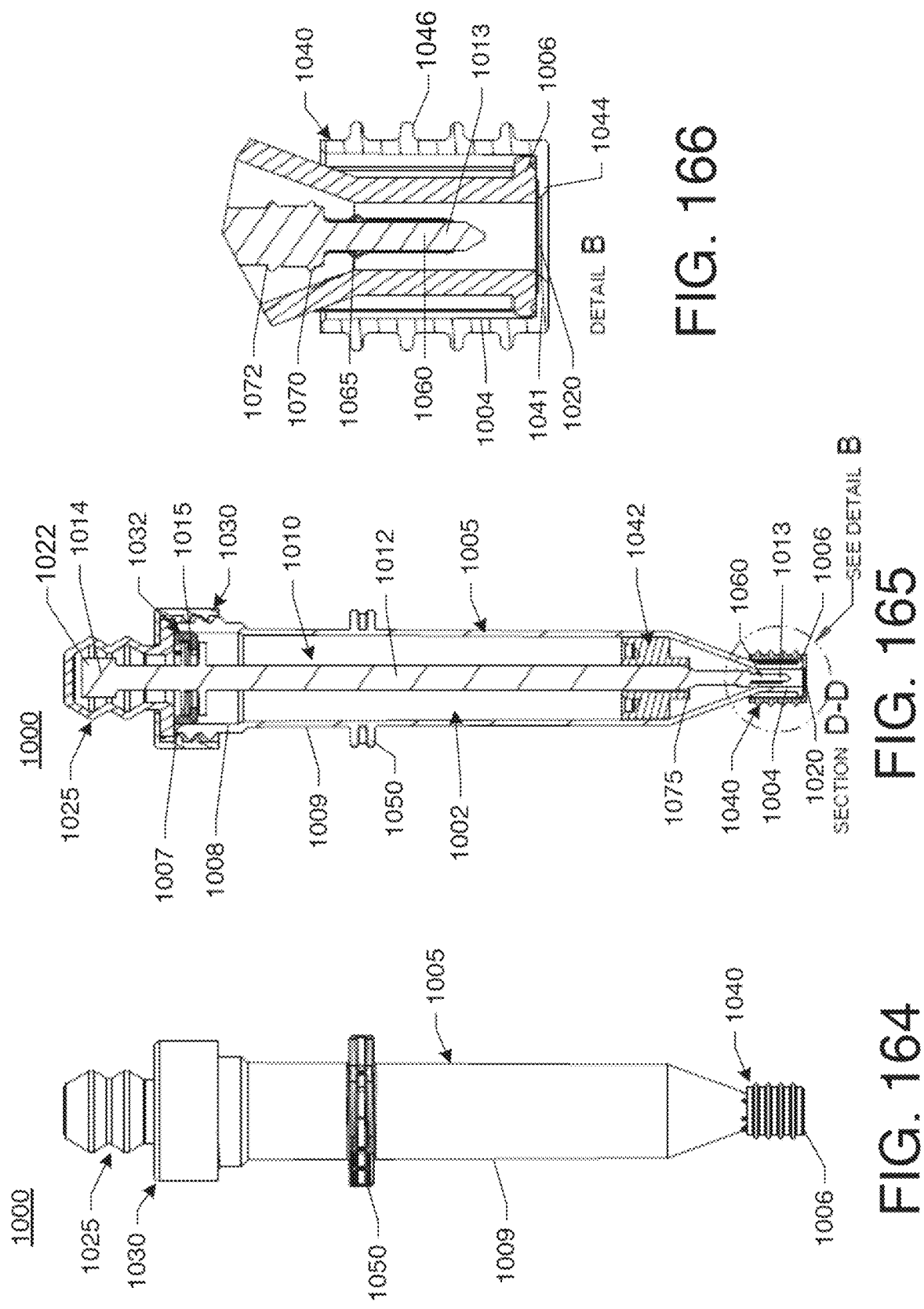

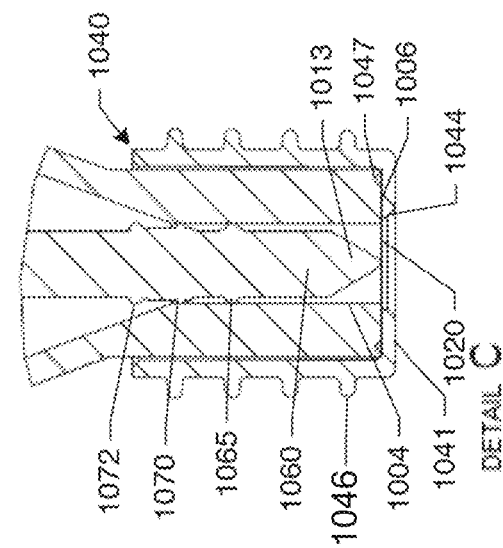
FIG. 171
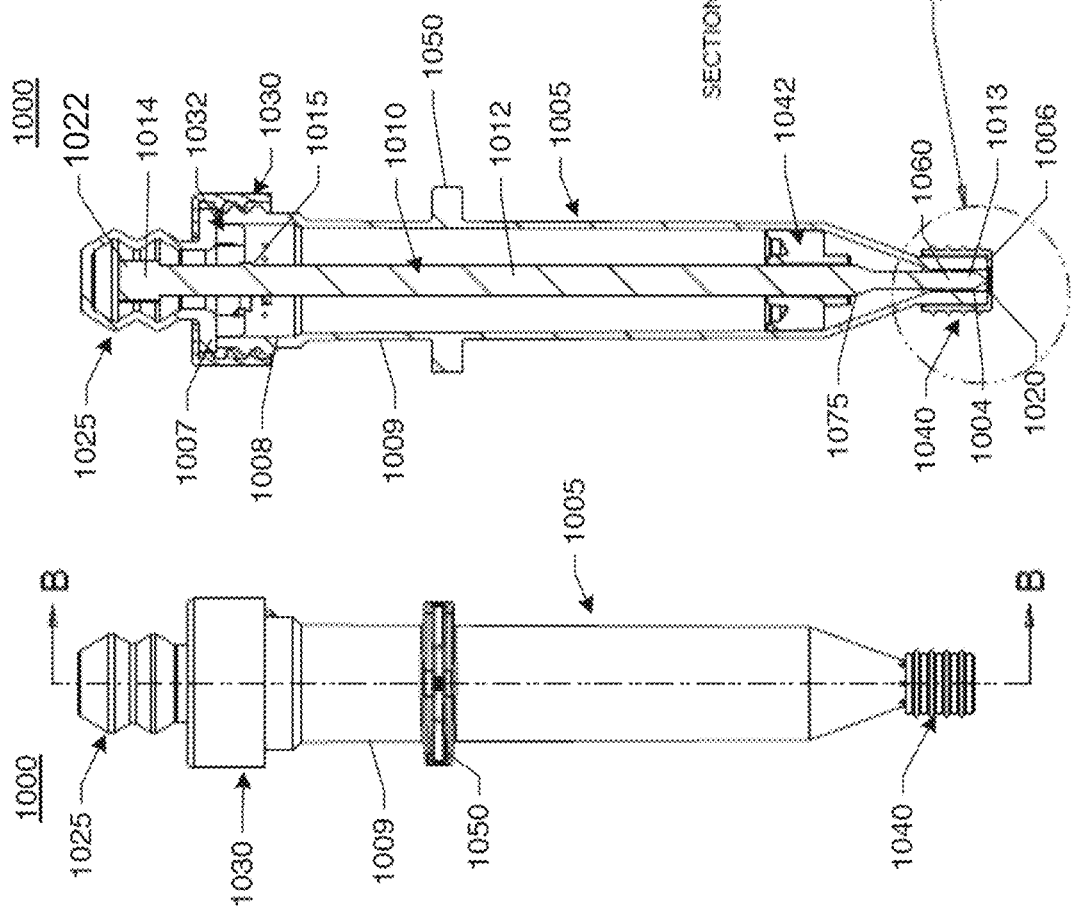
FIG. 170
FIG. 169

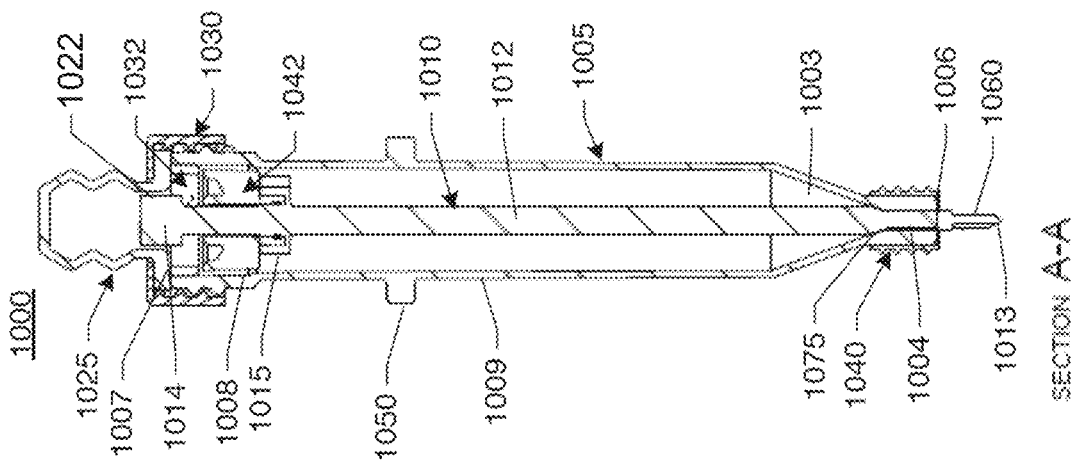
FIG. 174
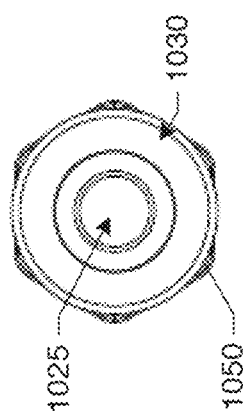
FIG. 173
FIG. 172

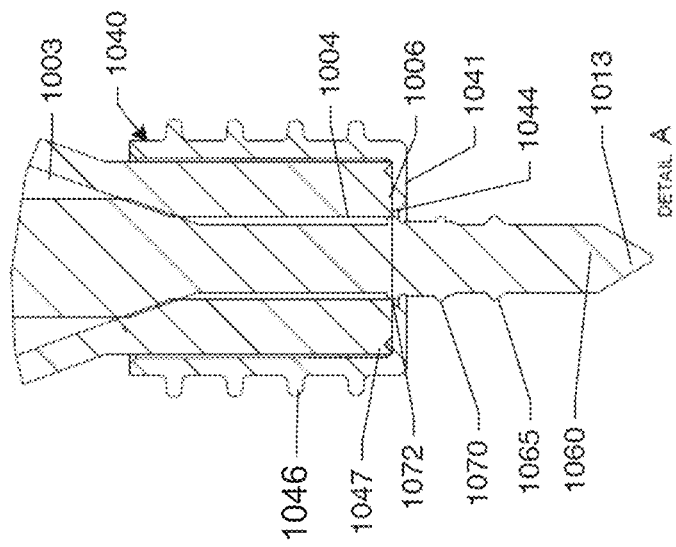
FIG. 177
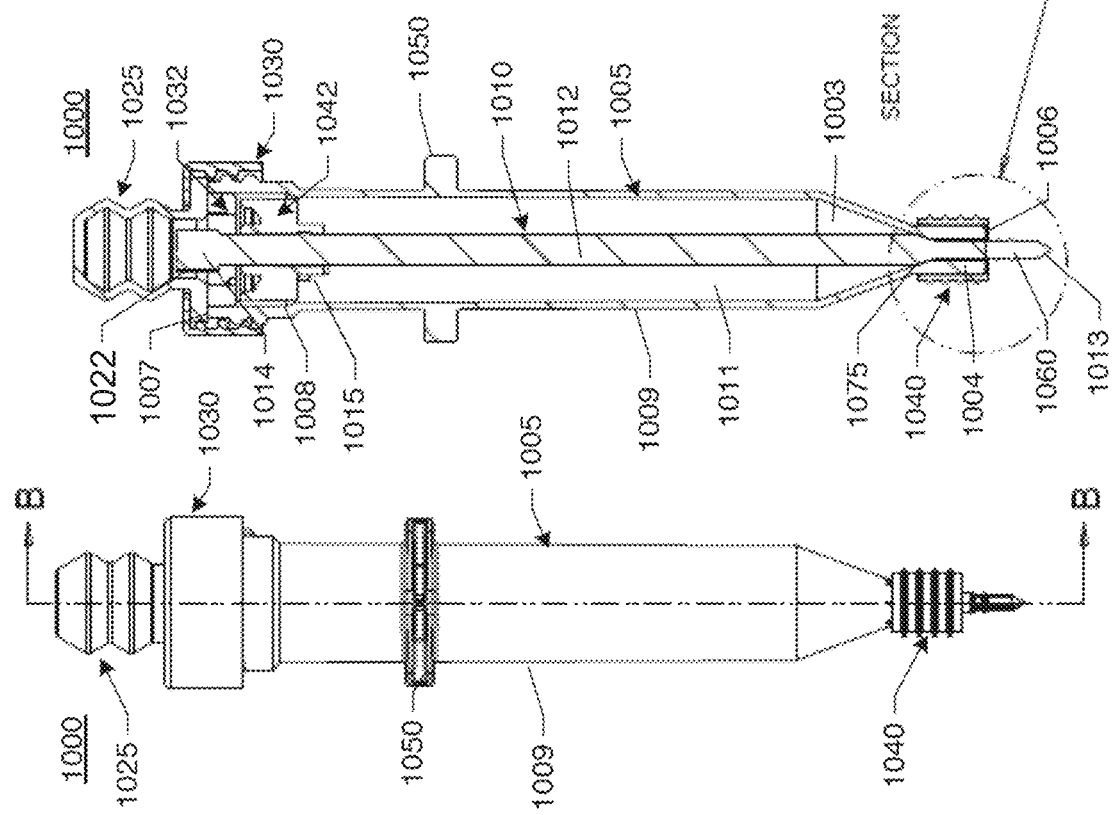
FIG. 176
FIG. 175

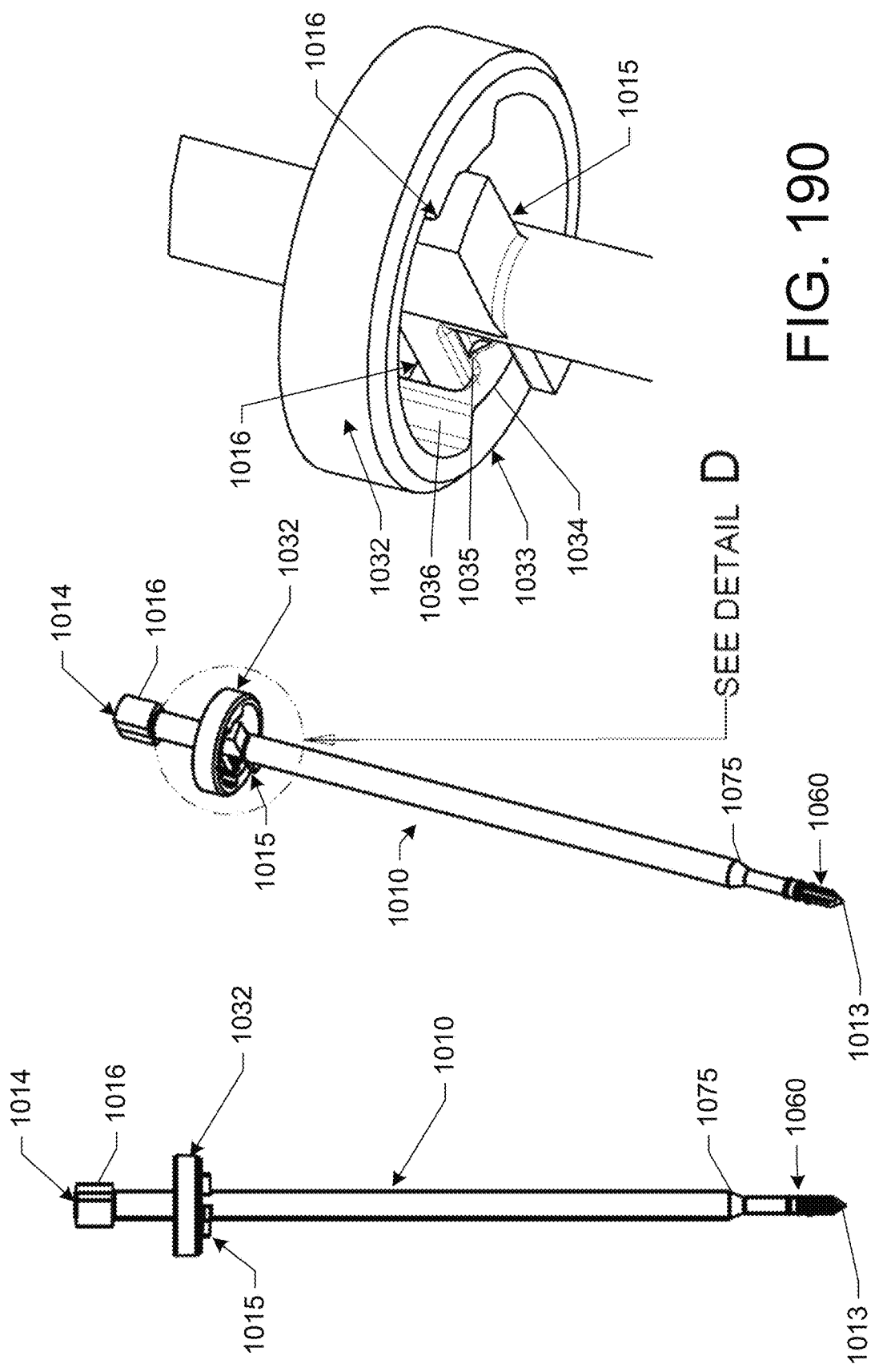

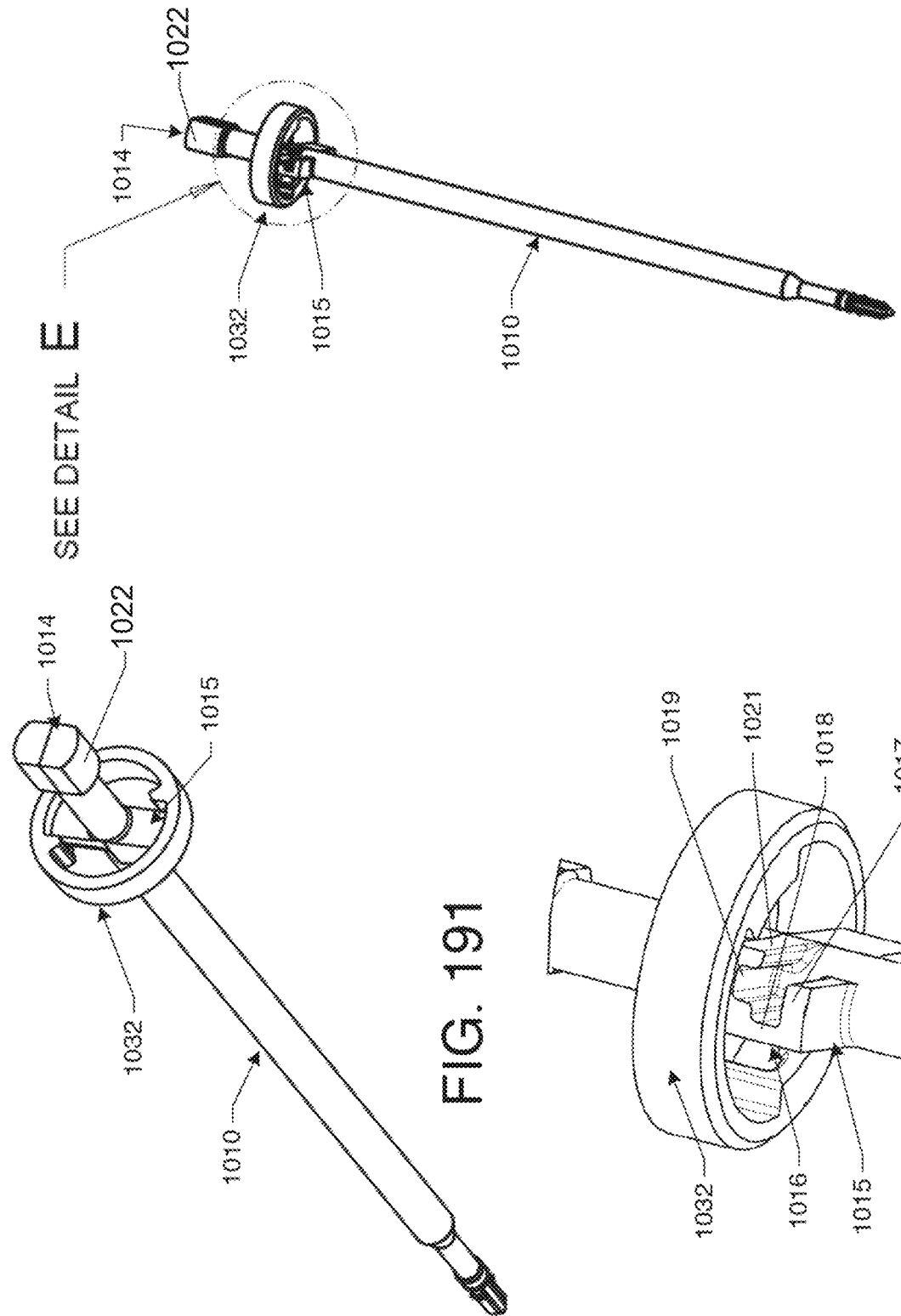

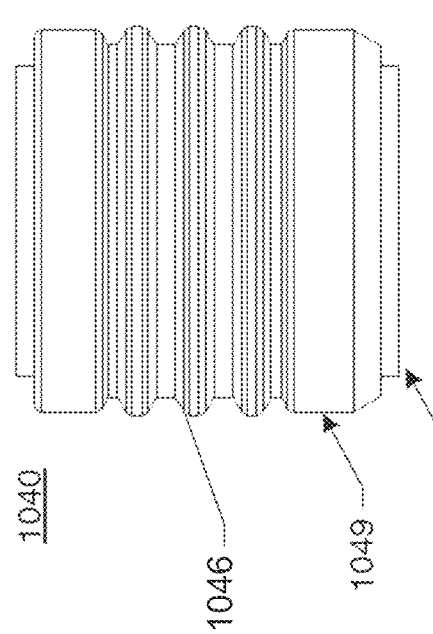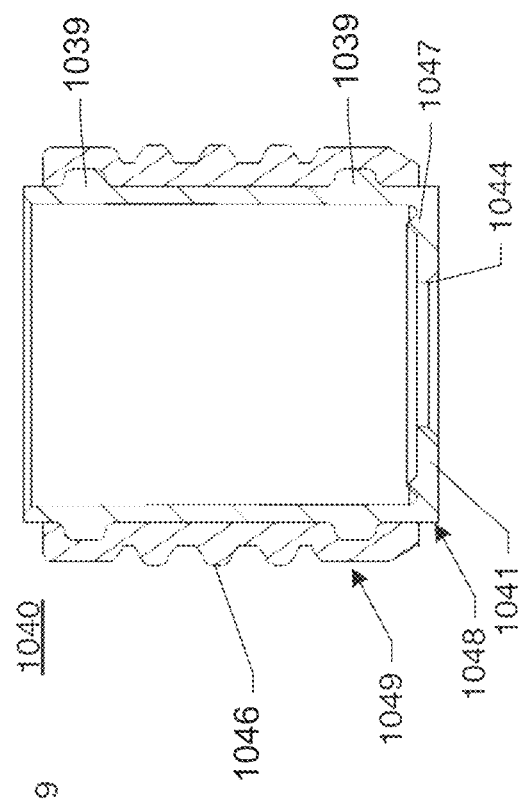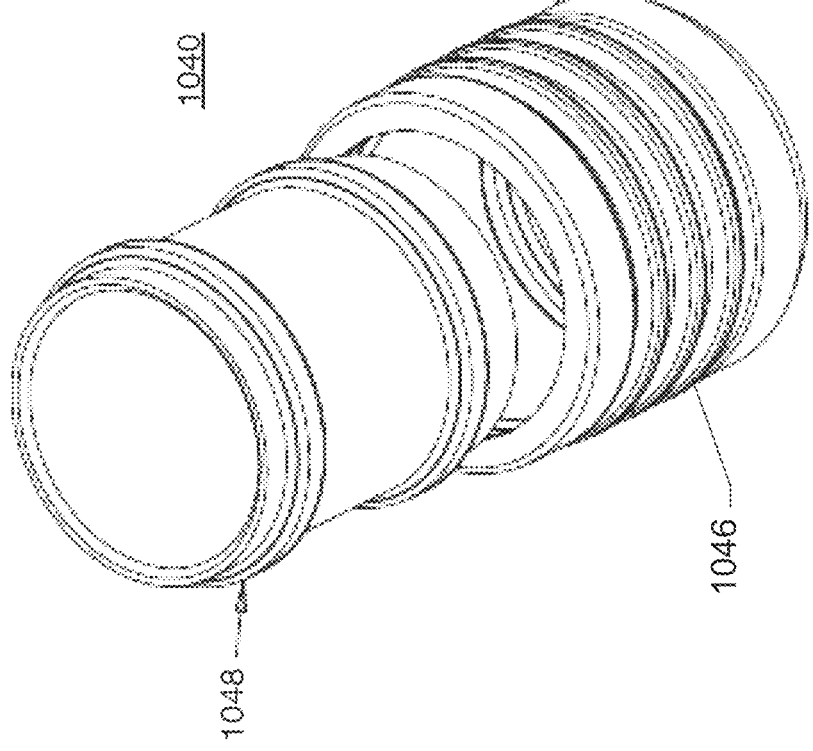

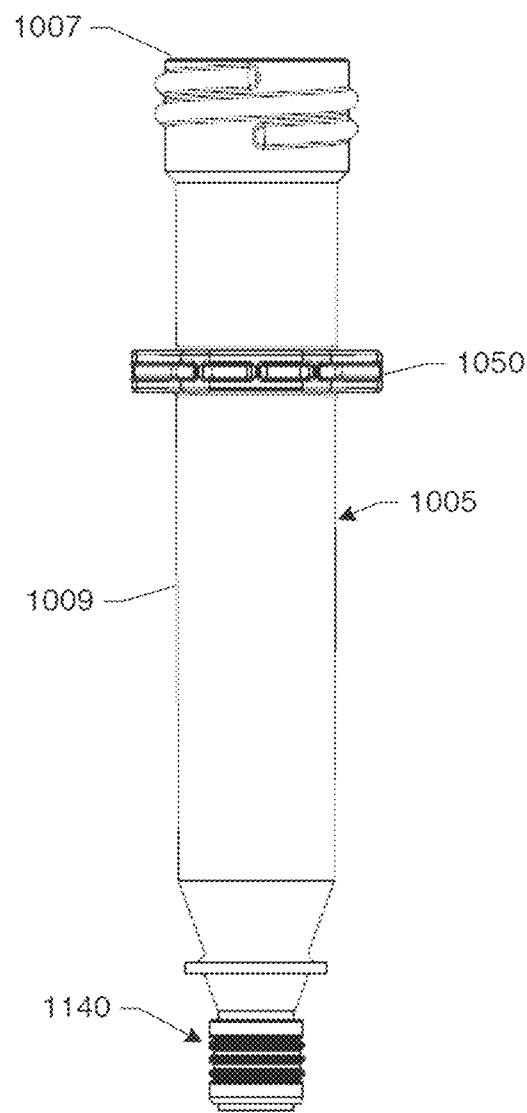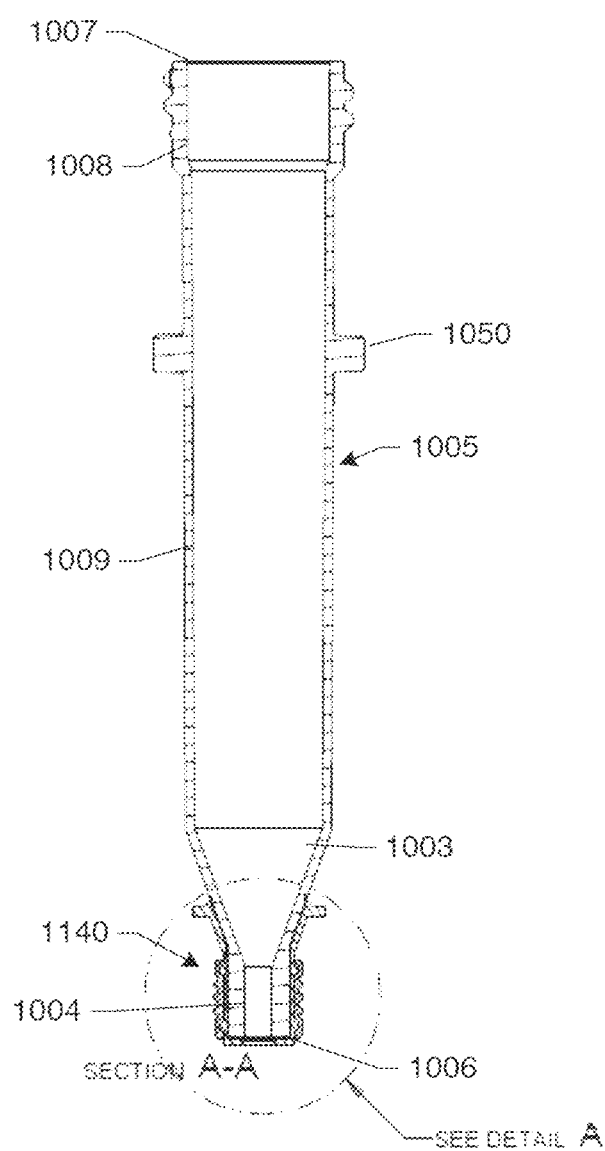
FIG. 201
FIG. 202

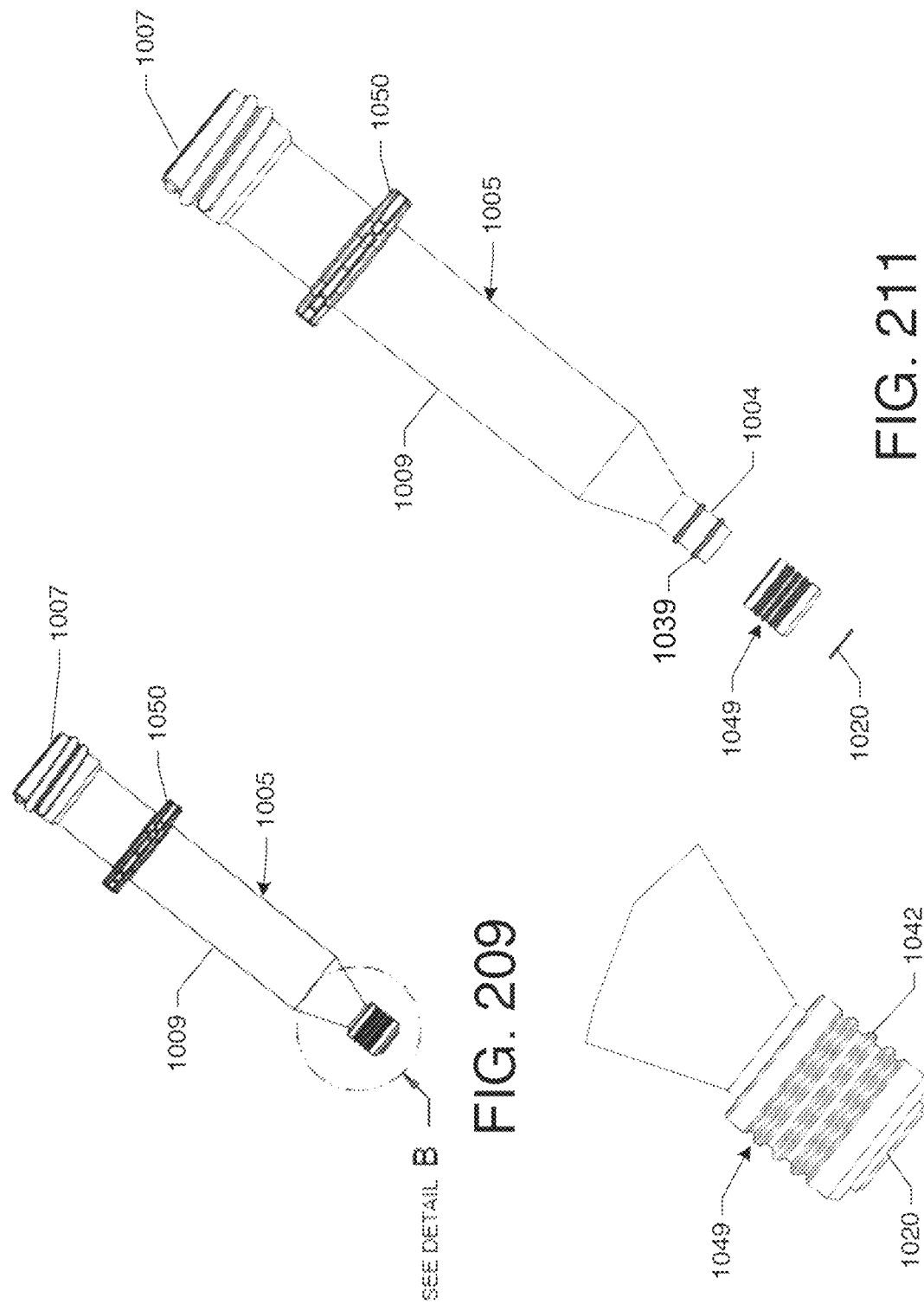

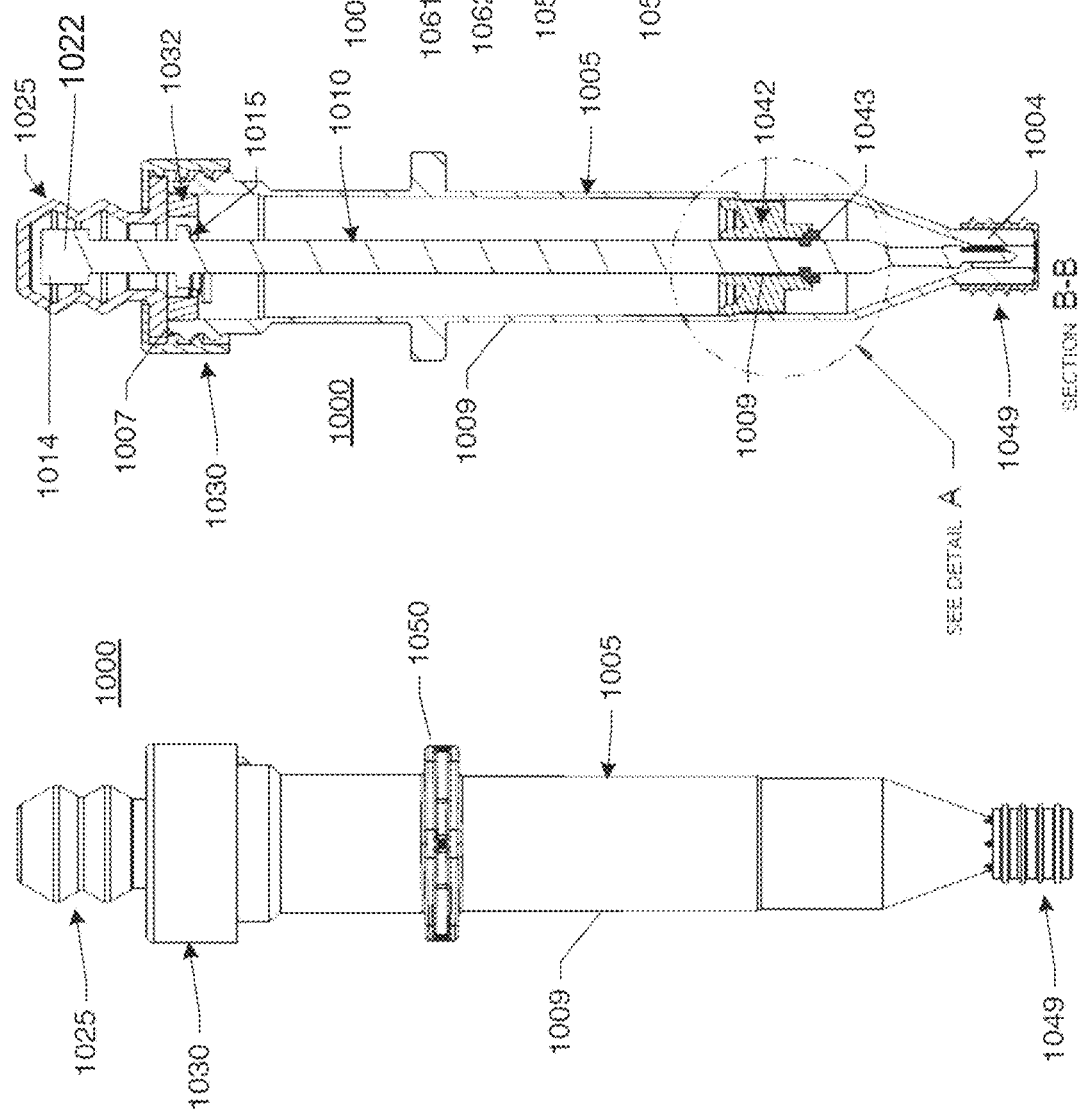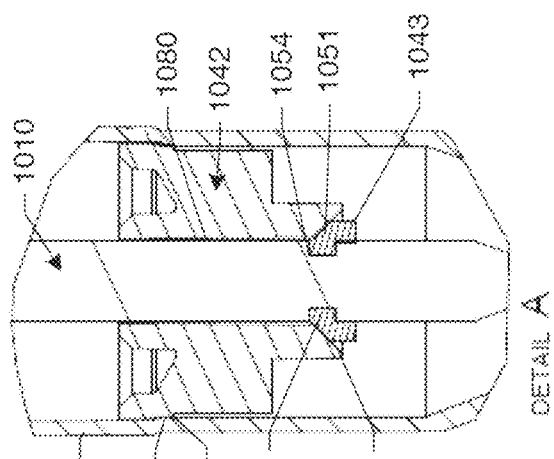
FIG. 214
FIG. 213
FIG. 212

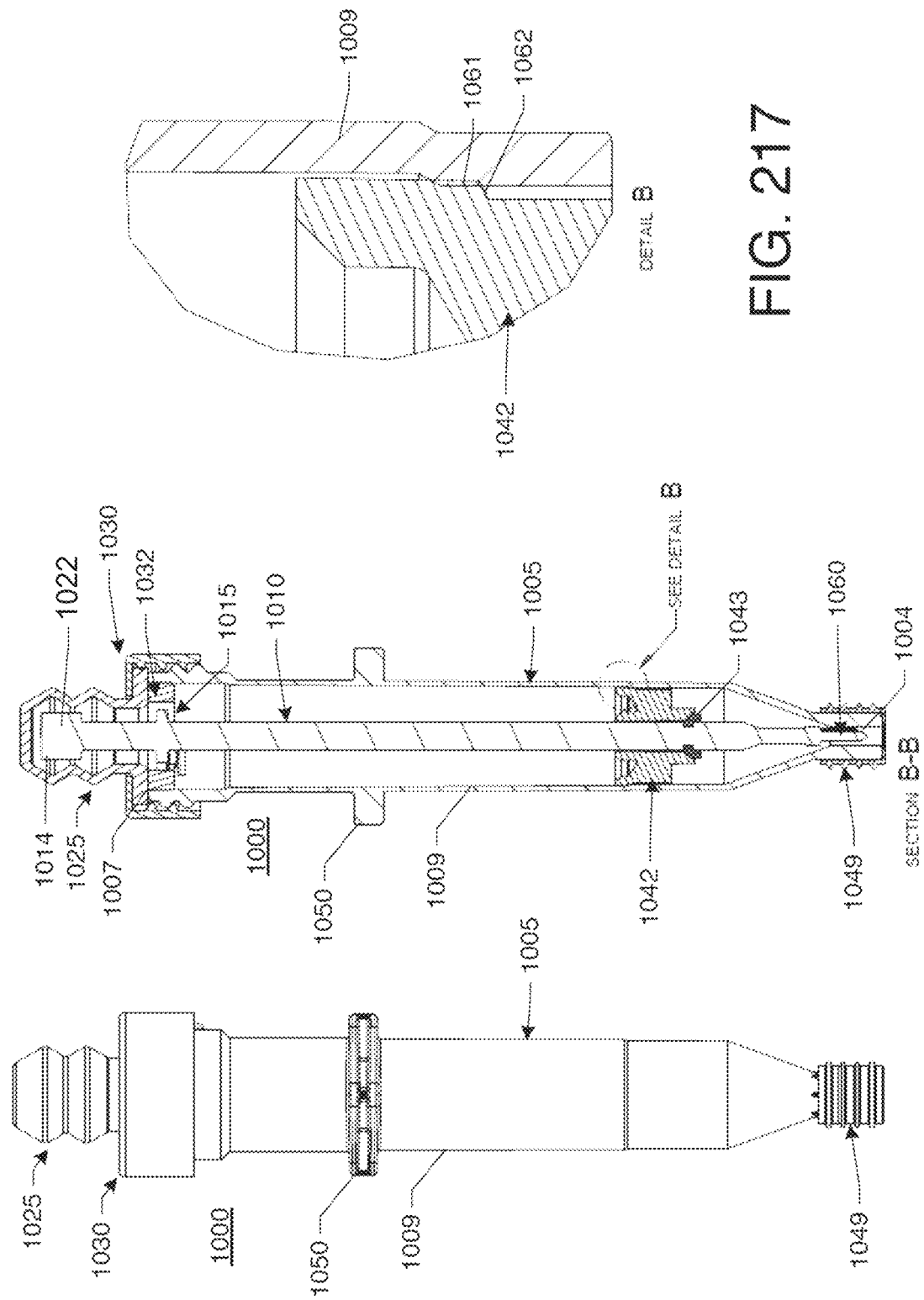

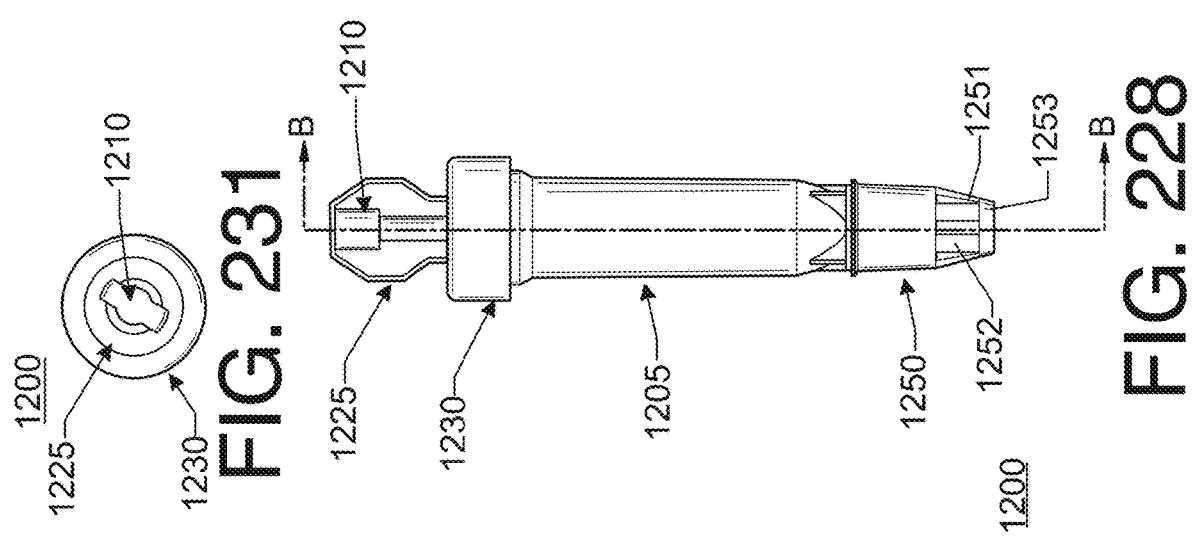

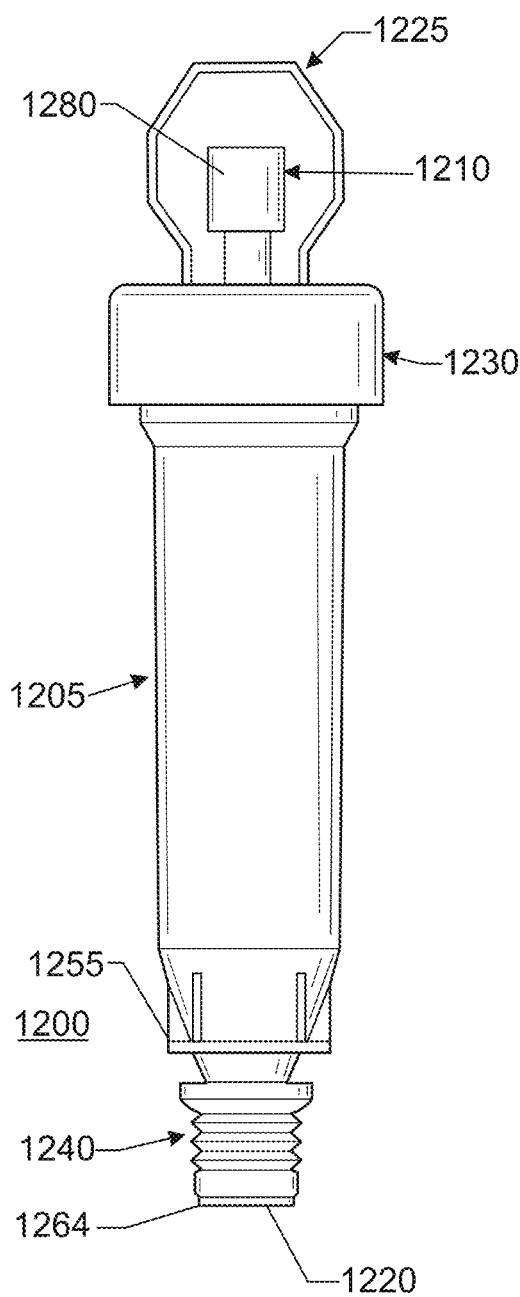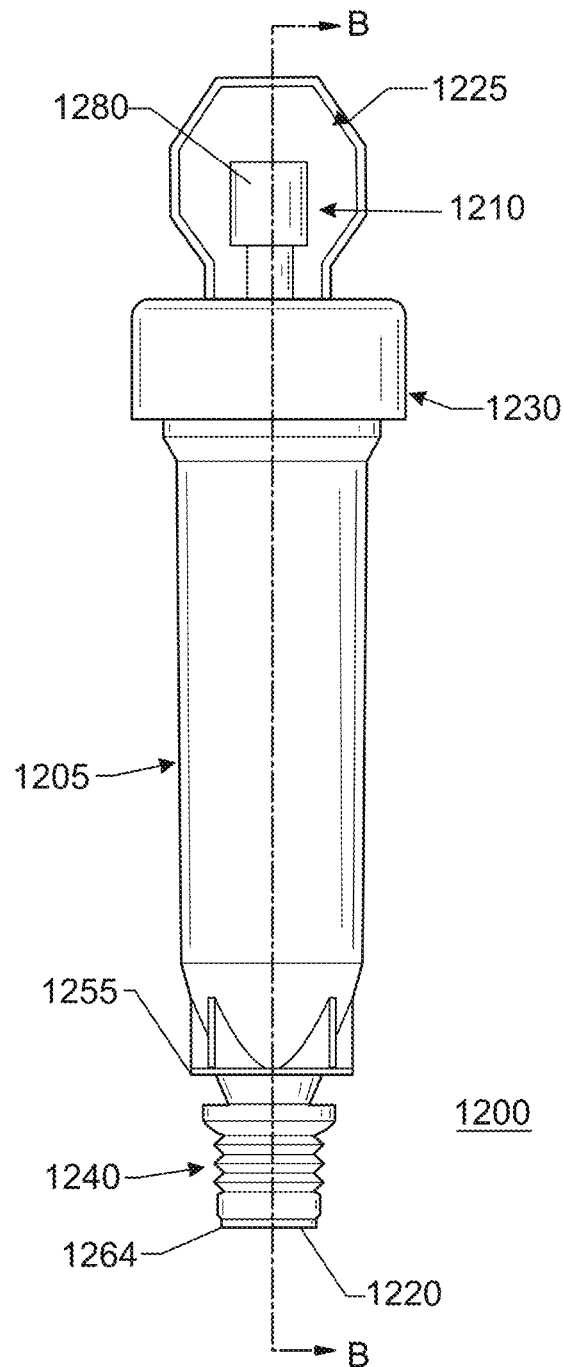

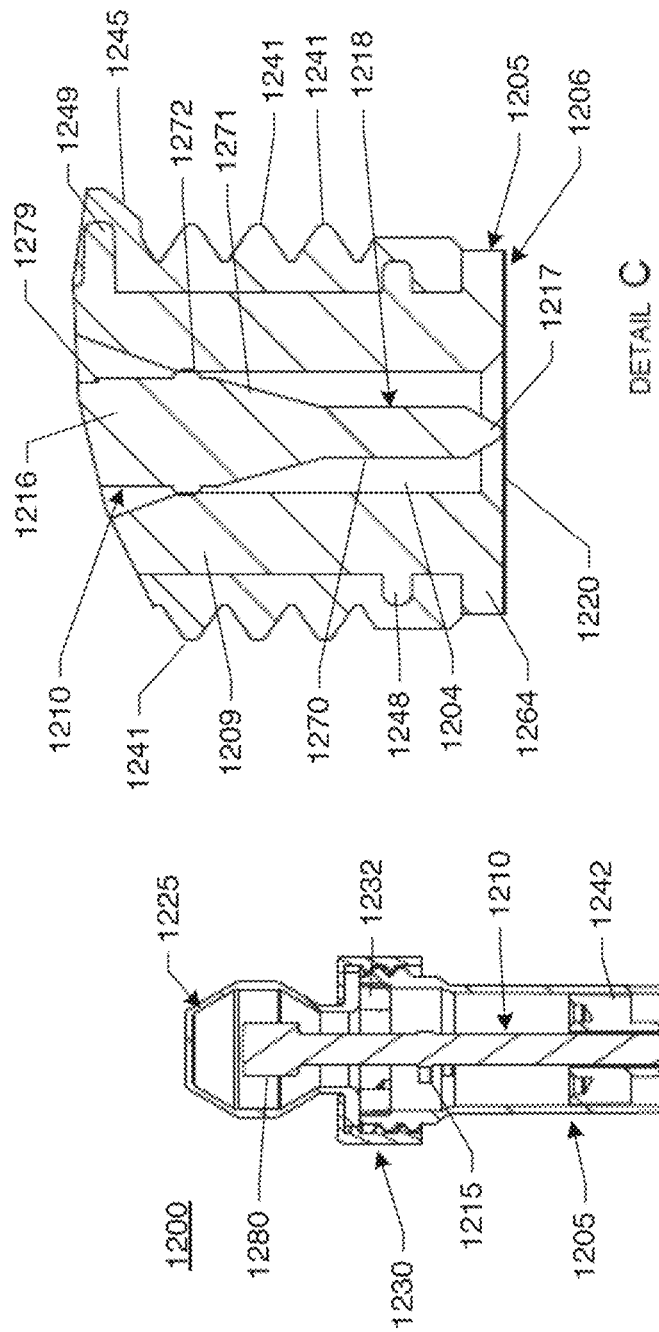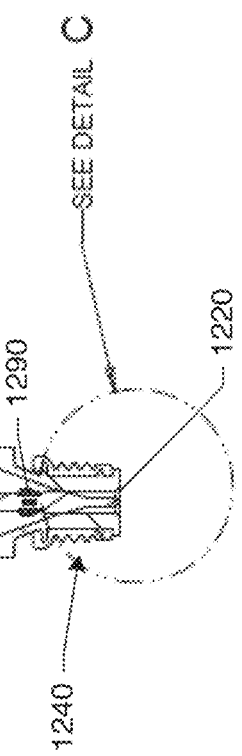
FIG. 235
FIG. 234

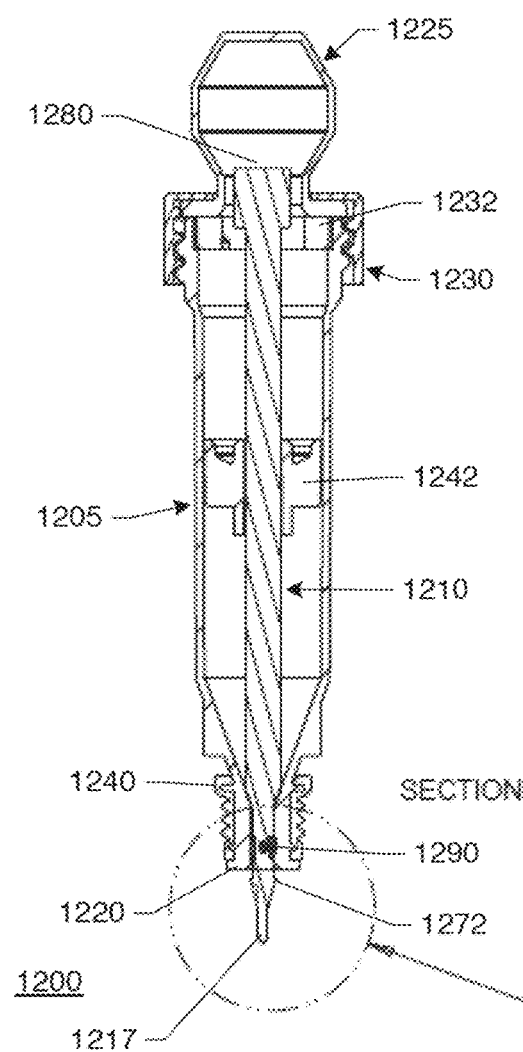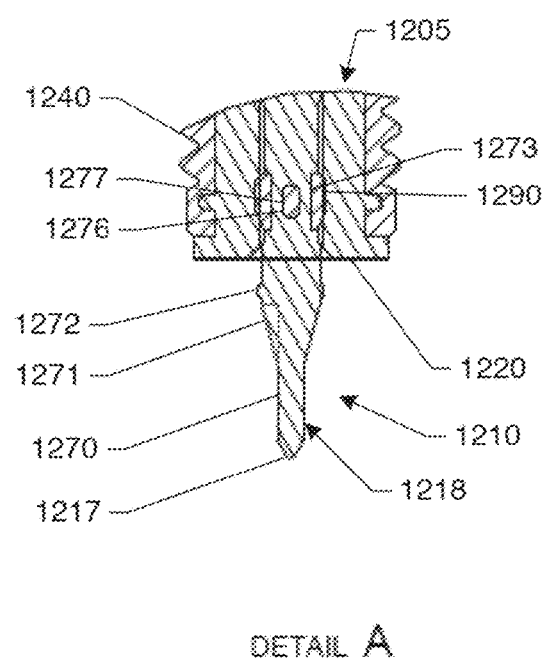
DETAIL A
FIG. 239
SECTION B-B
FIG. 238

DETAIL A

DETAIL C

DETAIL D

DETAIL A

DETAIL B

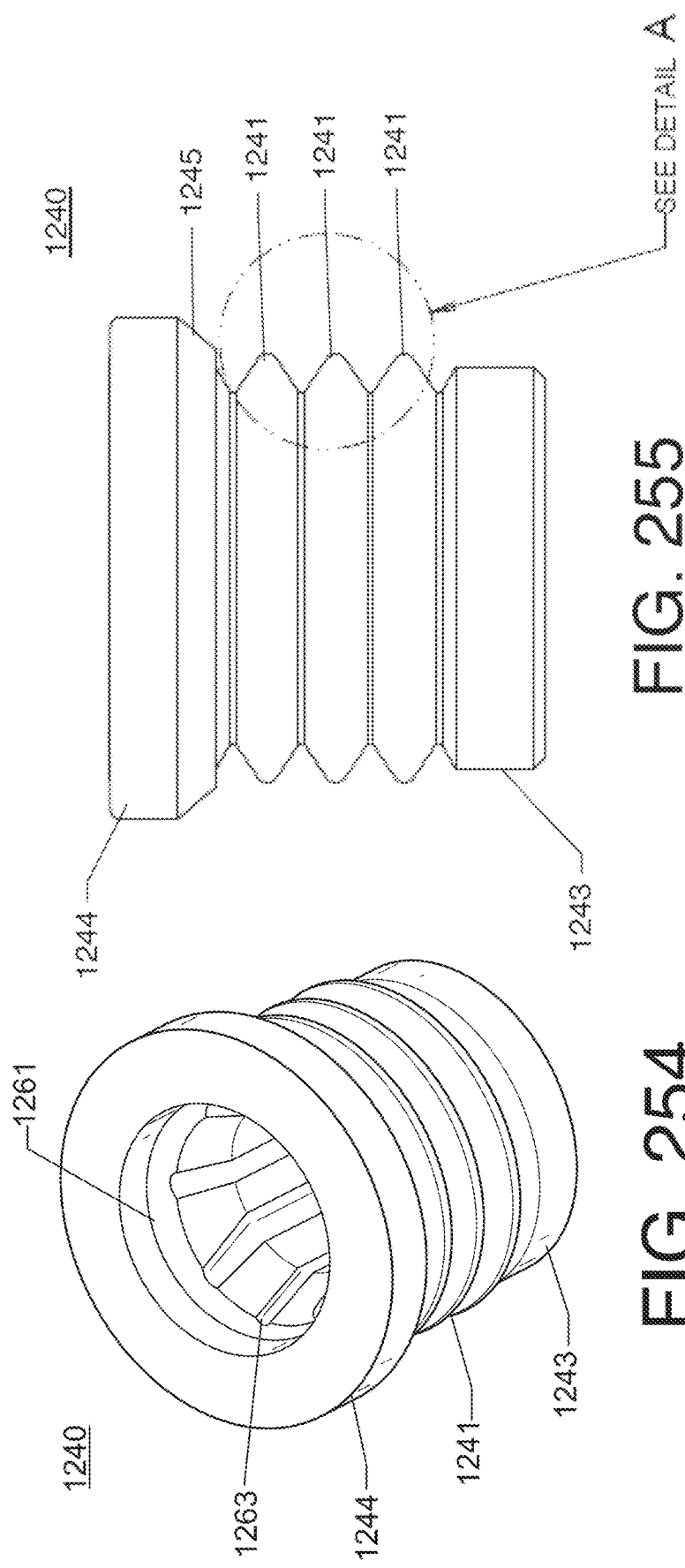

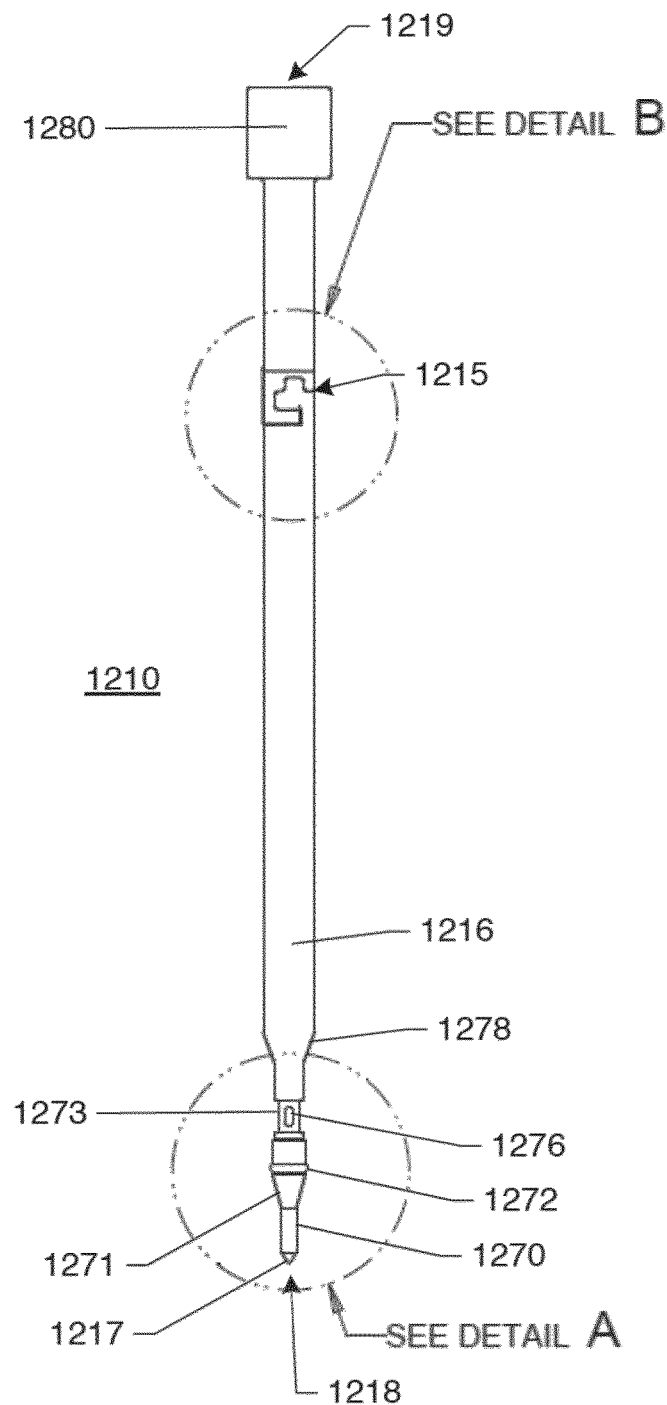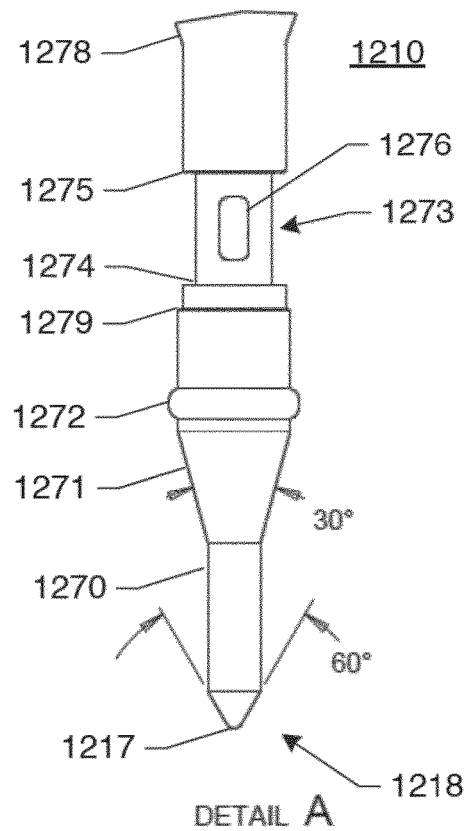
FIG. 265
FIG. 266

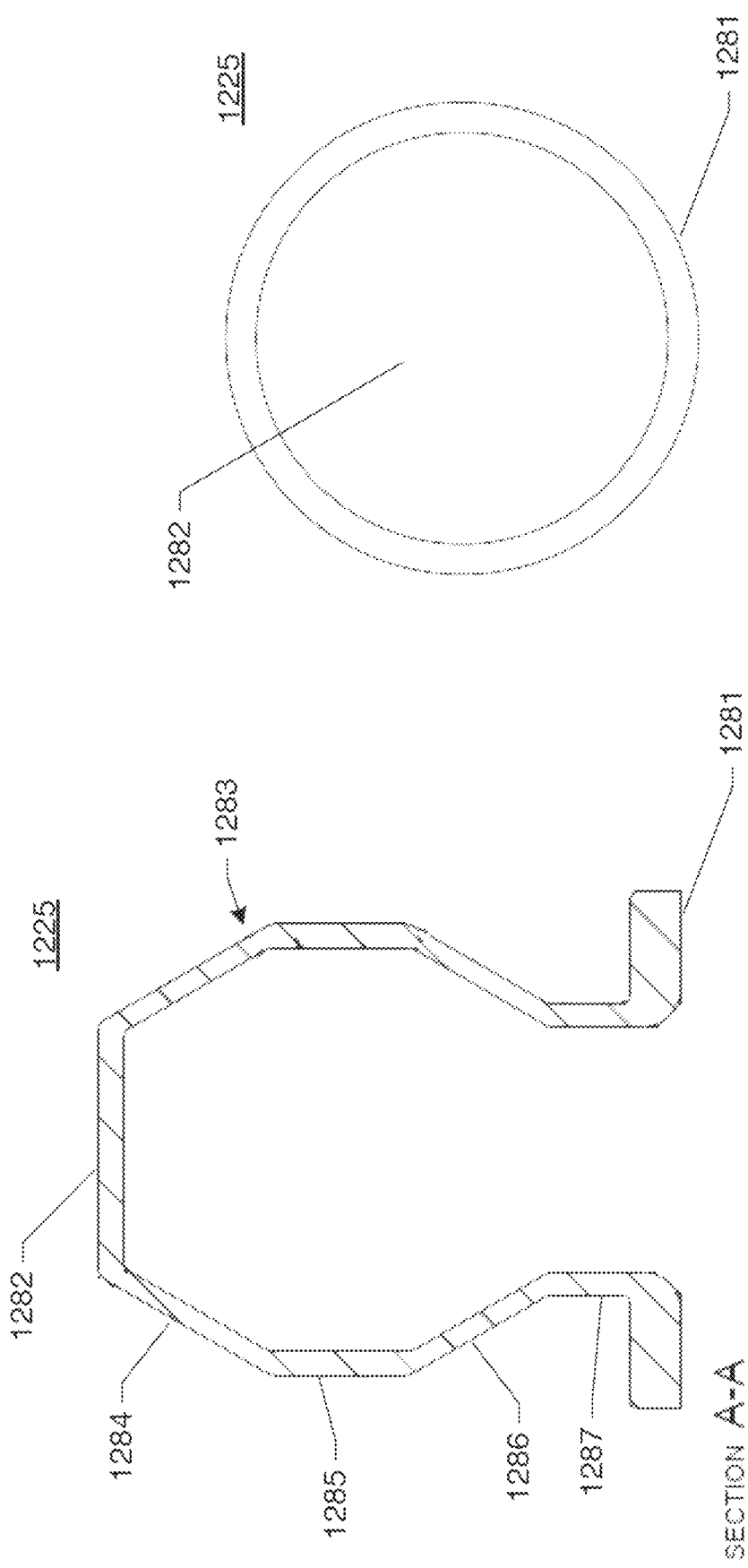

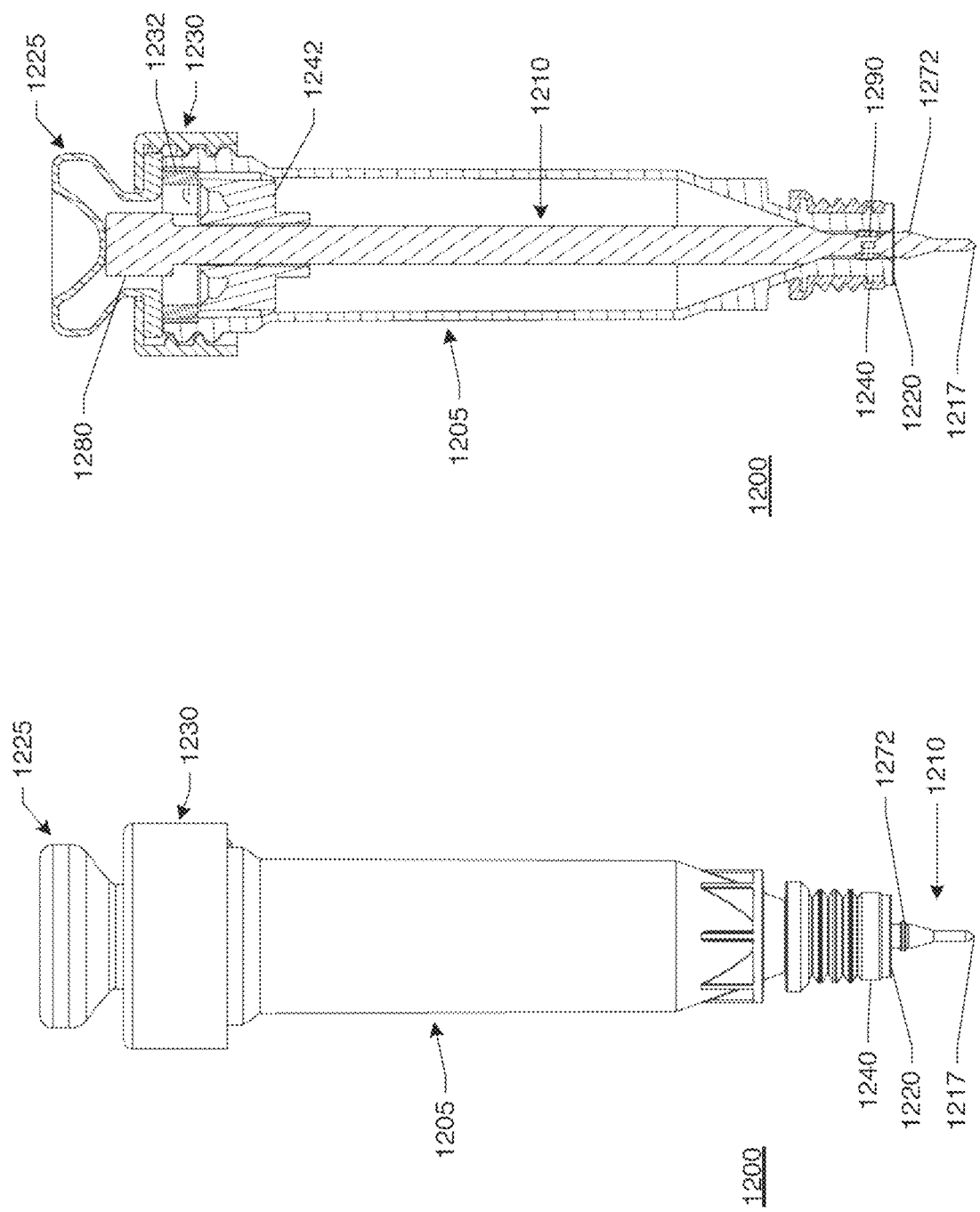

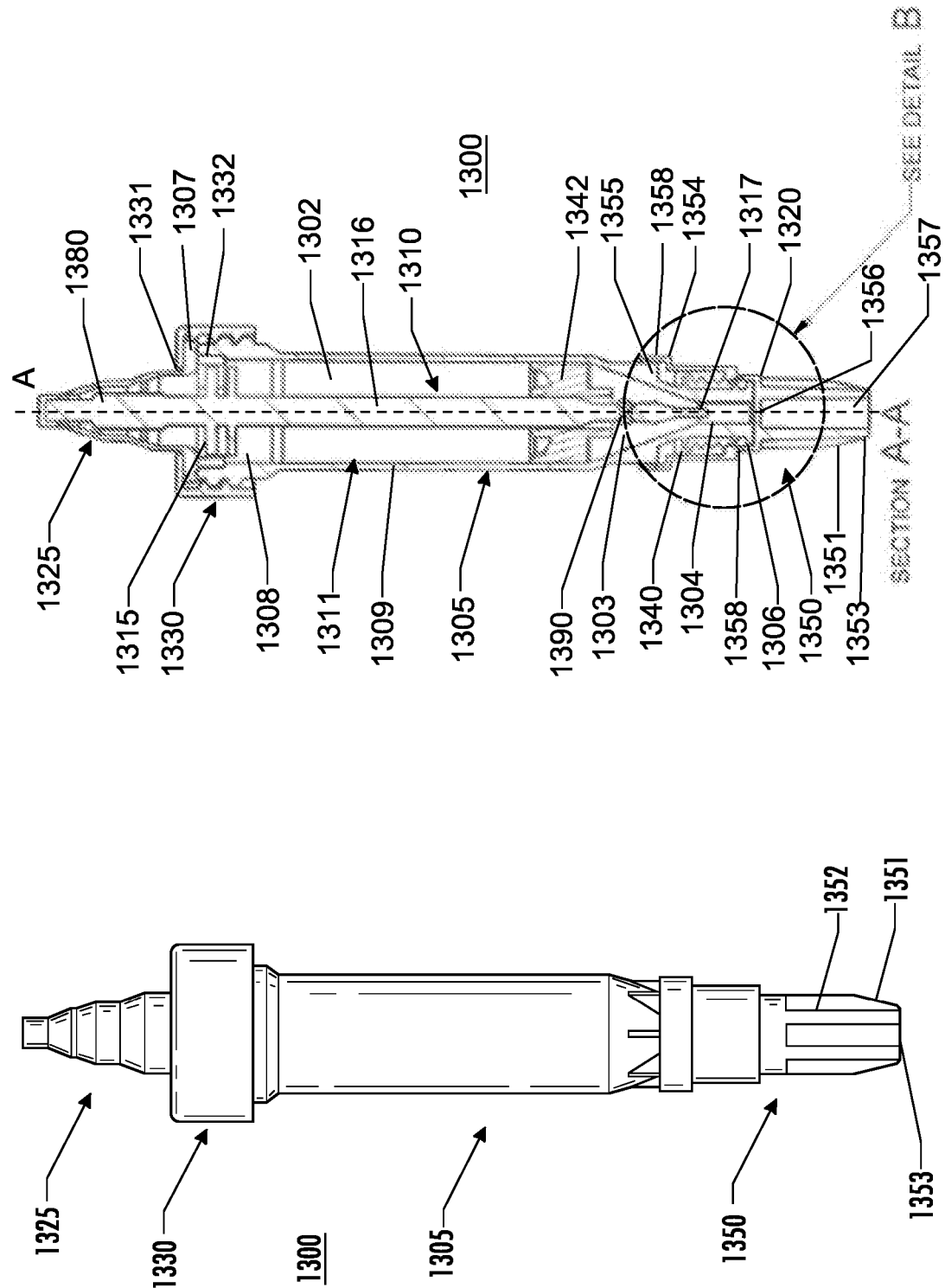

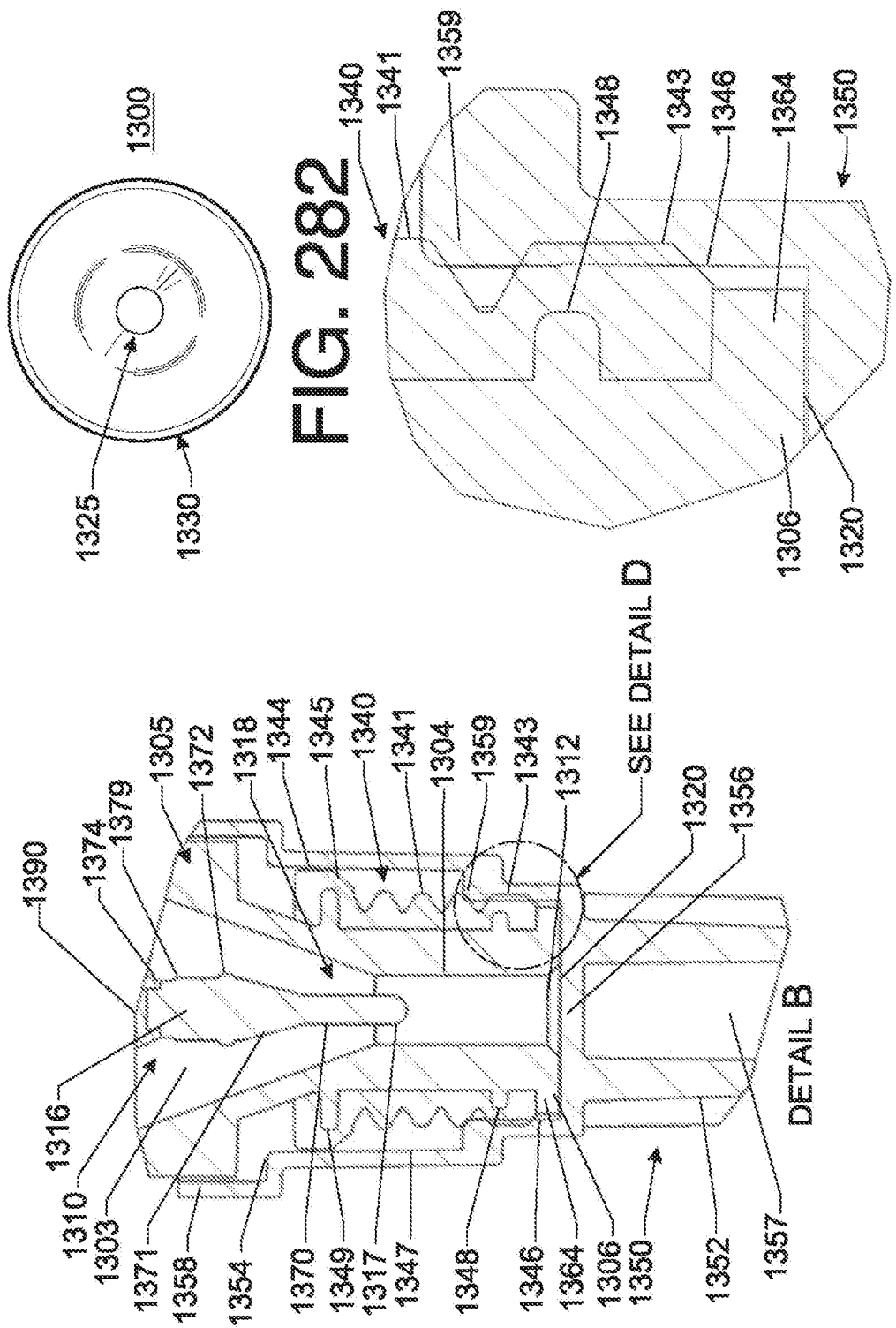

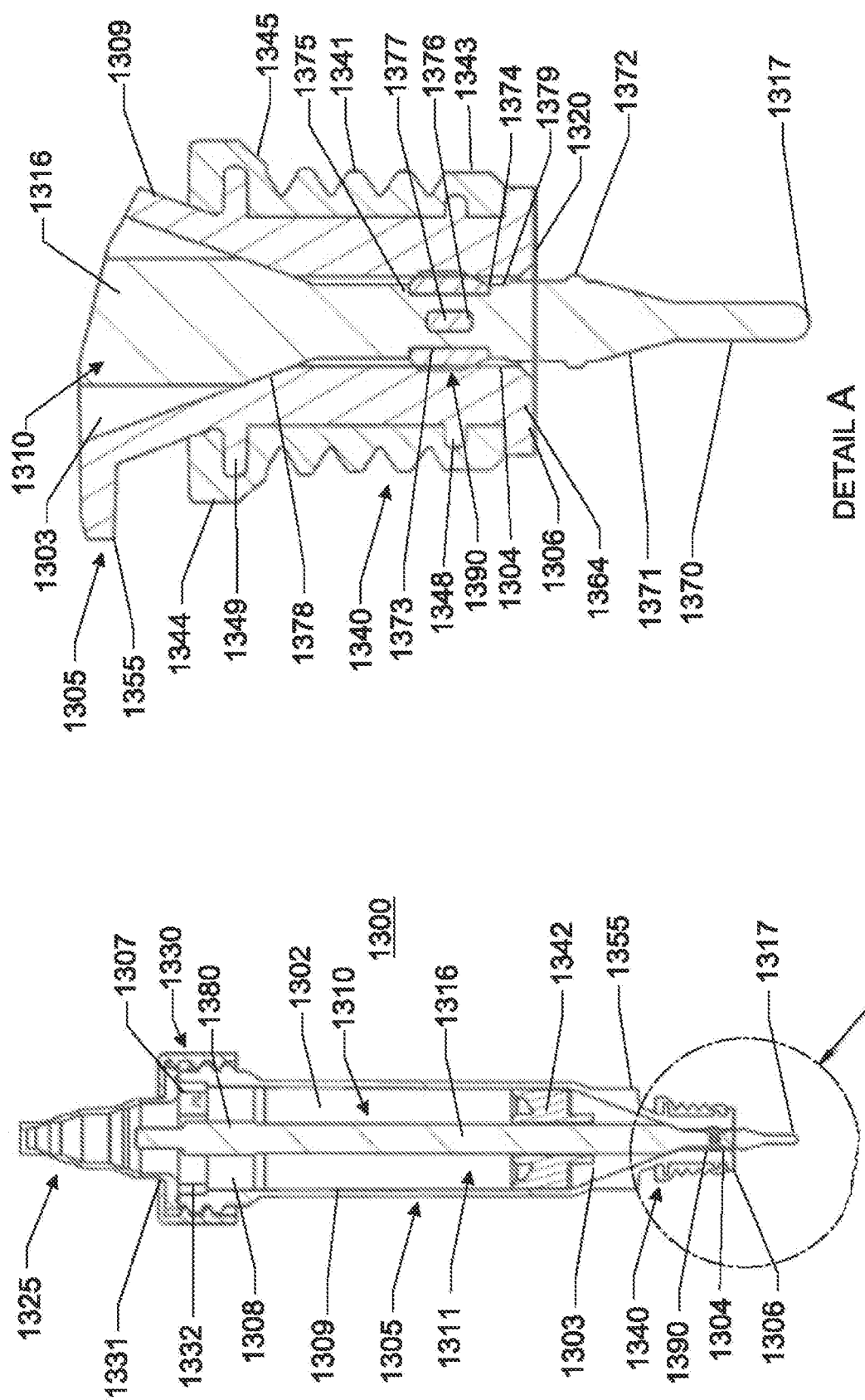

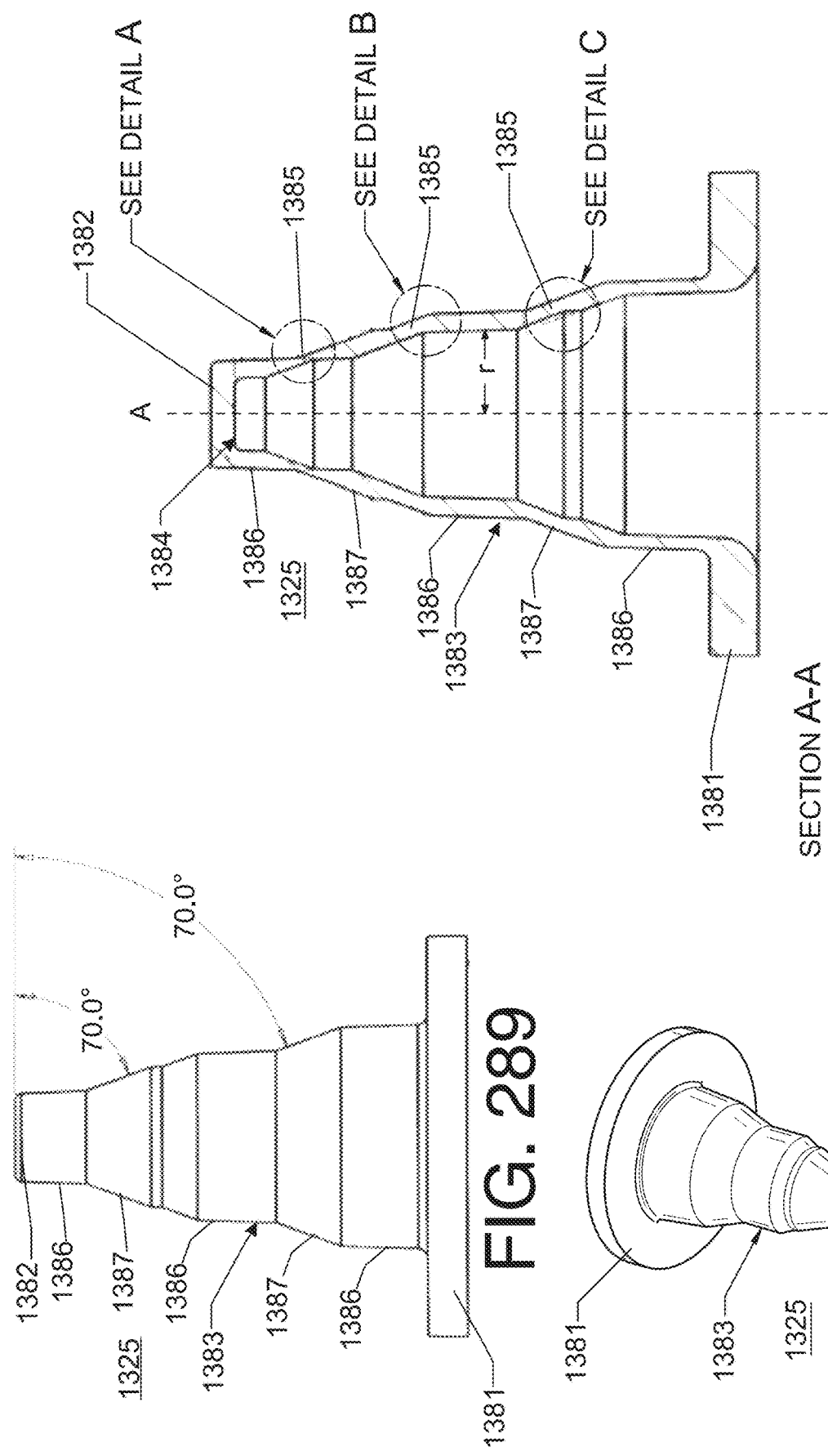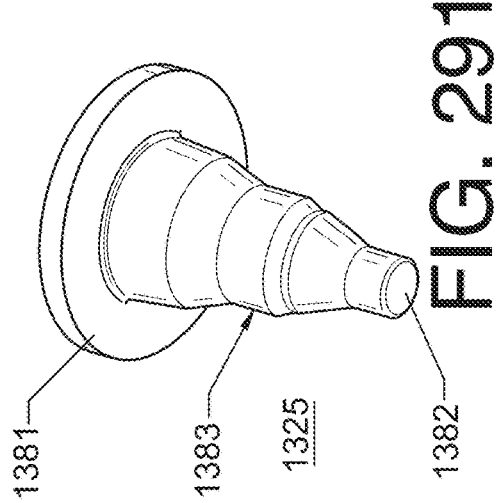

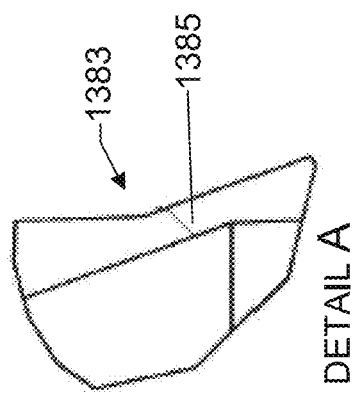
FIG. 293
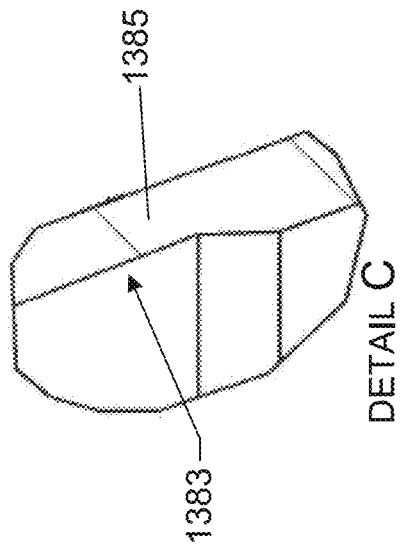
FIG. 295
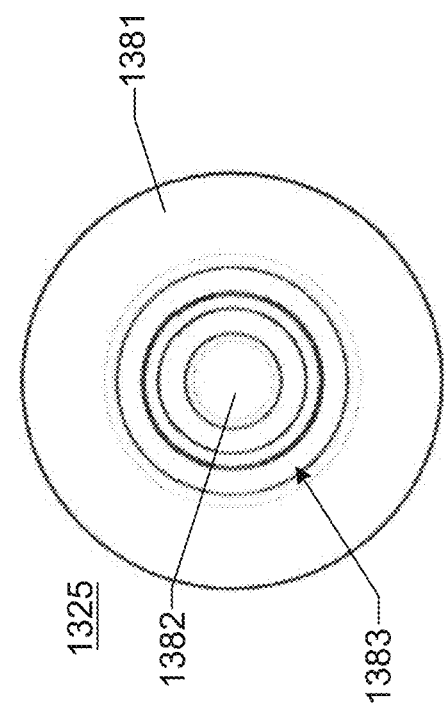
FIG. 292
FIG. 294

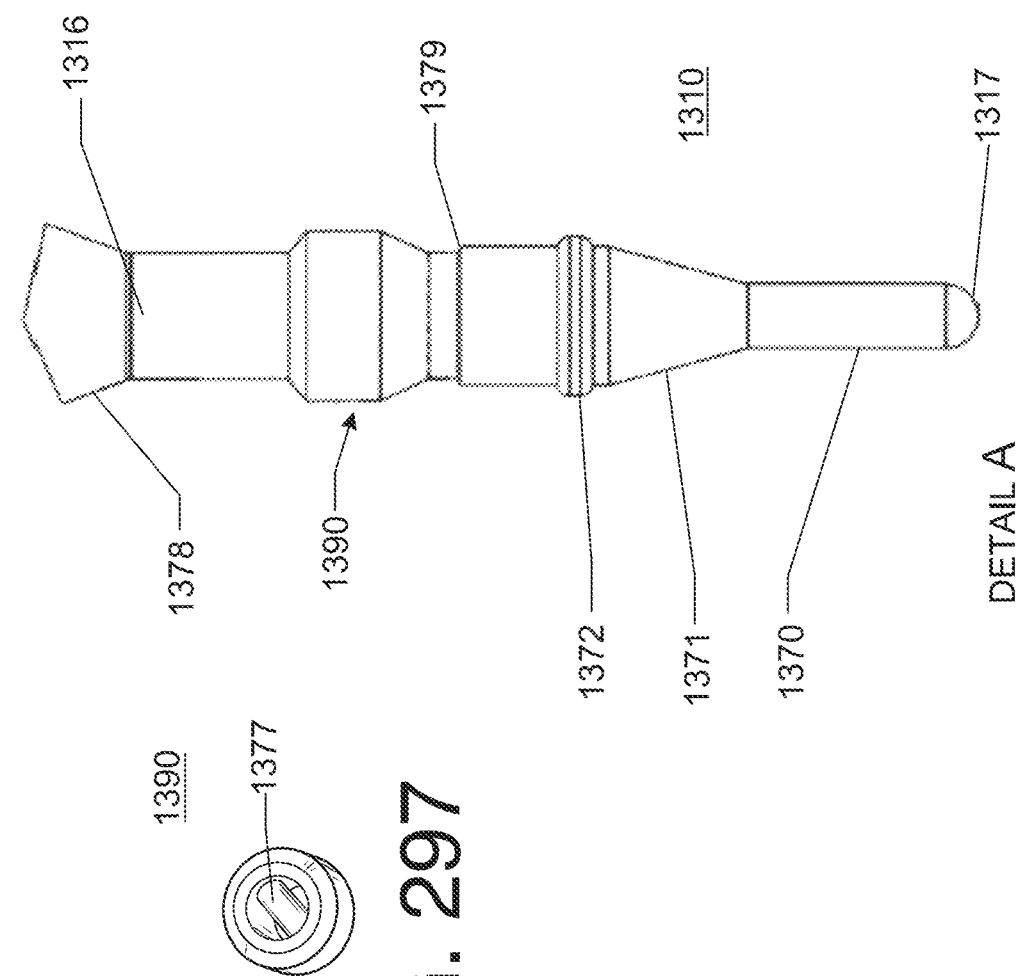
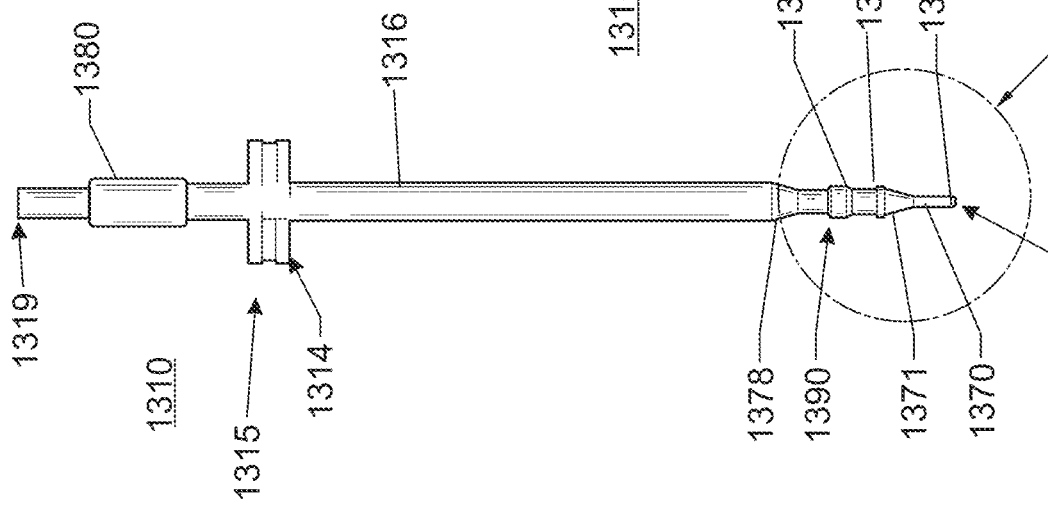

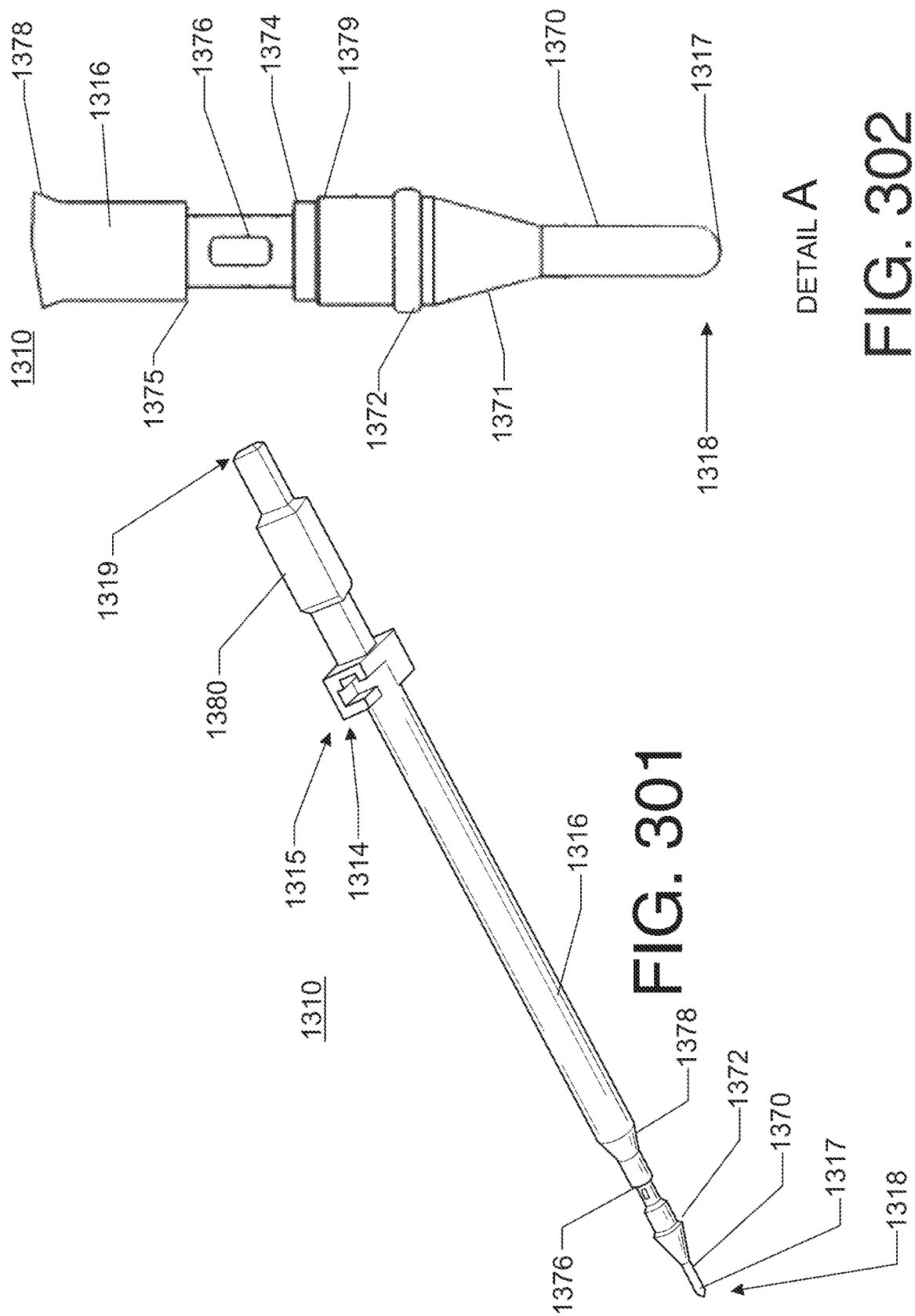

DETAIL C

DETAIL B

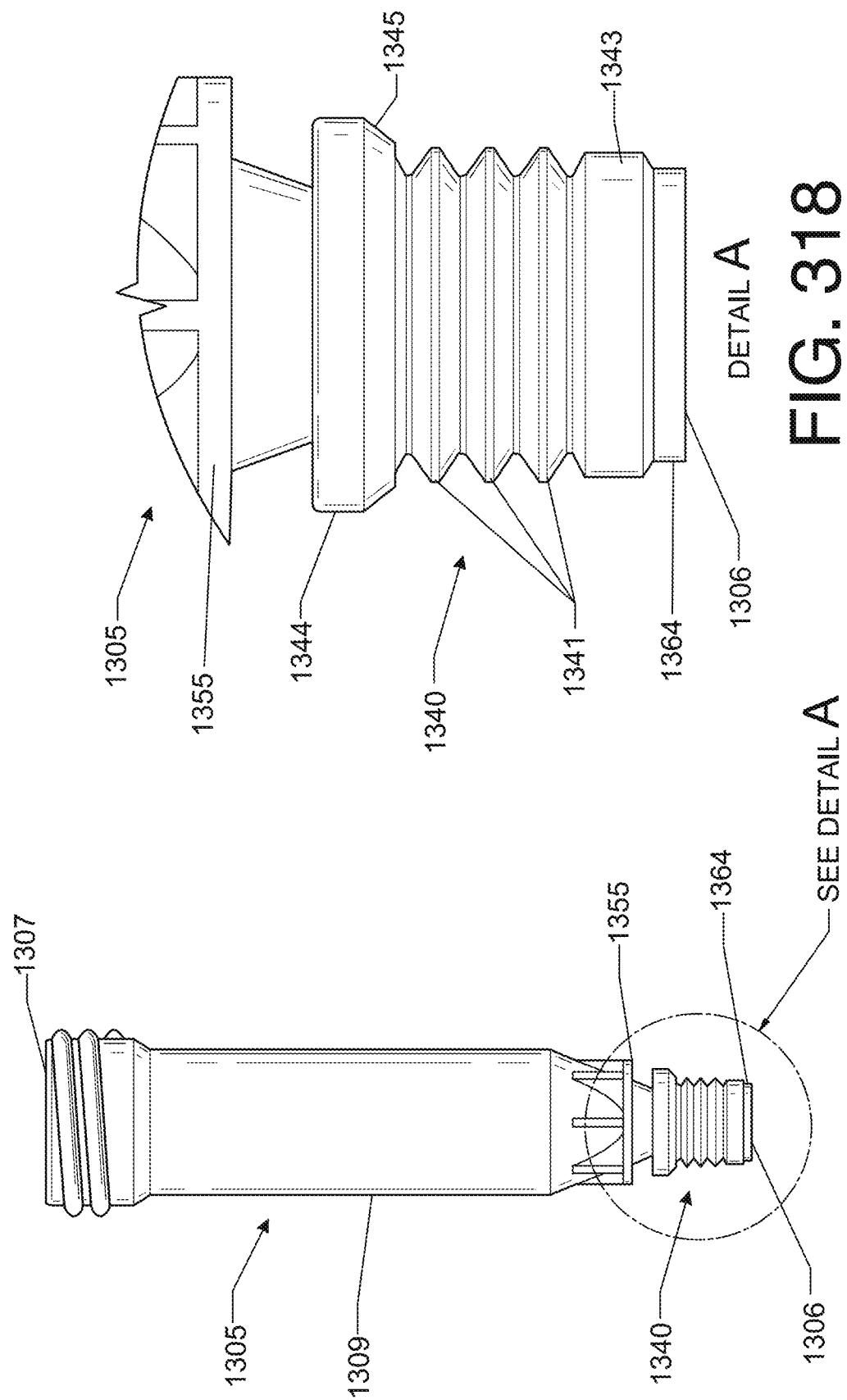

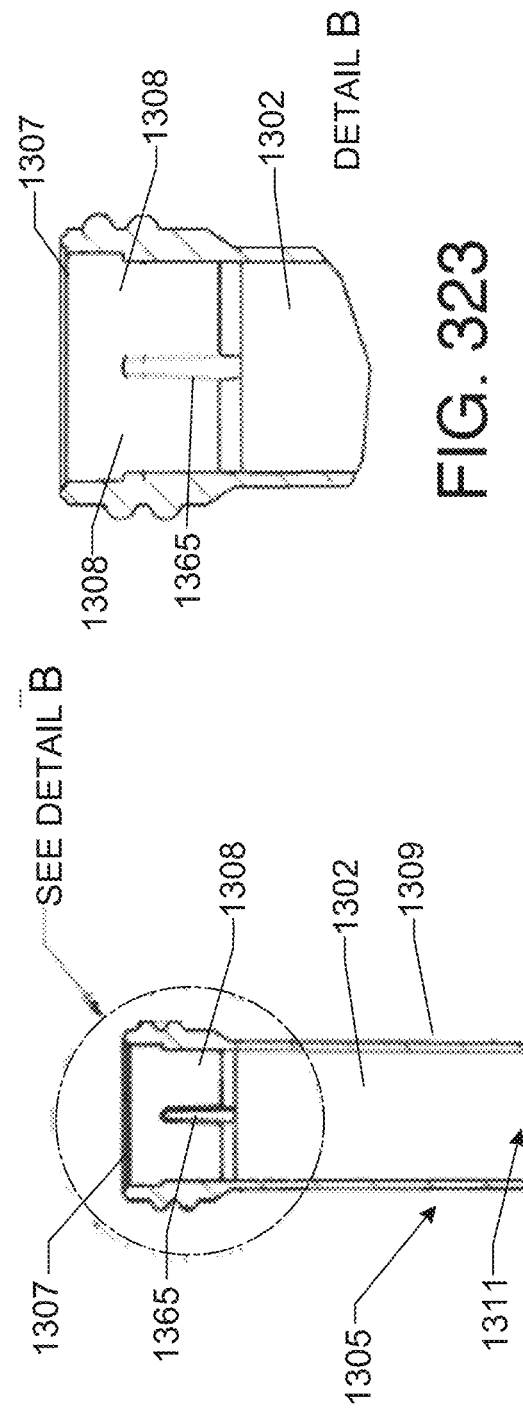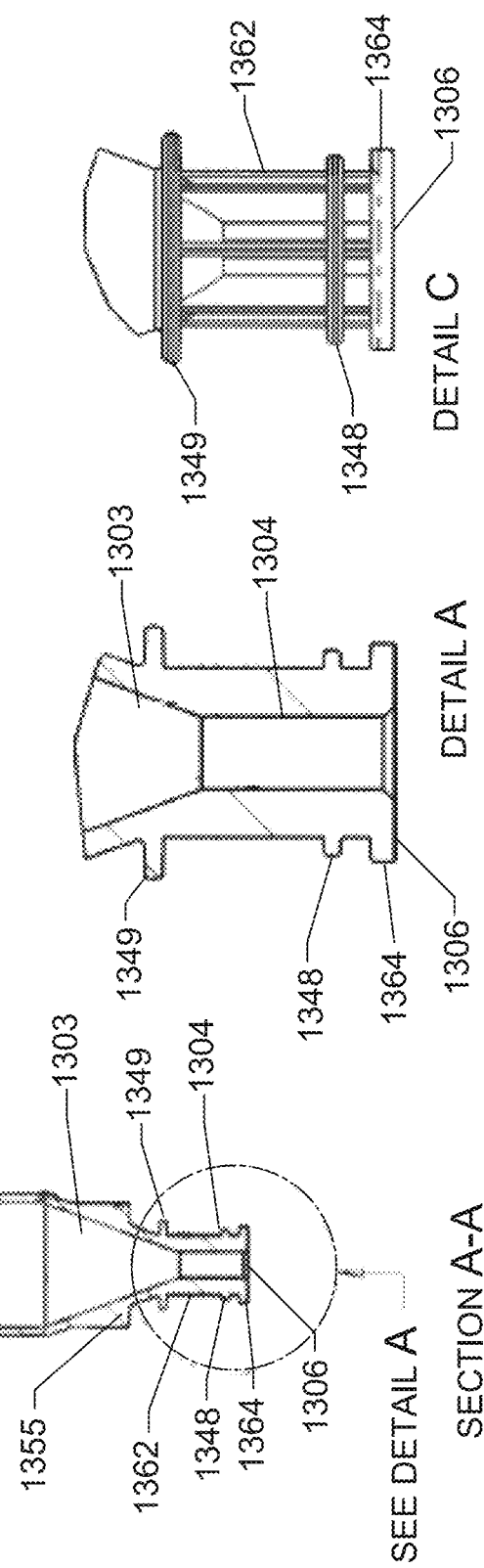

SECTION C-C

SECTION D-D

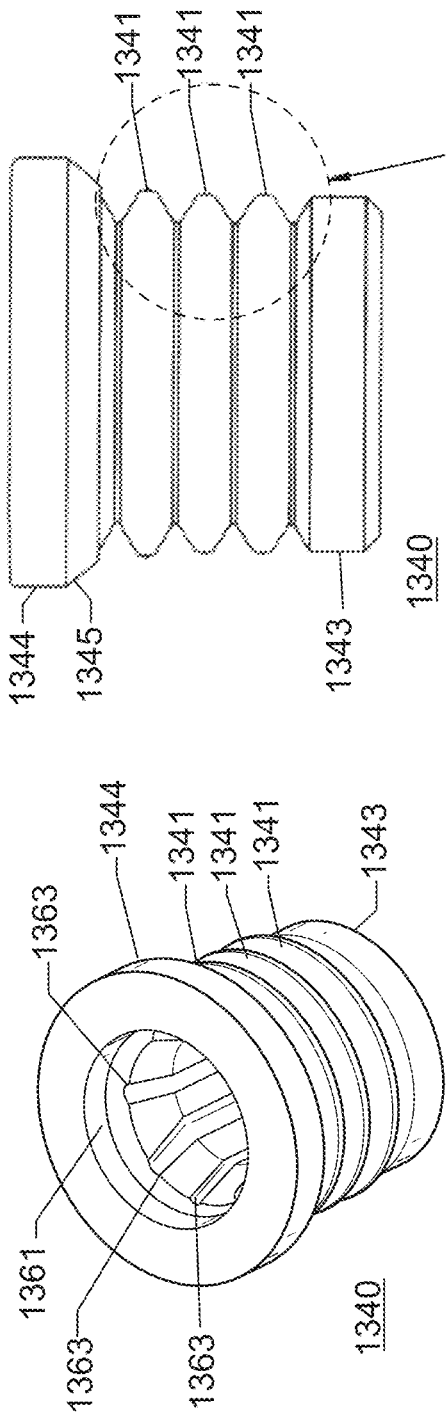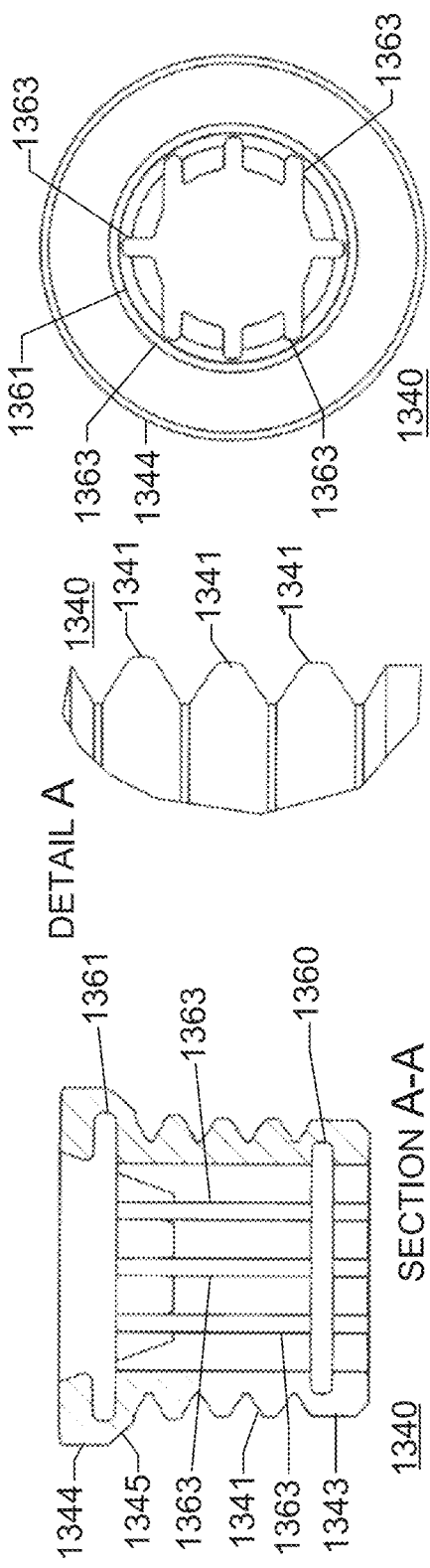
FIG. 330
FIG. 331
FIG. 332
FIG. 333
FIG. 334

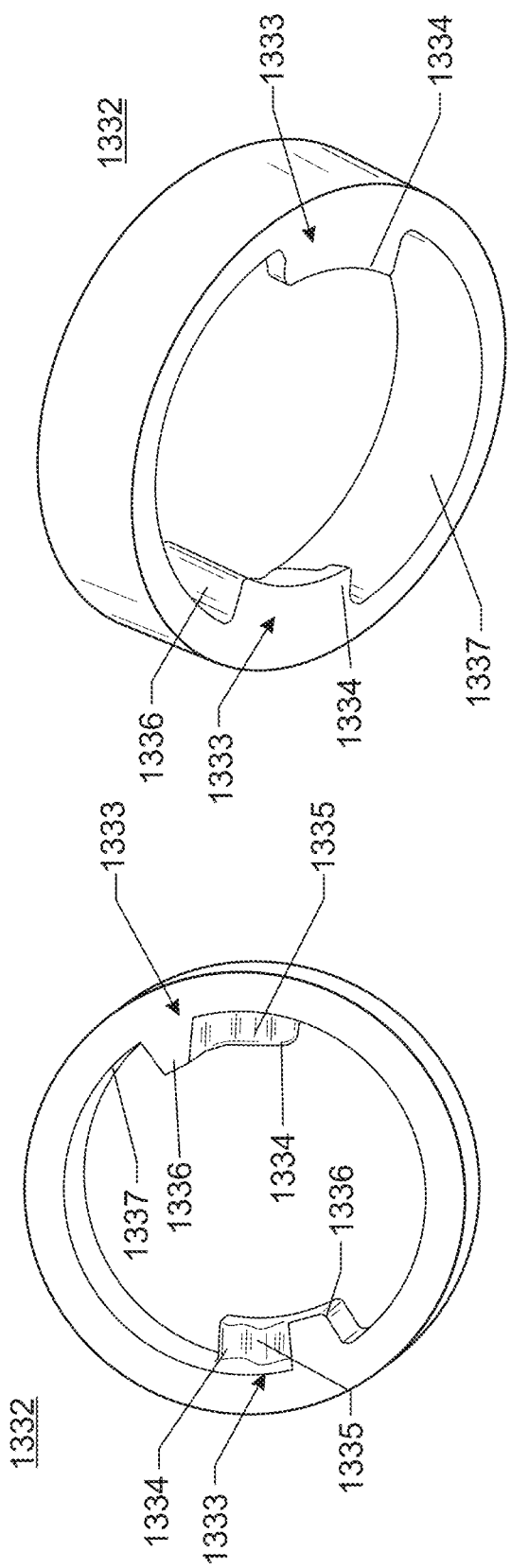
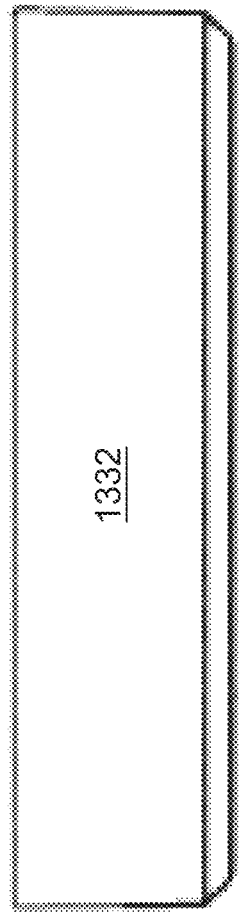
FIG. 339
FIG. 340
FIG. 341

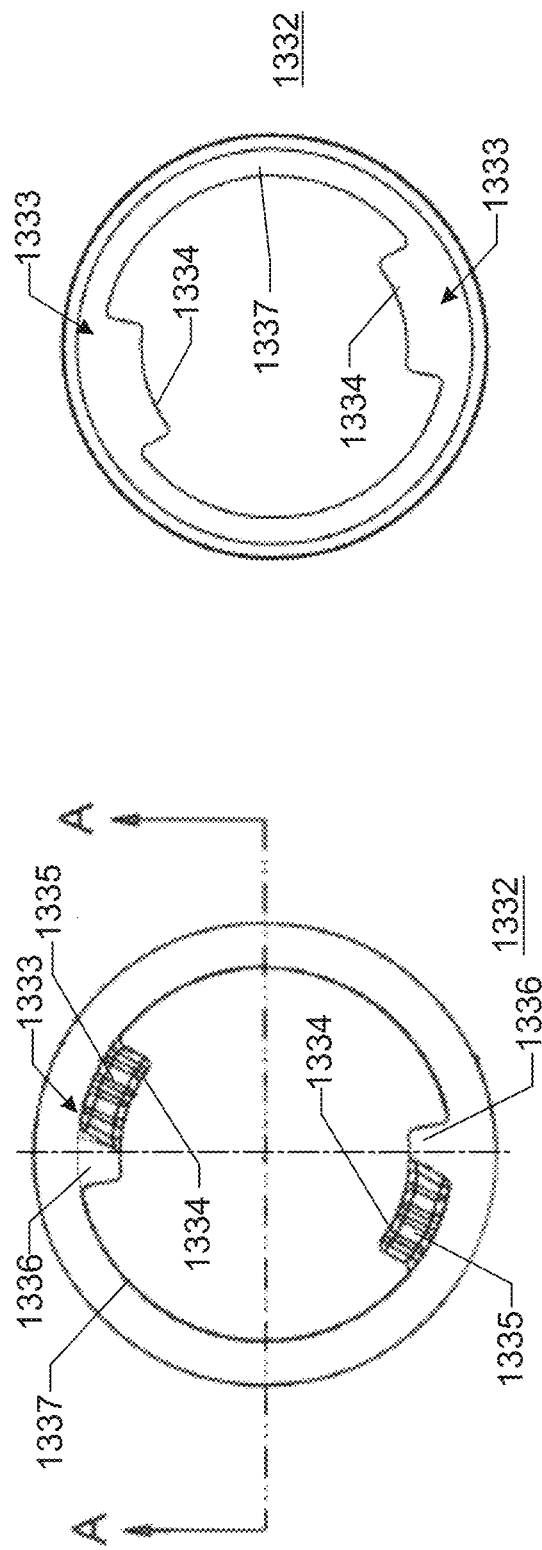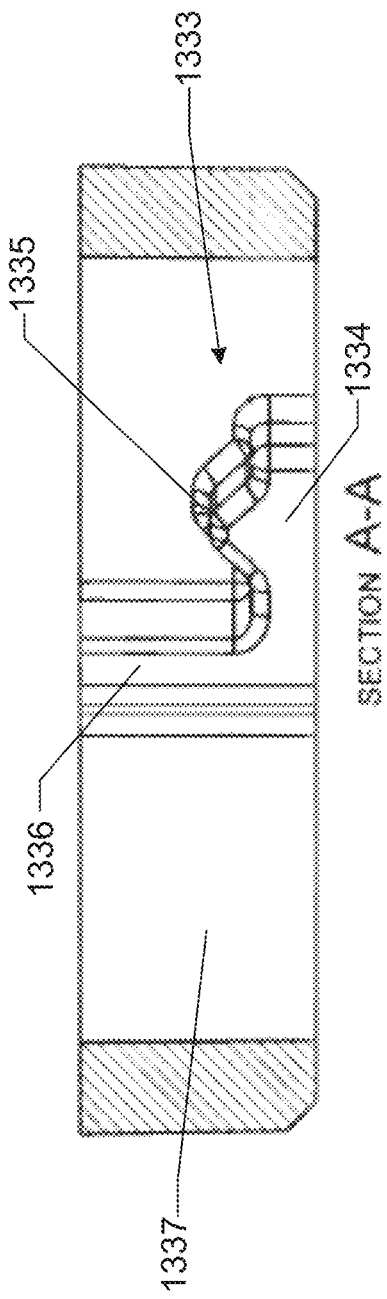

ISOLATION TUBE

CROSS-REFERENCE TO RELATED APPLICATIONS

This application is a continuation of U.S. application Ser. No. 16/046,275 (published as U.S. 2019/0046975), filed Jul. 26, 2018, which application claims the benefit of U.S. Provisional Application No. 62/537,731 entitled "Microbial Isolation Tube" and filed Jul. 27, 2017, and claims the benefit of U.S. Provisional Application No. 62/643,918 entitled "Microbial Isolation Tube" and filed Mar. 16, 2018. Each of the foregoing applications is hereby incorporated by reference herein in its entirety.

FIELD OF THE INVENTION

The present disclosure relates to a separation container and associated systems and methods for separating a sample via centrifugation and extracting a portion of the sample for use or testing.

BACKGROUND OF THE INVENTION

Sample preparation devices may typically separate a microorganism from a surrounding sample material (e.g., a blood sample) by centrifugation. Traditionally these systems require separate lysing, washing, decanting, and spinning steps, often requiring repeated washing, decanting, and spinning of the sample until the final, concentrated microorganism is obtained. Most, if not all, of these steps required separate user handling and different containers and equipment to perform.

Moreover, due to the wide variety of possible microorganisms that may be tested in the same separation container, the final properties of the concentrated microorganism (e.g., the density, viscosity, mass, etc.) may be difficult to predict. Many existing devices and methods require delicate handling and a precise application of force to transfer the microorganism into other testing apparatus after centrifugation. These processes are heavily dependent on user training and experience to obtain accurate, precise results. In addition, when handling dangerous microorganisms from sample material, it is often preferred to minimize human interaction with the sample as much as possible.

The inventors have identified a number of additional deficiencies and problems associated with conventional microbial separation products and other associated systems and methods. Through applied effort, ingenuity, and innovation, many of these identified problems have been solved by developing solutions that are included in embodiments of the present invention, many examples of which are described in detail herein.

BRIEF SUMMARY

Embodiments of the present invention herein include separation containers, centrifugation assemblies, and associated methods and systems for separating a sample via centrifugation and extracting a portion of the sample for use or testing. In some embodiments, a separation container may be provided for separating a sample via centrifugation and extracting a portion of the sample for use or testing. The separation container may include a body defining an internal chamber. The body may define an opening at a first end, and the body may be configured to receive the sample within the internal chamber. The separation container may further include a seal disposed across the opening, such that the seal may be configured to seal the opening of the body. The separation container may also include a plunger movably disposed at least partially inside the internal chamber. The plunger may be configured to be actuated to open the seal and extract the portion of the sample.

The body may define an axis extending from the first end to a second end. A longitudinal member of the plunger may be disposed on the axis. In some embodiments, the internal chamber may define a diameter radial to the axis, and the diameter may narrow from a collection diameter to a pellet diameter in a direction extending axially from the second end to the first end. At least a portion of the plunger may be configured to sealingly engage the body at a portion of the body corresponding to the pellet diameter. The at least the portion of the plunger may define a plunger diameter radial to a length of the longitudinal member, and the plunger diameter may be greater than the pellet diameter, and may define an interference fit between the plunger and the pellet region. In some embodiments, the plunger diameter may less than the collection diameter. The at least the portion of the plunger may include a sealing rib disposed circumferentially about the longitudinal member of the plunger, and the sealing rib may be configured to engage the body at the portion of the body corresponding to the pellet diameter.

In some embodiments, the plunger may be configured to allow the portion of the sample to pass by the plunger from a second end towards the first end during centrifugation, and the plunger may be configured to prevent a remaining part of the sample from traveling to the first end during actuation of the plunger, such that during actuation, the plunger may divide the internal chamber into two sub-chambers.

In some embodiments, the plunger may be buoyant in water or a density cushion material. In some further embodiments, the plunger may define a specific density of 0.95 or less relative to the water or the density cushion material. The plunger may further define a specific density of 0.9 or less relative to the water or the density cushion material. In some embodiments, the plunger may be buoyant in a mixture of the water and the density cushion material.

In some embodiments, the plunger may include one or more sealing ribs near a distal end that engage a narrow, pellet region of the separation container to seal the pellet region and apply a pressure to the microorganism sample. A blade or other pointed region of the plunger may then pierce the seal of the separation container from within the pressurized pellet region to express the microorganism from the separation container under pressure. The sealing rib(s) may prevent contamination of the sample by sealing the remaining fluid above the plunger from the microorganism sample, while also ensuring that the pellet is completely expressed from the pellet region.

In some embodiments, the plunger may define a point at a first distal end of a longitudinal member of the plunger, and the point may be configured to pierce the seal at the first opening to allow fluid communication between the internal chamber and an area outside the body via the opening.

The separation container may further include a flexible sealing member disposed at a second end of the body, and a second distal end of the plunger may be configured to extend at least partially into the flexible sealing member, such that compression of the flexible sealing member may actuate the plunger. The separation container may further include a cap secured to the body at the second end, and a portion of the flexible sealing member may be configured to be disposed between the cap and the body, and the cap may define an opening through which a second portion of the flexible sealing member and the second distal end of the plunger may be configured to extend. In some embodiments, the flexible sealing member may include a bellows gasket defining an open end configured to receive a portion of the plunger therein. The bellows gasket may further define a closed end configured to seal the internal chamber of the body.

In some embodiments, the separation container may include a sample collecting vessel configured to removably engage the body. The sample collecting vessel may be configured to surround the opening, such that the sample collecting vessel may be configured to collect the portion of the sample passing through the seal. The sample collecting vessel may contain fluids to facilitate the resuspension, testing, and/or growth of cells recovered from the sample portion.

The separation container may also include a rheological control member disposed in the internal chamber of the body. The rheological control member may define a barrier configured to reduce mixing of the sample and a density cushion. In some embodiments, the barrier of the rheological control member may define an annular structure disposed about the plunger. In some embodiments, the rheological control member may be buoyant in water and in a density cushion material.

In some embodiments, the seal may include a membrane, and in some embodiments, the membrane may include a foil sheet.

In another embodiment, a centrifugation assembly may be provided. The centrifugation assembly may include a separation container for separating a sample via centrifugation and extracting a portion of the sample for use or testing. In such embodiments, the separation container may include body defining an internal chamber. The body may define an opening at a first end, and the body may be configured to receive the sample within the internal chamber for centrifugation. The separation container of the centrifugation assembly may further include a seal disposed across the opening, such that the seal may be configured to seal the opening of the body. The separation container may also include a plunger movably disposed at least partially inside the internal chamber, and the plunger may be configured to be actuated to open the seal and extract the portion of the sample. The centrifuge assembly may also include a centrifuge cup configured to receive the separation container. The centrifuge cup may include a side wall configured to abut the body, and a bottom wall configured to abut the first end of the body. The bottom wall may be configured to support the seal of the separation container during centrifugation.

In yet another embodiment, a method for preparing viable and/or non-viable portions of a sample for testing may be provided. The method may include disposing the sample portion into a separation container. The separation container may include a body defining an internal chamber, and the body may define an opening at a first end. The separation container may further include a seal disposed across the opening, such that the seal may be configured to seal the opening of the body. The separation container may also include a plunger movably disposed at least partially inside the internal chamber, and the plunger may be configured to be actuated to open the seal. The separation container may further include a density cushion disposed in the internal chamber of the body. The method may include centrifuging the separation container to create a pellet from a portion of the sample within the internal chamber, and expressing the pellet from the opening in the body by depressing the plunger.

In some embodiments of the method, centrifuging the separation container to create the pellet may include allowing the portion of the sample to pass the plunger and collect at the first end of the body. Expressing the pellet may include depressing the plunger into sealing engagement with a portion of the body to create pressure between the plunger and the seal, and expelling the pellet from the opening under the pressure by opening the seal.

In some embodiments, the pellet may include viable portions of the sample suitable for a culture step.

In some embodiments, the pellet may include viable portions of the sample suitable for antibiotic susceptibility testing (AST) and phenotypic identification methods.

In some embodiments, the pellet may include portions of the sample suitable for identification by mass spectrometry (e.g. MALDI-TOF).

In some embodiments, the pellet may include portions of the sample suitable for other applications such as nucleic acid amplification techniques, spectroscopy techniques (e.g., Raman, FTIR), immunoassay techniques, probe-based assays, agglutination tests etc.).

In some embodiments, a rheological control member may be used that may seal between the plunger and the wall of the body to prevent mixing of the density cushion and the sample. In such embodiments, the rheological control member may be released by the wall when the wall expands outwardly during centrifugation.

In another embodiment, a separation container may be provided for separating a sample via centrifugation and extracting a portion of the sample for use or testing. The separation container may include a body defining an internal chamber. The body may include a wall at least partially bounding the internal chamber. The body may include an opening at a first end, and the body may define an axis extending from the first end to a second end. In some embodiments, an internal chamber defines a diameter radial to the axis, and the wall may be at least partially flexible such that the diameter of the internal chamber is a first diameter in a static state and the diameter of the internal chamber may expand to a second diameter during centrifugation. The body may be configured to receive the sample within the internal chamber. The separation container may further include a seal disposed across the opening, such that the seal may be configured to seal the opening of the body, and a plunger movably disposed at least partially inside the internal chamber. A longitudinal member of the plunger may be disposed on the axis of the body. The plunger may be configured to be actuated to open the seal and extract a portion of the sample. The separation container may further include a rheological control member disposed in the internal chamber. The rheological control member may define a bore through which the longitudinal member of the plunger is disposed, such that the rheological control member may be disposed between the longitudinal member and the wall. In some embodiments, the rheological control member may define an outermost diameter radial to the axis of the body. The outermost diameter of the rheological control member may be greater than the first diameter, and the second diameter may be greater than the outermost diameter of the rheological control member.

In some embodiments, the body may include a collection region defining the diameter. The body may include a widened region defining a greater diameter than the diameter of the collection region, and the greater diameter of the widened region may be greater than the outermost diameter of the rheological control member.

The wall may include an annular shoulder at which the diameter of the internal chamber changes. The first diameter may be defined on a narrow side of the annular shoulder in a static state, and the annular shoulder may be configured to engage the rheological control member.

In some embodiments, the rheological control member may include a second annular shoulder comprising a wide side defining the outermost diameter and a narrow side.

The separation container may include a gasket disposed circumferentially about the longitudinal member, and the gasket may be configured to seal an opening between the bore of the rheological control member and the plunger.

In another embodiment, a separation container and end cap assembly may be provided for separating a sample via centrifugation and extracting a portion of the sample for use or testing. The assembly may include a body, a seal, an end cap, and a plunger. The body may define an internal chamber, and the body may define an opening at a first end. The body may be configured to receive the sample within the internal chamber. The seal may be disposed across the opening, such that the seal may be configured to seal the opening of the body. The end cap may be at the first end, and the end cap may be attachable to the body. In some embodiments, the seal may be disposed between the end cap and the body. The plunger may be movably disposed at least partially inside the internal chamber, and the plunger may be configured to be actuated to open the seal and extract a portion of the sample.

In another embodiment, a separation container may be provided for separating a sample via centrifugation and extracting a portion of the sample for use or testing. The separation container may include a body, a seal, a plunger, and a flexible sealing member. The body may include an internal chamber, and the body may define a first opening at a first end and a second opening at a second end. The body may be configured to receive the sample within the internal chamber. In some embodiments, the seal may be disposed across the opening, such that the seal may be configured to seal the opening of the body. The plunger may be disposed at least partially inside the internal chamber, and the plunger may be configured to be actuated to open the seal and extract a portion of the sample. The flexible sealing member may at least partially cover the second opening. At least a portion of the plunger may be configured to extend at least partially into the flexible sealing member, such that compression of the flexible sealing member may actuate the plunger.

In some embodiments, the flexible sealing member may define a wall configured to at least partially surround the portion of the plunger. The wall may define an inwardly concave shape, such that the wall may be configured to flex outwardly from the plunger when the plunger is actuated. The flexible sealing member may include a first circumferential wall segment connected to a top of the flexible sealing member, a second circumferential wall segment connected to the first circumferential wall segment, and a third circumferential wall segment connected to the second circumferential wall segment. The second circumferential wall segment may be concentric about a longitudinal axis of the plunger. The first circumferential wall segment and the second circumferential wall segment may each be angled at least partially inwardly towards the plunger from their respective connections to the second circumferential wall segment.

BRIEF DESCRIPTION OF THE SEVERAL VIEWS OF THE DRAWINGS

Figure 1:
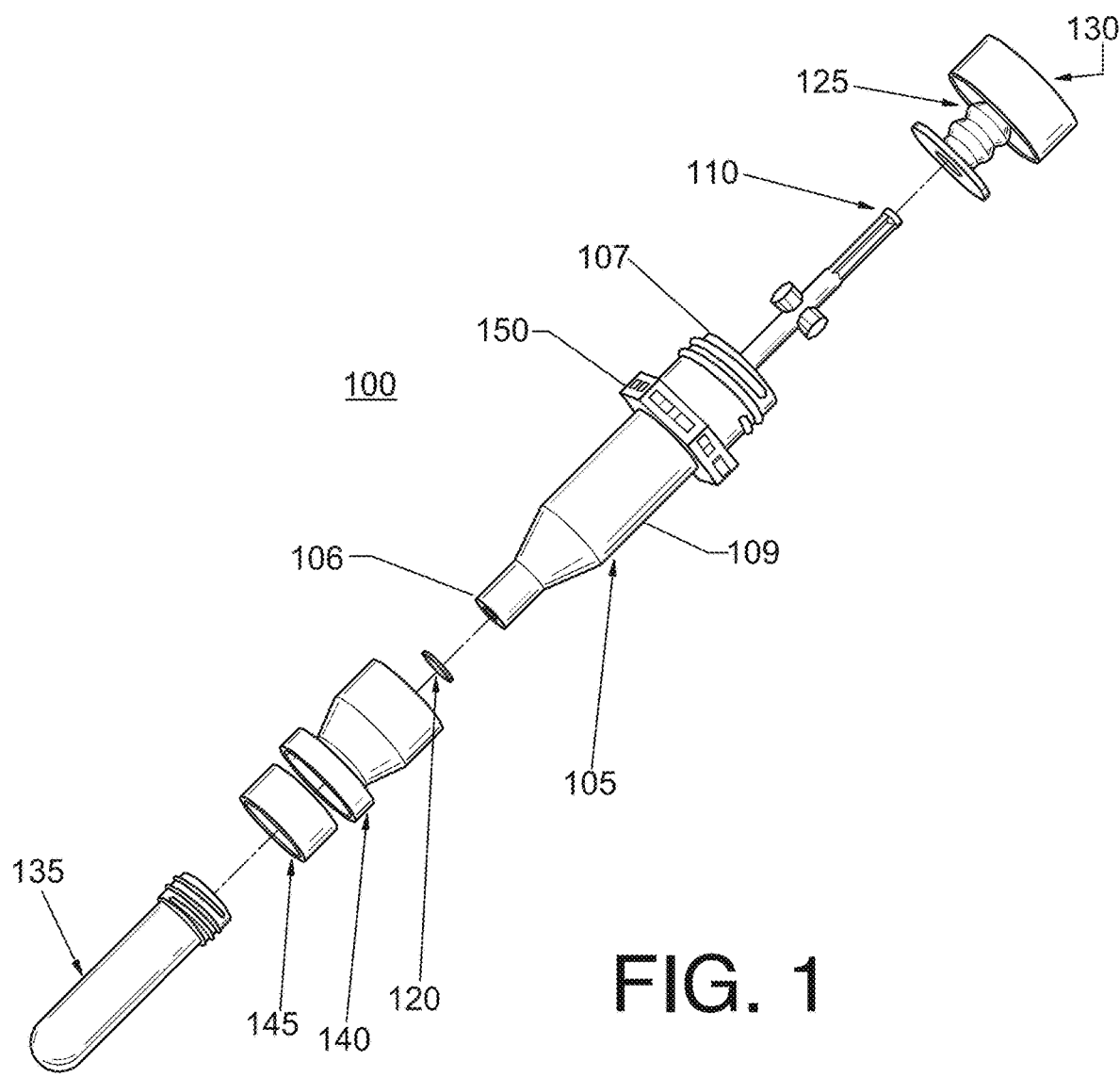
Figure 14:
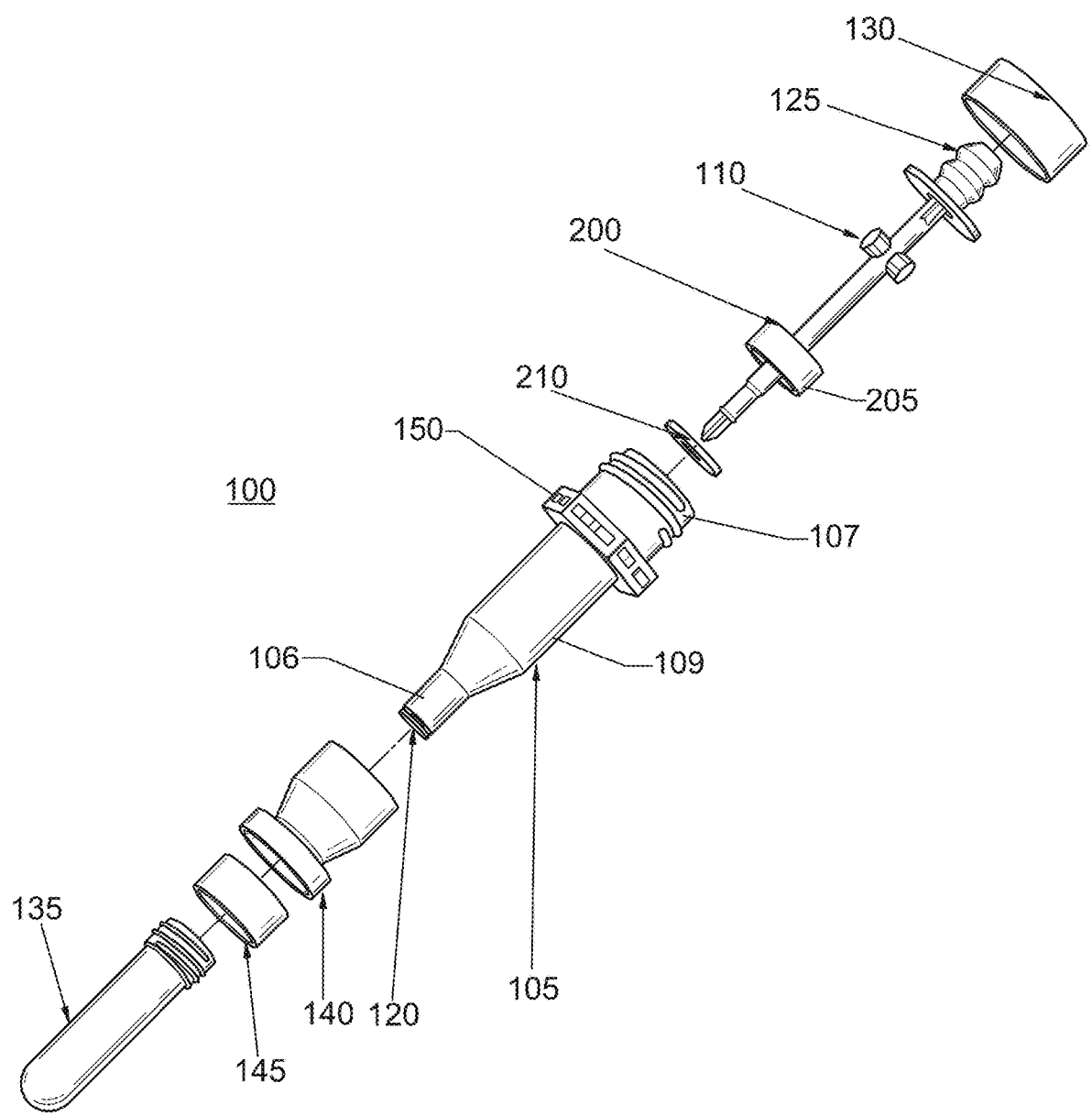
Figure 24:
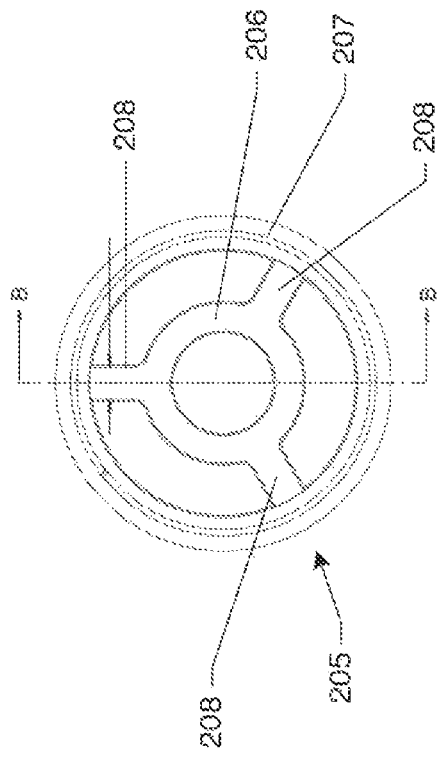
Figure 23:
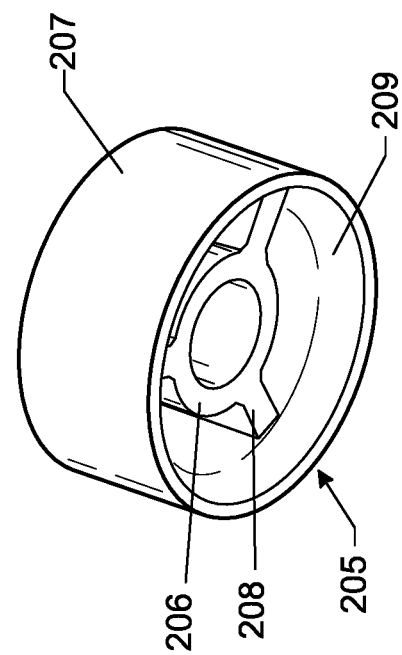
Figure 26:
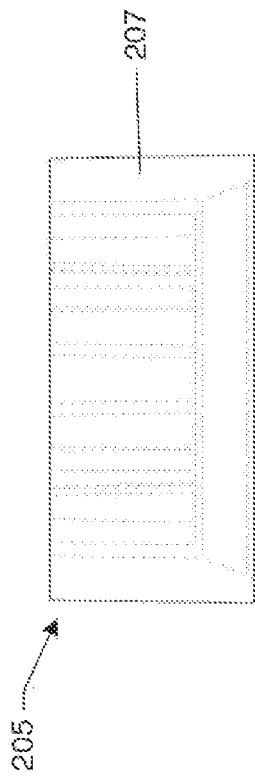
Figure 25:
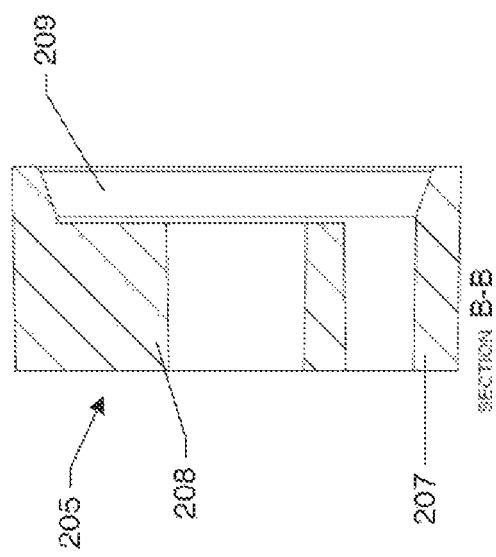
Figure 32:
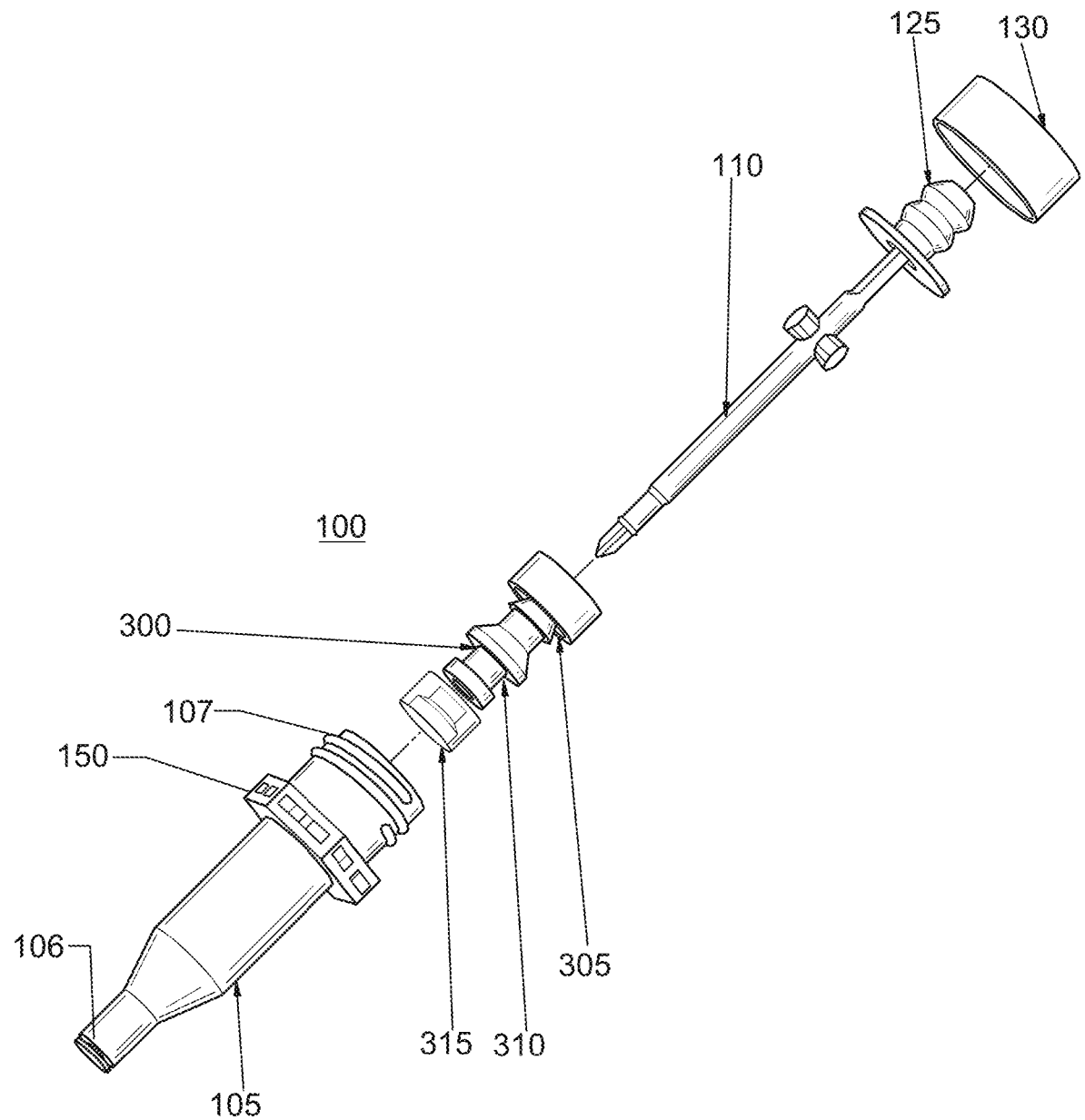
Figures 45, 46, 47:
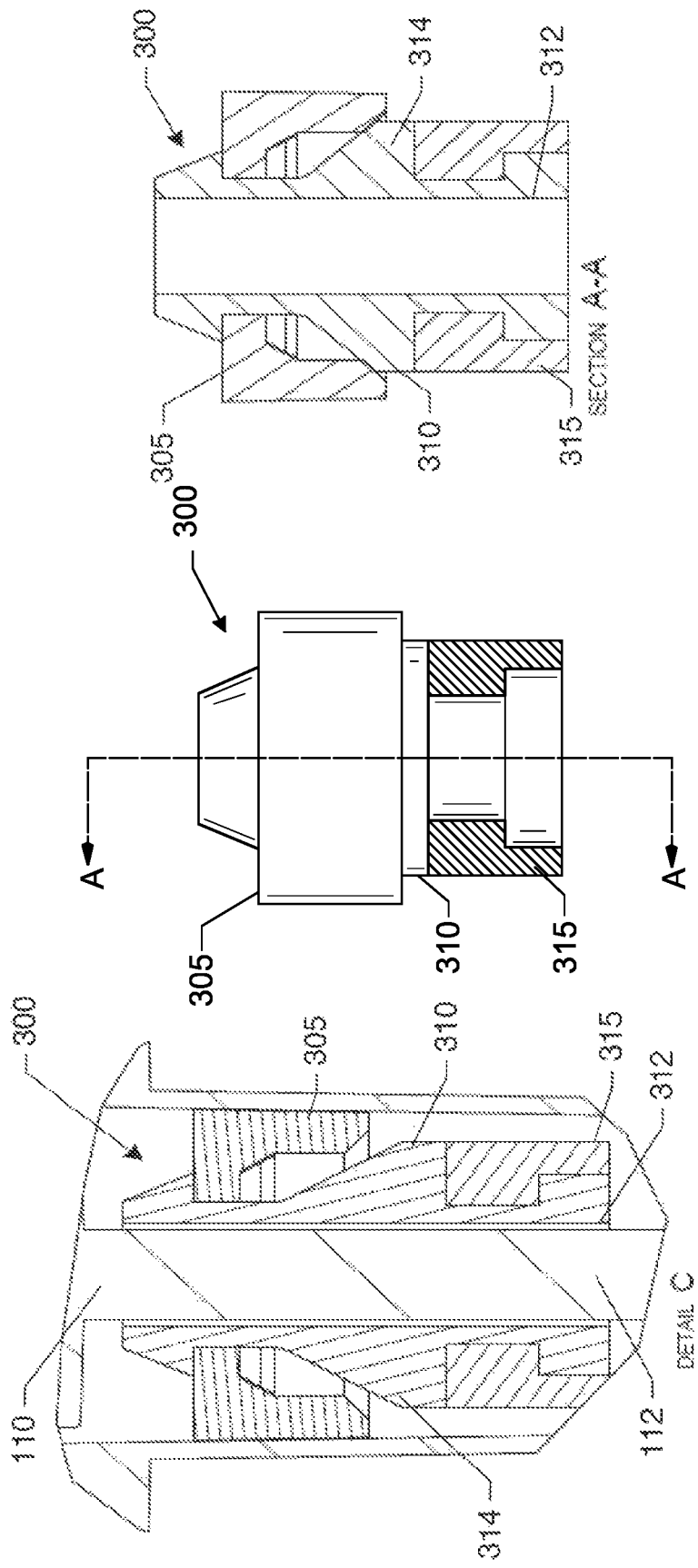
Figures 48, 49:
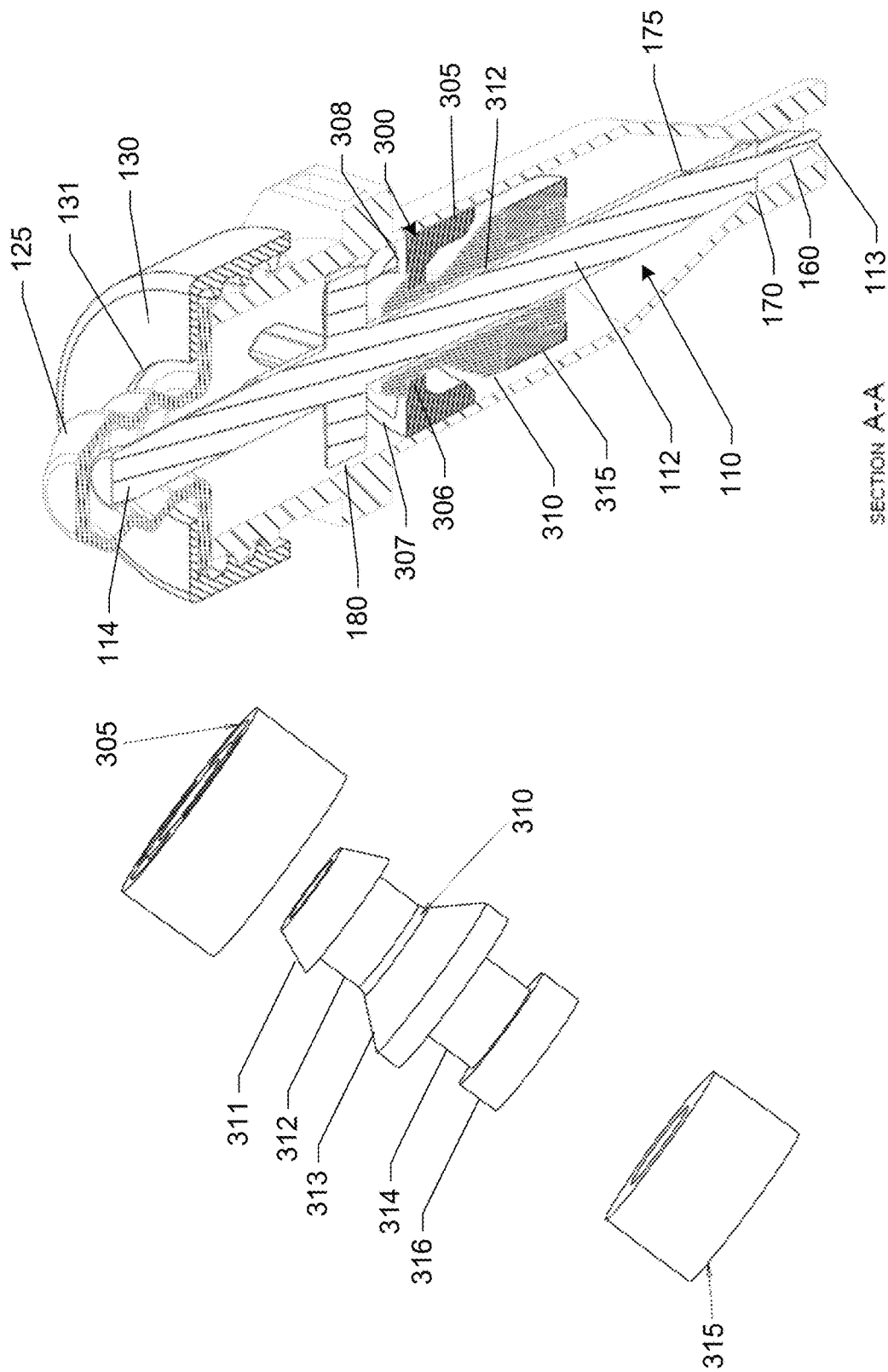
Figure 50:
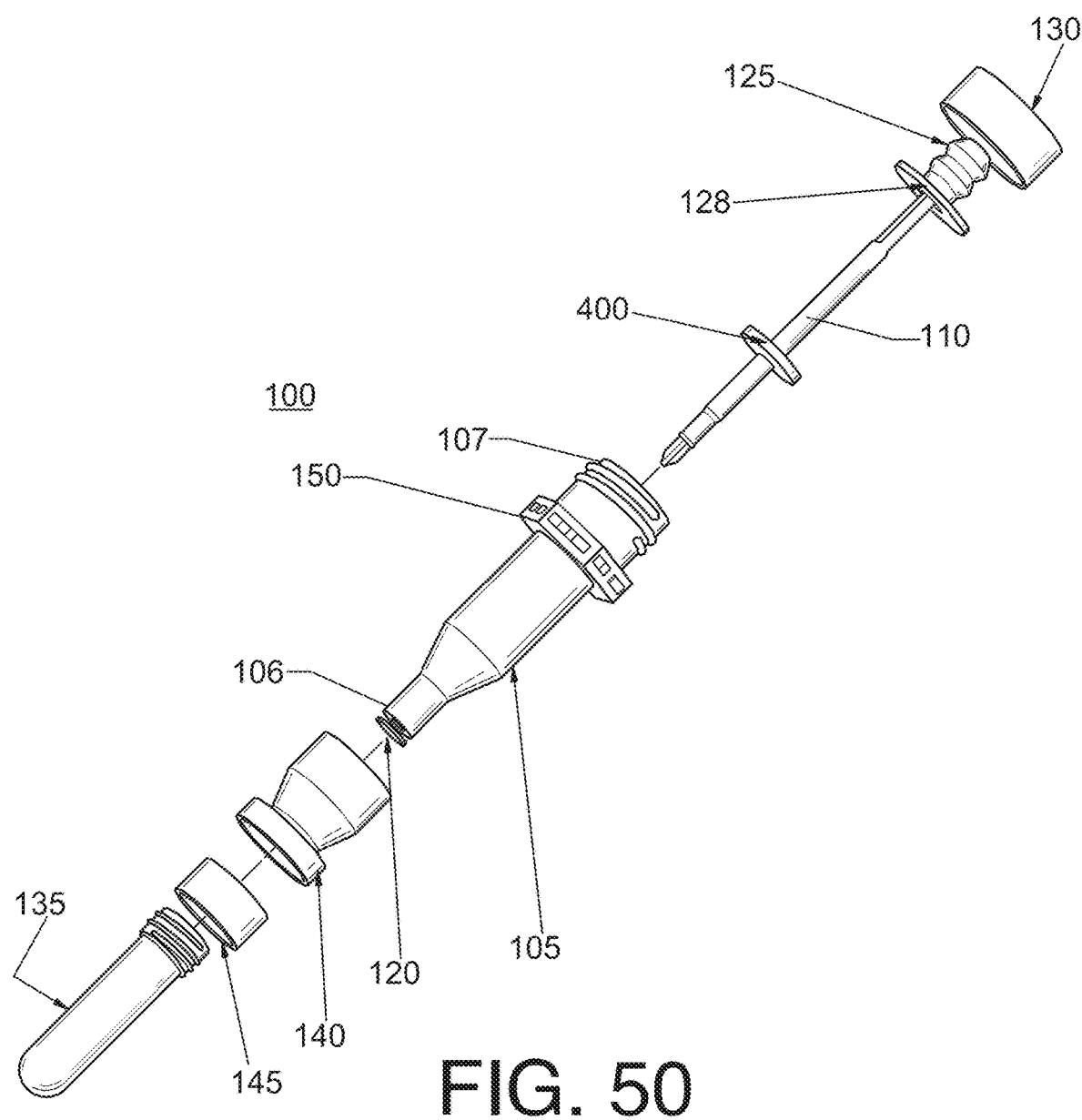
Figure 68:
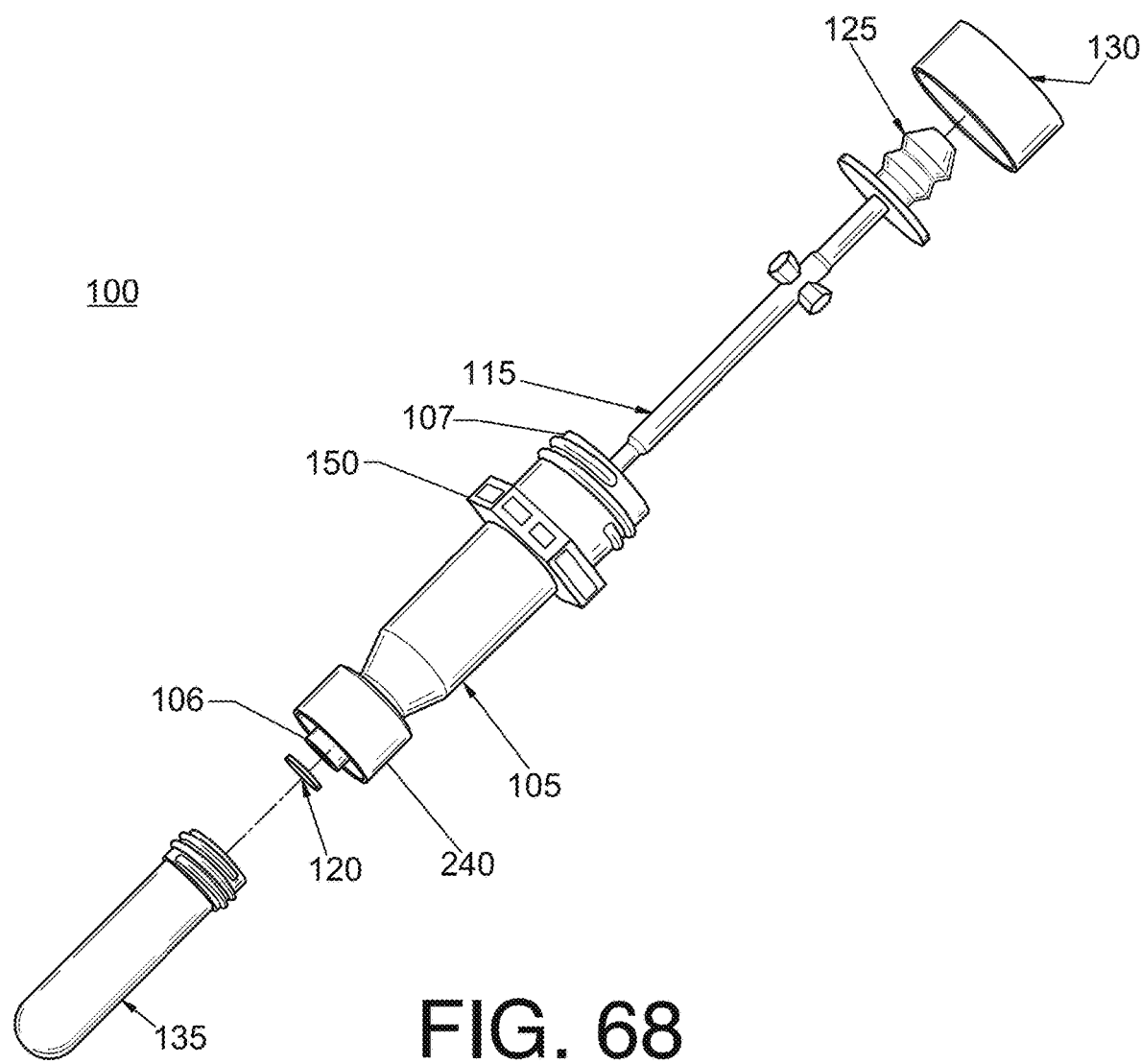
Figure 84:
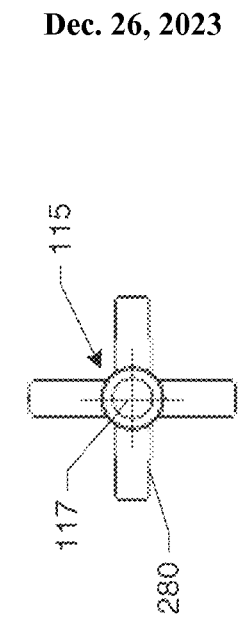
Figure 85:
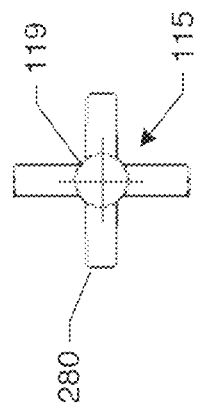
Figure 82:
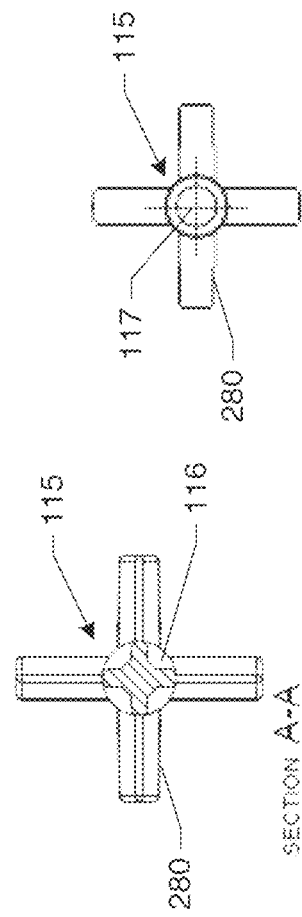
Figure 83:
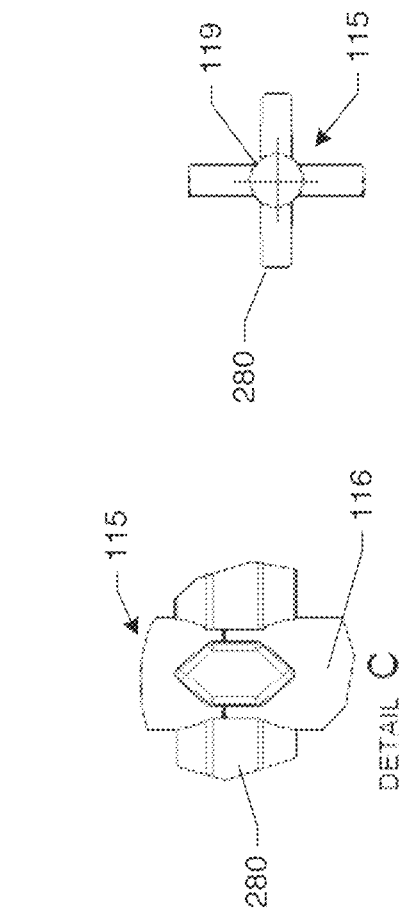
Figure 81:
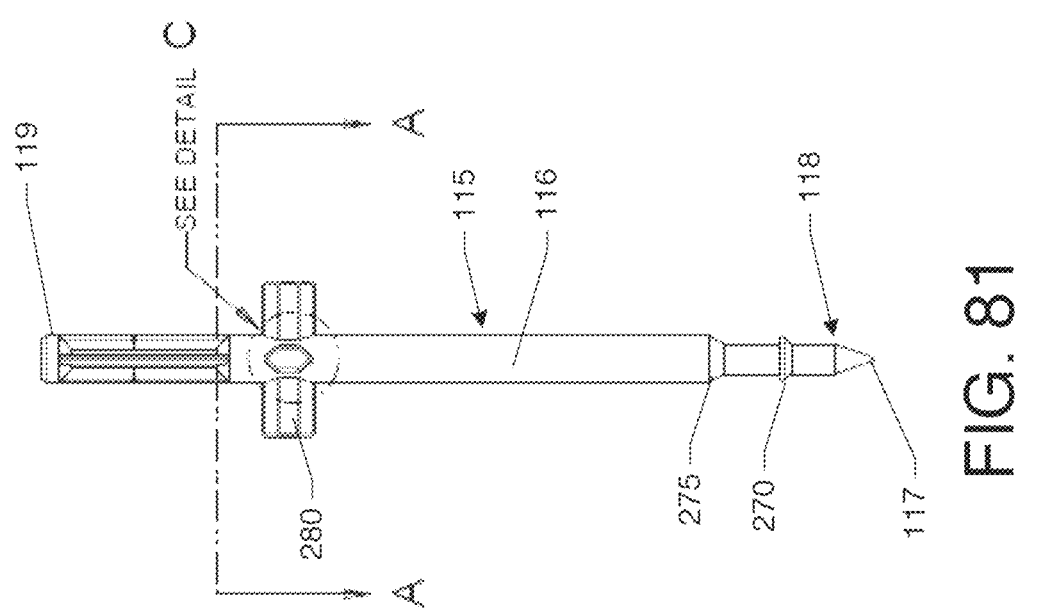
Figure 87:
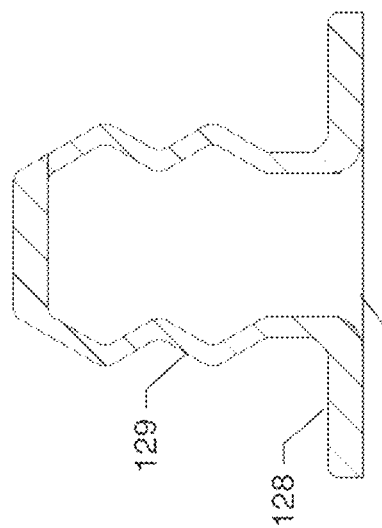
Figure 90:
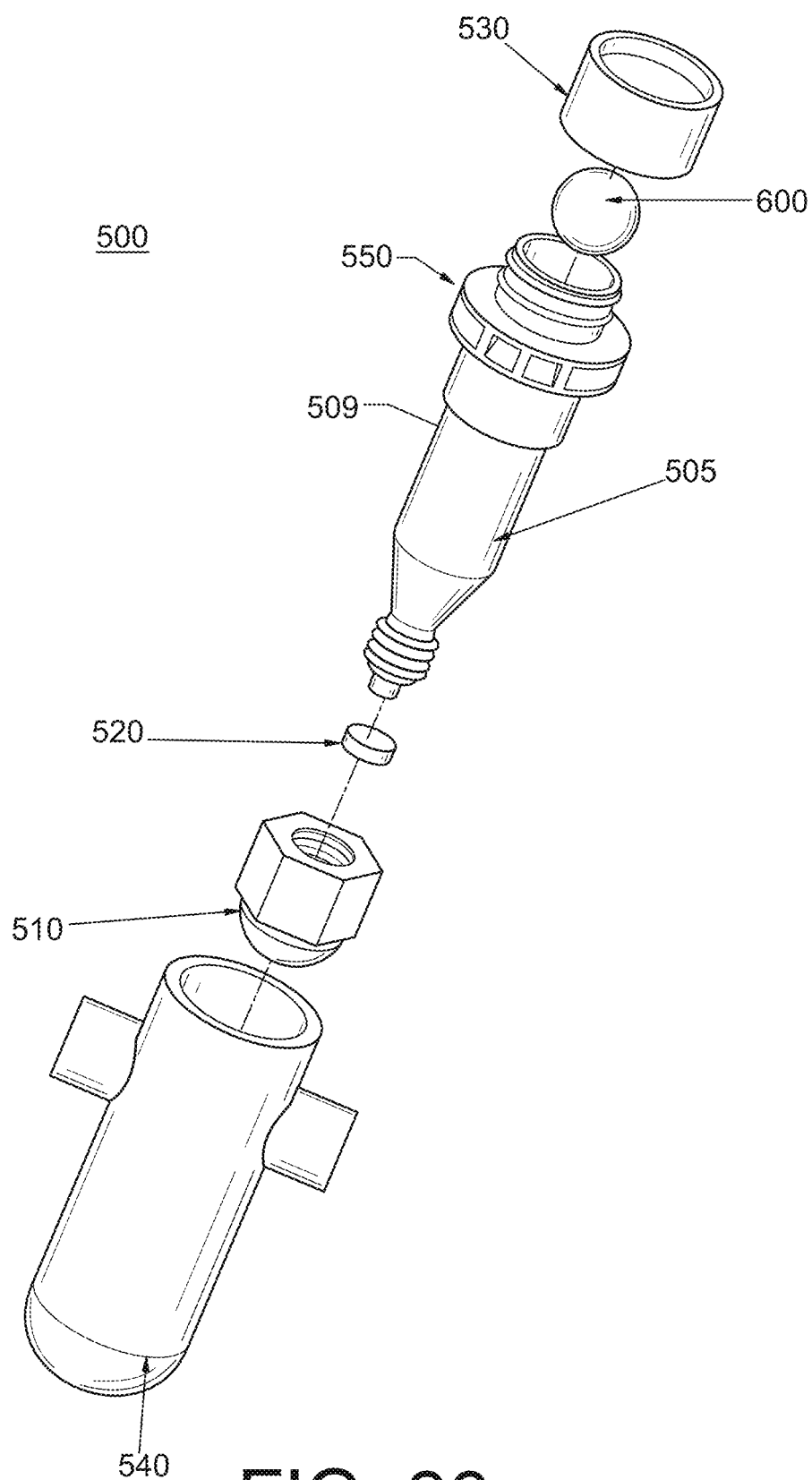
Figure 92:
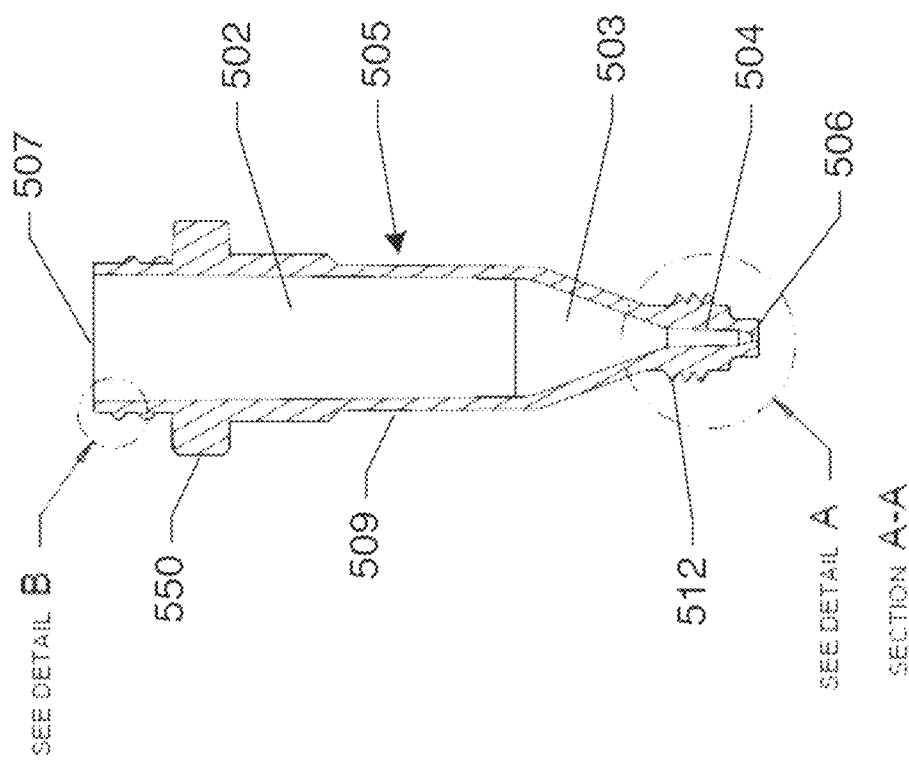
Figure 91:
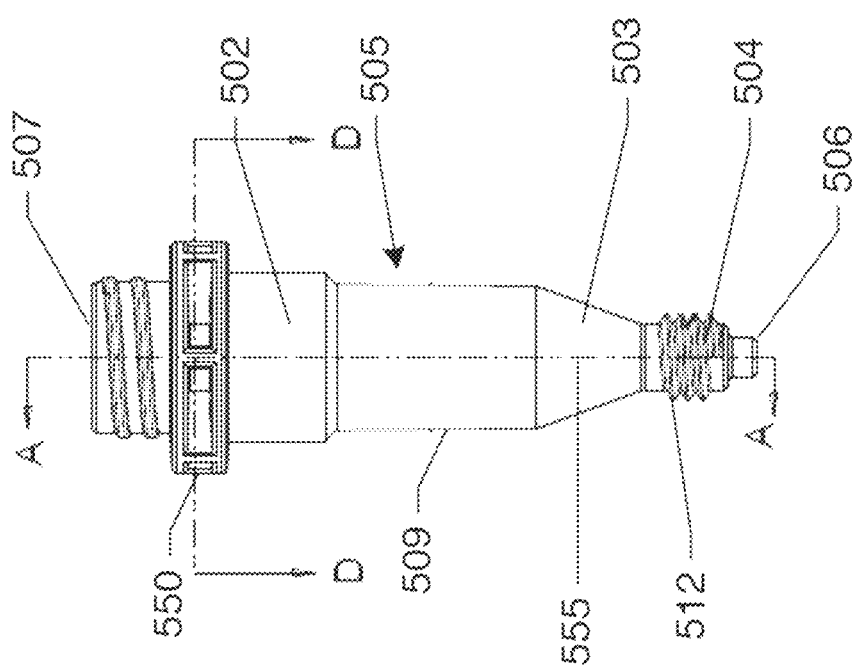
Figure 97:
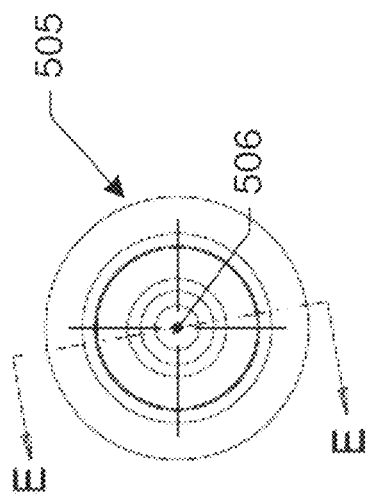
Figure 98:
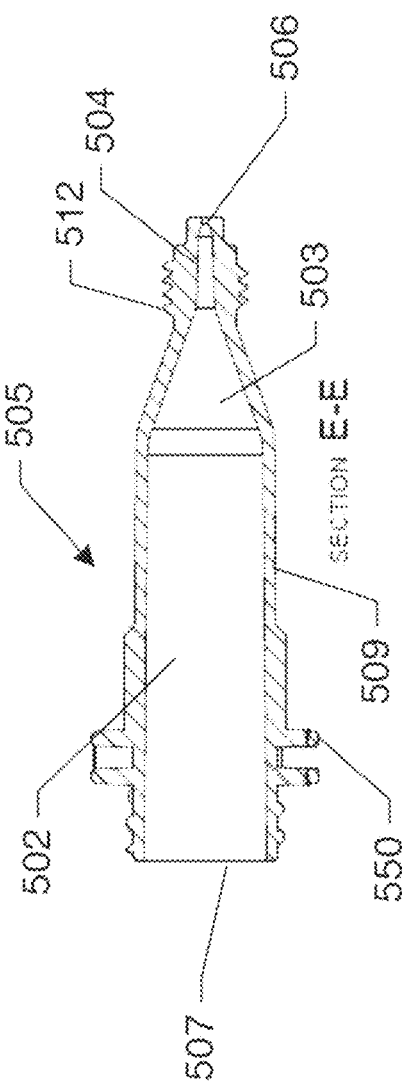
Figure 96:
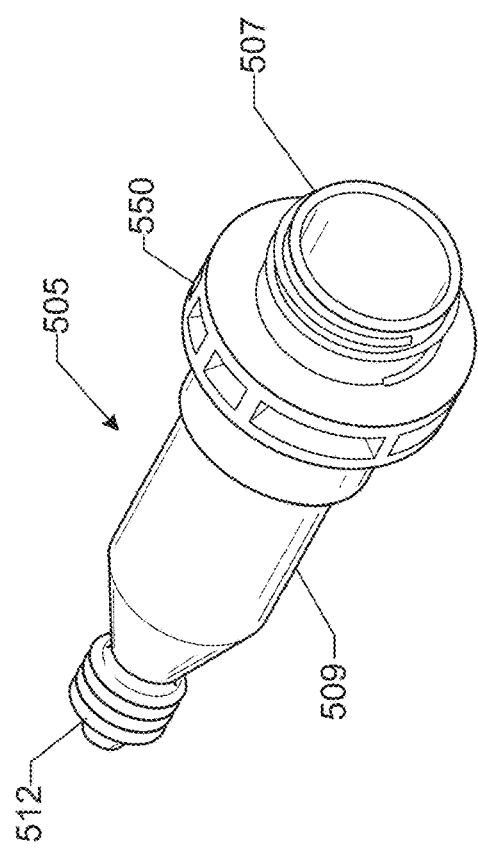
Figure 102:
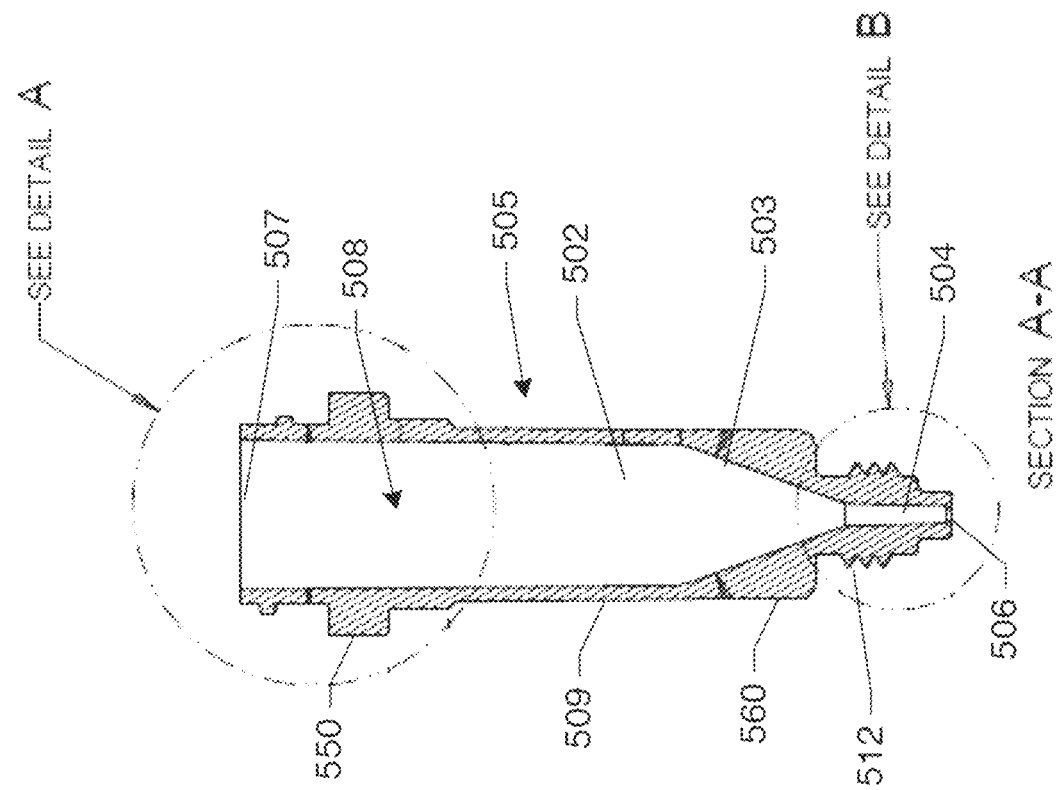
Figure 101:
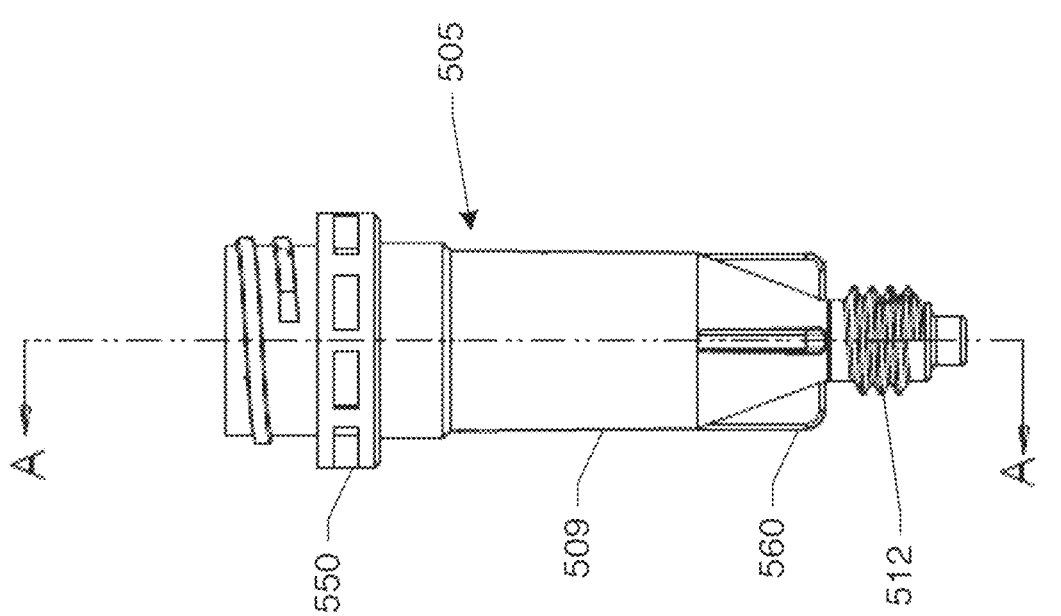
Figure 104:
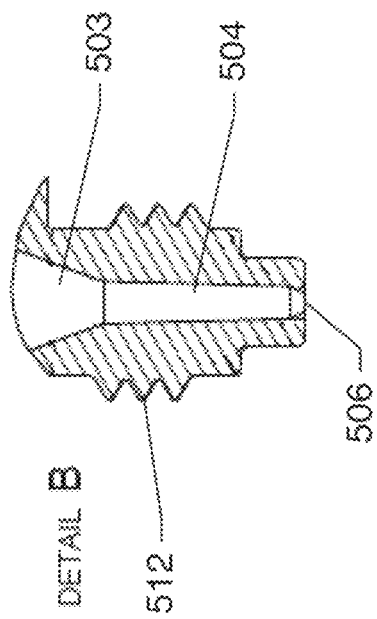
Figure 105:
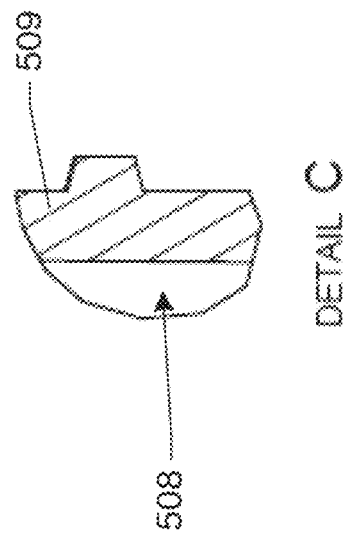
Figure 103:
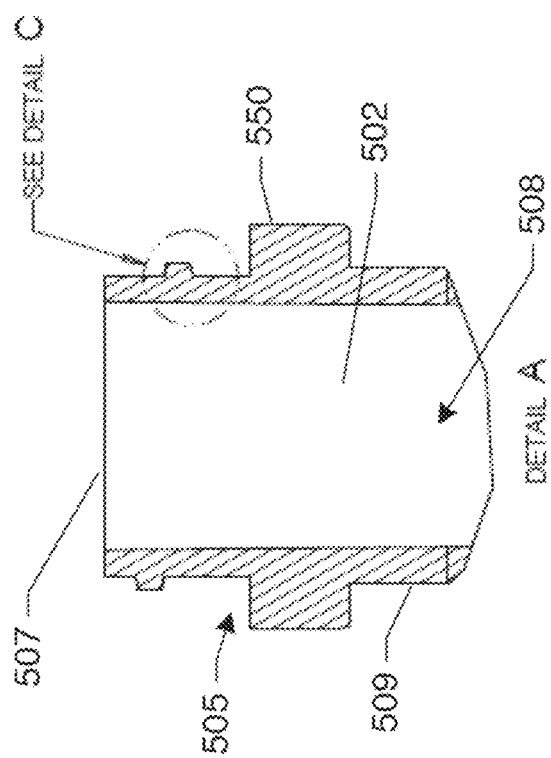
Figure 107:
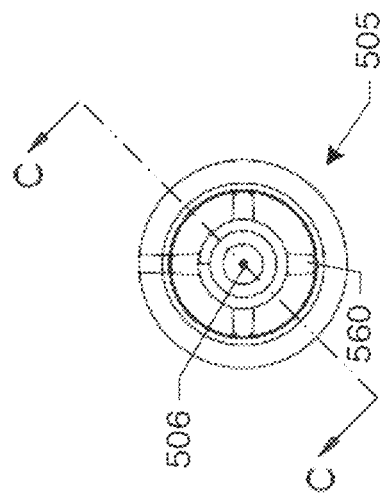
Figure 108:
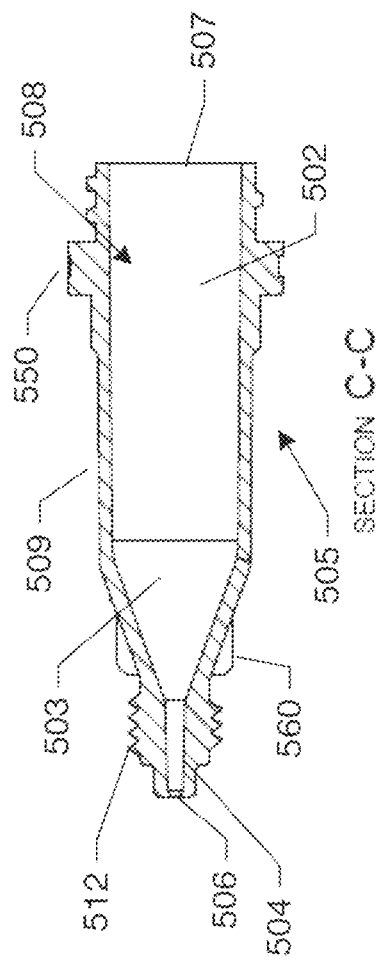
Figure 106:
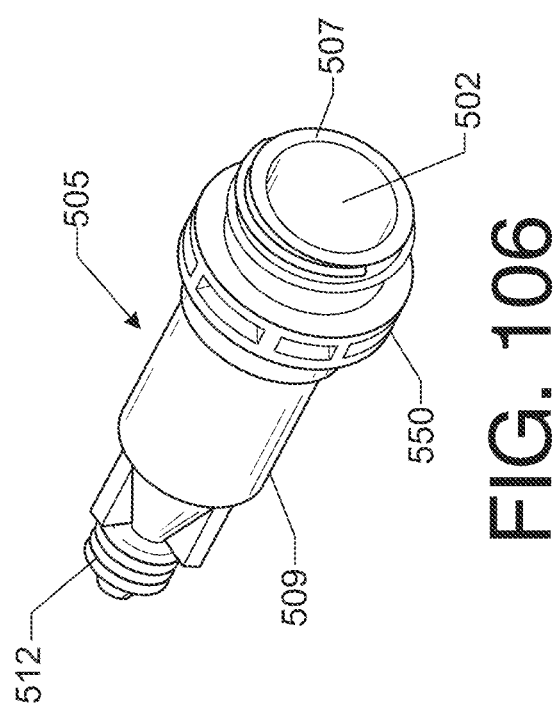
Figure 110:
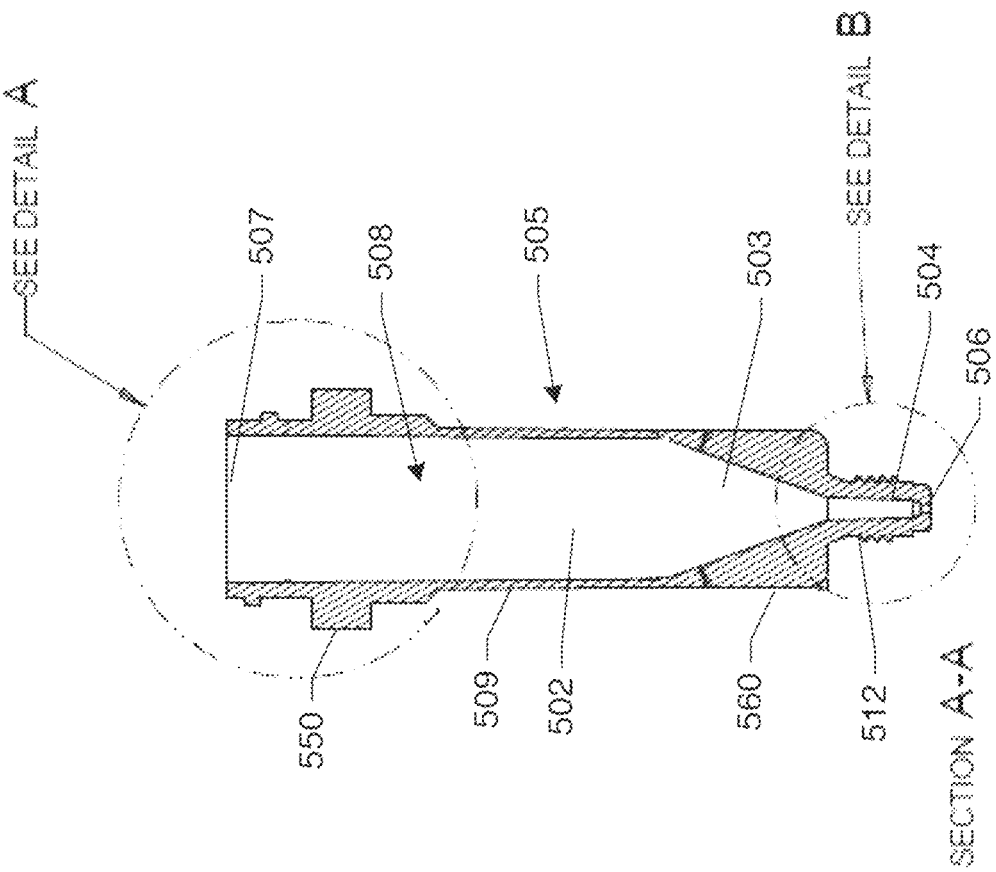
Figure 109:
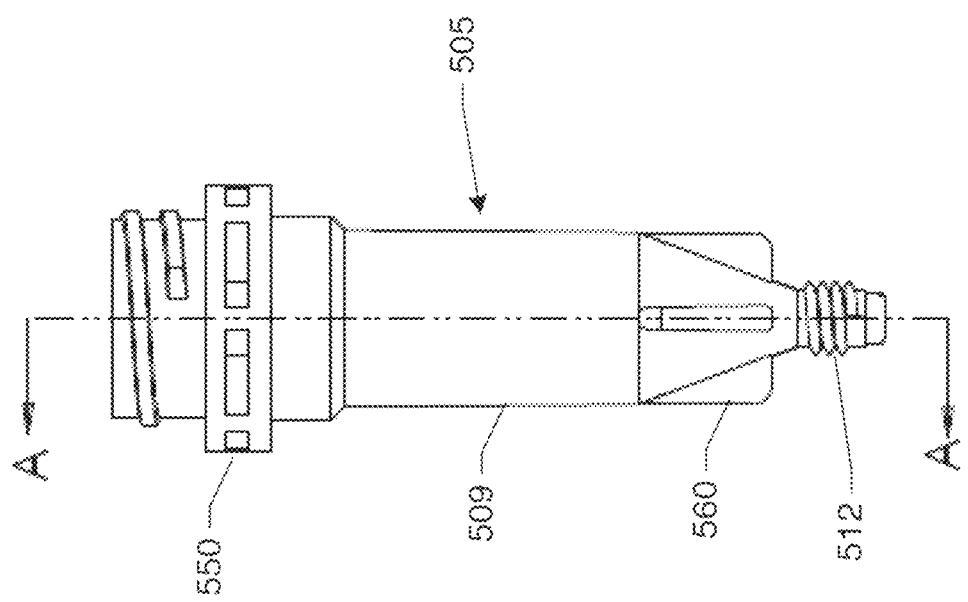
Figure 112:
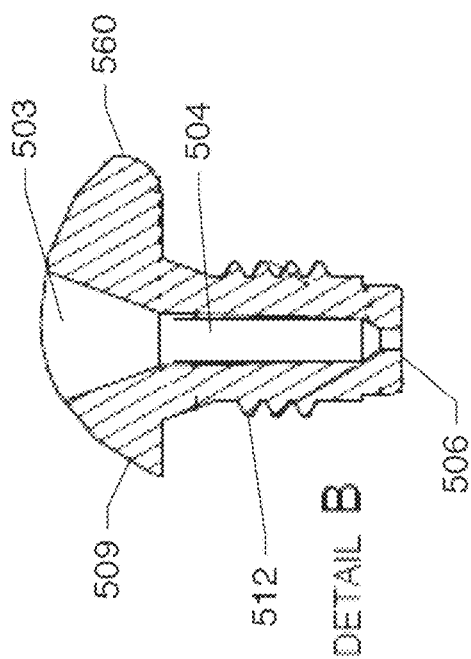
Figure 111:
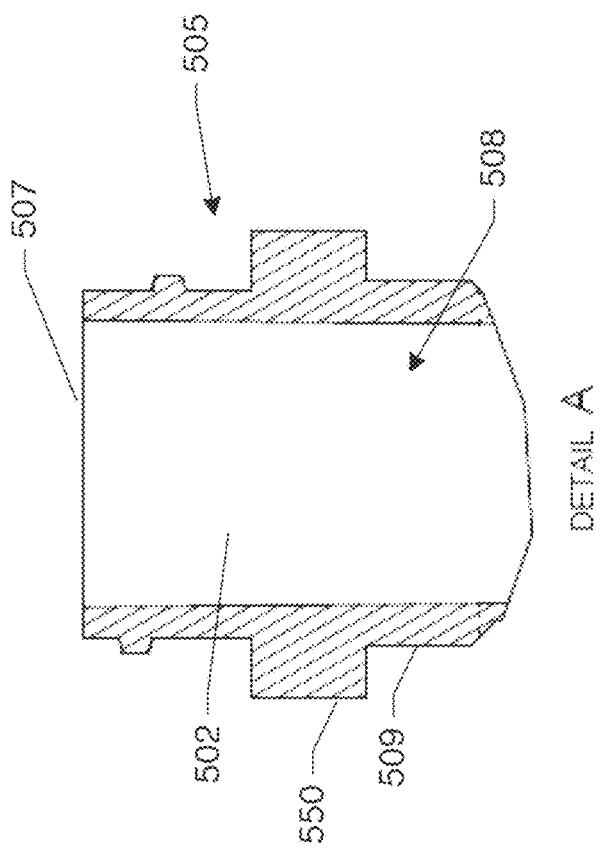
Figure 114:
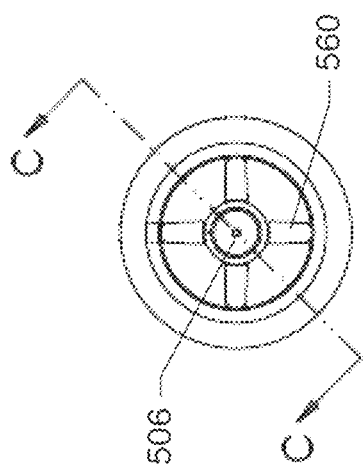
Figure 113:
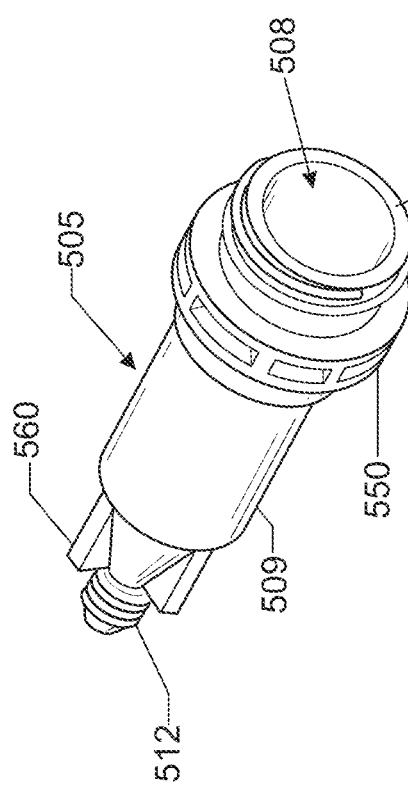
Figure 115:
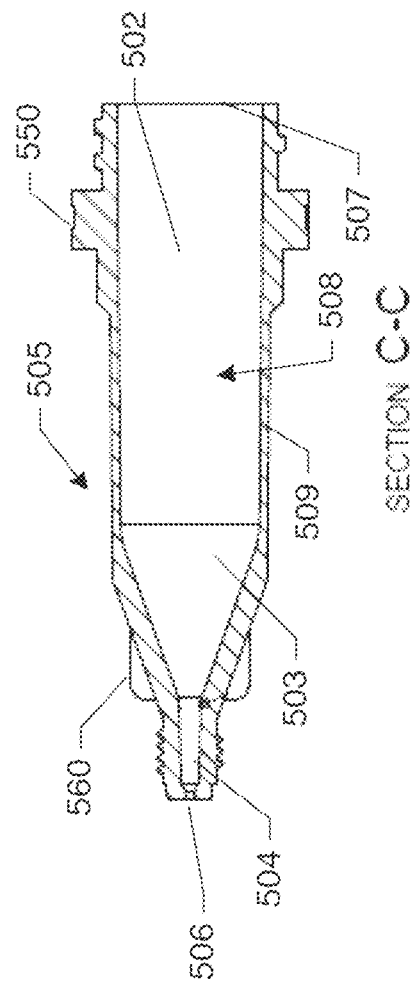
Figure 121:
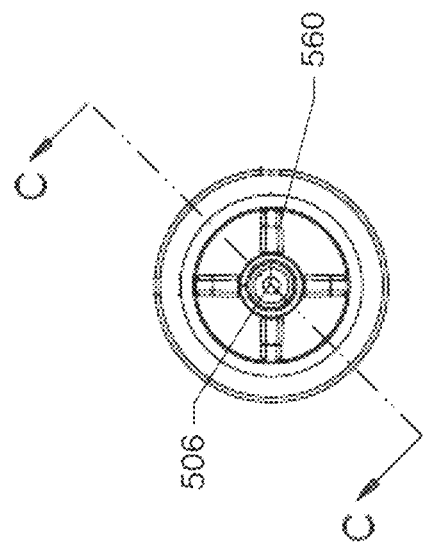
Figure 122:
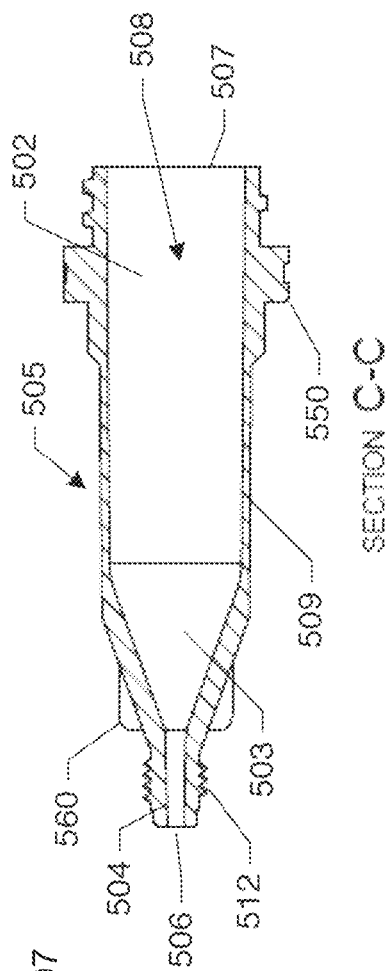
Figure 120:
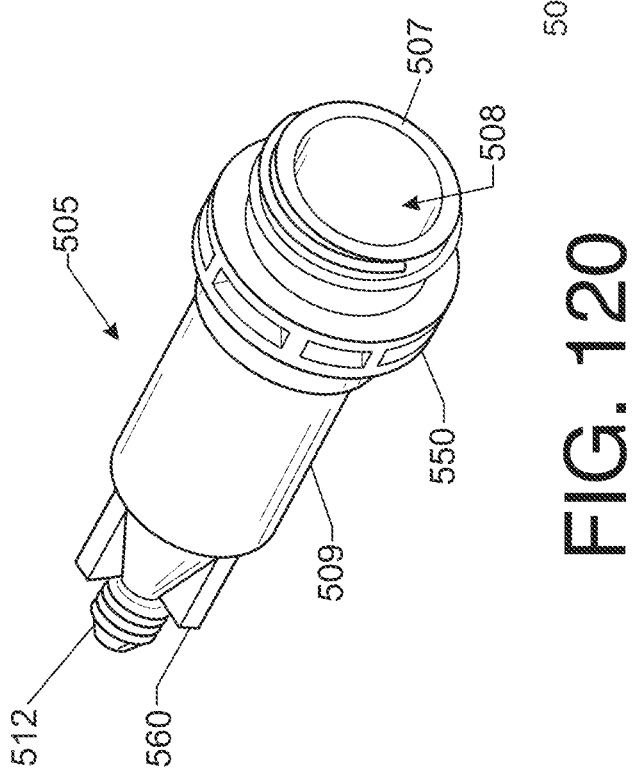
Figure 129:
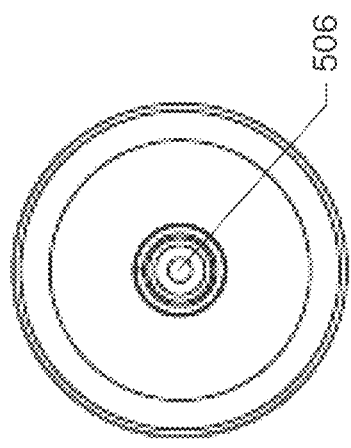
Figure 127:
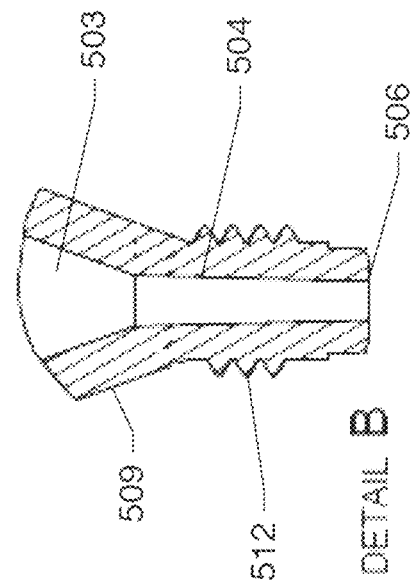
Figure 128:
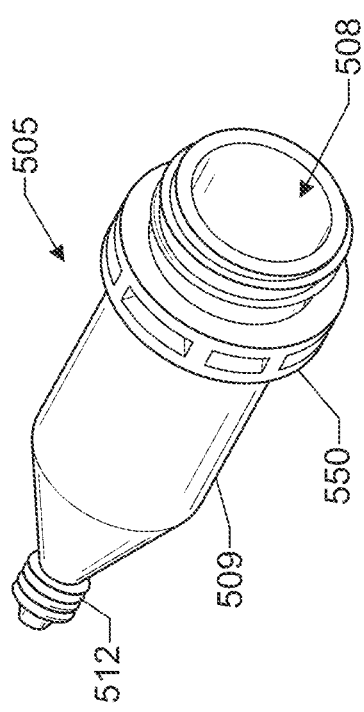
Figure 126:
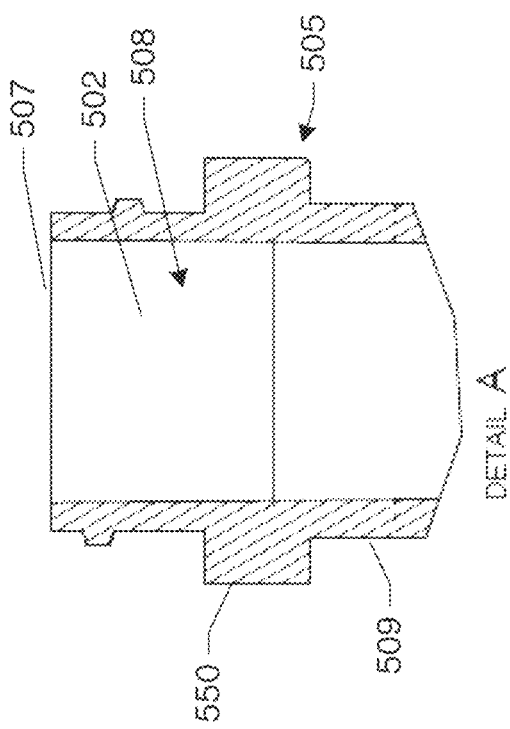
Figures 130, 131, 132:
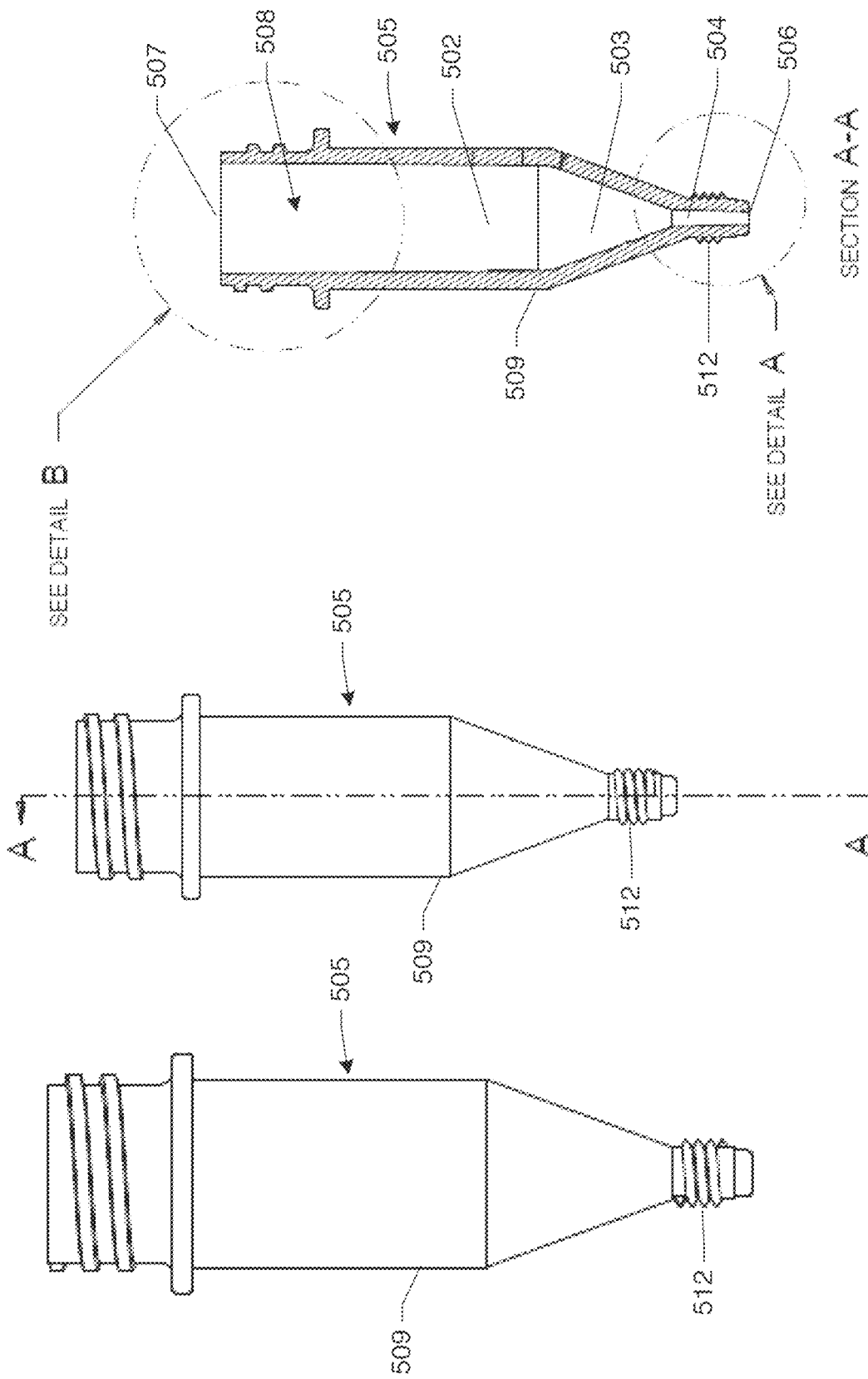
Figure 136:
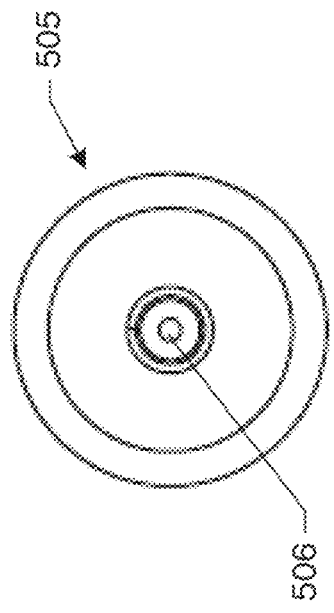
Figure 134:
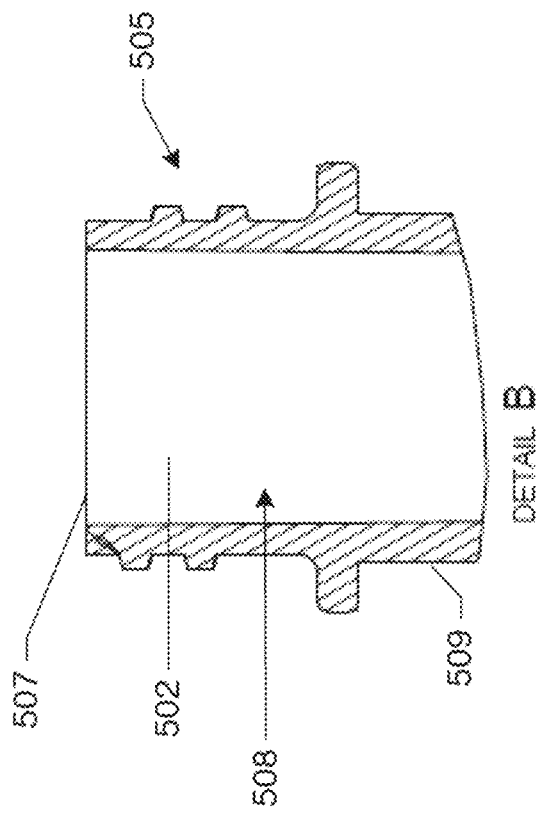
Figure 135:
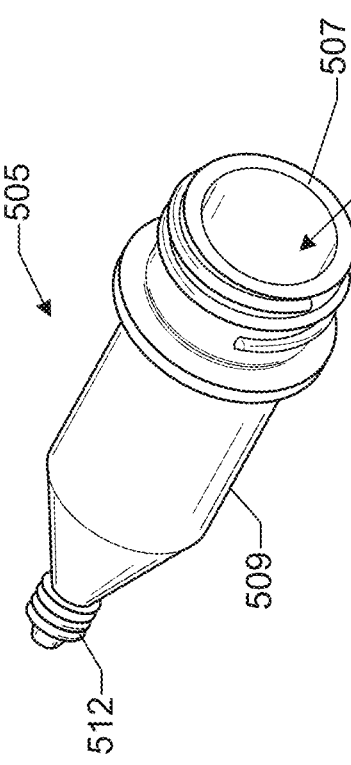
Figure 133:
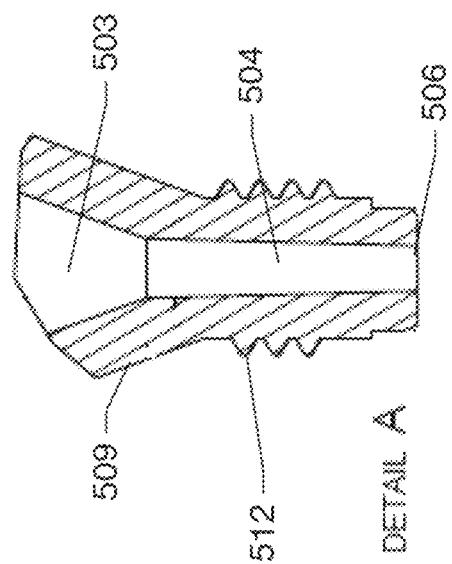
Figure 138:
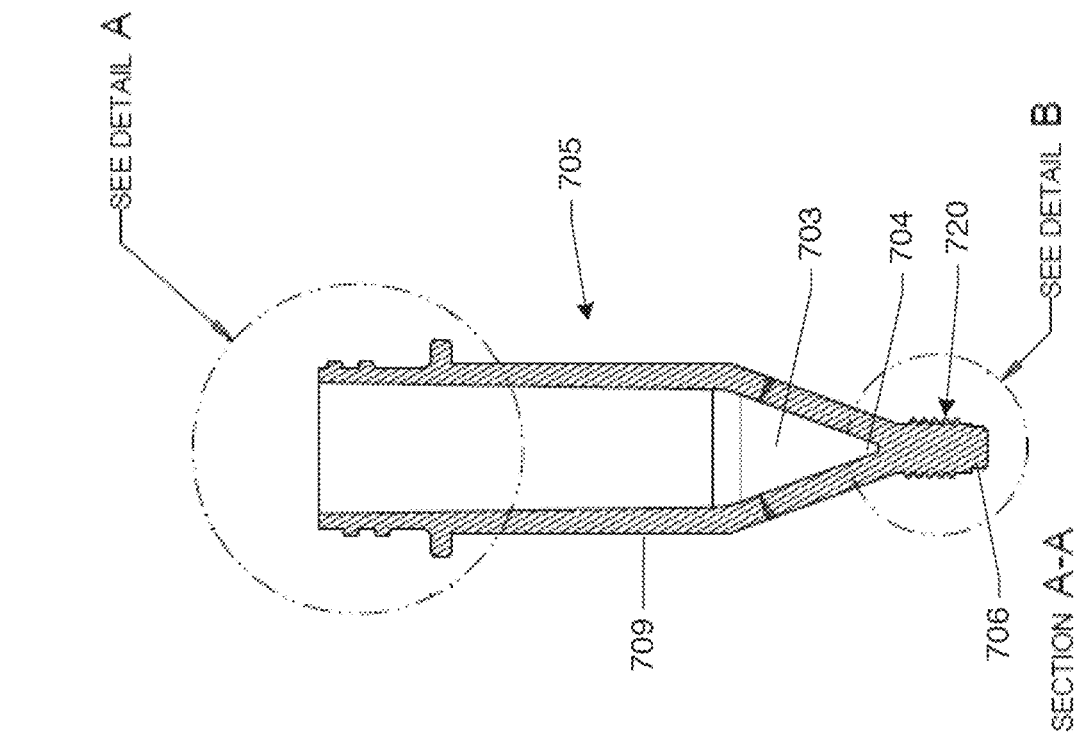
Figure 137:
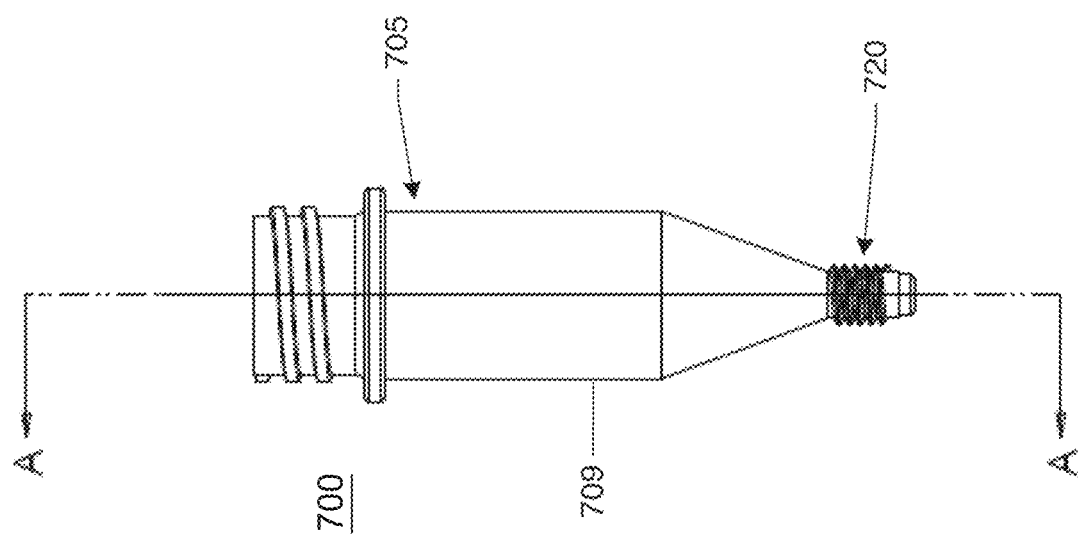
Figure 140:
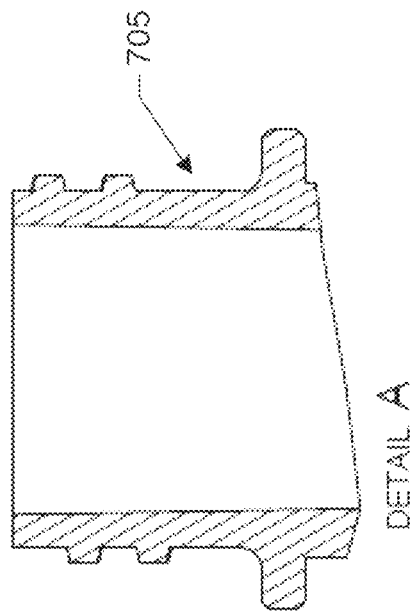
Figure 141:
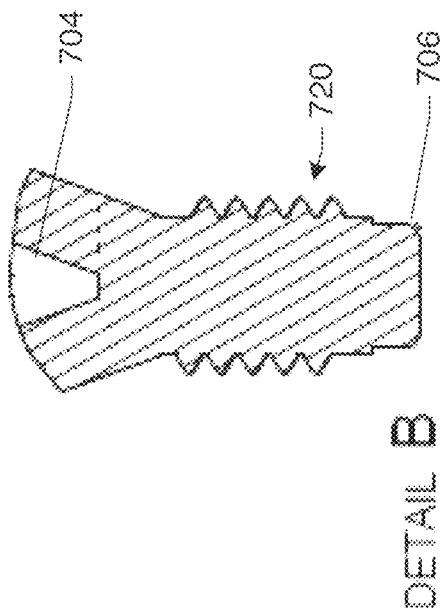
Figure 139:
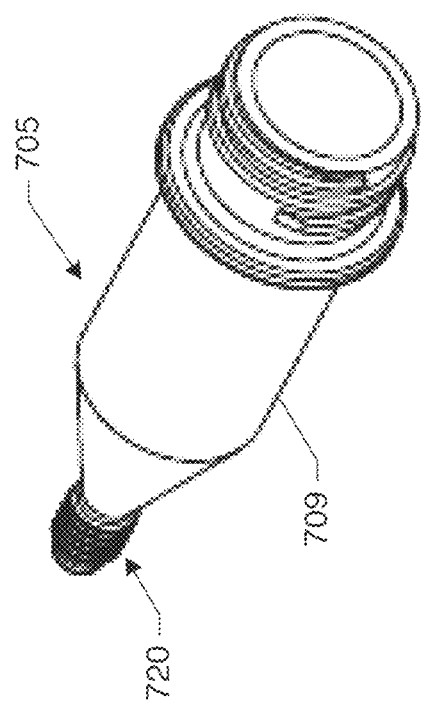
Figure 144:
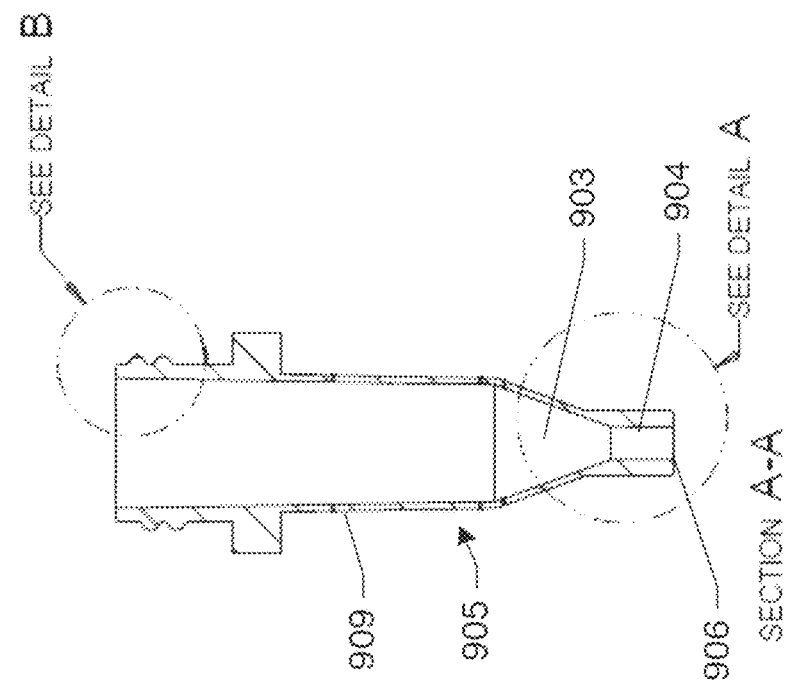
Figure 143:
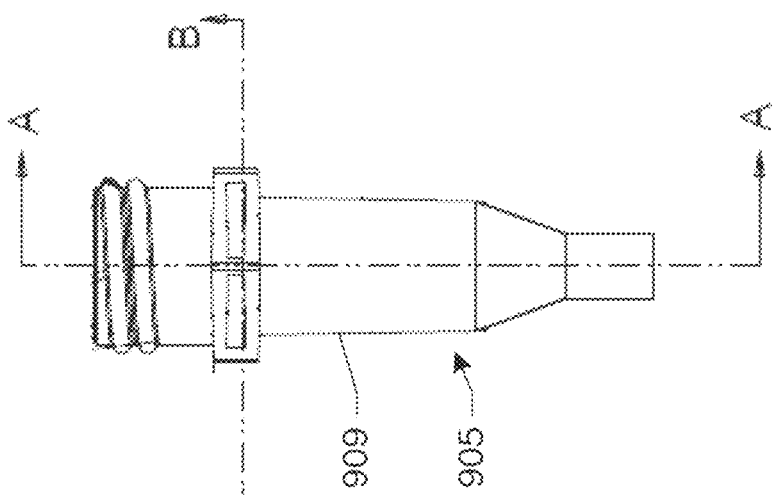
Figure 142:
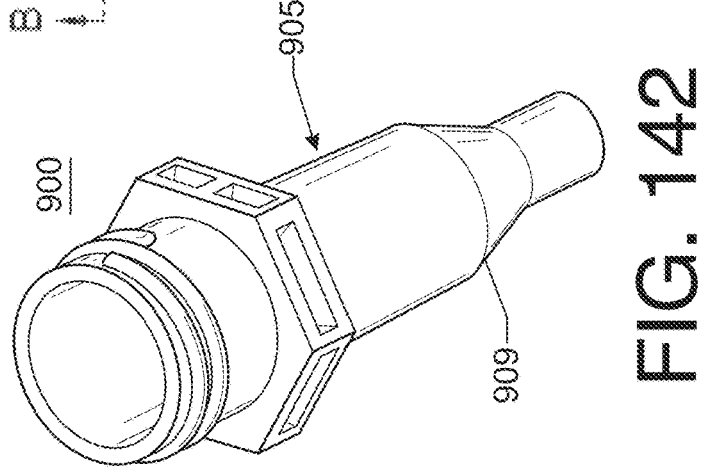
Figure 146:
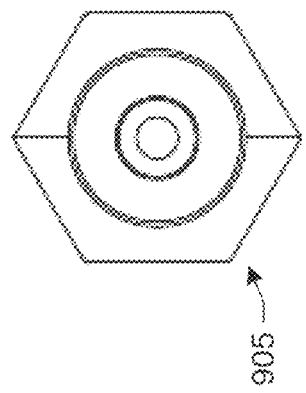
Figure 145:
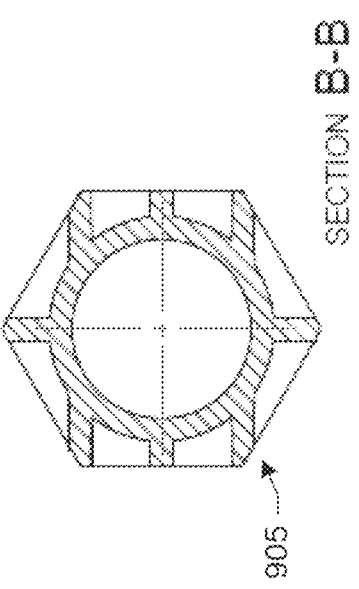

Having thus described the disclosure in general terms, reference will now be made to the accompanying drawings, which are not drawn to scale, and wherein:

FIG. 1 shows an exploded view of a separation container according to some embodiments discussed herein;

FIG. 2 shows a side elevation view of the separation container of FIG. 1;

FIG. 3 shows a cross-sectional view of FIG. 2 taken along Section A-A;

FIG. 4 shows a top plan view of the separation container of FIG. 1;

FIG. 5 shows another side elevation view of the separation container of FIG. 1 showing the plunger in a raised position and the seal intact;

FIG. 6 shows a cross-sectional view of the separation container of FIG. 5;

FIG. 7 shows a detail view of the pellet region and first distal end of the plunger of Detail B in FIG. 5;

FIG. 8 shows a side elevation view of the separation container of FIG. 1 showing the plunger in a depressed position and the seal being opened;

FIG. 9 shows a cross-sectional view of the separation container of FIG. 8;

FIG. 10 shows a top plan view of the separation container of FIG. 8;

FIG. 11 shows another side elevation view of the separation container of FIG. 8;

FIG. 12 shows a cross-sectional view of FIG. 11 taken along Section B-B;

FIG. 13 shows a detail view of the pellet region and first distal end of the plunger of Detail A in FIG. 12;

FIG. 14 shows an exploded view of a separation container according to with some embodiments discussed herein;

FIG. 15 shows a side elevation view of the separation container of FIG. 14 showing the plunger in a raised position and the seal intact;

FIG. 16 shows a cross-sectional view of the separation container of FIG. 15 taken along Section A-A;

FIG. 17 shows a top plan view of the separation container of FIG. 14;

FIG. 18 shows another side elevation view of the separation container of FIG. 14 showing the plunger in a raised position;

FIG. 19 shows a cross-sectional view of the separation container of FIG. 18 taken along Section B-B;

FIG. 20 shows another cross-sectional view of the separation container of FIG. 18 taken along Section B-B;

FIG. 21 shows a detail view of the rheological control member of Detail A in FIG. 20;

FIG. 22 shows a detail view of the pellet region and first distal end of the plunger of Detail B in FIG. 19;

FIG. 23-26 show various views of the barrier of the rheological control member of the separation container of FIG. 14;

FIG. 27-31 show various views of the adaptor of the separation container of FIG. 14;

FIG. 32 shows an exploded view of a separation container according to some embodiments discussed herein;

FIG. 33 shows a side elevation view of the separation container of FIG. 32 showing the plunger in a raised position and the seal intact;

FIG. 34 shows a cross-sectional view of the separation container of FIG. 33 taken along Section A-A;

FIG. 35 shows a top plan view of the separation container of FIG. 32;

FIG. 36 shows another side elevation view of the separation container of FIG. 32 showing the plunger in a raised position;

FIG. 37 shows a cross-sectional view of the separation container of FIG. 36 taken along Section B-B;

FIG. 38 shows a detail view of the pellet region and first distal end of the plunger of Detail B in FIG. 37;

FIG. 39 shows a side elevation view of a body and cap of the separation container of FIG. 32;

FIG. 40 shows a cross-sectional view of the body, cap, and rheological control member of FIG. 39 taken along Section A-A;

FIG. 41 shows a top plan view of the body, cap, and rheological control member of FIG. 40;

FIG. 42 shows a side elevation view of a body and cap of the separation container of FIG. 32;

FIG. 43 shows a cross-sectional view of the body, cap, and rheological control member of FIG. 42 taken along Section B-B;

FIG. 44 shows a detail view of the first end of the body of Detail A in FIG. 43;

FIG. 45 shows a cross-sectional view of the rheological control member of FIG. 32;

FIG. 46 shows a side elevation view of the rheological control member of FIG. 32;

FIG. 47 shows another cross-sectional view of the rheological control member of FIG. 32;

FIG. 48 shows an exploded view of the rheological member of FIG. 32;

FIG. 49 shows a perspective, cross-sectional view of the separation container of FIG. 32;

FIG. 50 shows an exploded view of a separation container according to some embodiments discussed herein;

FIG. 51 shows a side elevation view of the separation container of FIG. 50 showing the plunger in a raised position and the seal intact;

FIG. 52 shows a cross-sectional view of the separation container of FIG. 51 taken along Section A-A;

FIG. 53 shows a top plan view of the separation container of FIG. 50;

FIG. 54 shows another side elevation view of the separation container of FIG. 50 showing the plunger in a raised position;

FIG. 55 shows a cross-sectional view of the separation container of FIG. 54 taken along Section B-B;

FIG. 56 shows a detail view of the pellet region and first distal end of the plunger of Detail B in FIG. 55;

FIG. 57-67 show various views of a plunger 110 according to some embodiments discussed herein, including a perspective view (FIG. 57); side views (FIGS. 58, 64); detail views (FIGS. 59-60, 63, 66-67); a top view (FIG. 61); a bottom view (FIG. 62); and a downward cross-sectional view (FIG. 65);

FIG. 68 shows an exploded view of a separation container according to some embodiments discussed herein;

FIG. 69 shows a side elevation view of the separation container of FIG. 68 showing the plunger in a raised position and the seal intact;

FIG. 70 shows a cross-sectional view of the separation container of FIG. 69 taken along Section A-A;

FIG. 71 shows a top plan view of the separation container of FIG. 68;

FIG. 72 shows a detail view of the pellet region and first distal end of the plunger of Detail A of FIG. 70;

FIG. 73 shows a side elevation view of the separation container of FIG. 68 showing the plunger in a depressed position and the seal being opened;

FIG. 74 shows a cross-sectional view of the separation container of FIG. 73 taken along Section A-A;

FIG. 75 shows a top plan view of the separation container of FIG. 73;

FIG. 76 shows a detail view of the pellet region and first distal end of the plunger of Detail B in FIG. 74;

FIG. 77-85 show various views of a plunger 115 according to some embodiments discussed herein, including a perspective view (FIG. 77); side views (FIGS. 78, 81); detail views (FIGS. 79-80, 83); a top view (FIG. 85); a bottom view (FIG. 84); and a downward cross-sectional view (FIG. 82);

FIGS. 86-89 show various views of the flexible sealing member of the separation container of FIGS. 1, 14, 32, 50, and 68;

FIG. 90 shows an exploded view of a separation container and centrifuge cup according to some embodiments discussed herein;

FIG. 91 shows a side elevation view of the body of the separation container of FIG. 90;

FIG. 92 shows a cross-sectional view of the body of FIG. 91 taken along Section A-A;

FIG. 93 shows a cross-sectional view of the body of FIG. 91 taken along Section D-D;

FIG. 94 shows a detail view of the second end of the body and cap threads of Detail B of FIG. 92;

FIG. 95 shows a detail view of the pellet region of the body of Detail A of FIG. 92;

FIG. 96 shows a perspective view of a body of a separation container according to some embodiments discussed herein;

FIG. 97 shows a bottom plan view of the body of FIG. 96;

FIG. 98 shows a cross-sectional view of the body of FIG. 97 taken along Section E-E;

FIG. 99 shows a side elevation view of the separation container and centrifuge cup of FIG. 90;

FIG. 100 shows a cross-sectional view of the separation container and centrifuge cup of FIG. 99 taken along Section A-A;

FIG. 101 shows a side elevation view of a body of a separation container according to some embodiments discussed herein;

FIG. 102 shows a cross-sectional view of the body of FIG. 101 taken along Section A-A;

FIG. 103 shows a detail view of the second end of the body of Detail A of FIG. 102;

FIG. 104 shows a detail view of the first end and pellet region of the body of Detail B of FIG. 102;

FIG. 105 shows a detail view of the wall of the body of Detail C of FIG. 103;

FIG. 106 shows a perspective view of the body of FIG. 101;

FIG. 107 shows a bottom plan view of the body of FIG. 106;

FIG. 108 shows a cross-sectional view of the body of FIG. 107 taken along Section C-C;

FIG. 109 shows a side elevation view of a body of a separation container according to some embodiments discussed herein;

FIG. 110 shows a cross-sectional view of the body of FIG. 109 taken along Section A-A;

FIG. 111 shows a detail view of the second end of the body of Detail A of FIG. 110;

FIG. 112 shows a detail view of the first end and pellet region of the body of Detail B of FIG. 110;

FIG. 113 shows a perspective view of the body of FIG. 109;

FIG. 114 shows a bottom plan view of the body of FIG. 113;

FIG. 115 shows a cross-sectional view of the body of FIG. 114 taken along Section C-C;

FIG. 116 shows a side elevation view oft a body of a separation container according to some embodiments discussed herein;

FIG. 117 shows a cross-sectional view of the body of FIG. 116 taken along Section A-A;

FIG. 118 shows a detail view of the second end of the body of Detail A of FIG. 117;

FIG. 119 shows a detail view of the first end and pellet region of the body of Detail B of FIG. 117;

FIG. 120 shows a perspective view of a body of a separation container according to some embodiments discussed herein;

FIG. 121 shows a bottom plan view of the body of FIG. 120;

FIG. 122 shows a cross-sectional view of the body of FIG. 121 taken along Section C-C;

FIG. 123 shows a side elevation view of a body of a separation container according to some embodiments discussed herein;

FIG. 124 shows another side elevation view of the body of FIG. 124;

FIG. 125 shows a cross-sectional view of the body of FIG. 124 taken along Section A-A;

FIG. 126 shows a detail view of the second end of the body of Detail A of FIG. 125;

FIG. 127 shows a detail view of the first end and pellet region of the body of Detail B of FIG. 125;

FIG. 128 shows a perspective view of the body of FIG. 123;

FIG. 129 shows a bottom plan view of the body of FIG. 123;

FIG. 130 shows a side elevation view of a body of a separation container according to some embodiments discussed herein;

FIG. 131 shows another side elevation view of the body of FIG. 130;

FIG. 132 shows a cross-sectional view of the body of FIG. 131 taken along Section A-A;

FIG. 133 shows a detail view of the first end and pellet region of the body of Detail A of FIG. 132;

FIG. 134 shows a detail view of the second end of the body of Detail B of FIG. 132;

FIG. 135 shows a perspective view of the body of FIG. 130;

FIG. 136 shows a bottom plan view of the body of FIG. 130;

FIG. 137 shows a side elevation view of a body of a separation container according to some embodiments discussed herein;

FIG. 138 shows a cross-sectional view of the body of FIG. 137 taken along Section A-A;

FIG. 139 shows a perspective view of the body of FIG. 137;

FIG. 140 shows a detail view of the second end of the body of Detail A of FIG. 138;

FIG. 141 shows a detail view of the first end and pellet region of the body of Detail B of FIG. 138;

FIG. 142 shows a perspective view of a body of a separation container according to some embodiments discussed herein;

FIG. 143 shows a side elevation view of the body of FIG. 142;

FIG. 144 shows a cross-sectional view of the body of FIG. 143 taken along Section A-A;

FIG. 145 shows a cross-sectional view of the body of FIG. 143 taken along Section B-B;

FIG. 146 shows a bottom plan view of the body of FIG. 142

Figure 148:
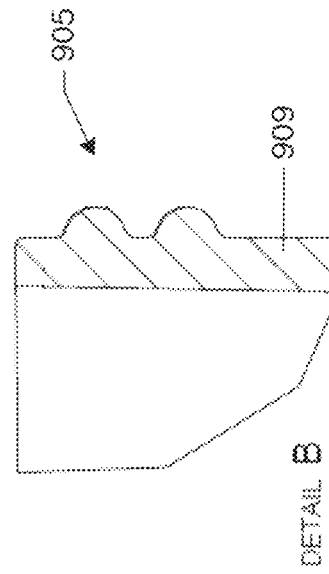
Figure 147:
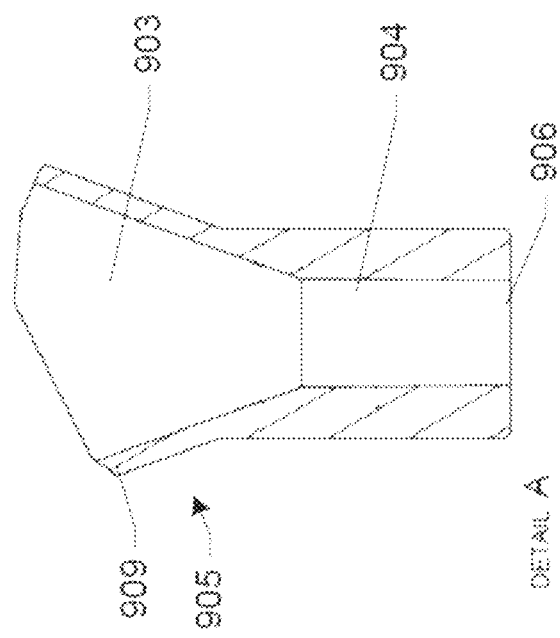
Figure 150:
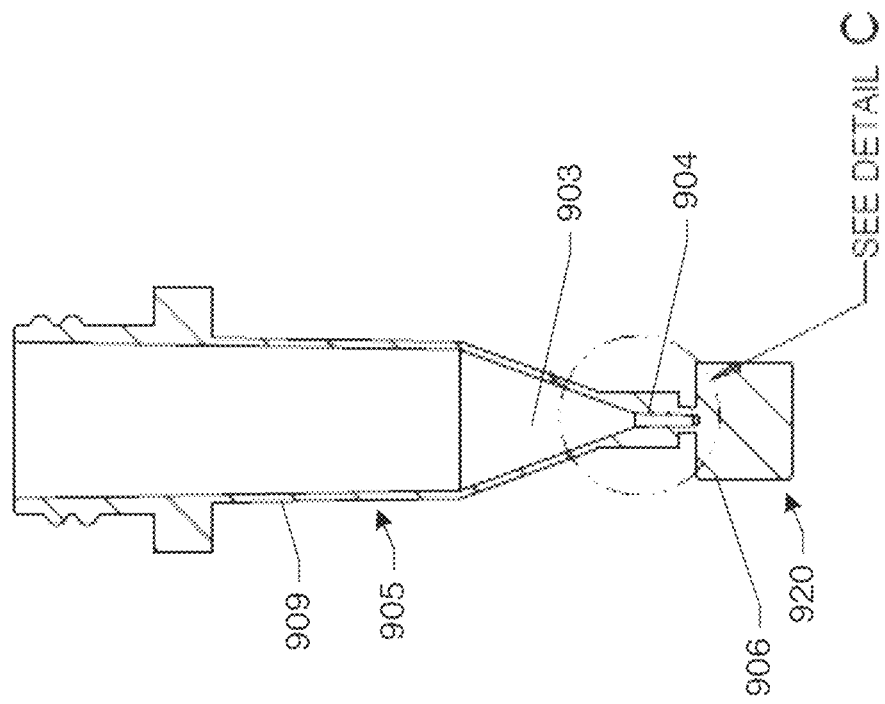
Figure 149:
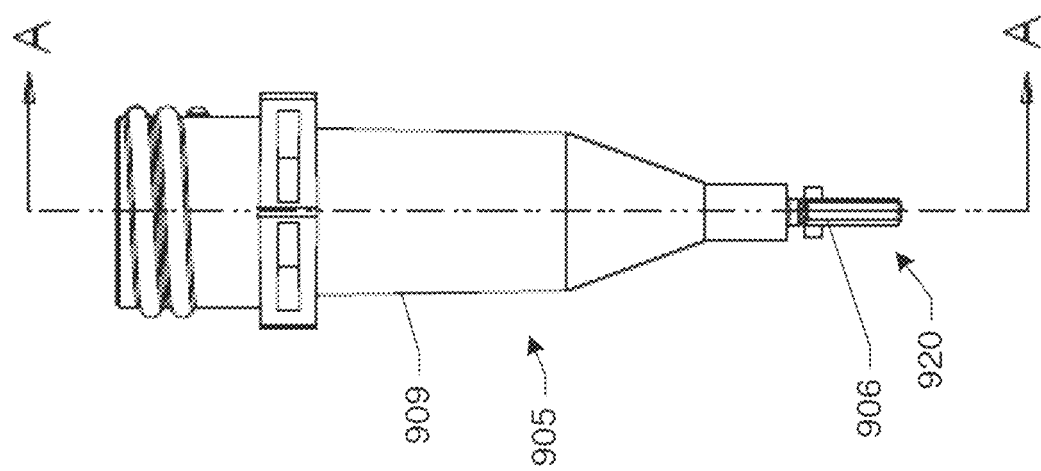
Figure 152:
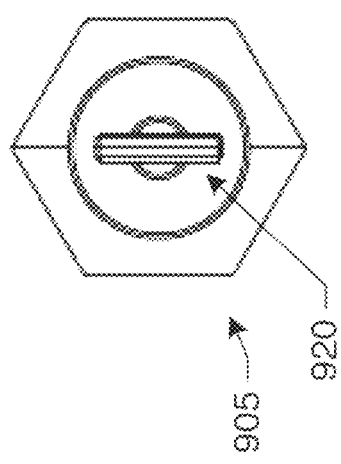
Figure 153:
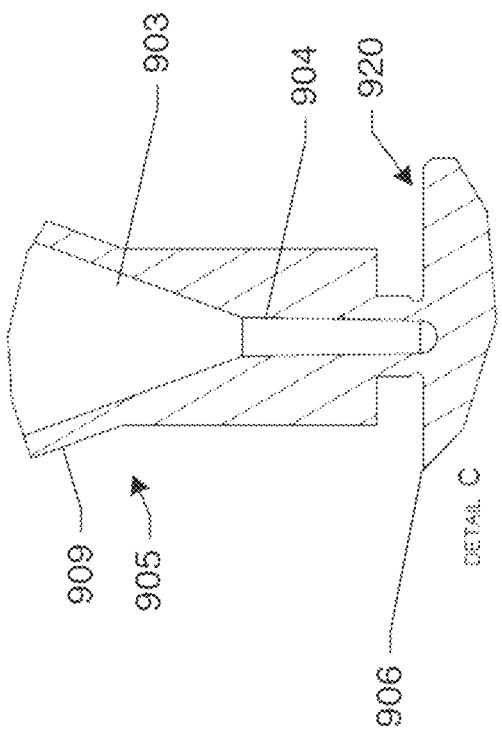
Figure 151:
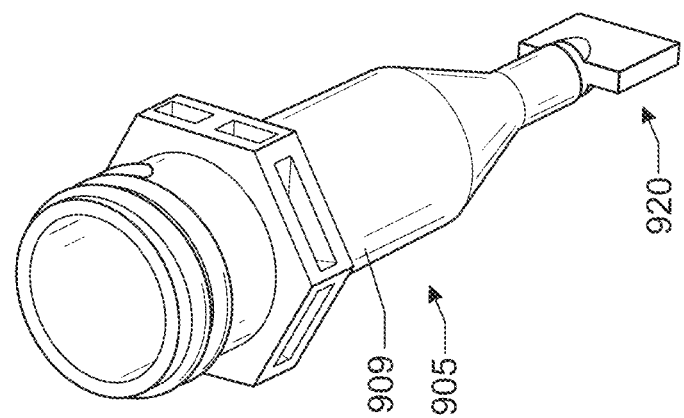
Figure 155:
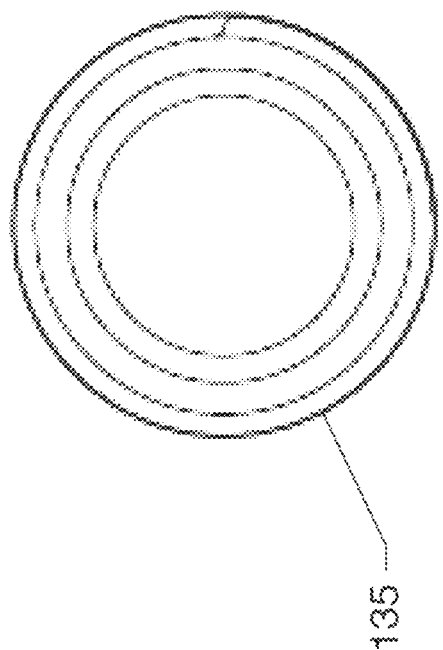
Figure 154:
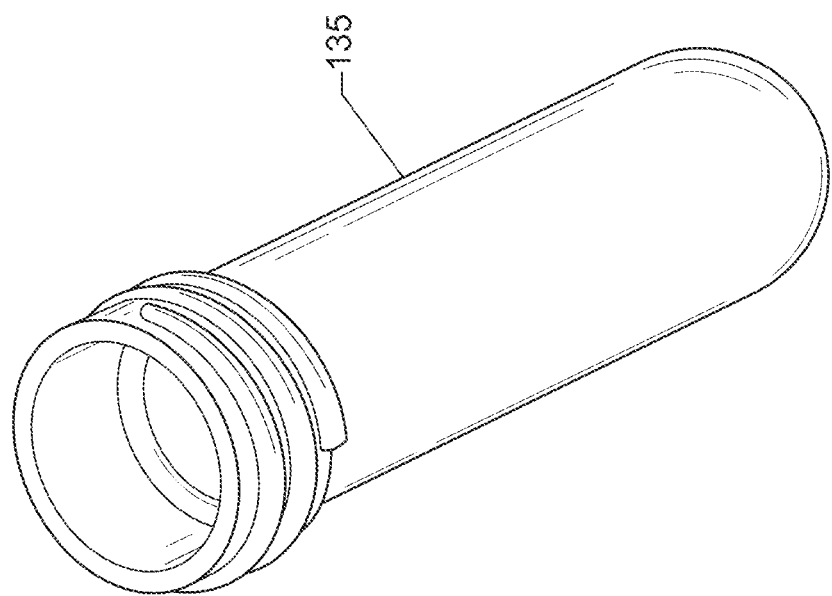
Figure 157:
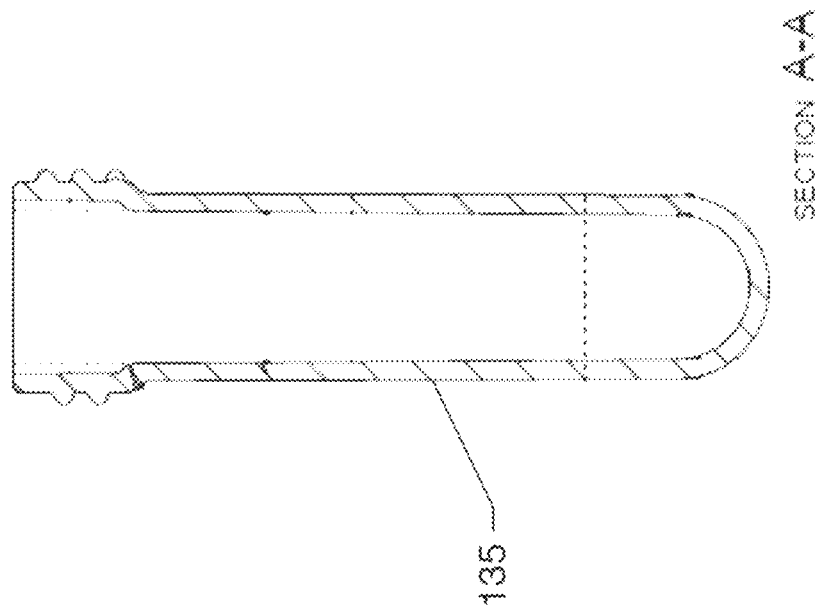
Figure 156:
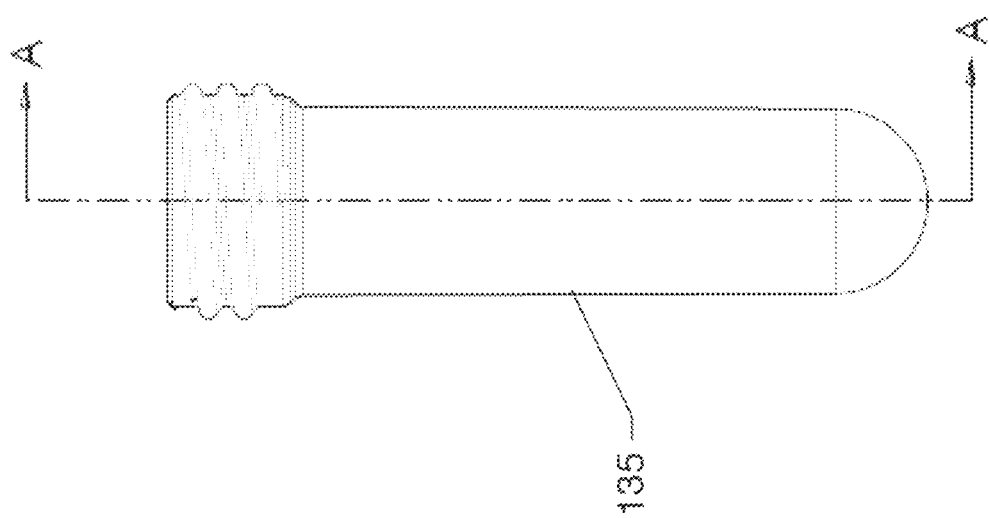
Figure 168:
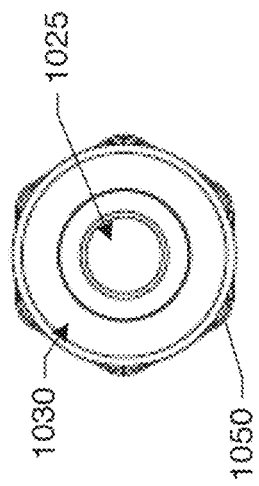
Figure 167:
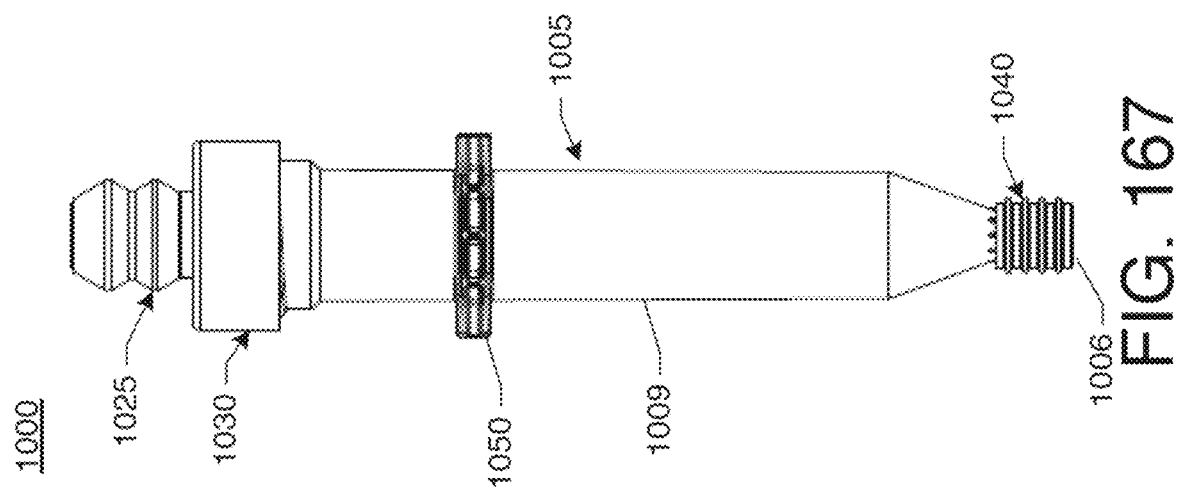
Figure 178:
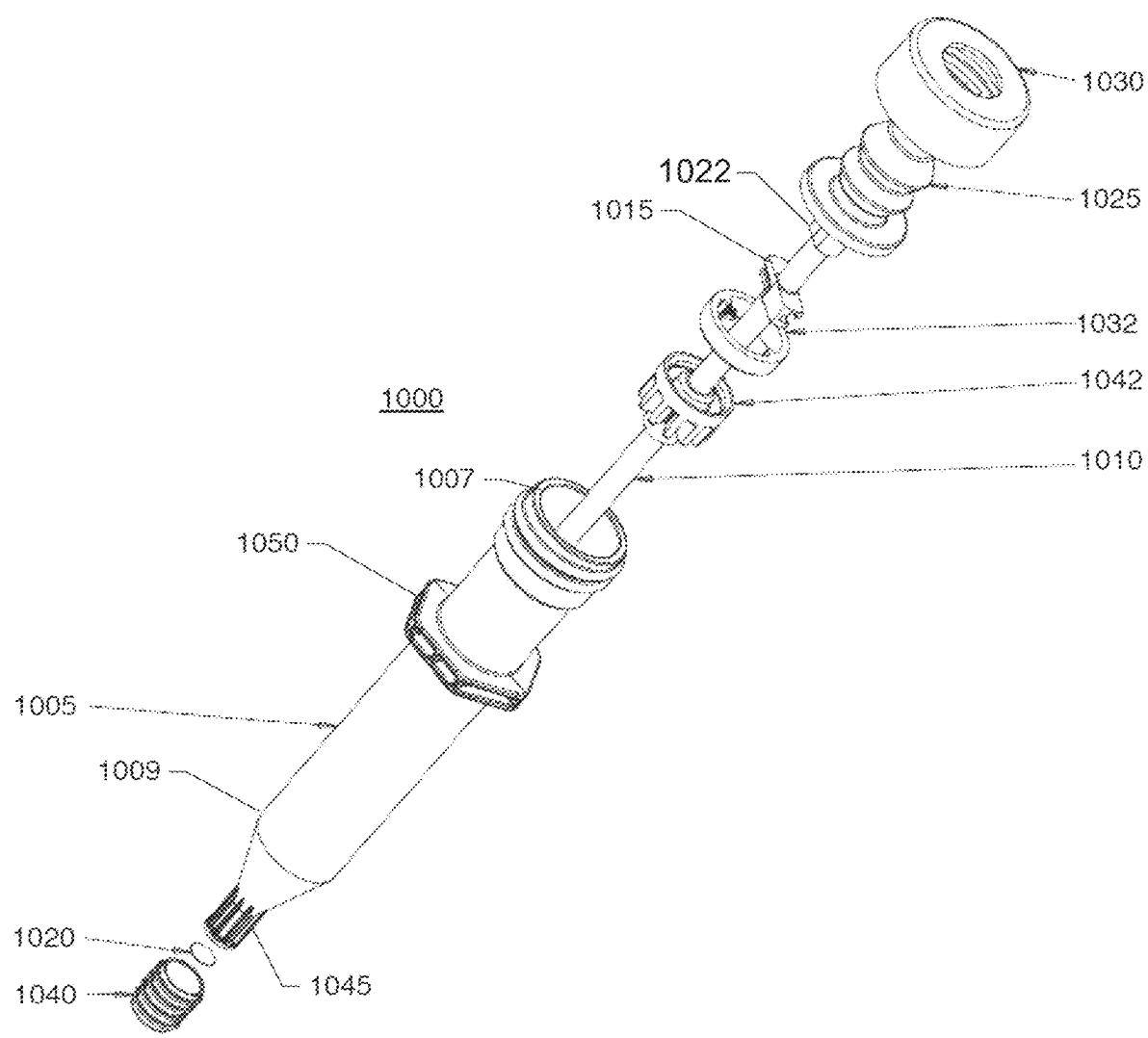
Figure 179:
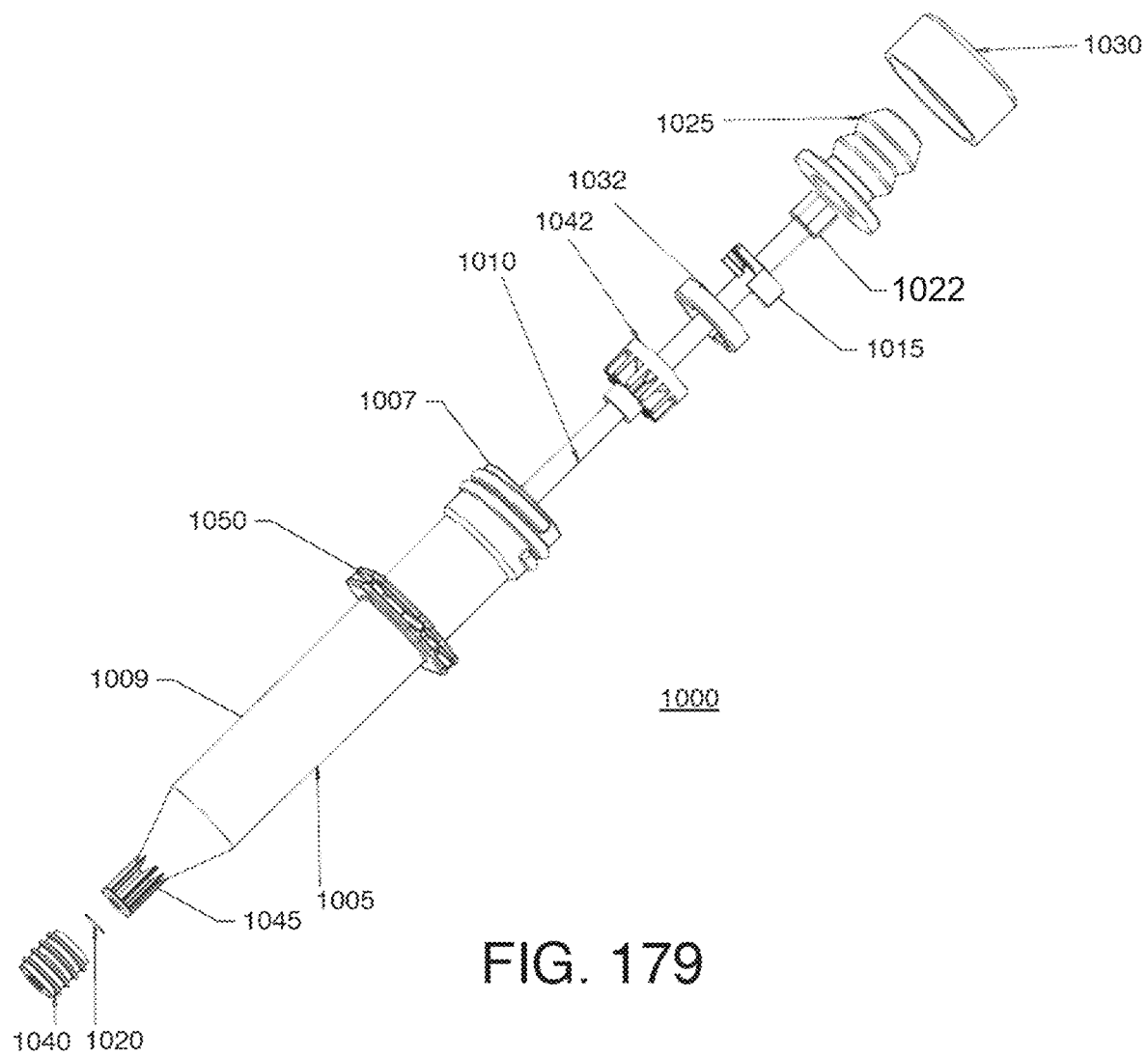
Figure 180:
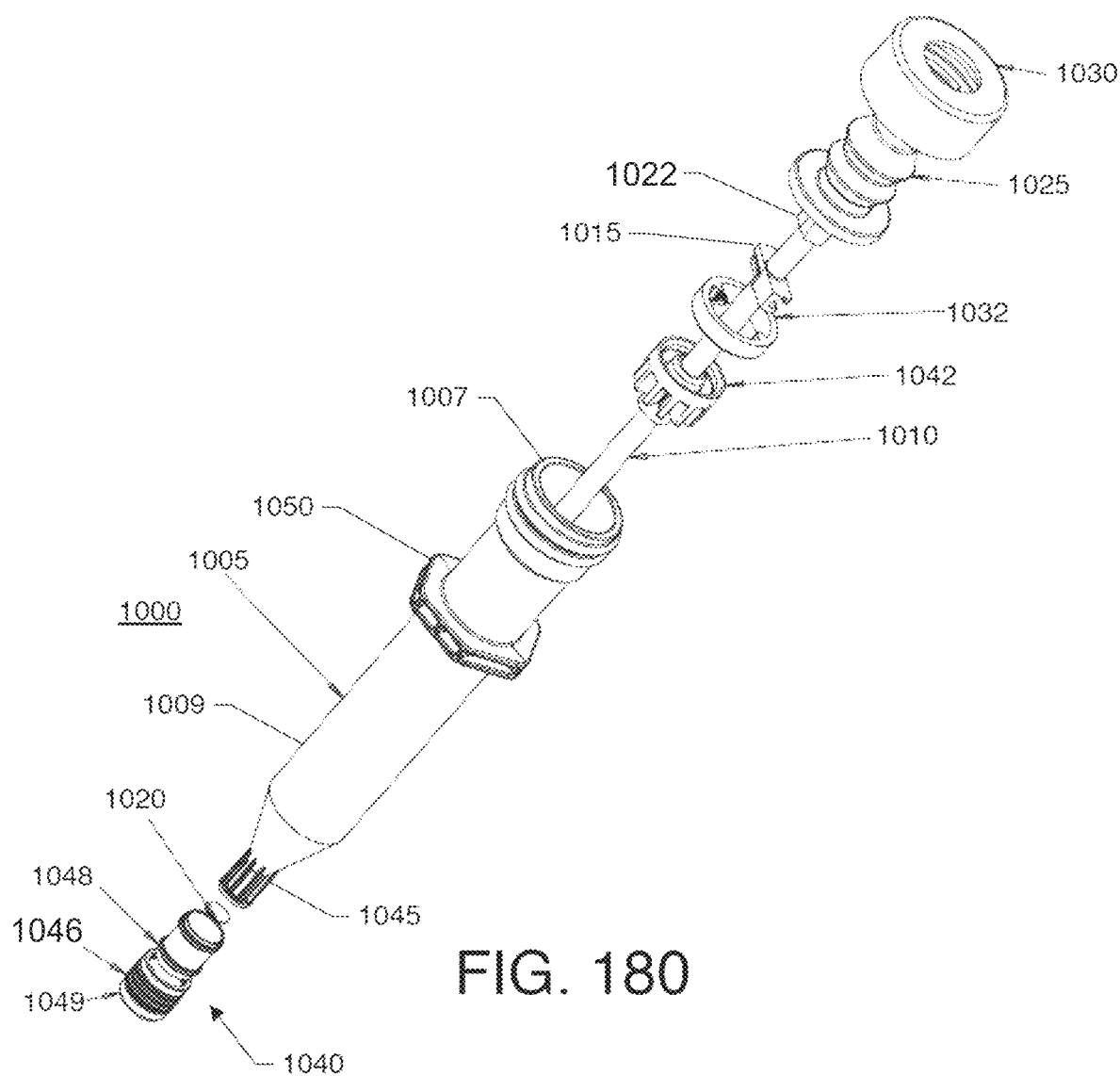
Figure 181:
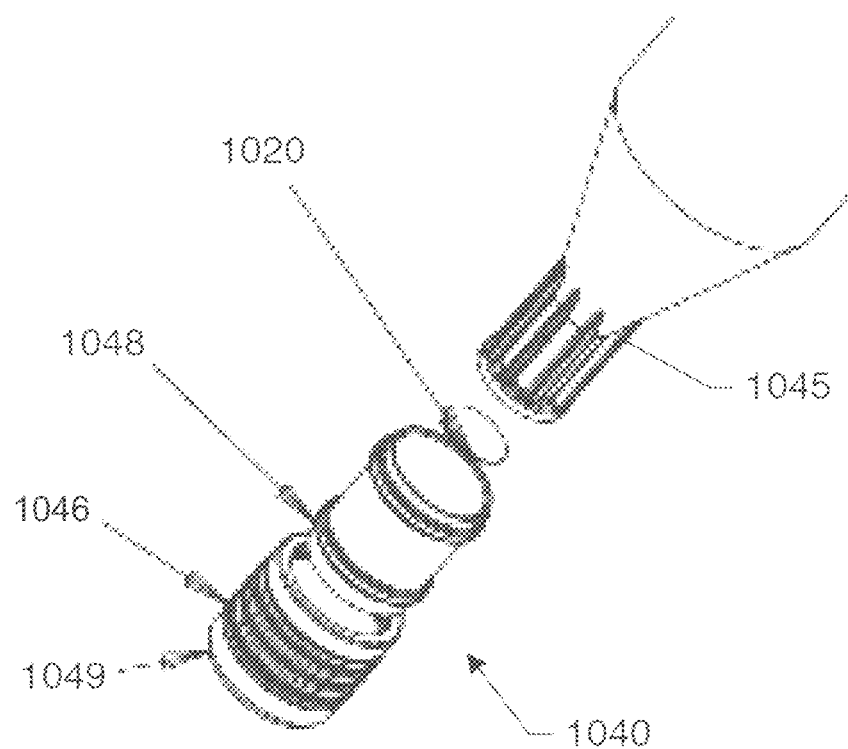
Figure 182:
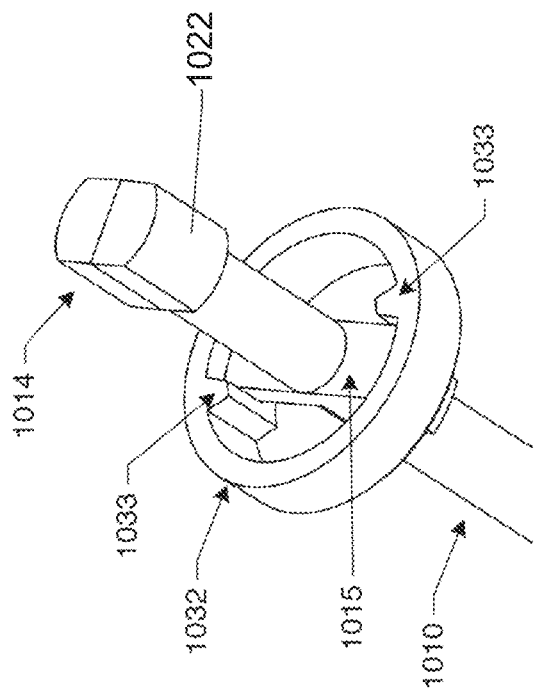
Figure 183:
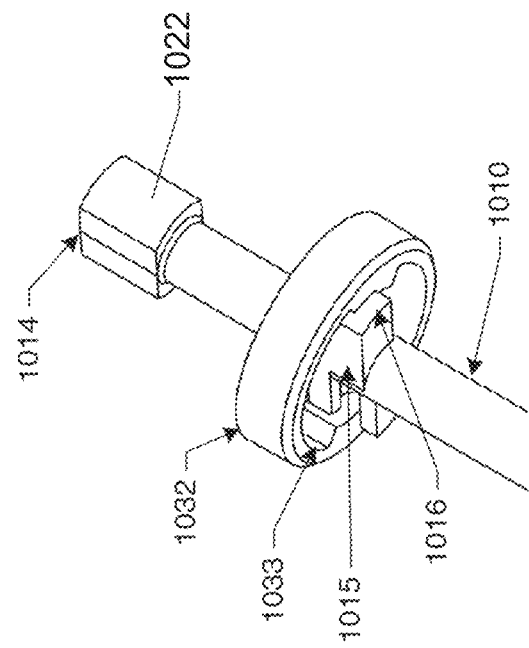
Figures 186, 187:
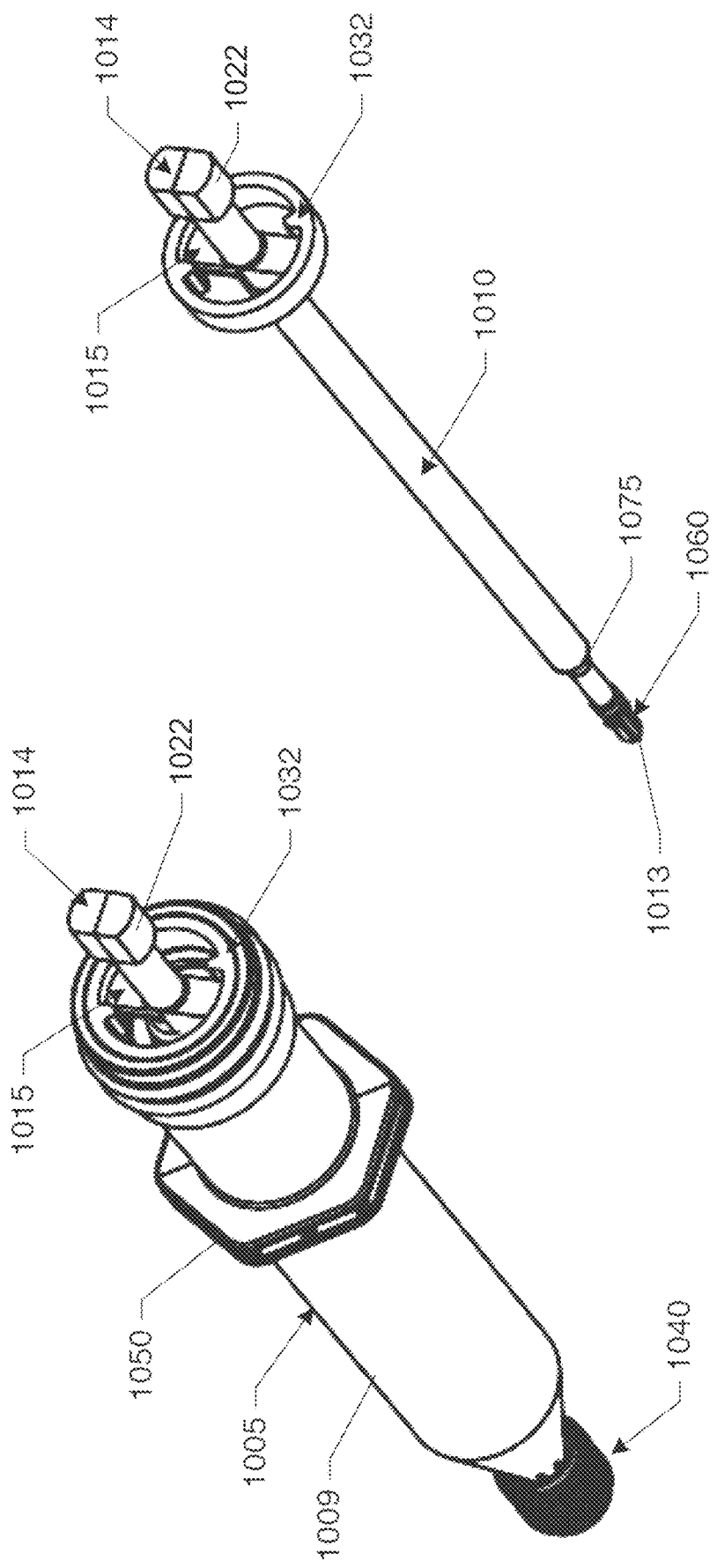
Figures 194, 195:
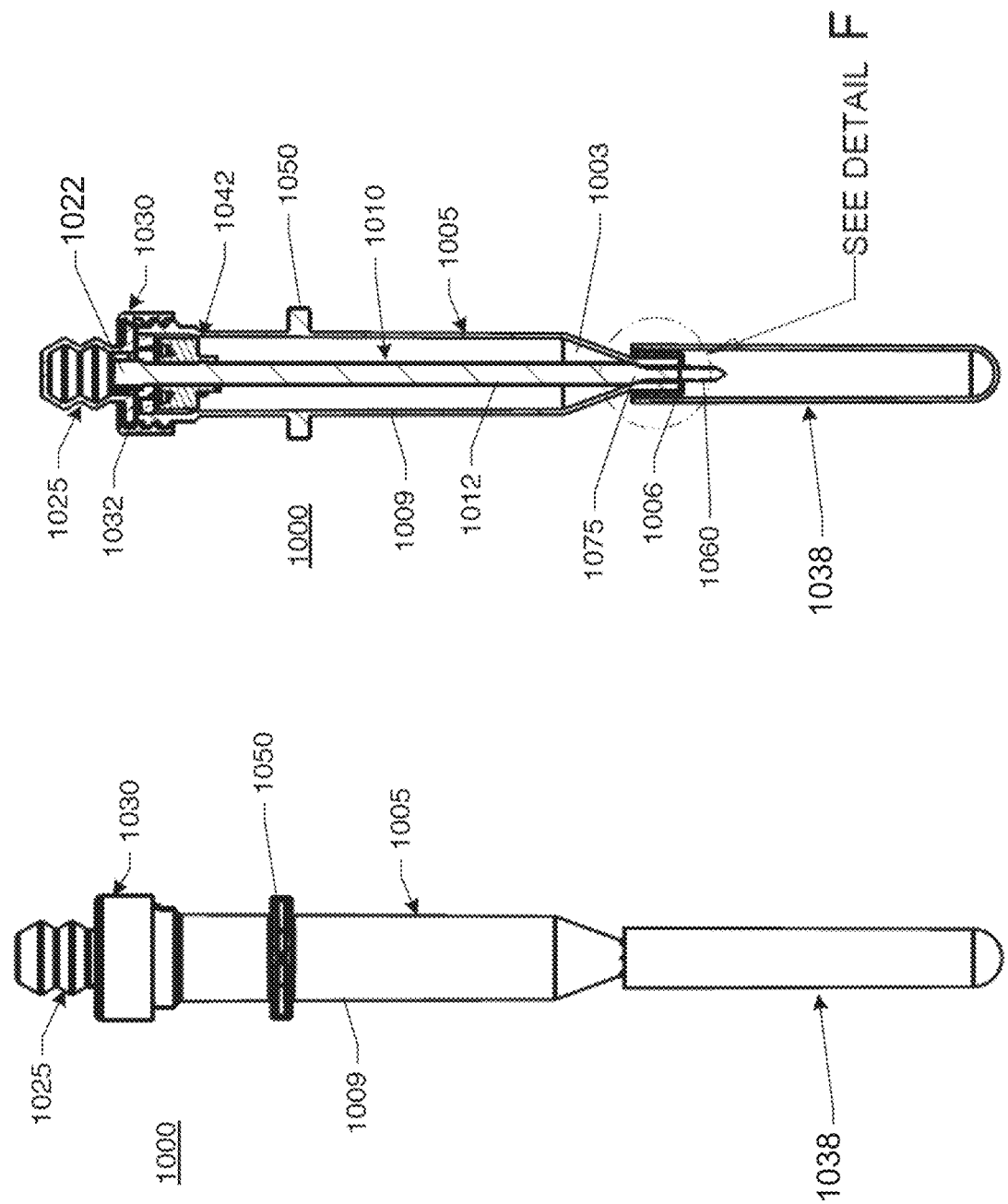
Figure 197:
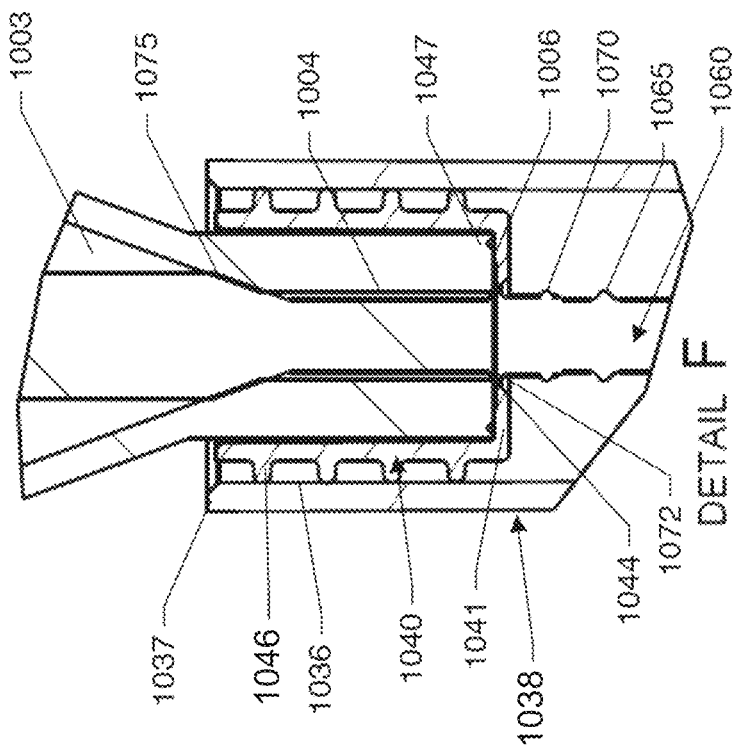
Figure 196:
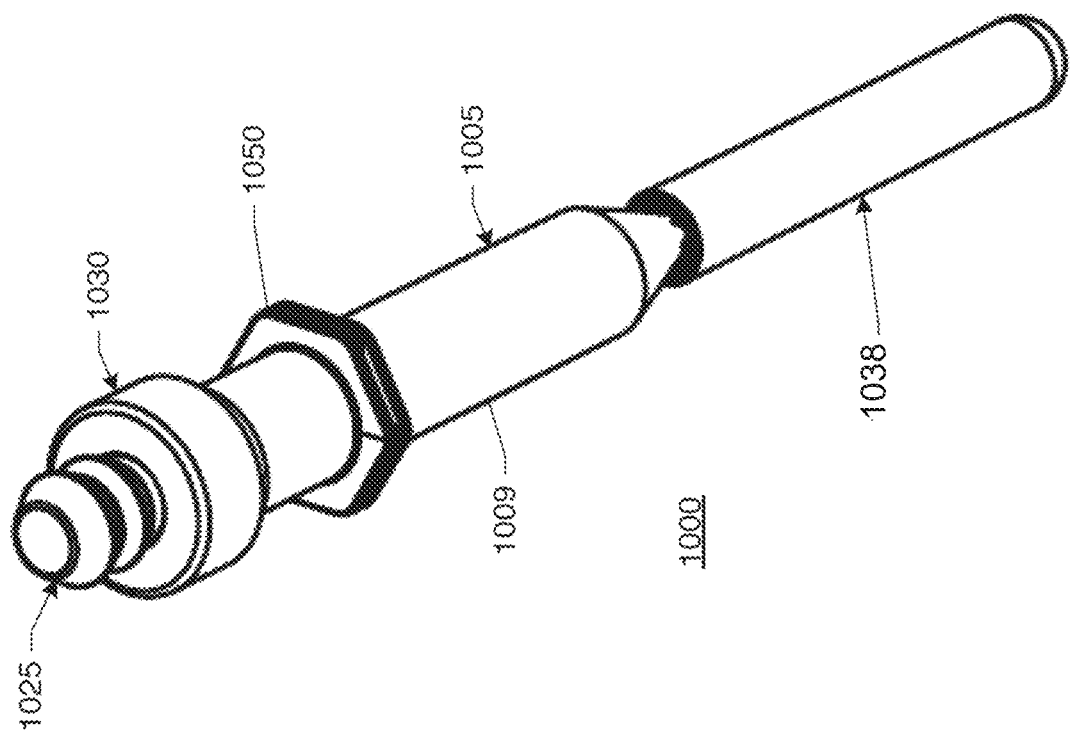
Figure 205:
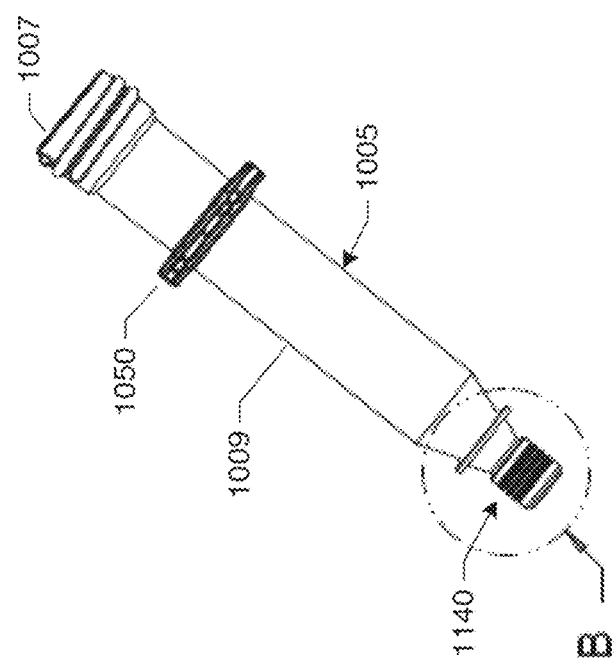
Figure 203:
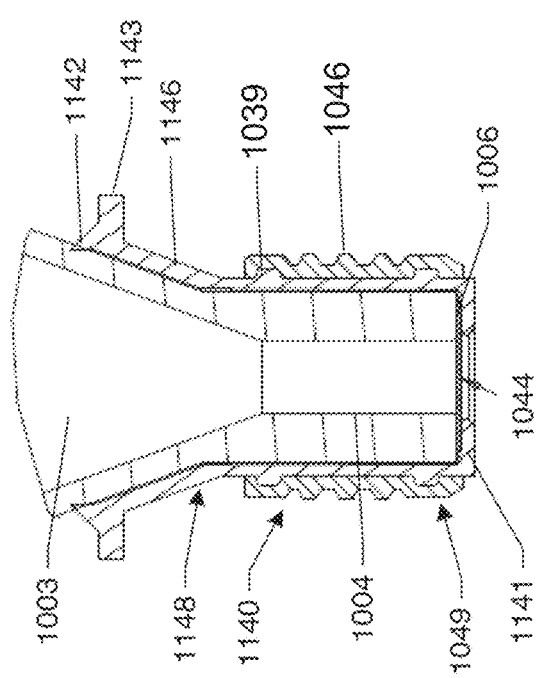
Figure 204:
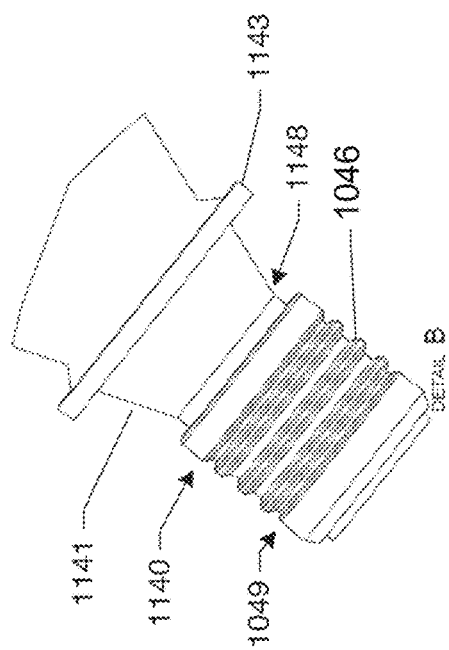
Figures 206, 207, 208:
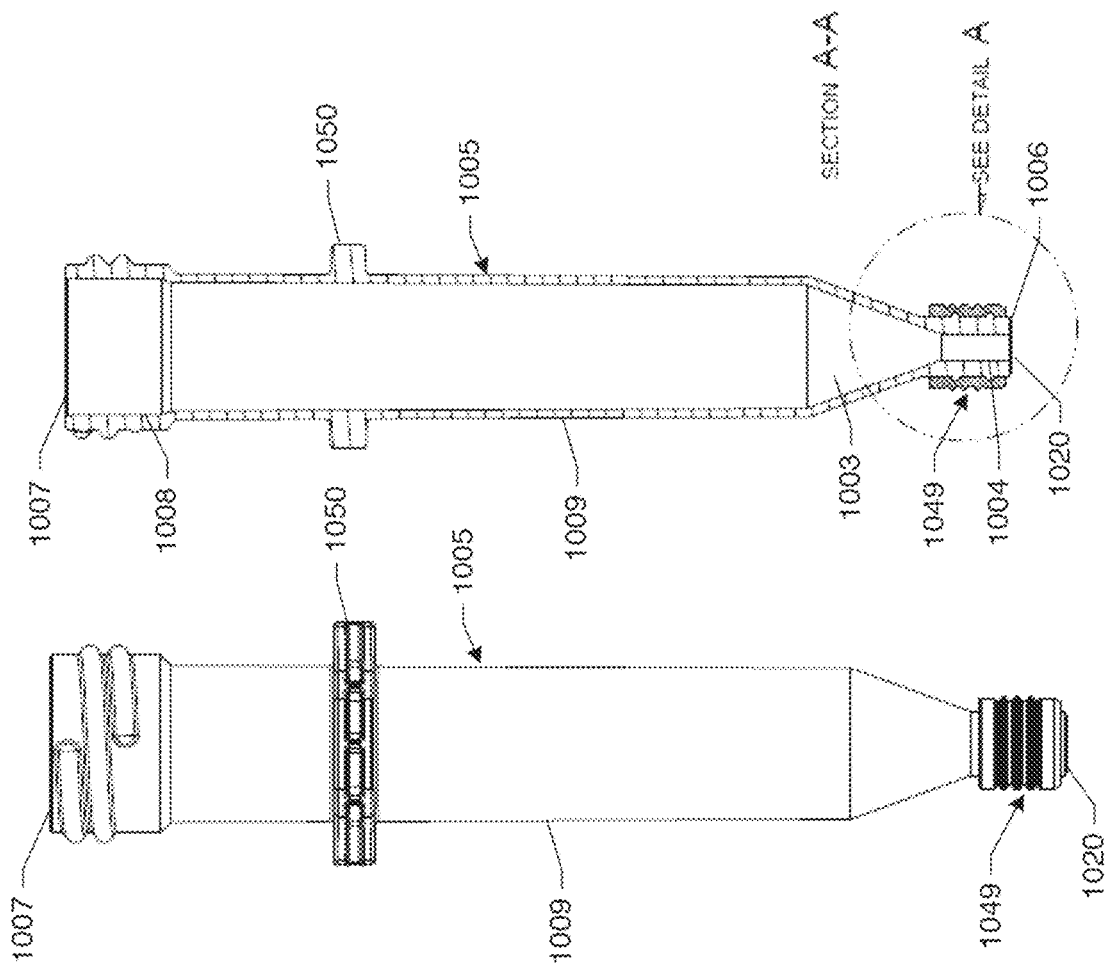
Figure 218:
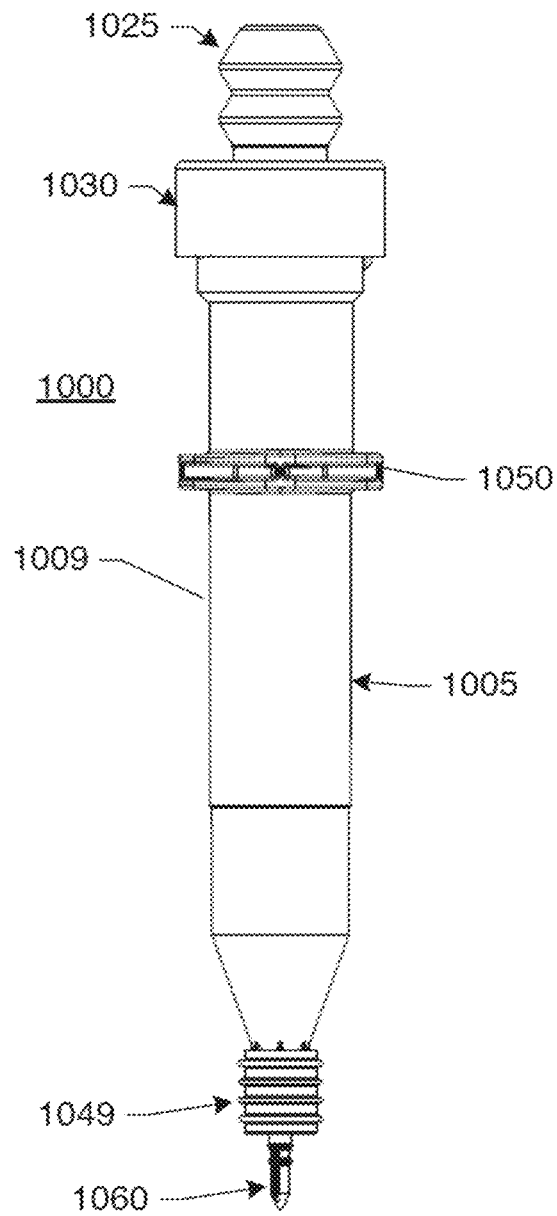
Figure 219:
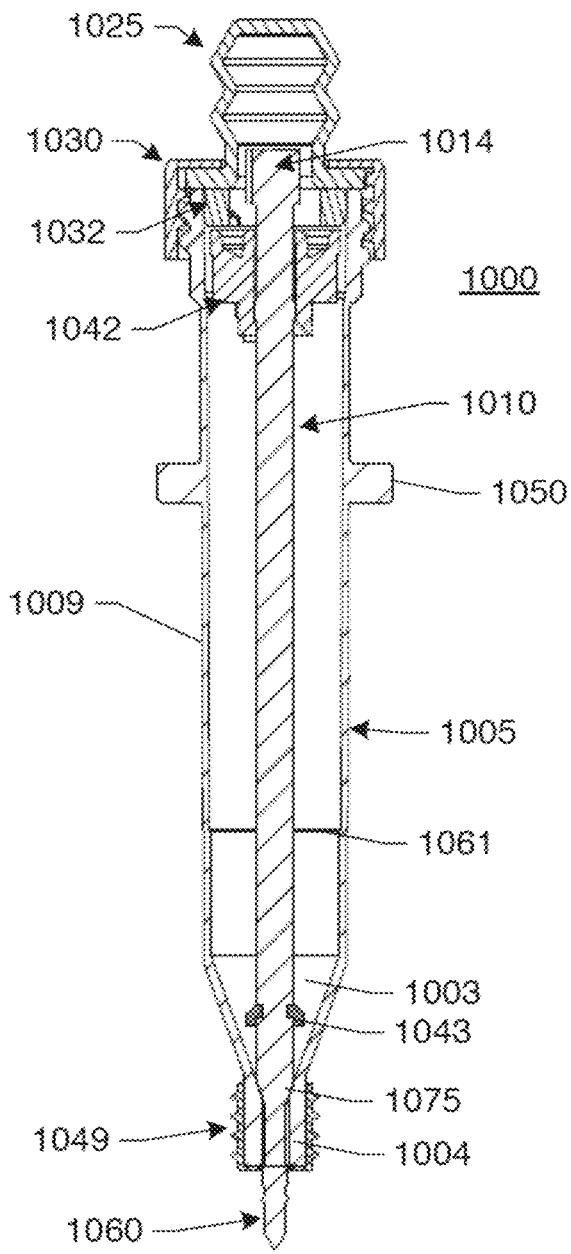
Figure 220:
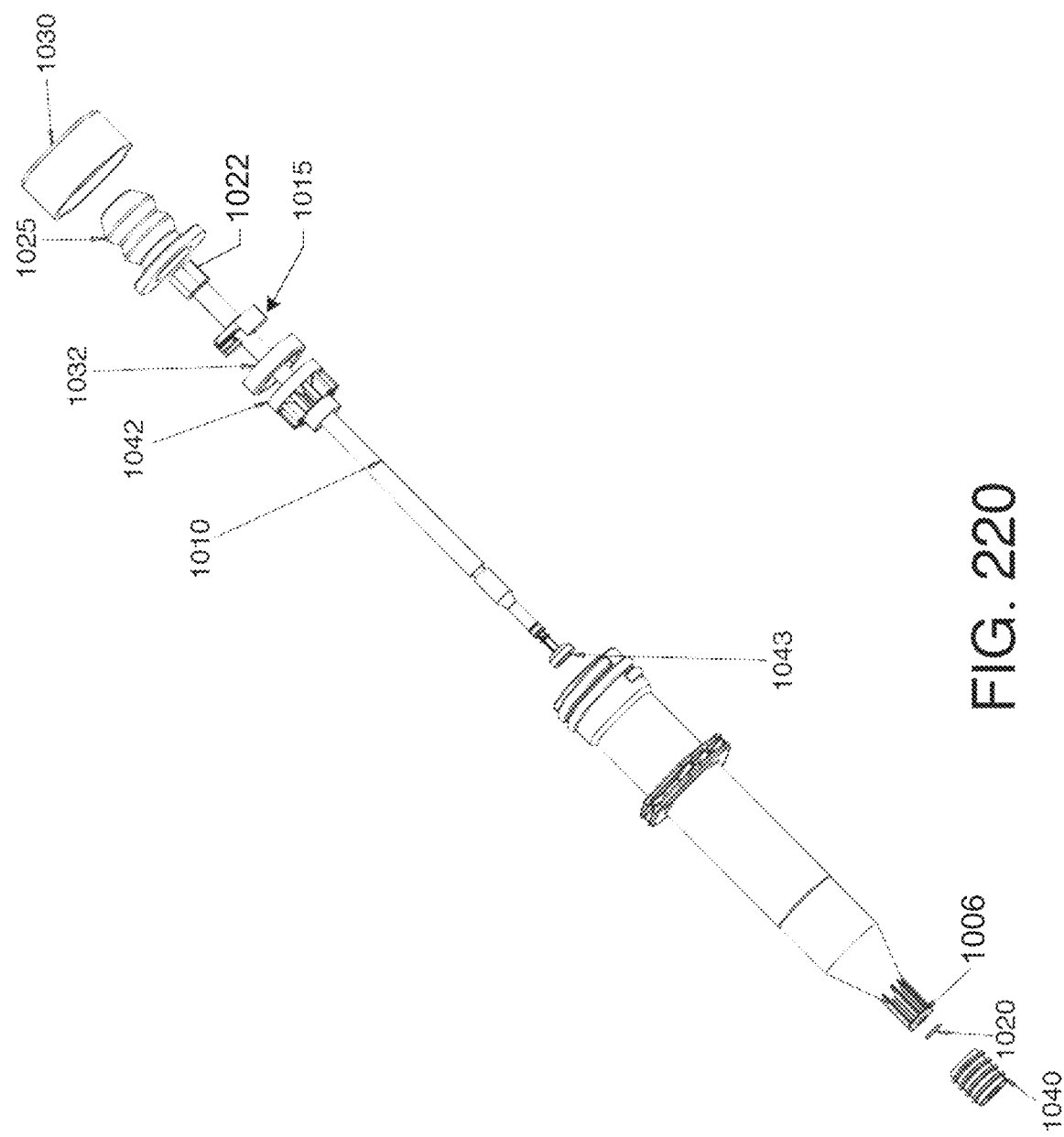
Figure 222:
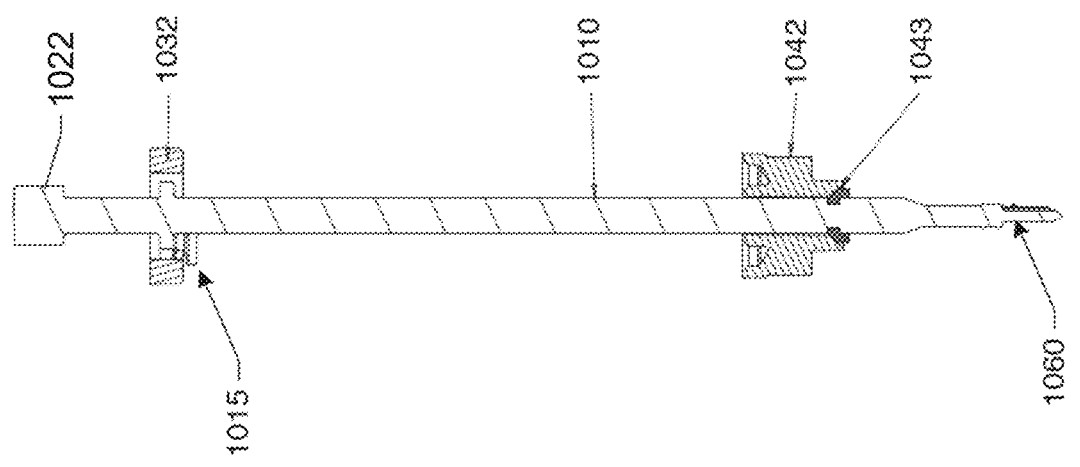
Figure 221:
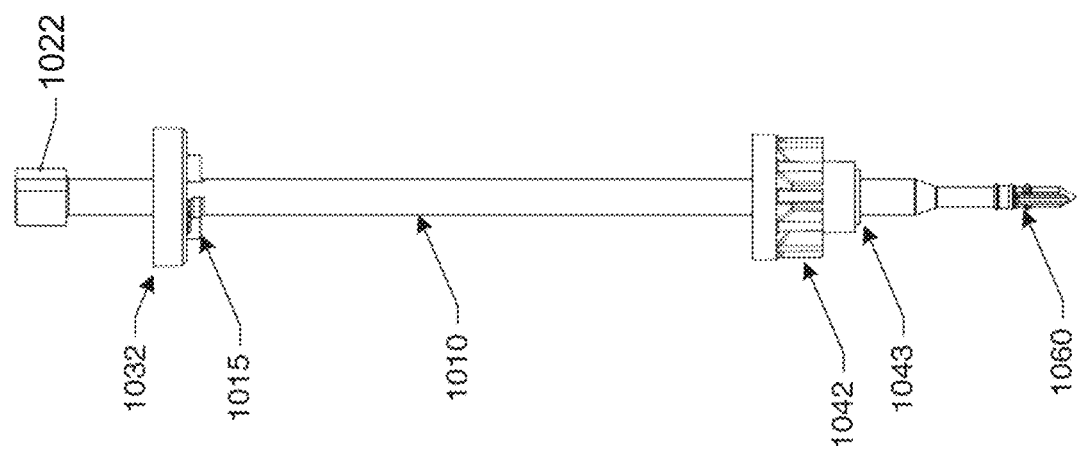
Figure 223:
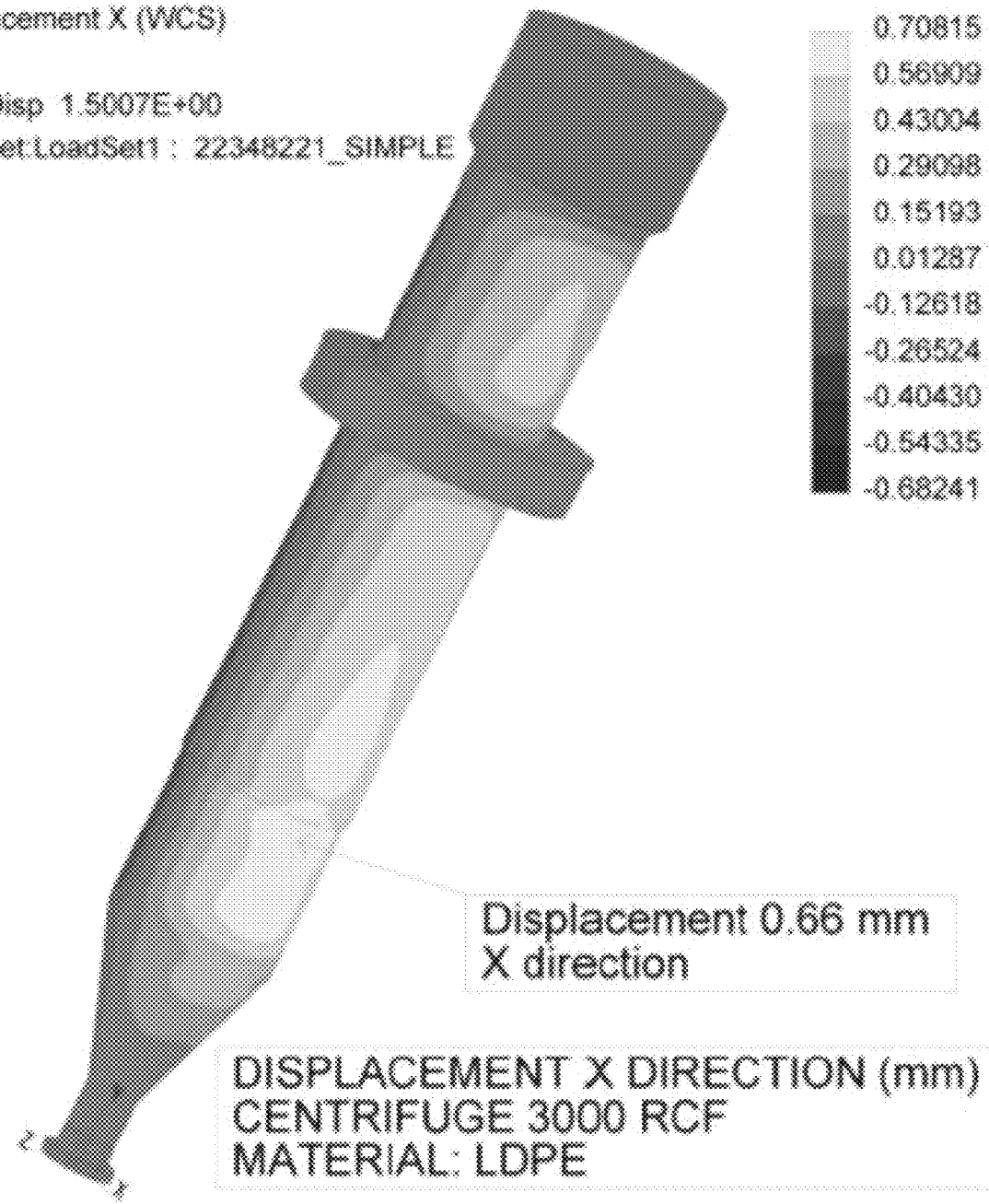
Figure 224:
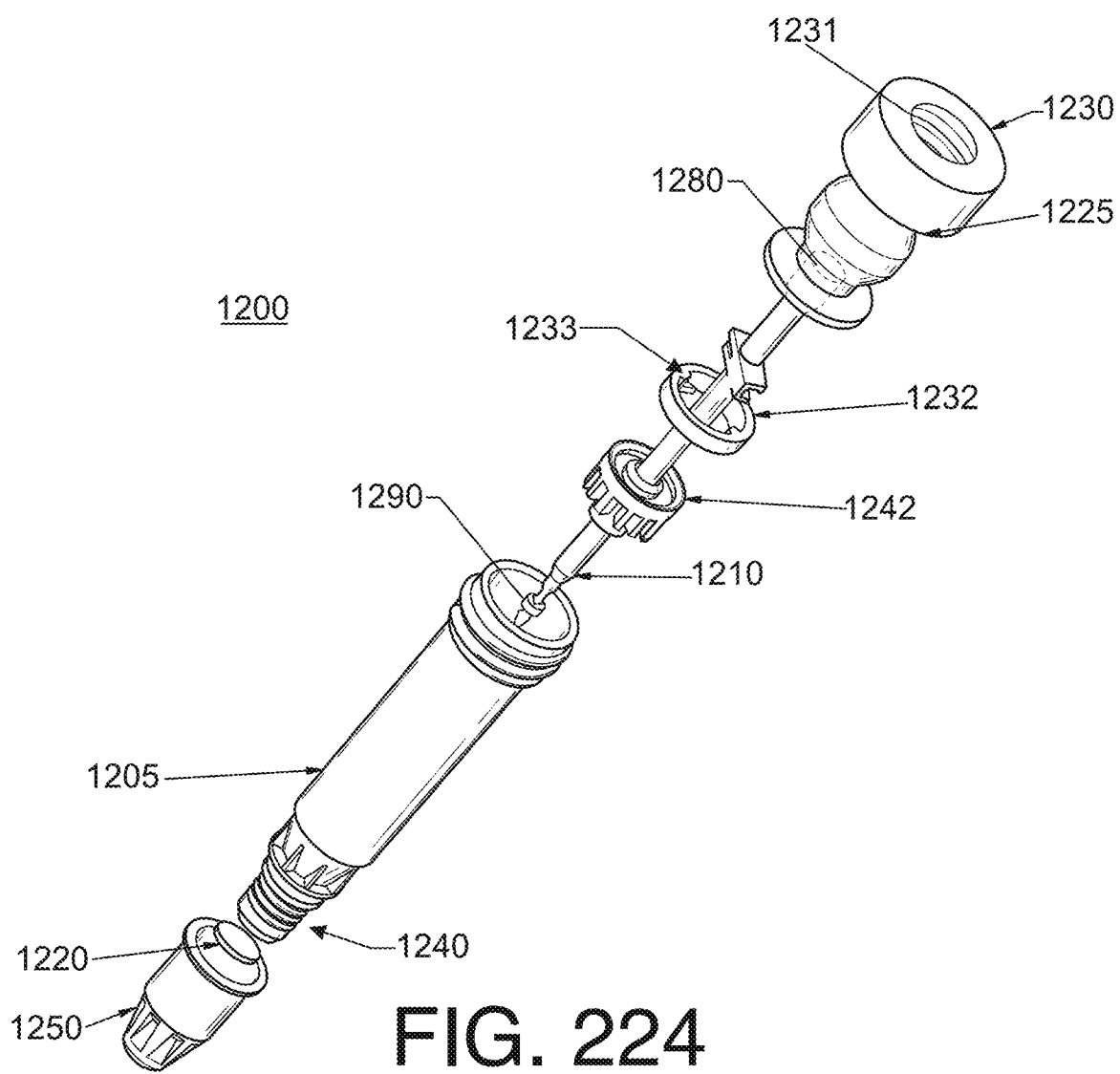
Figure 227:
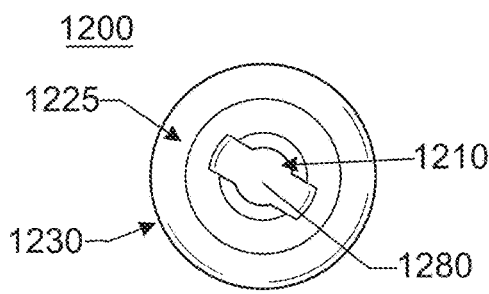
Figure 225:
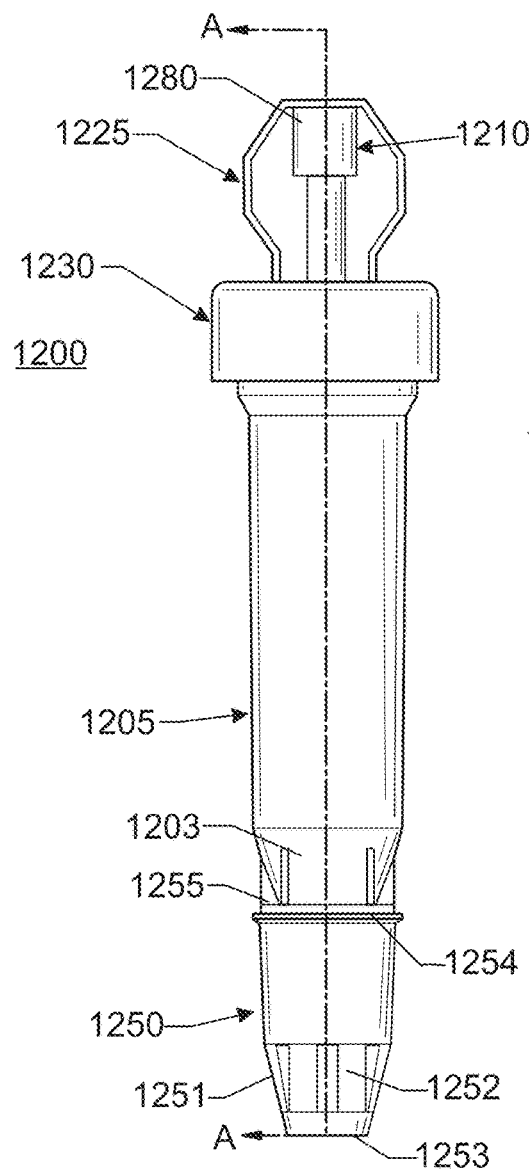
Figure 226:
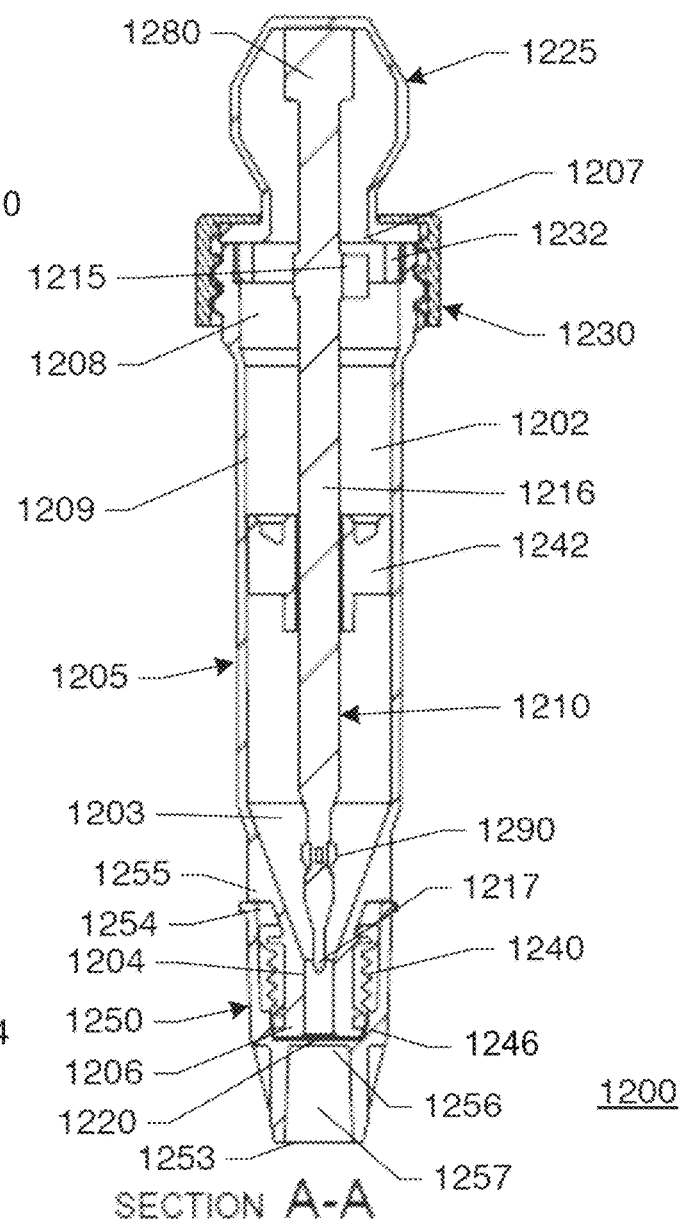
Figure 236:
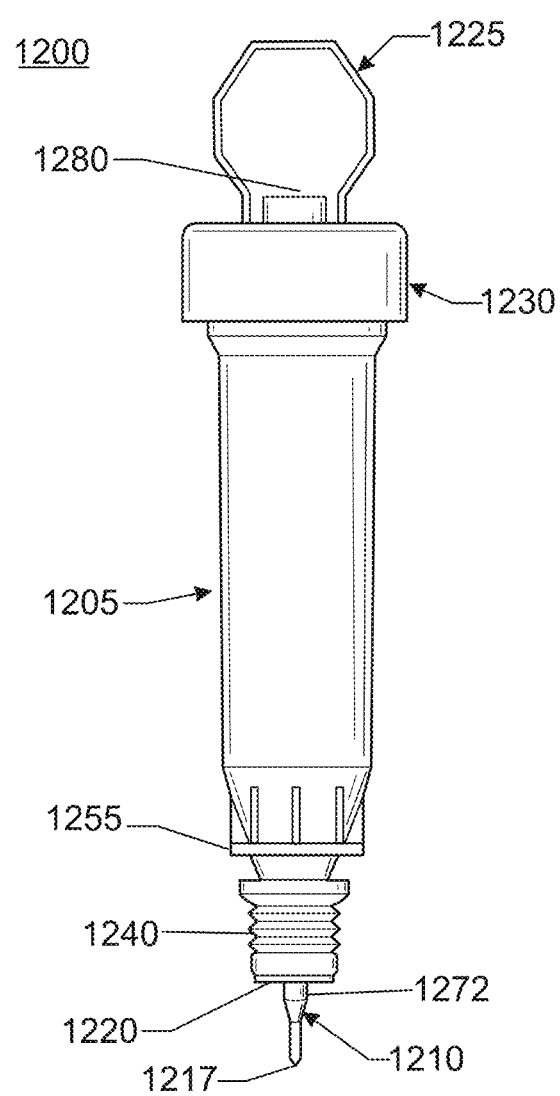
Figure 237:
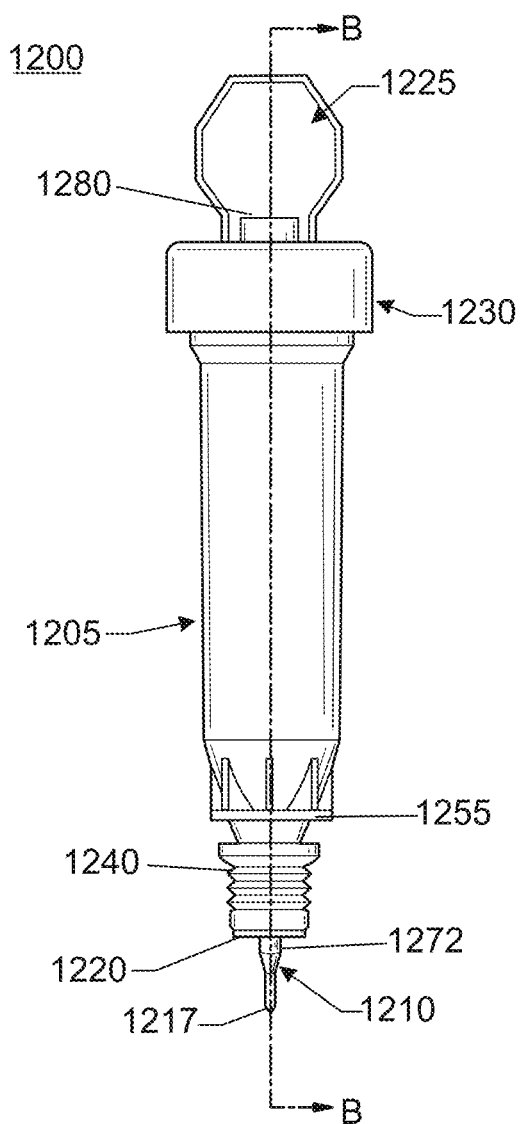
Figure 240:
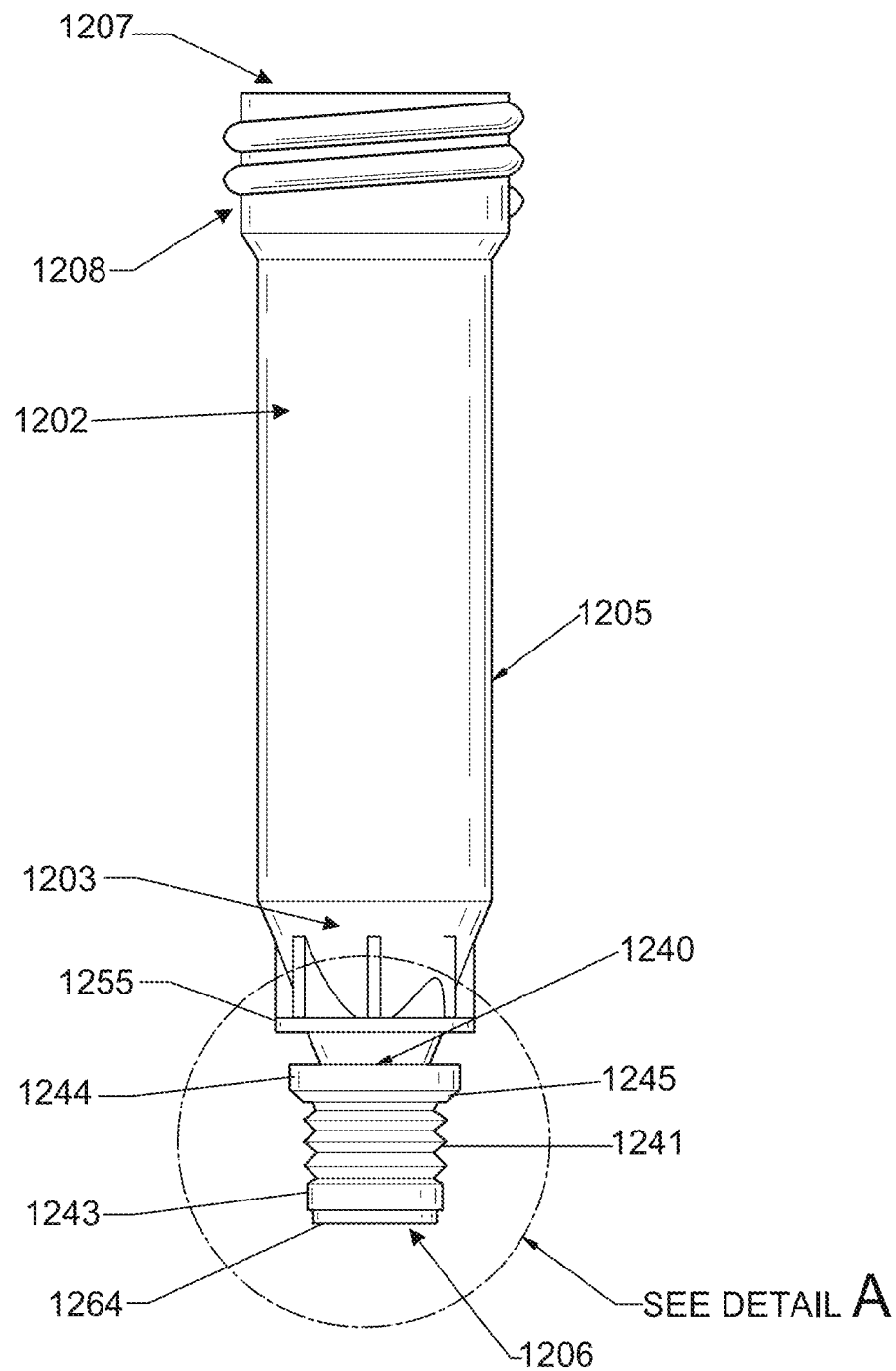
Figure 241:
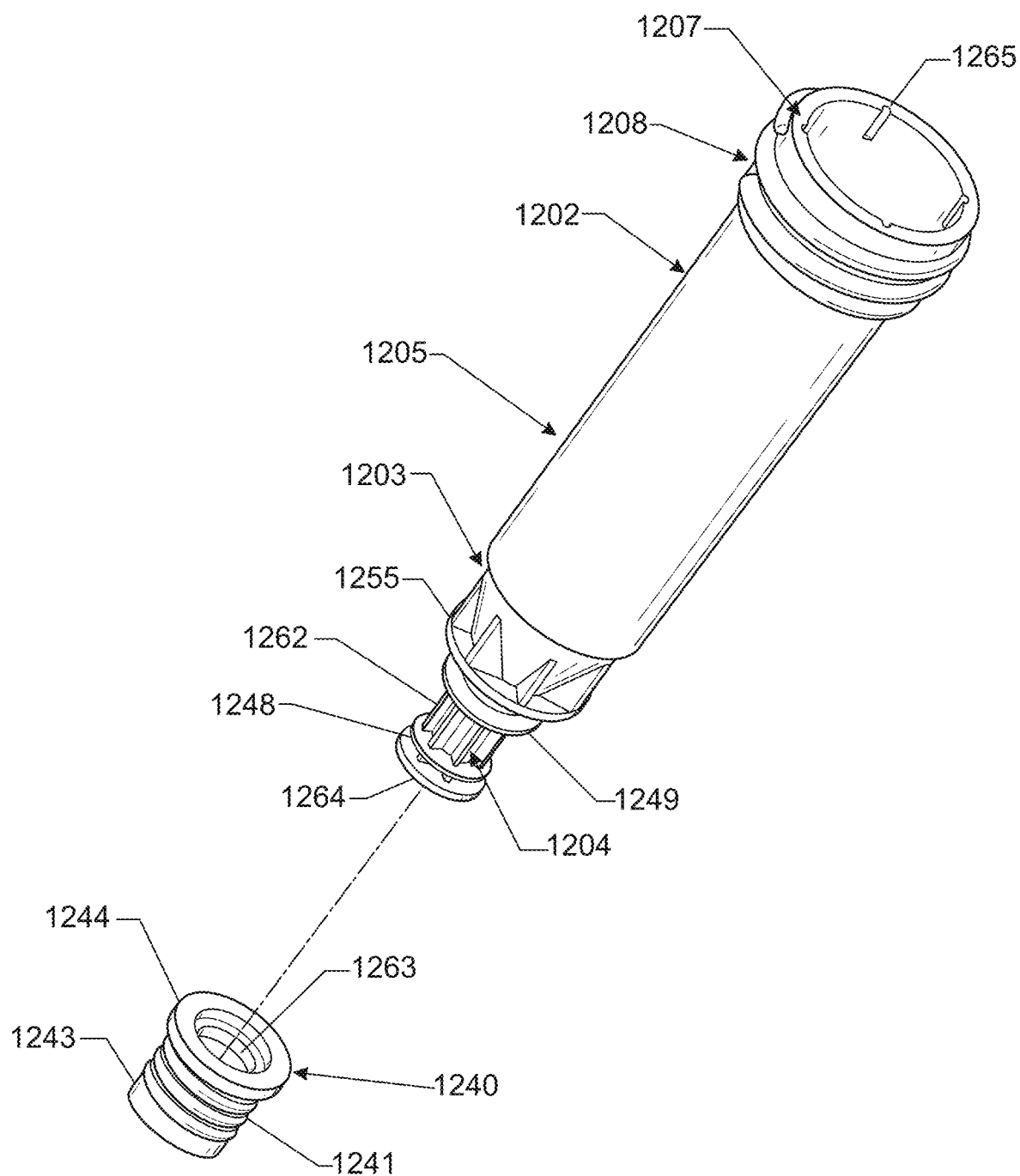
Figure 242:
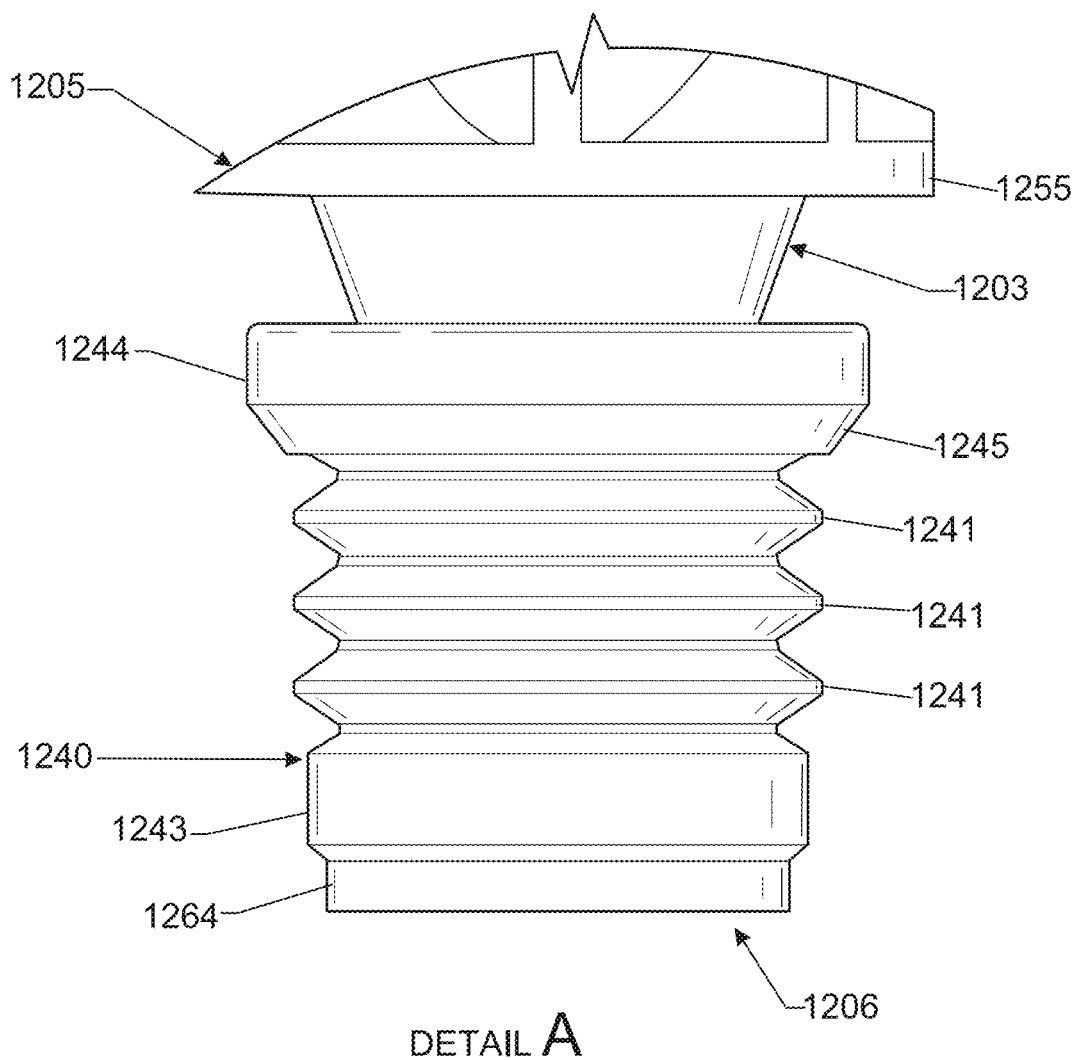
Figures 243, 244, 245:
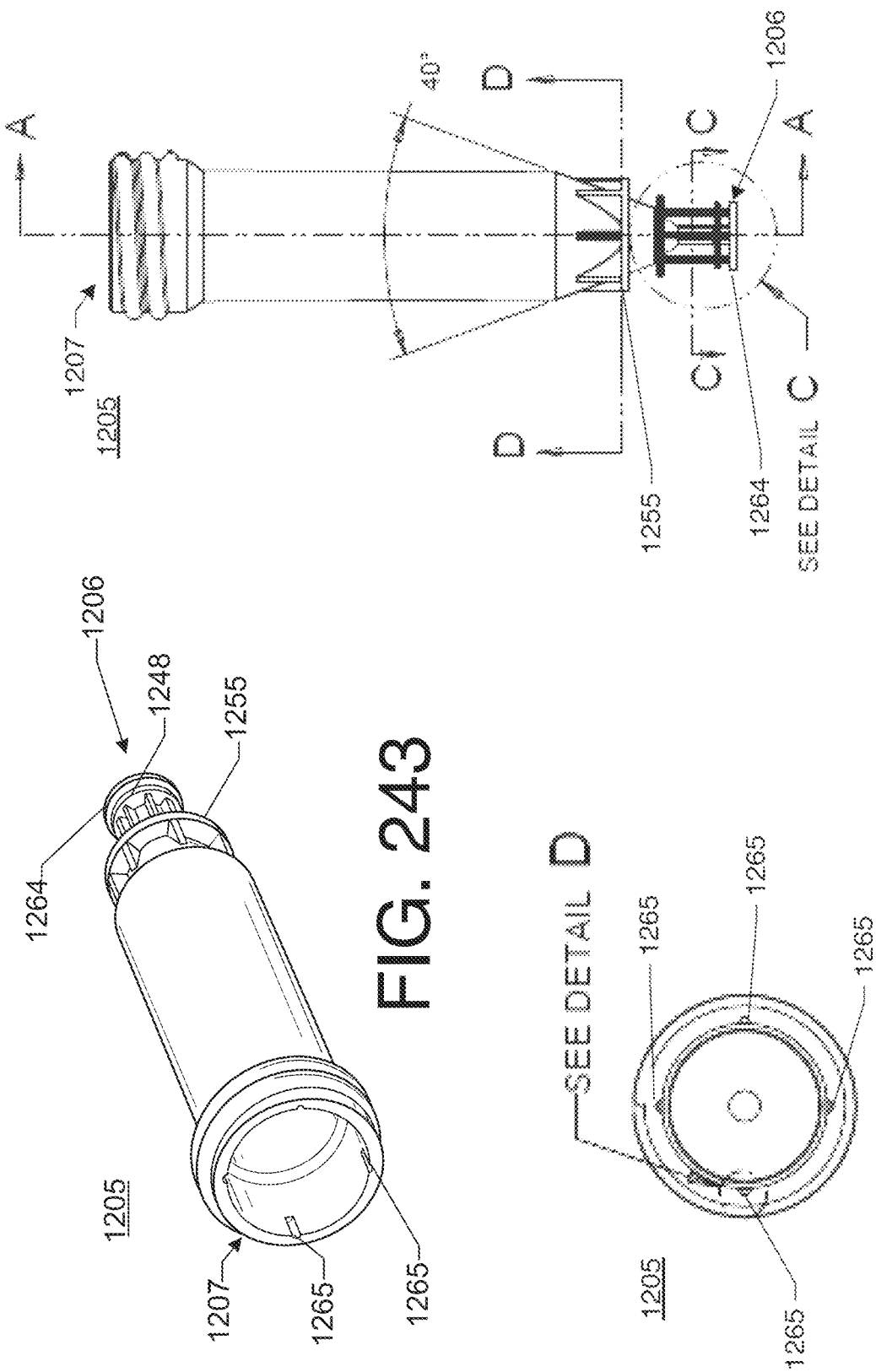
Figures 246, 247:
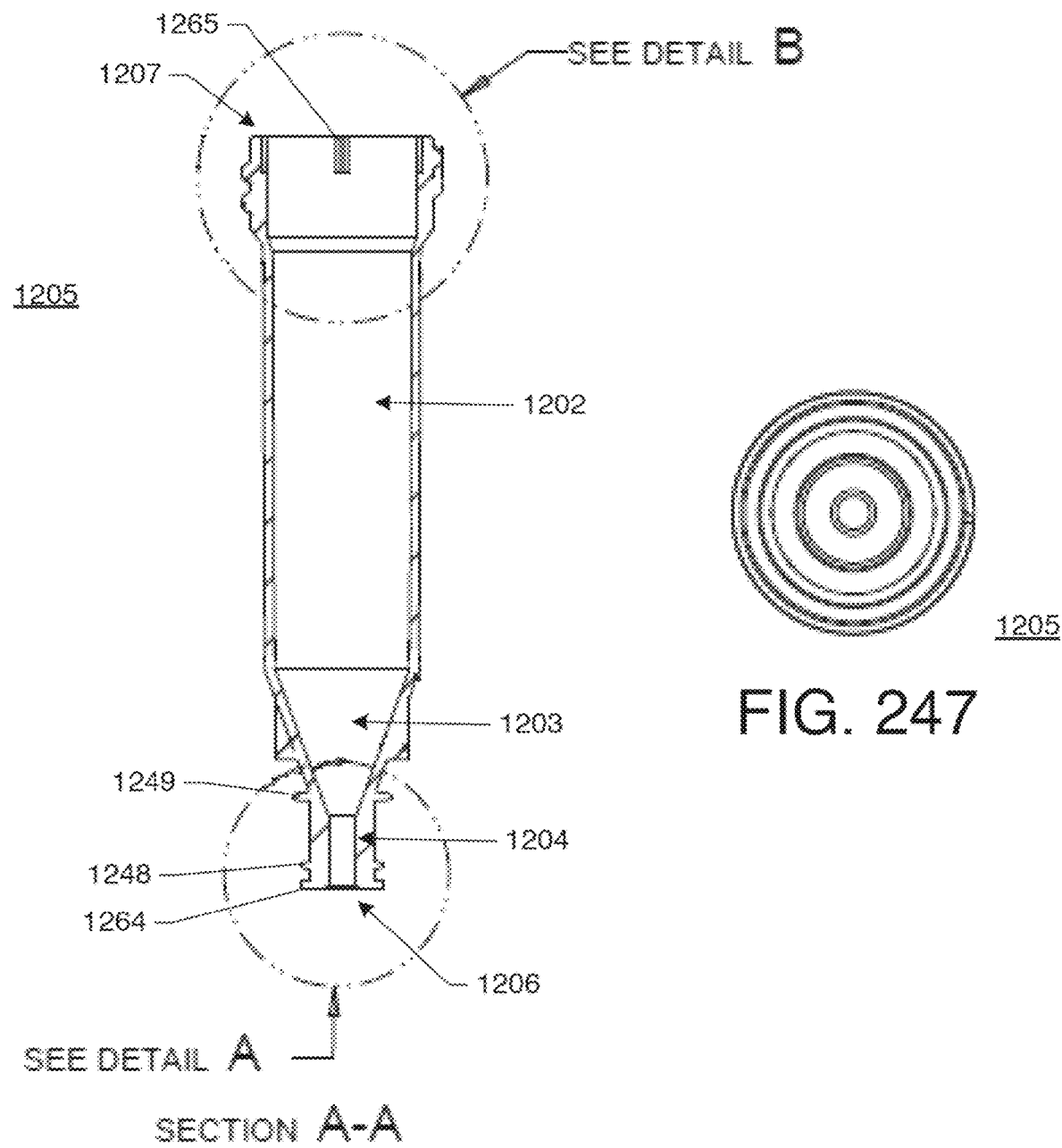
Figure 250:
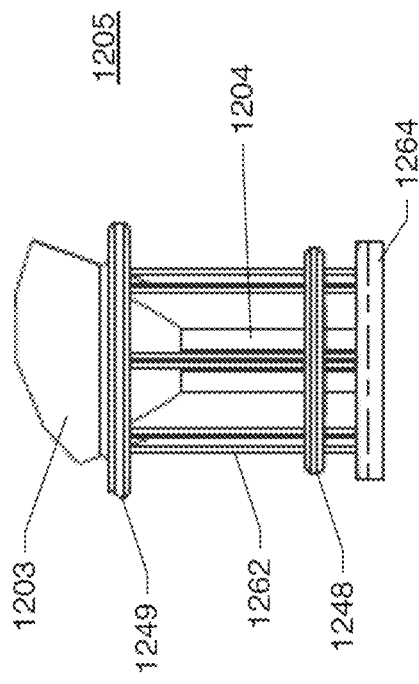
Figure 251:
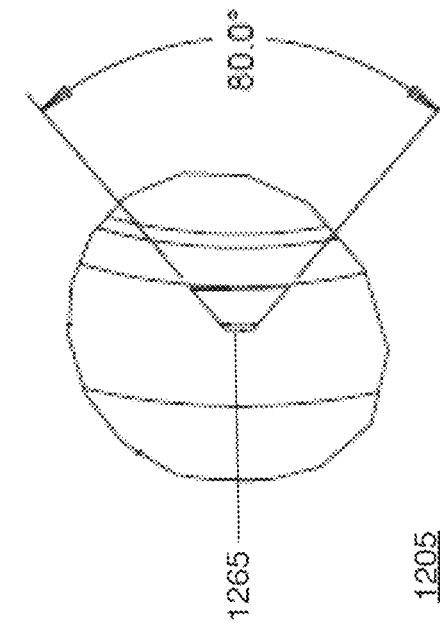
Figure 248:
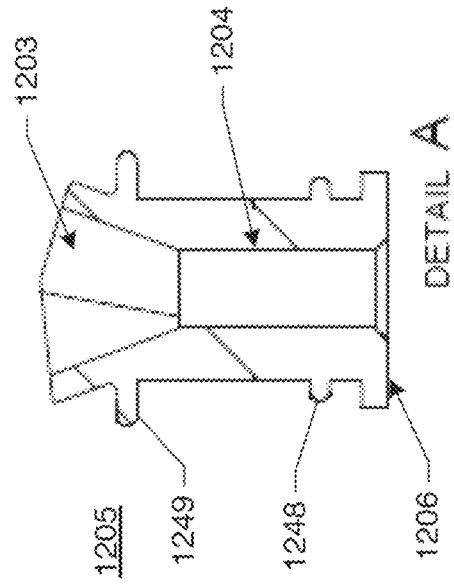
Figure 249:
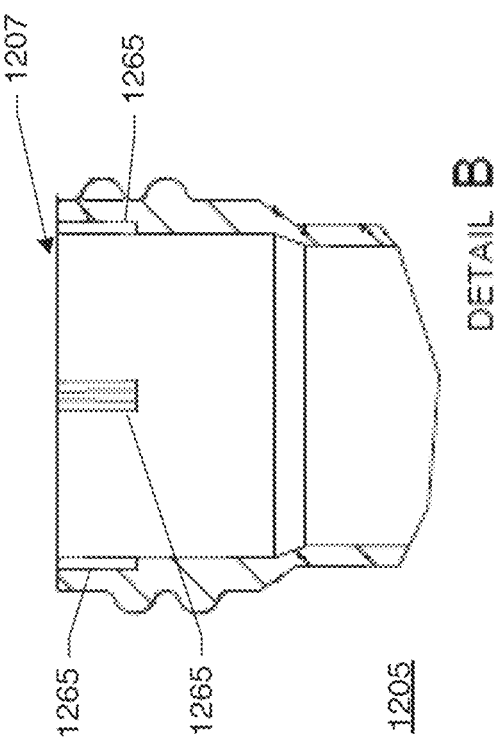
Figure 253:
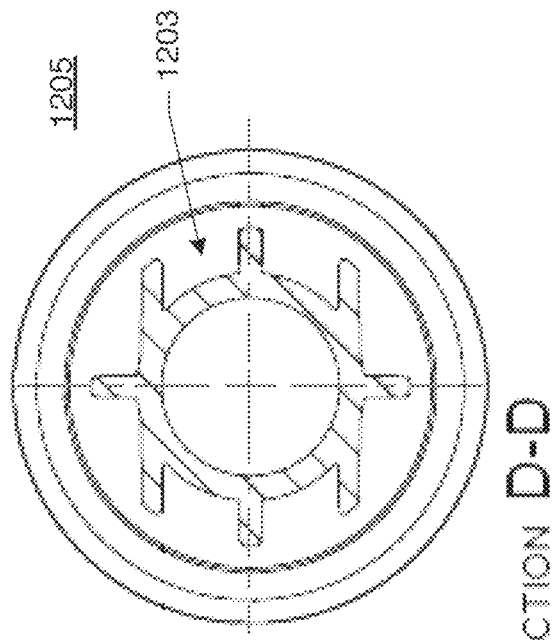
Figure 252:
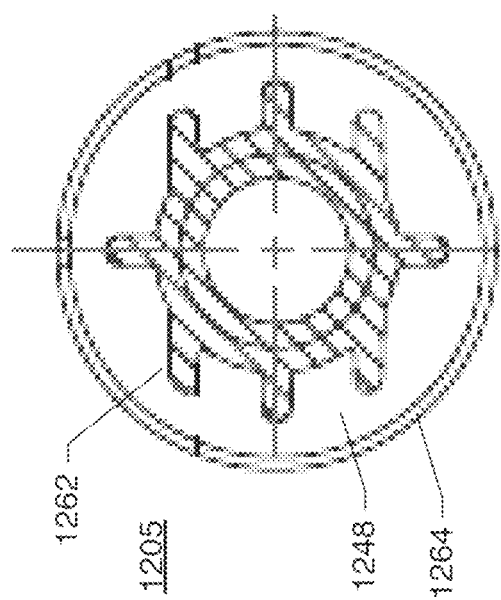
Figure 257:
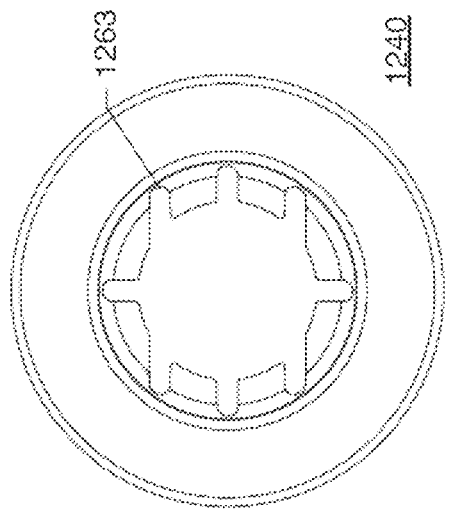
Figure 258:
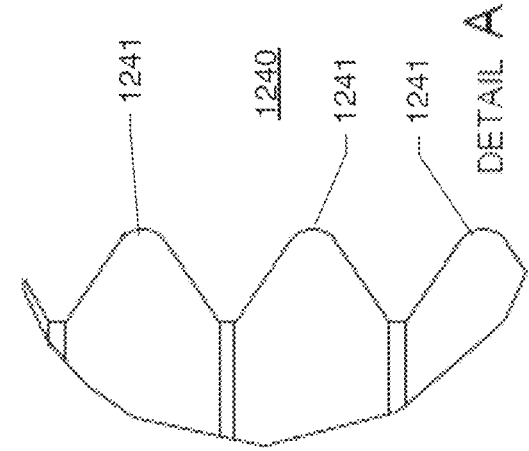
Figure 256:
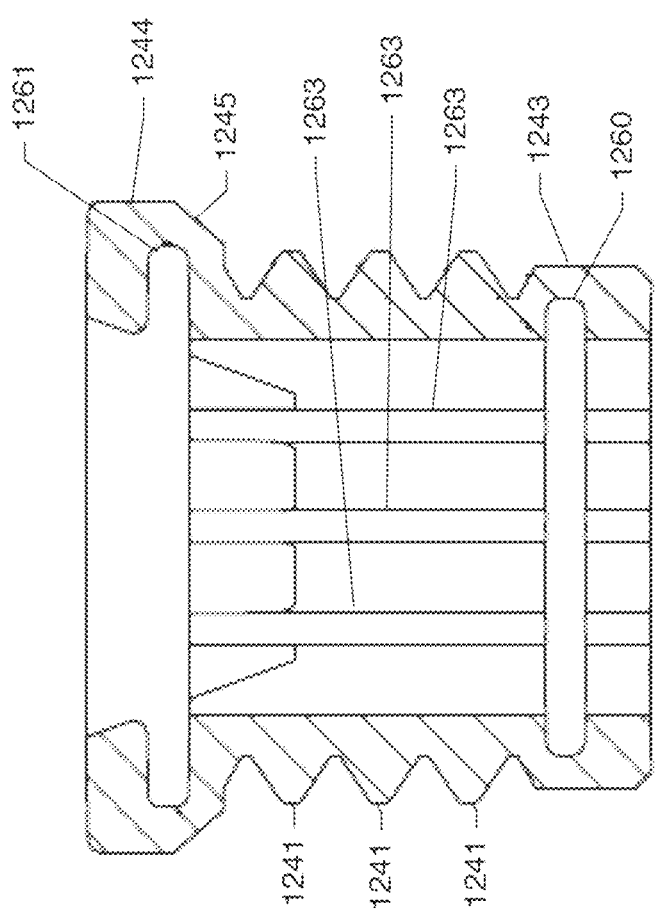
Figure 259:
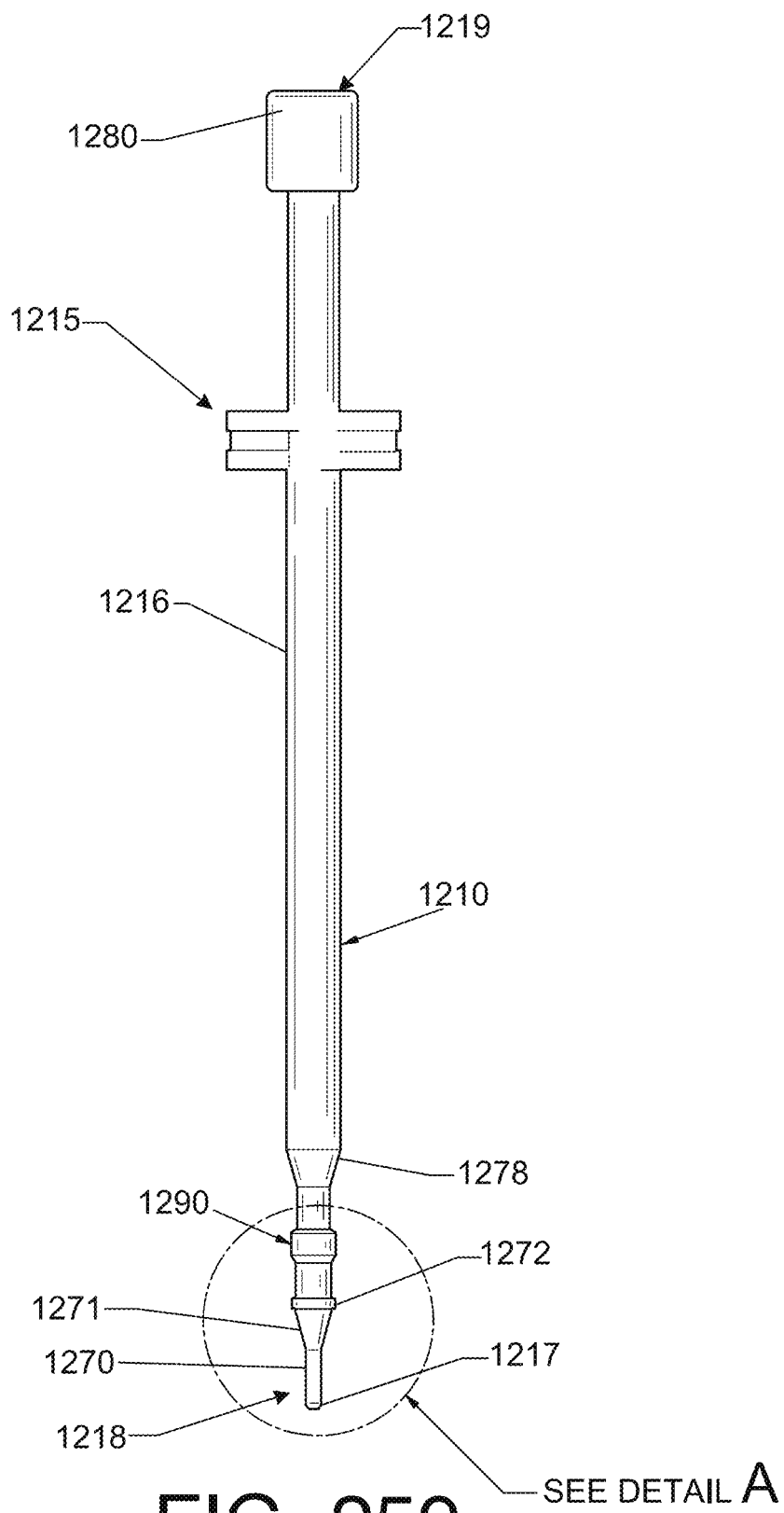
Figure 261:
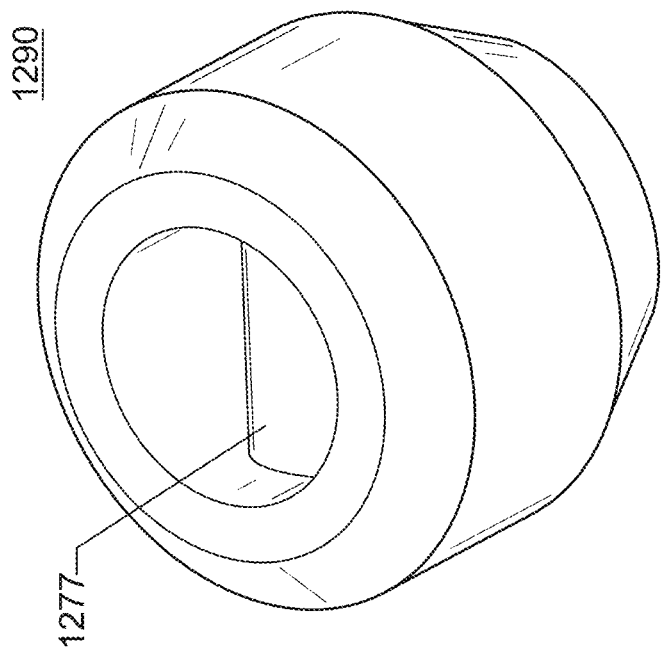
Figure 260:
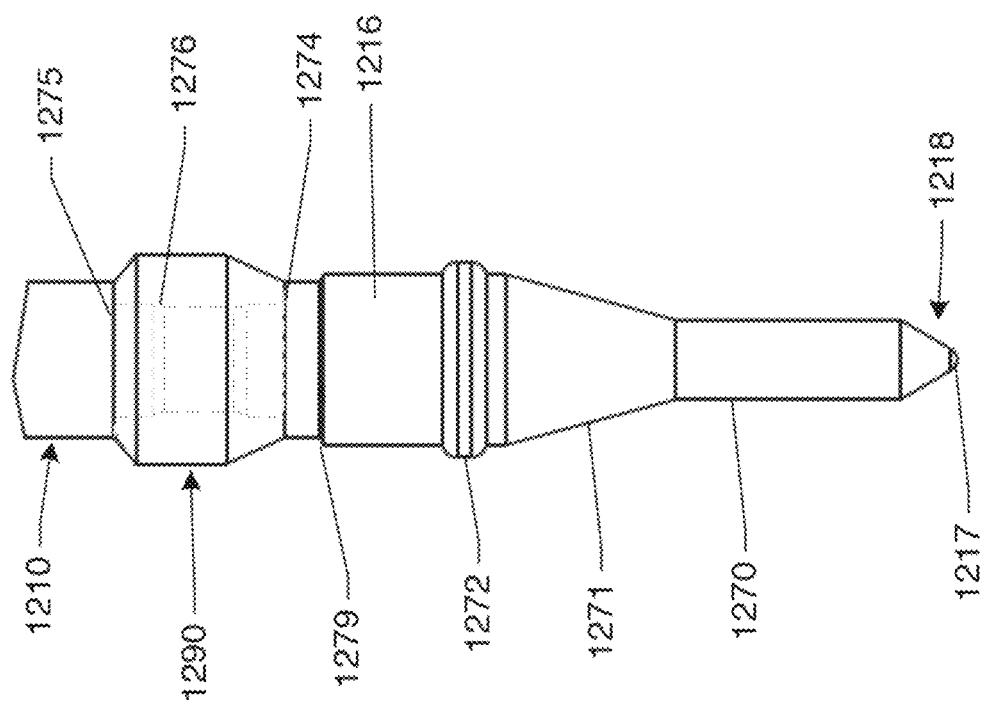
Figure 262:
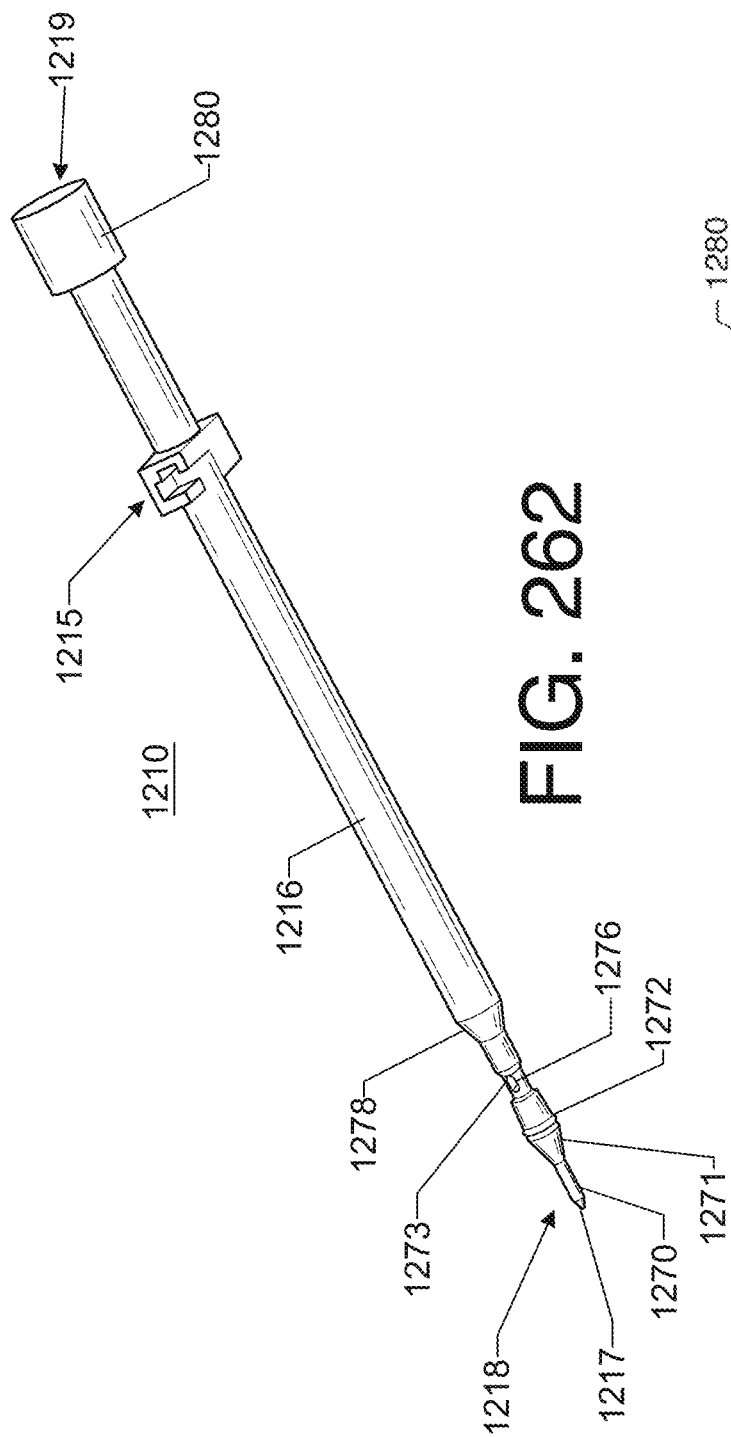
Figure 264:
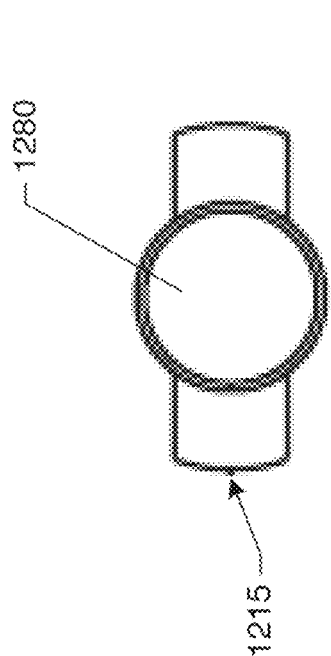
Figure 263:
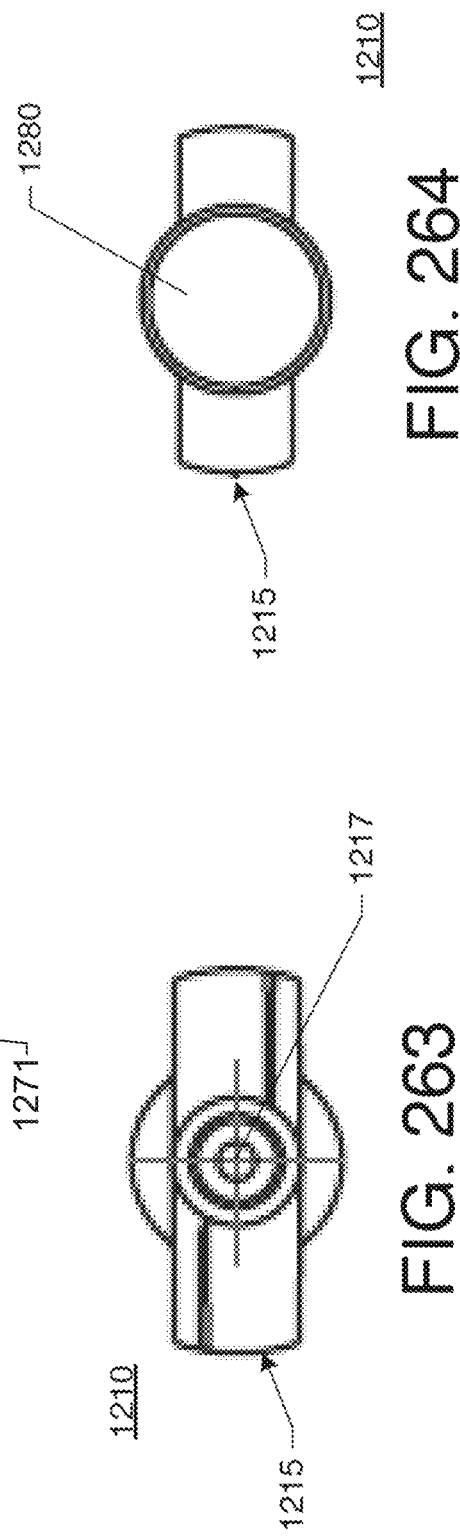
Figures 267, 268:
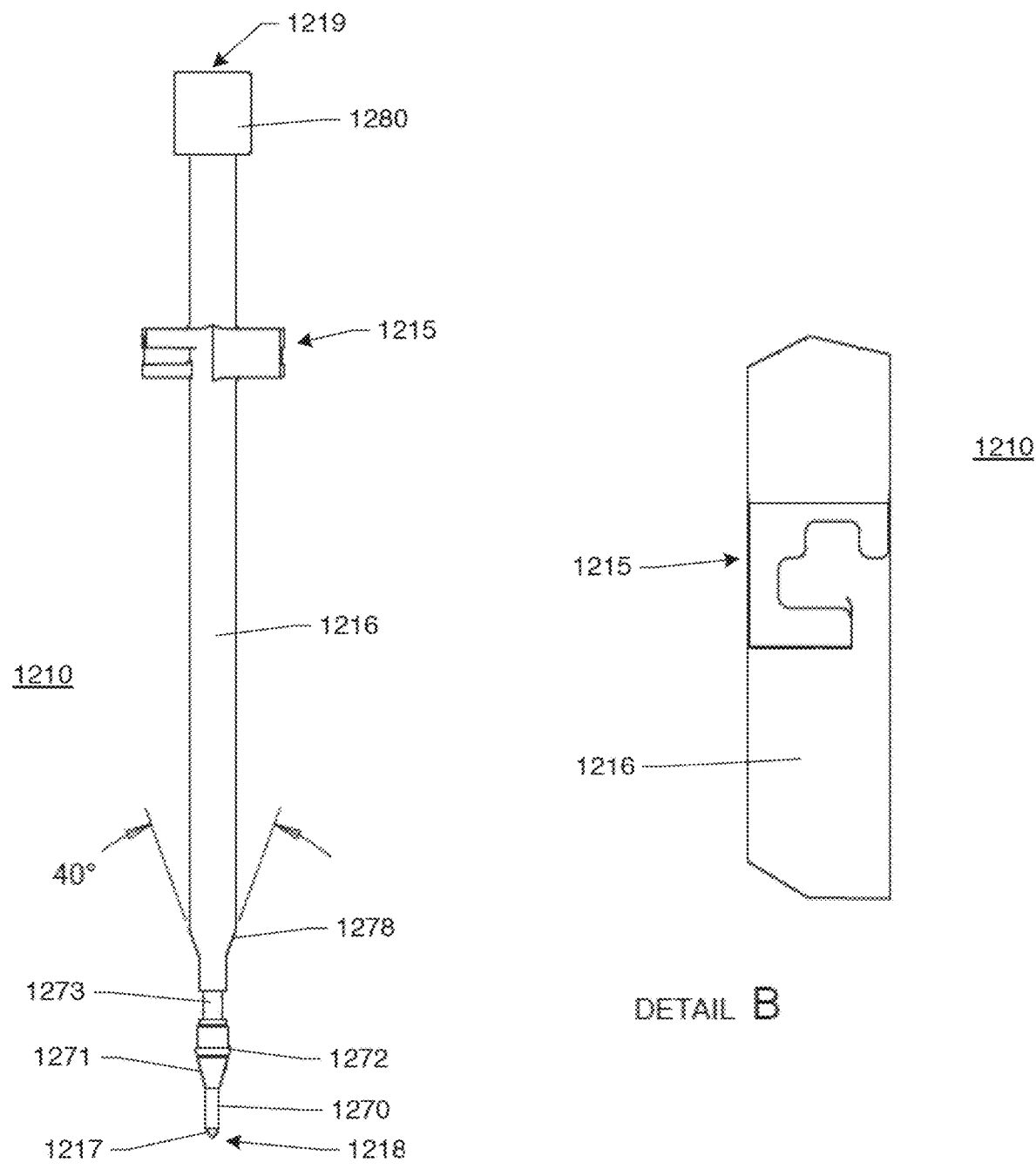
Figure 270:
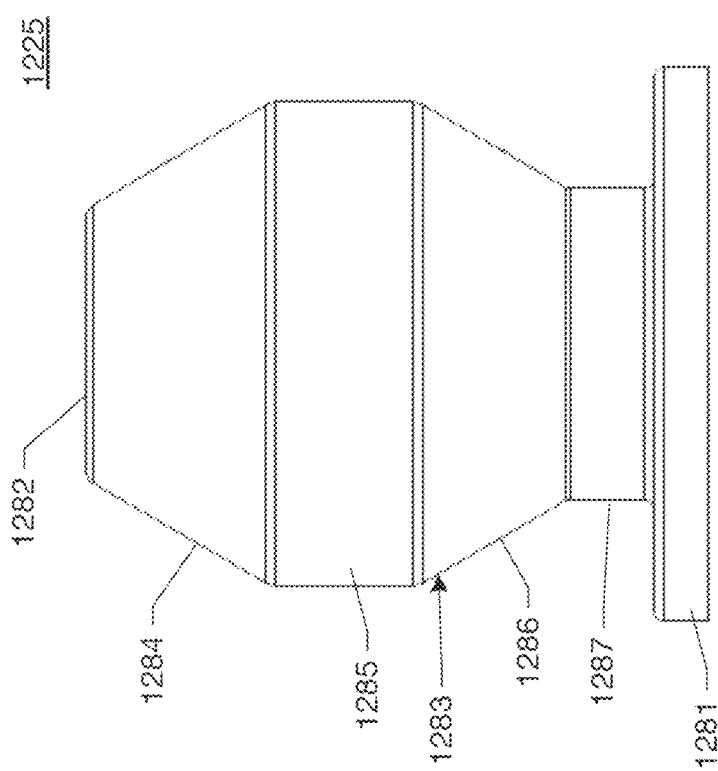
Figure 269:
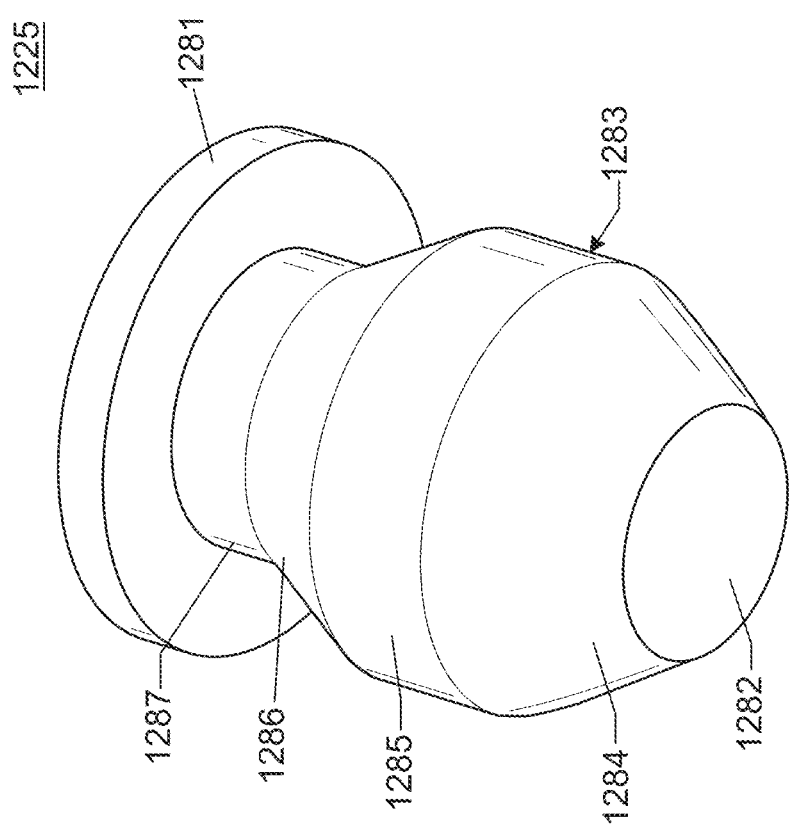
Figure 273:
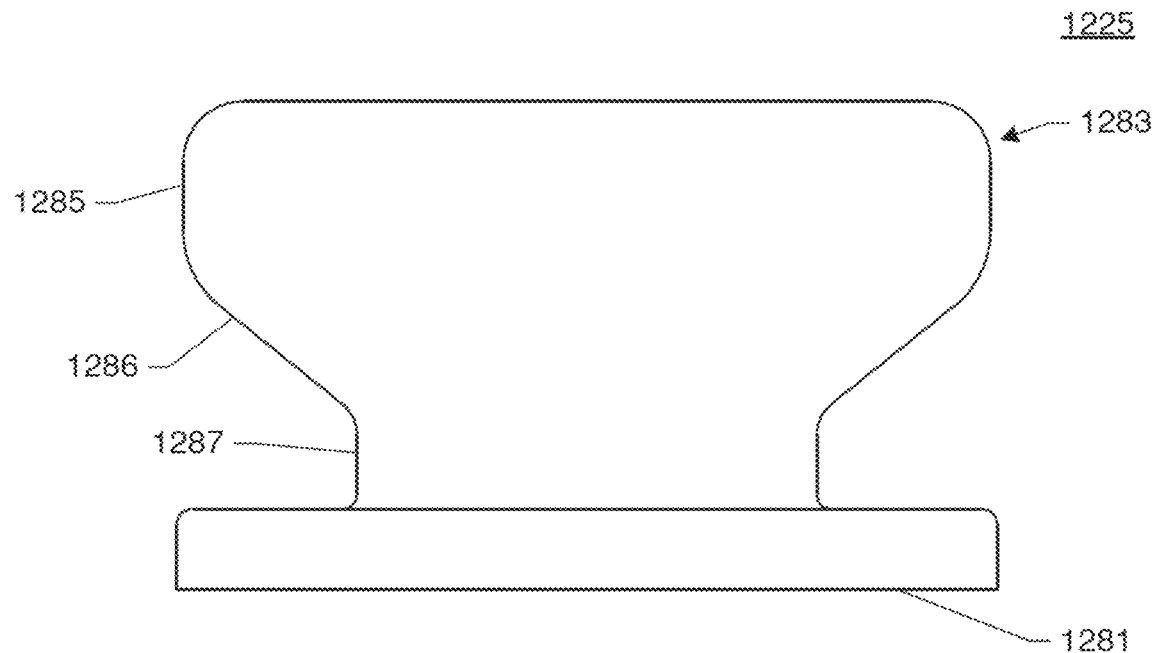
Figure 274:
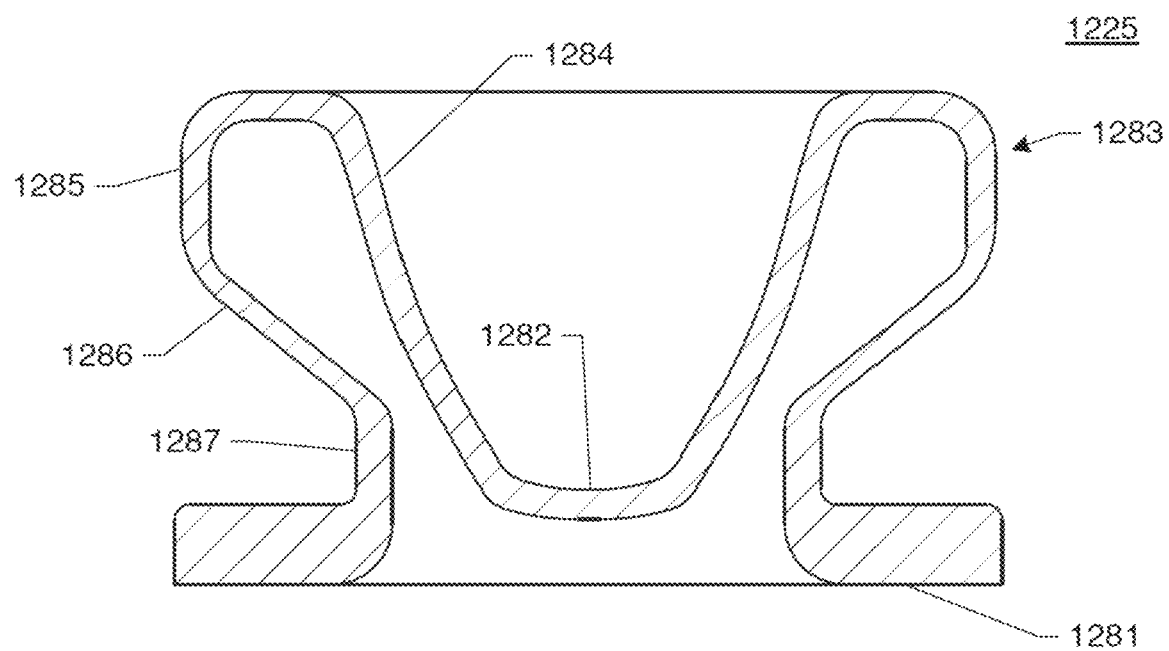
Figure 277:
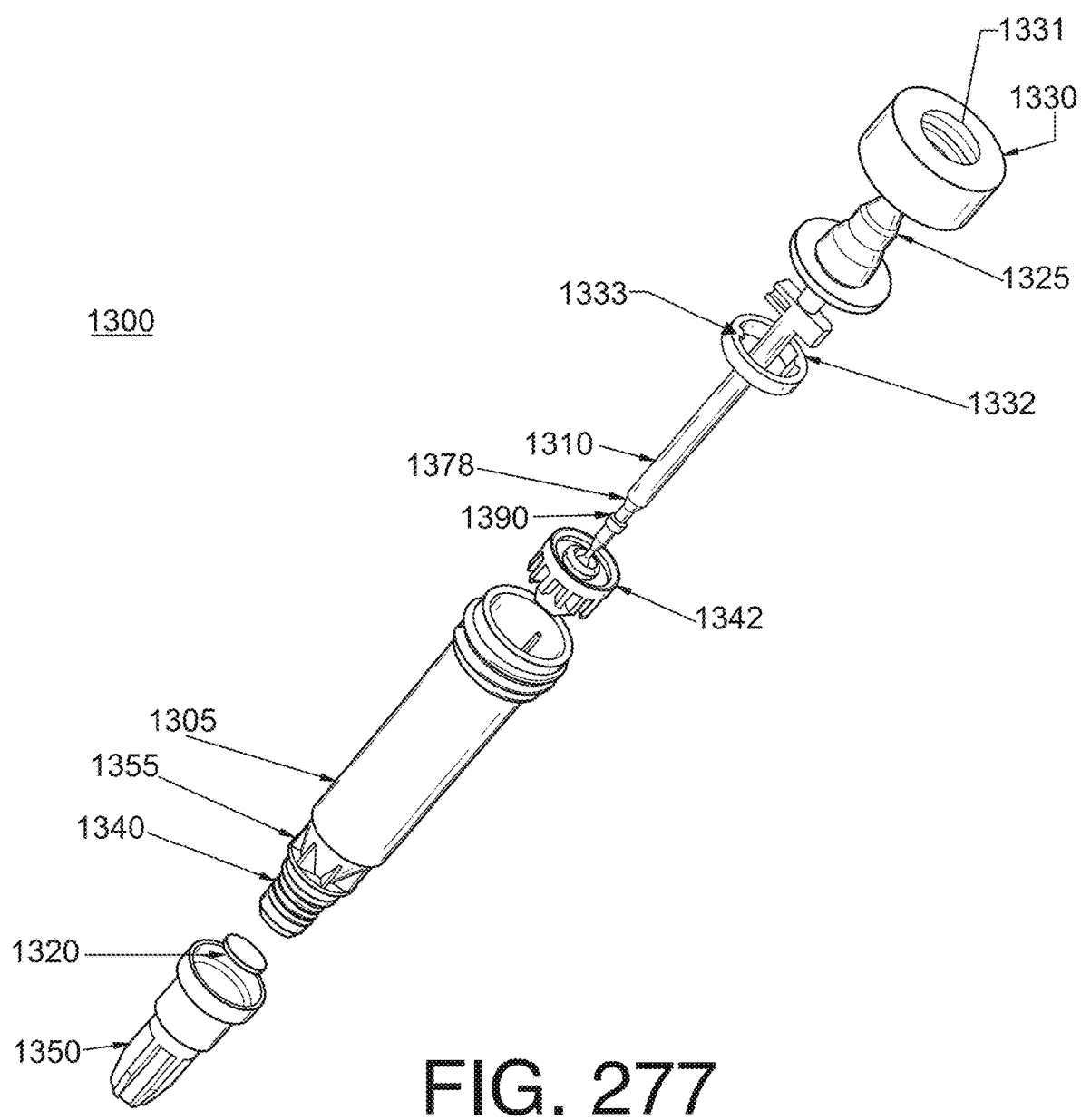
Figure 284:
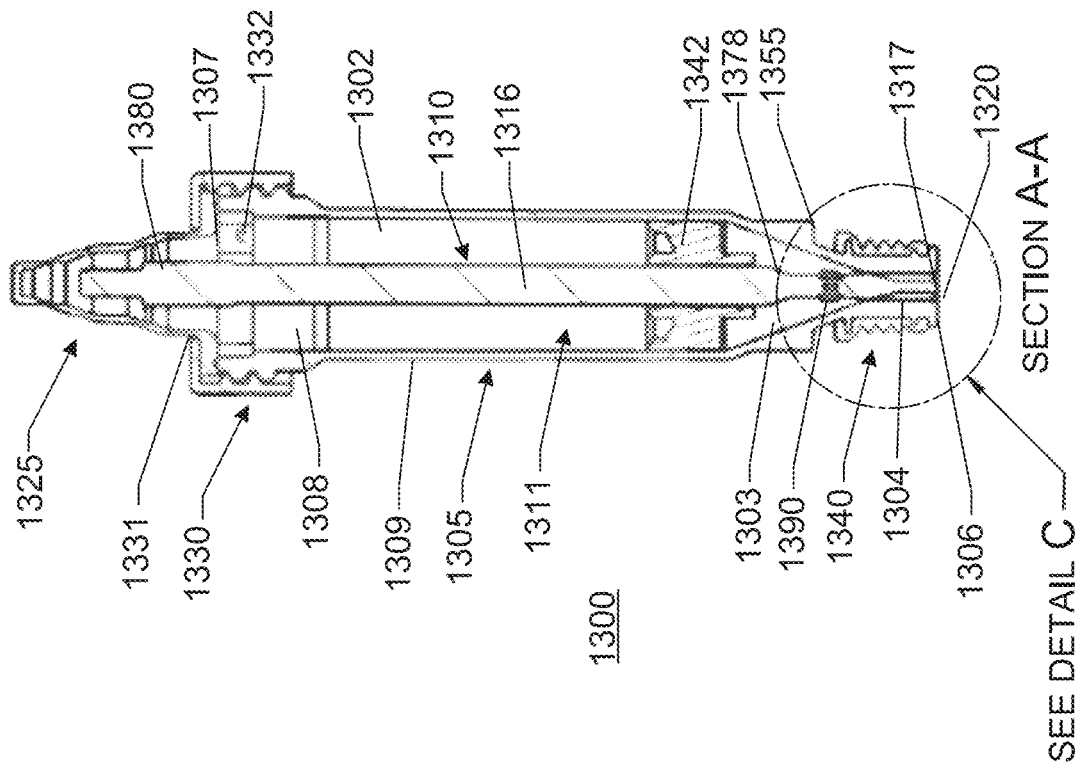
Figure 283:
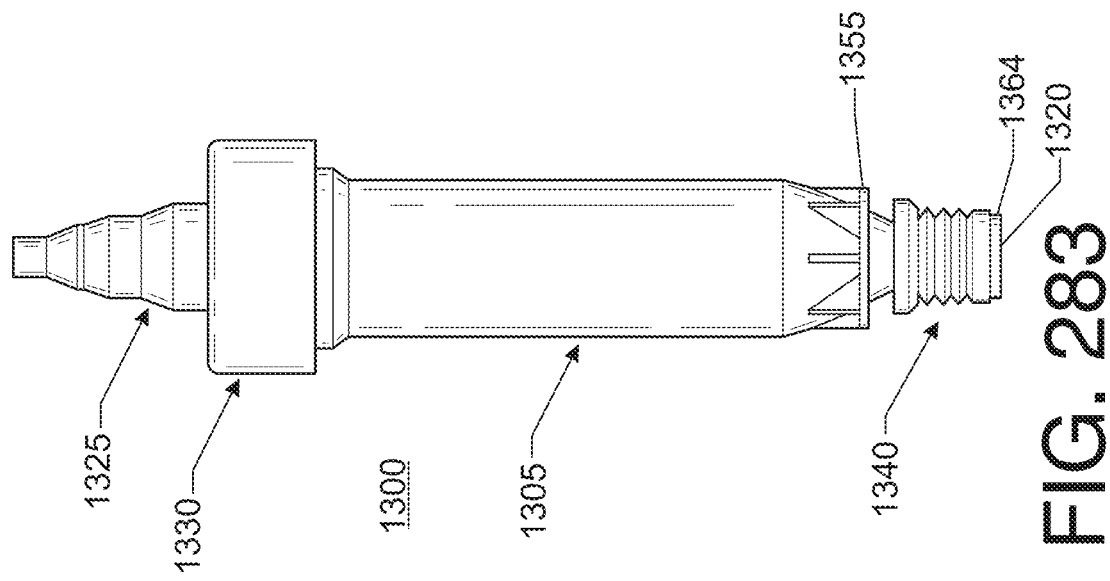
Figure 286:
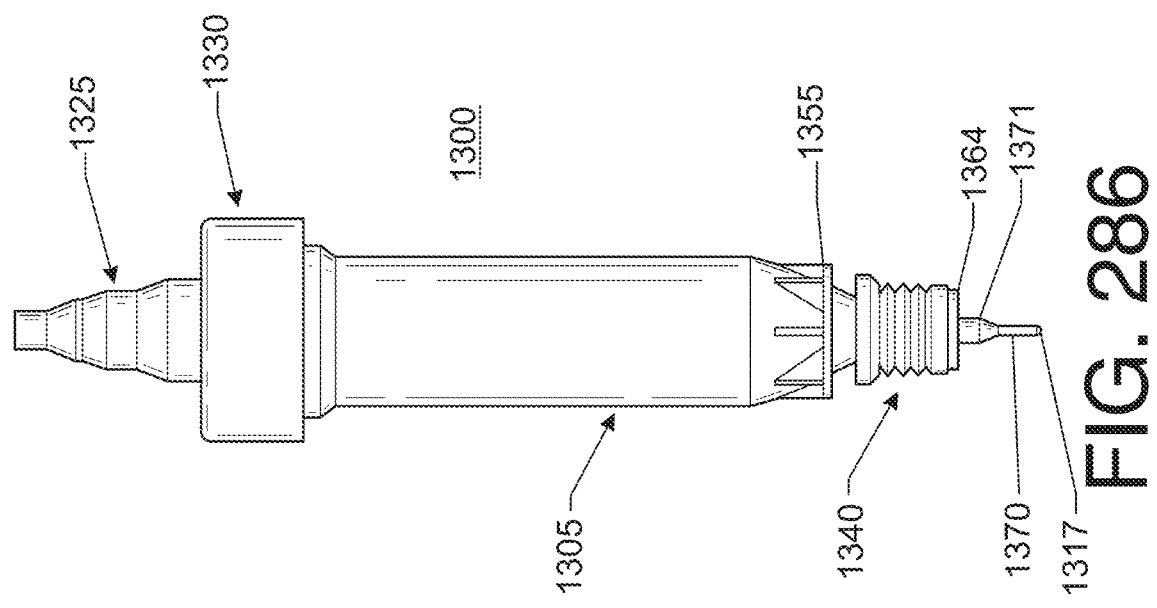
Figure 285:
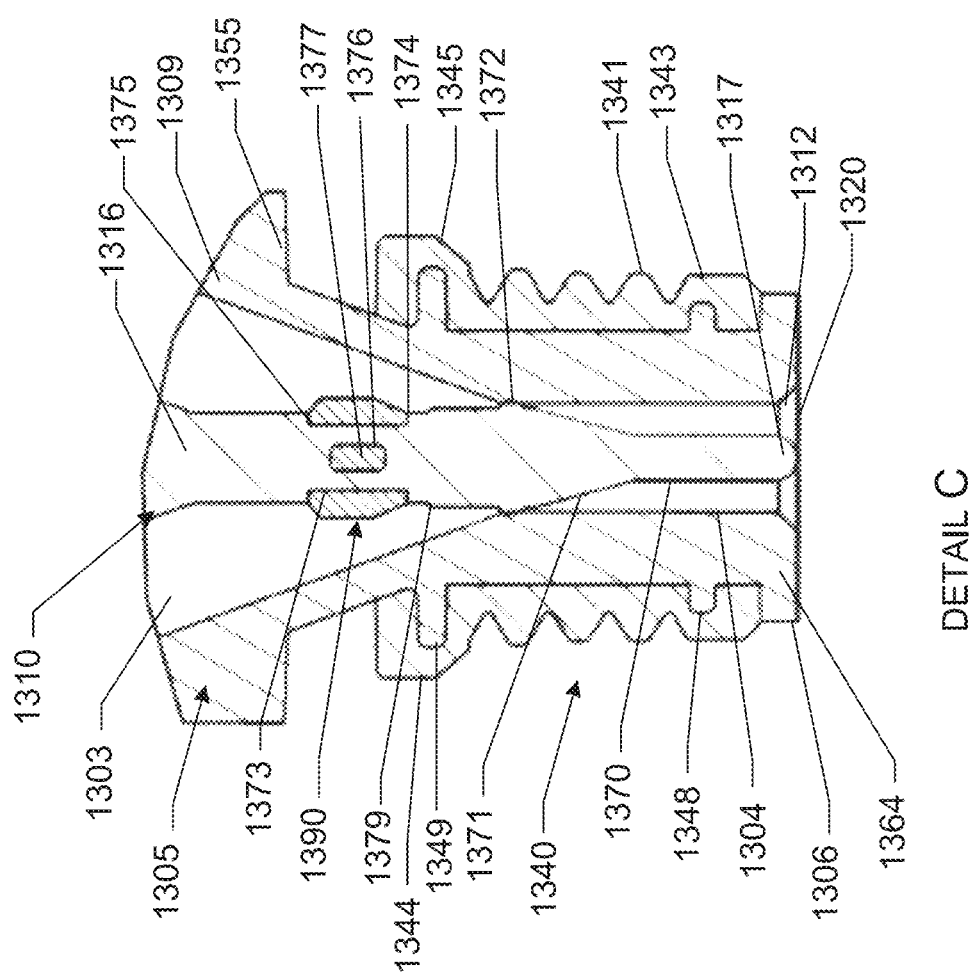
Figure 300:
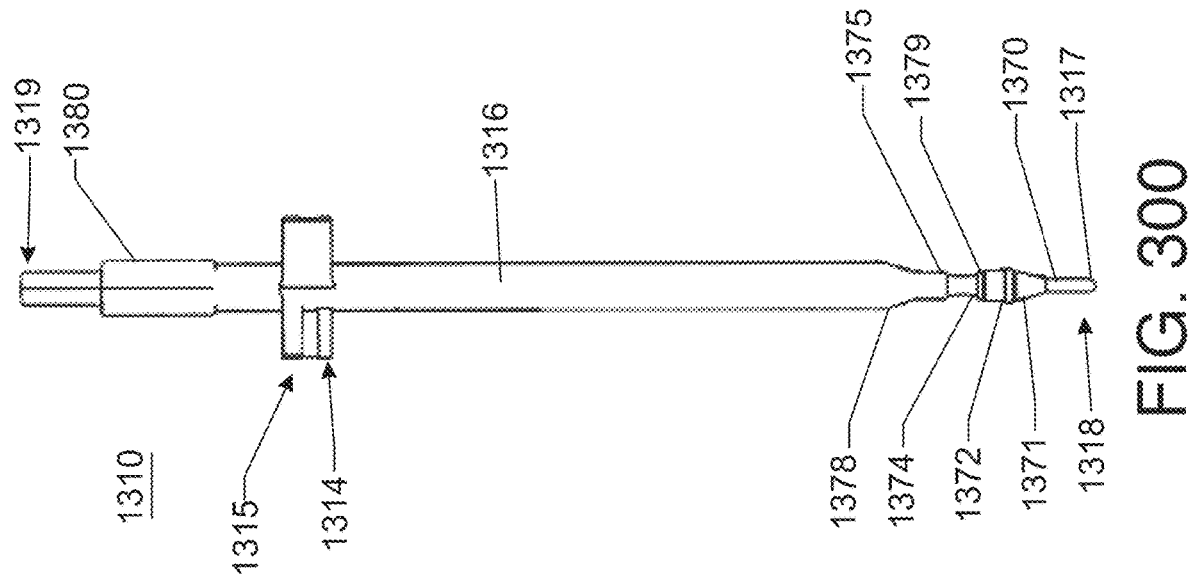
Figure 299:
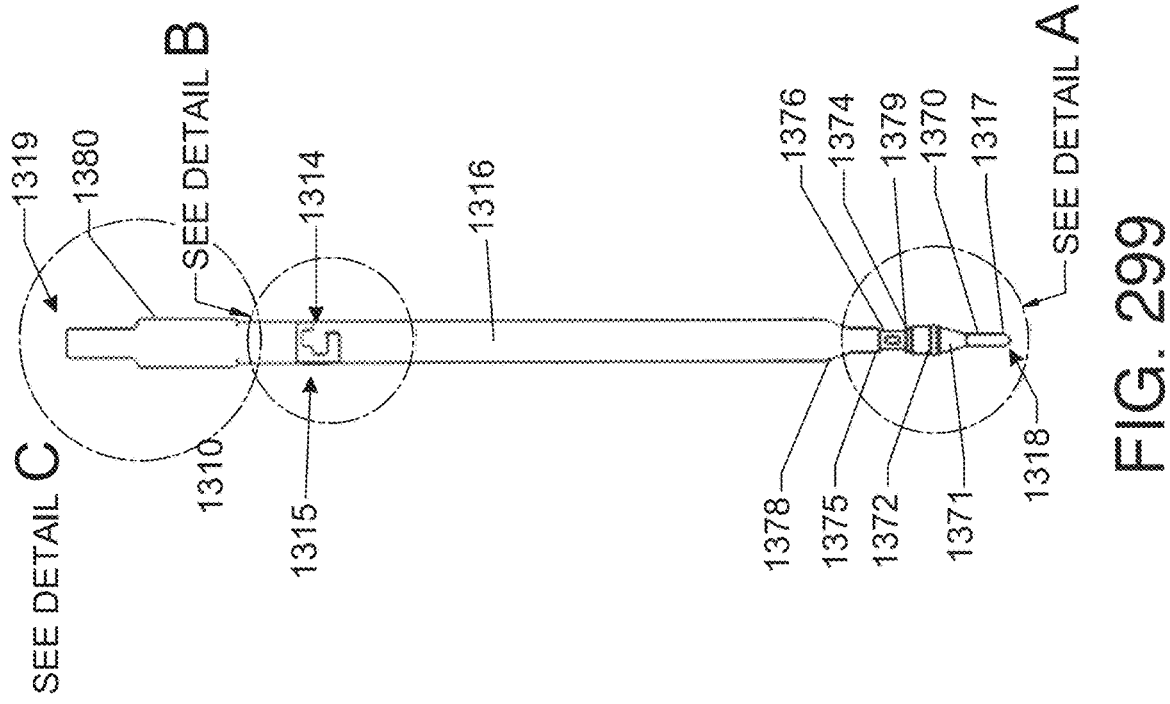
Figure 304:
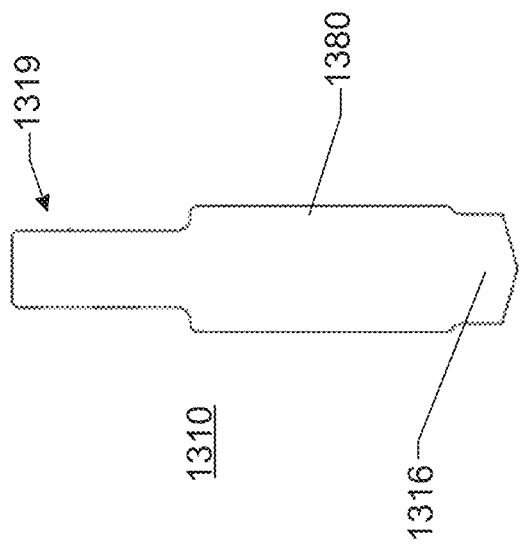
Figure 306:
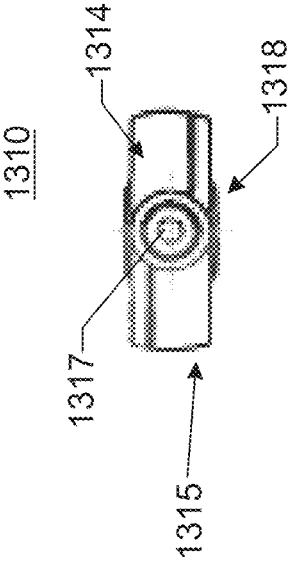
Figure 303:
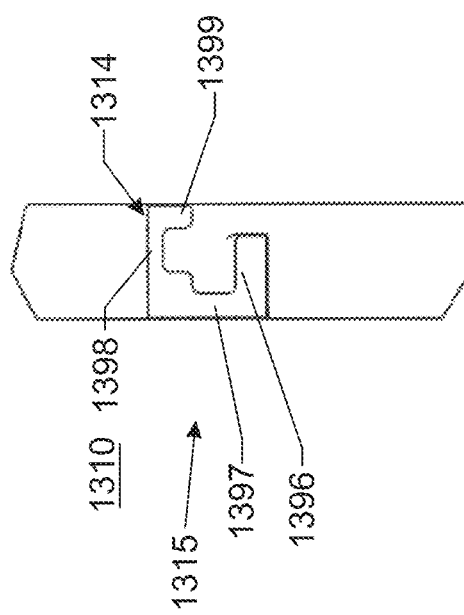
Figure 305:
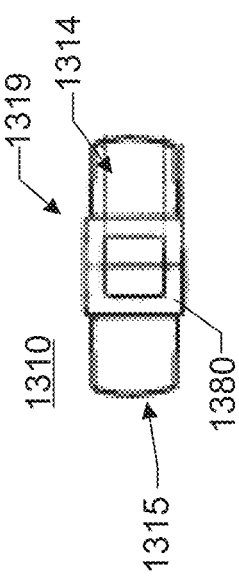
Figure 308:
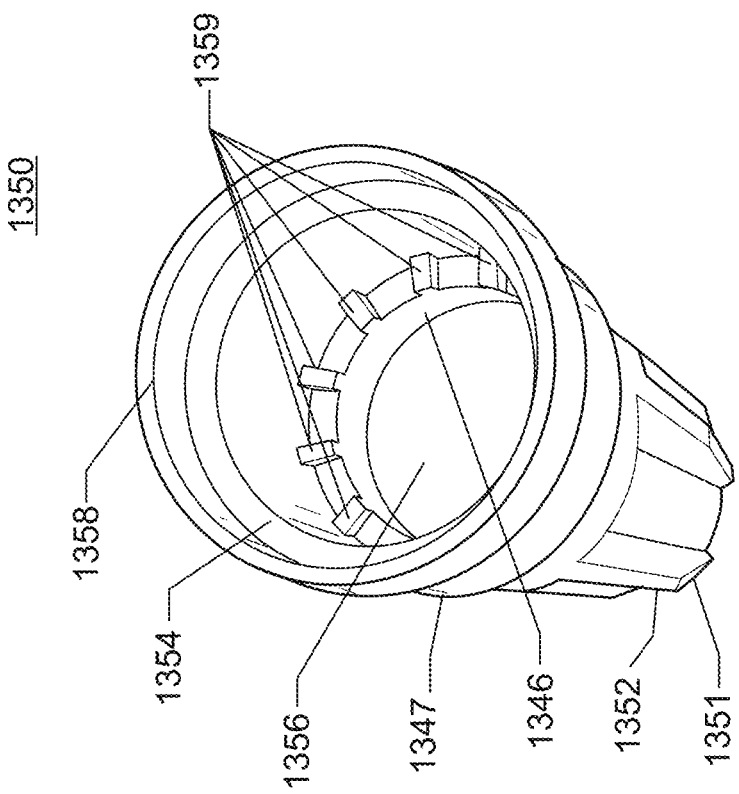
Figure 307:
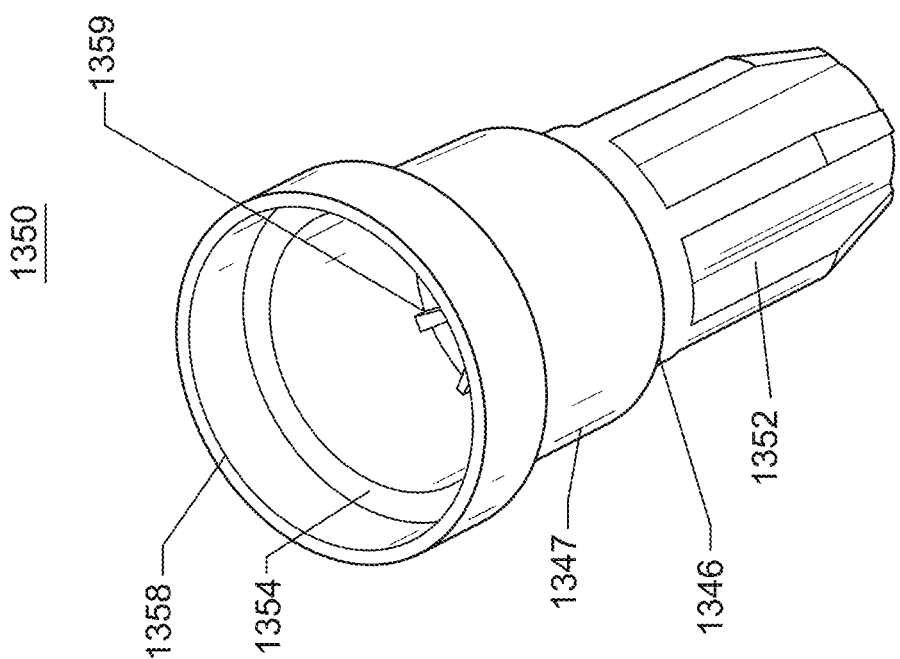
Figure 310:
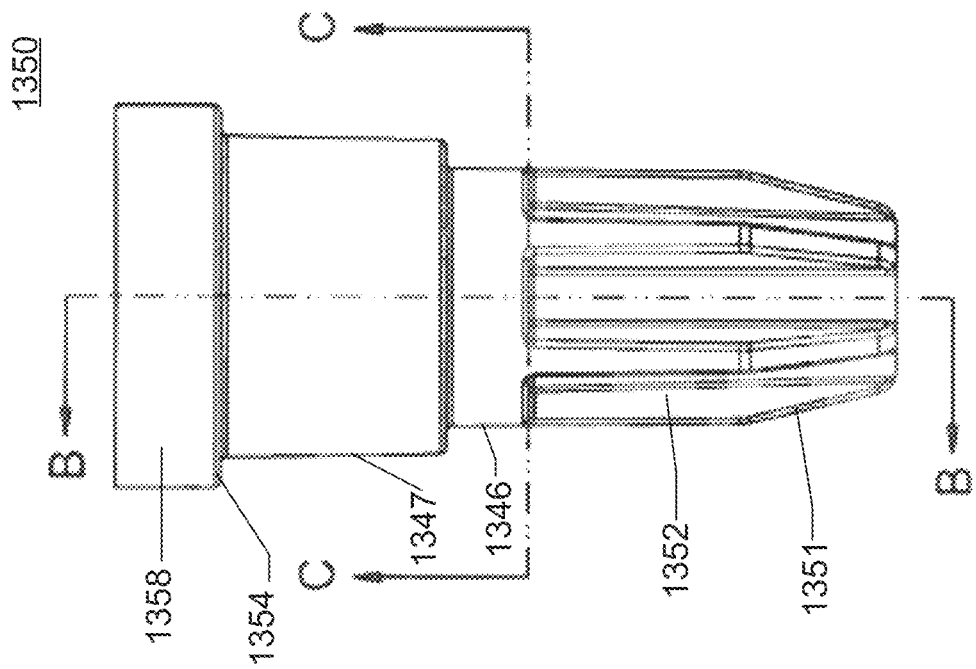
Figure 309:
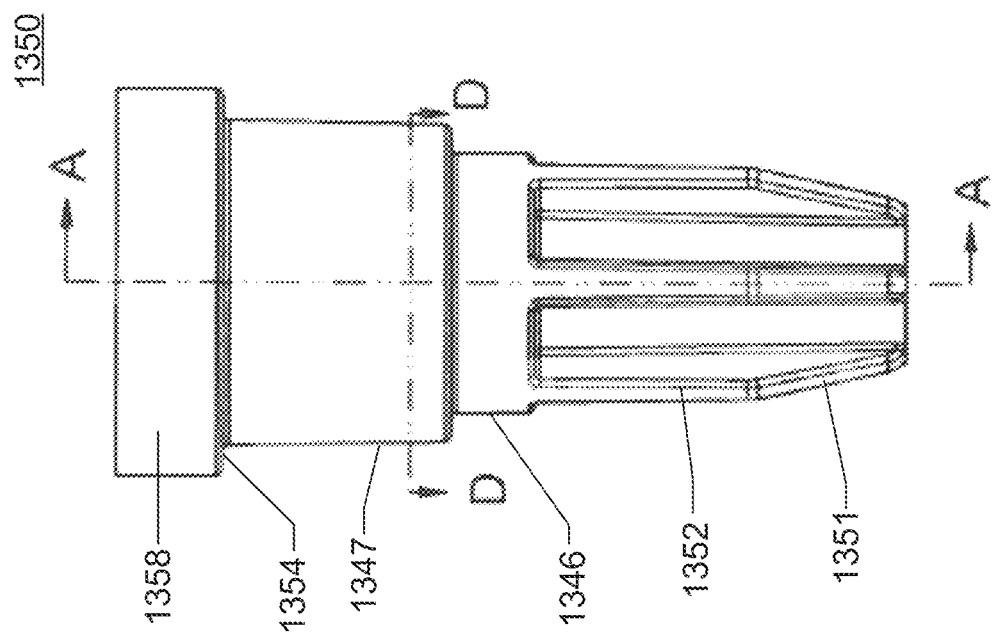
Figure 312:
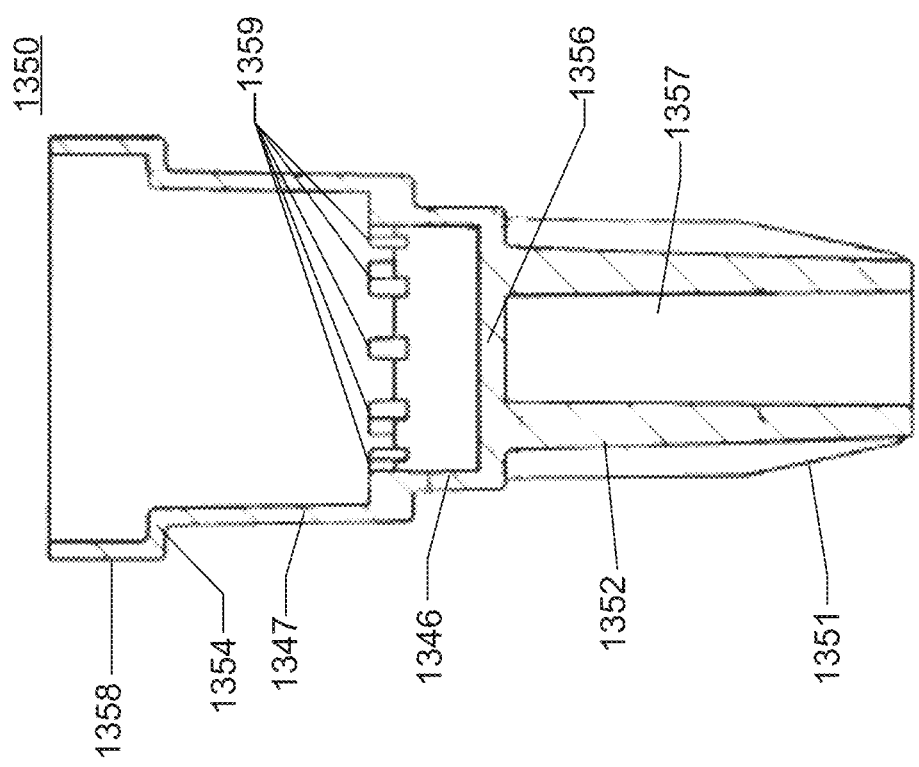
Figure 311:
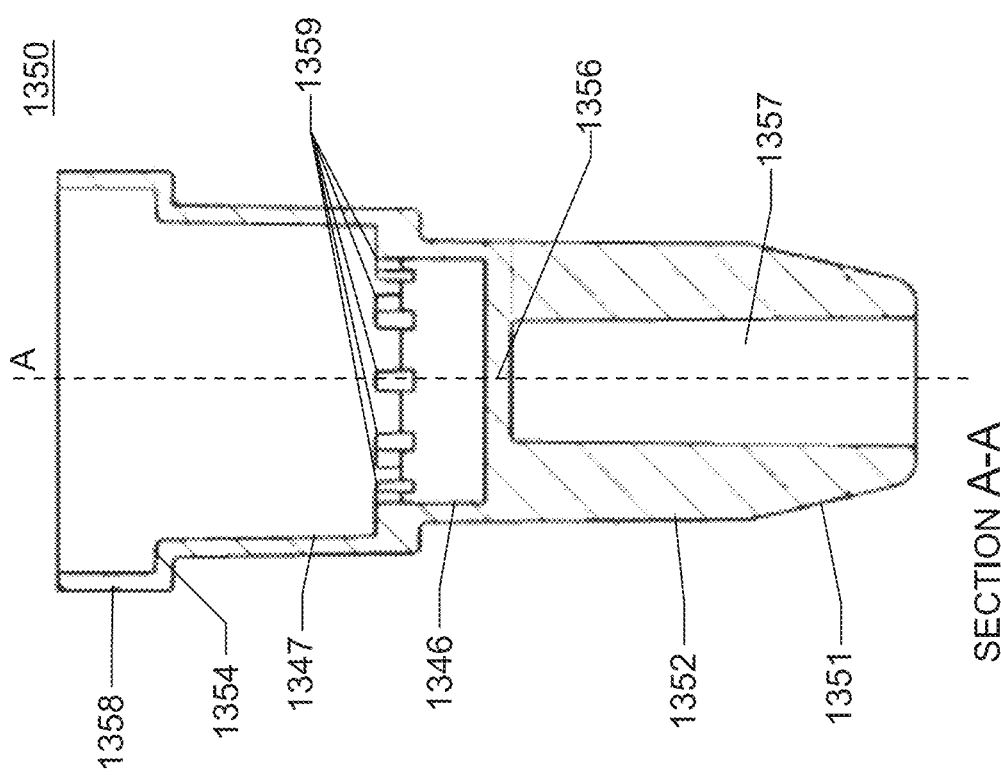
Figure 314:
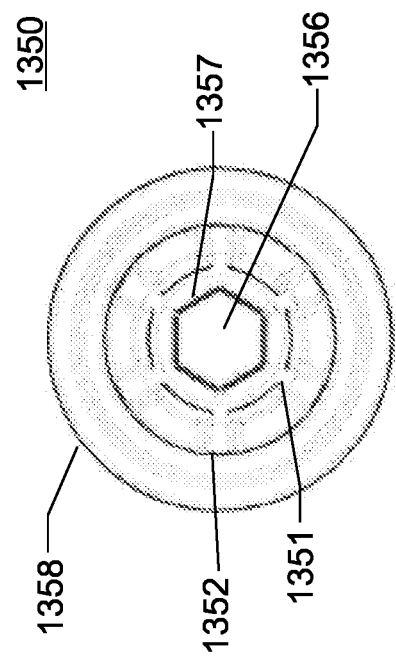
Figure 316:
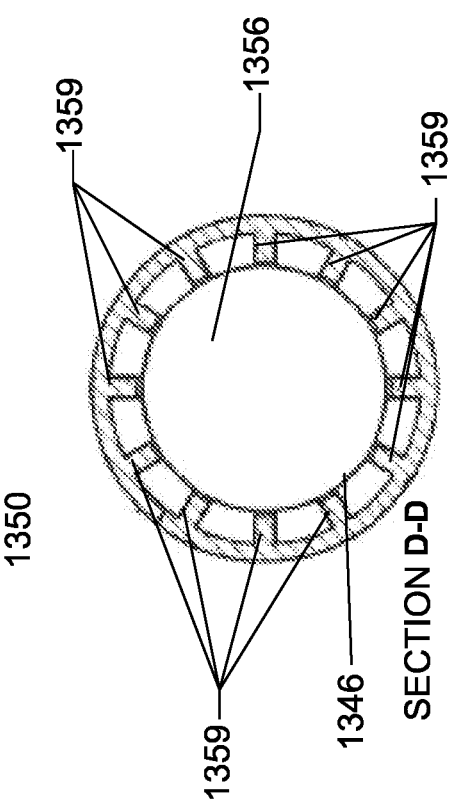
Figure 313:
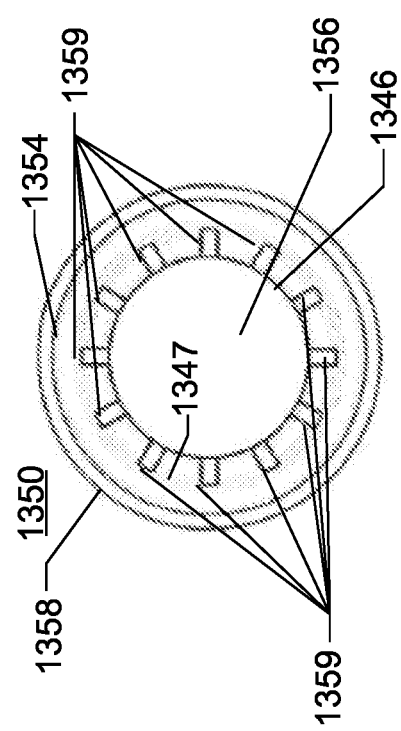
Figure 315:
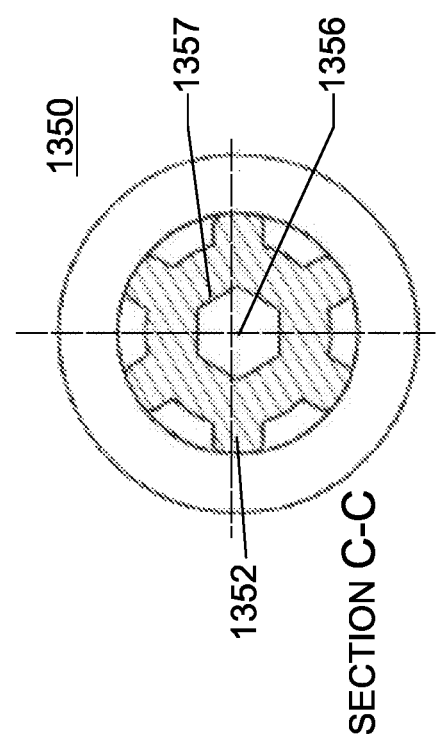
Figure 319:
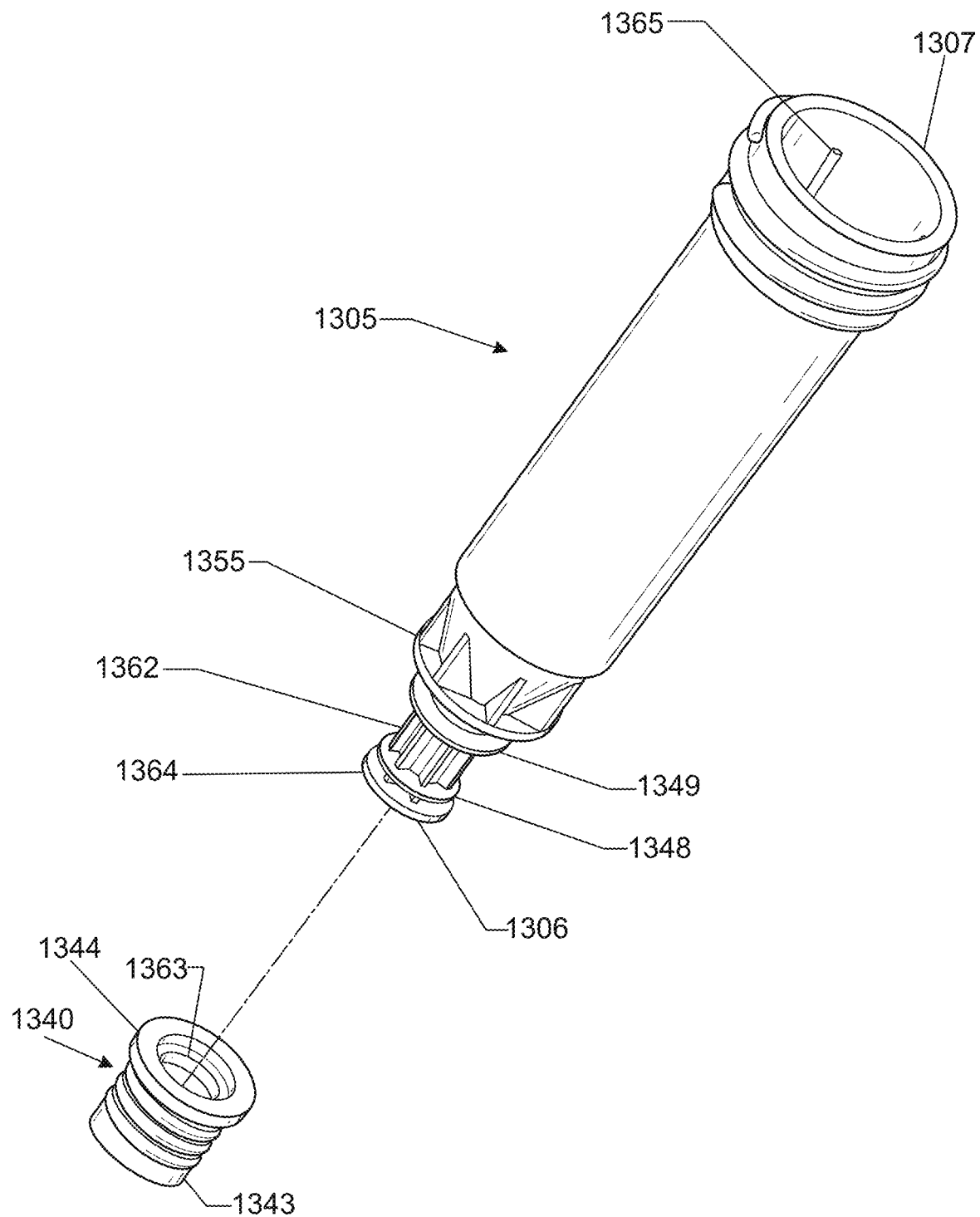
Figures 320, 321:
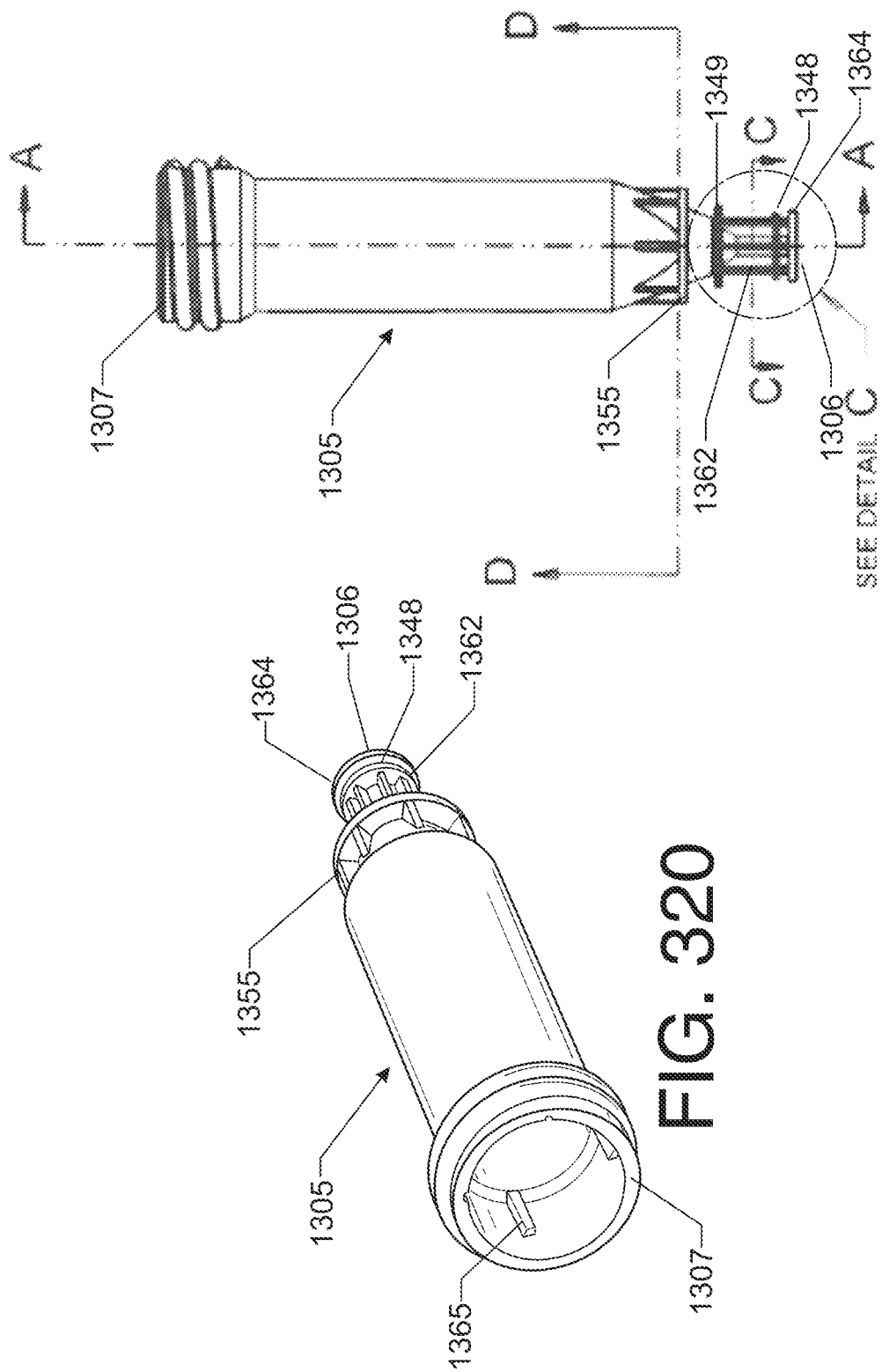
Figure 327:
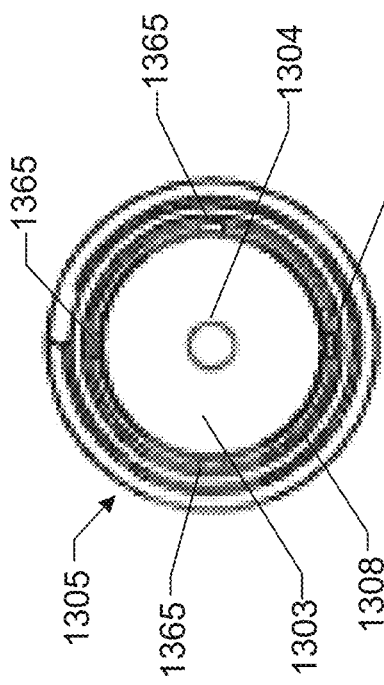
Figure 326:
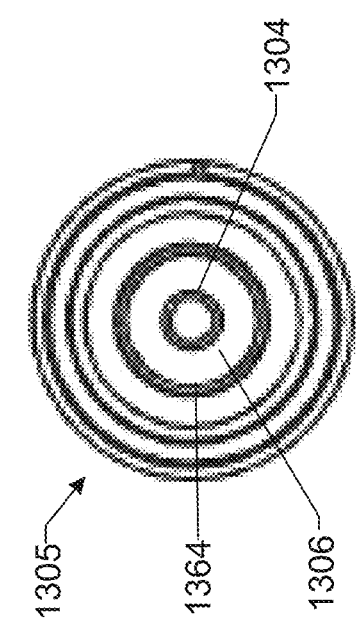
Figure 329:
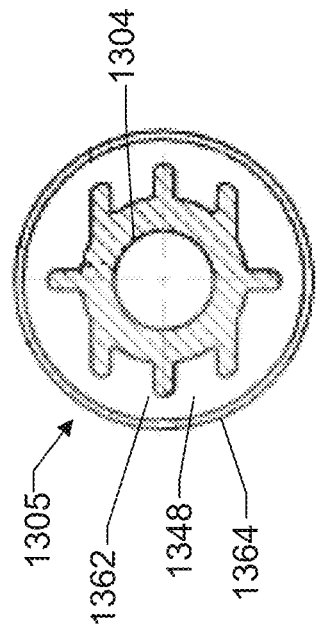
Figure 328:
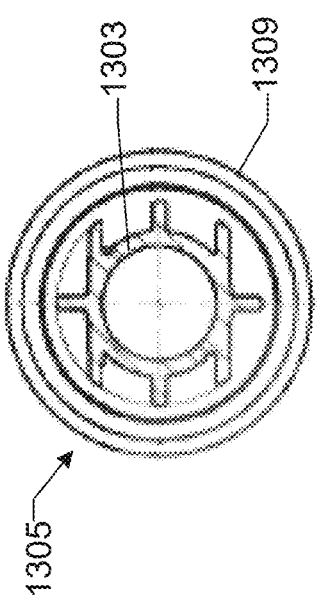
Figure 336:
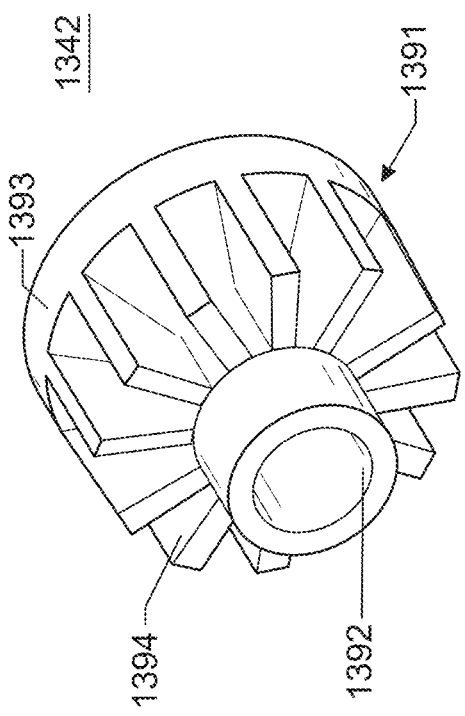
Figure 338:
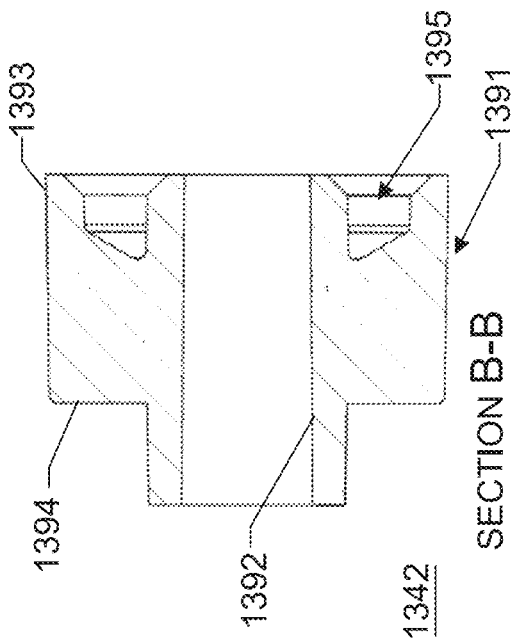
Figure 335:
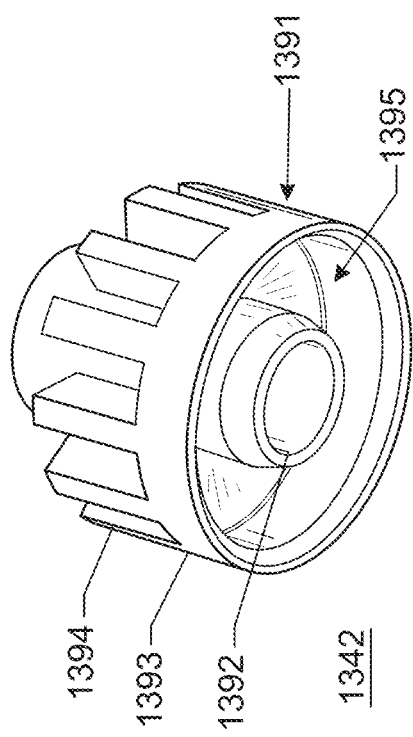
Figure 337:
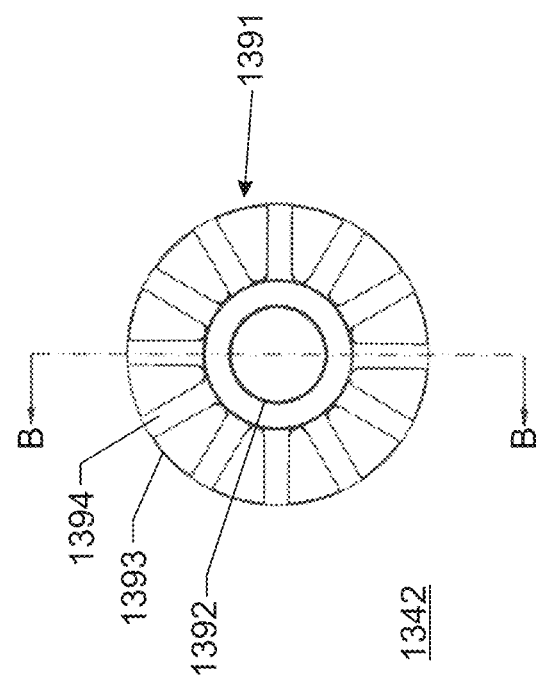

FIG. 147 shows a detail view of the first end and pellet region of the body of Detail A of FIG. 144;

FIG. 148 shows a detail view of the second end of the body of Detail B of FIG. 144;

FIG. 149 shows a side elevation view of the body of FIG. 142 having a pull tab according to some embodiments discussed herein;

FIG. 150 shows a cross-sectional view of the body of FIG. 149 taken along Section A-A;

FIG. 151 shows a perspective view of the body of FIG. 149;

FIG. 152 shows a bottom plan view of the body of FIG. 149;

FIG. 153 shows a detail view of the pull tab, first end of the body, and pellet region of Detail C of FIG. 150;

FIGS. 154-157 show various views of a sample collecting vessel according to some of the embodiments discussed herein;

FIG. 158 shows MALDI-TOF ID Results for Recovered Suspensions in Example 1;

FIGS. 159-160 shows a comparison of historical colony control results versus VITEK2 AST card results for the Suspension of Example 1;

FIG. 161 shows a side elevation view of another embodiment of a separation container having a raised plunger according to some embodiments discussed herein;

FIG. 162 shows a top plan view of the separation container of FIG. 161;

FIG. 163 shows a cross-sectional view of the separation container of FIG. 161;

FIG. 164 shows another side elevation view of the separation container of FIG. 161;

FIG. 165 shows another cross-sectional view of the separation container of FIG. 161;

FIG. 166 shows a portion of the cross-sectional view of FIG. 165 showing Detail B;

FIG. 167 shows another side elevation view of the separation container of FIG. 161;

FIG. 168 shows another top plan view of the separation container of FIG. 161;

FIG. 169 shows another side elevation view of the separation container of FIG. 161;

FIG. 170 shows a cross-sectional view of the separation container of FIG. 169 taken along section B-B with the plunger in a piercing position according to some embodiments discussed herein;

FIG. 171 shows a portion of the cross-sectional view of FIG. 170 showing Detail C;

FIG. 172 shows another side elevation view of the separation container of FIG. 161 with the plunger down according to some embodiments discussed herein;

FIG. 173 shows a top elevation view of the separation container of FIG. 172;

FIG. 174 shows a cross-sectional view of the separation container of FIG. 172 taken along section A-A;

FIG. 175 shows another side elevation view of the separation container of FIG. 172;

FIG. 176 shows a cross-sectional view of the separation container of FIG. 175 taken along section B-B;

FIG. 177 shows a portion of the cross-sectional view of FIG. 176 showing Detail A;

FIG. 178 shows an exploded view of the separation container of FIG. 161;

FIG. 179 shows another exploded view of the separation container of FIG. 161;

FIG. 180 shows an exploded view of another embodiment of a separation container according to some embodiments discussed herein;

FIG. 181 shows a portion of the exploded view of FIG. 180;

FIGS. 182-185 and 187-193 show a plunger and a retainer according to some embodiments discussed herein;

FIG. 186 shows the plunger and retainer of FIGS. 182-185 and 187-193 inserted into a body according to some embodiments discussed herein;

FIG. 194 shows a separation container having a sample collecting vessel according to some embodiments discussed herein;

FIG. 195 shows a cross-sectional view of the separation container of FIG. 194;

FIG. 196 shows a perspective view of the separation container of FIG. 194;

FIG. 197 shows a portion of the cross-sectional view of FIG. 195 showing Detail F;

FIG. 198 shows an exploded view of a two-piece coupling cap according to some embodiments discussed herein;

FIG. 199 shows a side elevation view of the two-piece coupling cap of FIG. 198;

FIG. 200 shows a cross-sectional view of the two-piece coupling cap of FIG. 198;

FIG. 201 shows a side elevation view of another embodiment of a body and coupling cap according to some embodiments discussed herein;

FIG. 202 shows a cross-sectional view of the body and coupling cap of FIG. 201;

FIG. 203 shows a portion of the cross-sectional view of FIG. 202 showing Detail A;

FIG. 204 shows a portion of the side view of FIG. 205 showing Detail B;

FIG. 205 shows another side view of the body and coupling cap of FIG. 201;

FIG. 206 shows a side elevation view of another embodiment of a body and coupling cap according to some embodiments discussed herein;

FIG. 207 shows a cross-sectional view of the body and coupling cap of FIG. 206;

FIG. 208 shows a portion of the cross-sectional view of FIG. 207 showing Detail A;

FIG. 209 shows another side view of the body and coupling cap of FIG. 206;

FIG. 210 shows a portion of the side elevation view of the body and coupling cap of FIG. 209 showing Detail B;

FIG. 211 shows an exploded view of the body and coupling cap of FIG. 206;

FIG. 212 shows a side elevation view of yet another embodiment of a separation container according to some embodiments discussed herein;

FIG. 213 shows a cross-sectional view of the separation container of FIG. 212;

FIG. 214 shows a portion of the cross-sectional view of the separation container of FIG. 212 showing Detail A;

FIG. 215 shows another side elevation view of the separation container of FIG. 212;

FIG. 216 shows a cross-sectional view of the separation container of FIG. 215;

FIG. 217 shows a portion of the cross-sectional view of FIG. 216 showing Detail B;

FIG. 218 shows a side elevation of the separation container of FIG. 212 with the plunger down according to some embodiments discussed herein;

FIG. 219 shows a cross-sectional view of the separation container of FIG. 218 showing the rheological control member having floated to the top of the body according to some embodiments discussed herein;

FIG. 220 shows an exploded view of the separation container of FIG. 212;

FIG. 221 shows a side elevation view of the plunger, retainer, and rheological control member of FIG. 213;

FIG. 222 shows a cross-sectional view of the plunger, retainer, and rheological control member of FIG. 221;

FIG. 223 shows a finite element analysis of the deformation of a low density polyethylene body during centrifugation;

FIG. 224 shows an exploded perspective view of another separation container according to some embodiments discussed herein;

FIG. 225 shows a side elevation view of the separation container of FIG. 224;

FIG. 226 shows a cross-sectional view of the separation container of FIG. 225 taken along line A-A;

FIG. 227 shows a top plan view of the separation container of FIG. 224;

FIG. 228 shows a side elevation view of the separation container of FIG. 225 rotated ninety degrees;

FIG. 229 shows a cross-sectional view of the separation container of FIG. 228 taken along line B-B;

FIG. 230 shows a partial cross-sectional view of a portion of the separation container indicated as Detail B in FIG. 229;

FIG. 231 shows a top plan view of the separation container of FIG. 224;

FIG. 232 shows a side elevation view of the separation container of FIG. 224 without a cap according to some embodiments discussed herein;

FIG. 233 shows a side elevation view of the separation container of FIG. 232 rotated ninety degrees;

FIG. 234 shows a cross-sectional view of the separation container of FIG. 233 taken along line B-B;

FIG. 235 shows a partial cross-sectional view of a portion of the separation container indicated as Detail C in FIG. 234;

FIG. 236 shows a side elevation view of the separation container of FIG. 224 without a cap and with the plunger depressed according to some embodiments discussed herein;

FIG. 237 shows a side elevation view of the separation container of FIG. 236 rotated ninety degrees;

FIG. 238 shows a cross-sectional view of the separation container of FIG. 237 taken along line B-B;

FIG. 239 shows a partial cross-sectional view of a portion of the separation container indicated as Detail A in FIG. 238;

FIG. 240 shows a side elevation view of the body and coupling member of the separation container of FIG. 224 according to some embodiments discussed herein;

FIG. 241 shows an exploded view of the body and coupling member of FIG. 240;

FIG. 242 shows a partial side elevation view of a portion of the body and the coupling member indicated as Detail A in FIG. 240;

FIG. 243 shows a perspective view of the body of FIG. 224 according to some embodiments discussed herein;

FIG. 244 shows a top plan view of the body of FIG. 243;

FIG. 245 shows a side elevation view of the body of FIG. 243;

FIG. 246 shows a cross-sectional view of the body of FIG. 245 taken along line A-A;

FIG. 247 shows a bottom plan view of the body of FIG. 243;

FIG. 248 shows a partial cross-sectional view of a portion of the body indicated as Detail A in FIG. 246;

FIG. 249 shows a partial cross-sectional view of a portion of the body indicated as Detail B in FIG. 246;

FIG. 250 shows a partial side elevation view of a portion of the body indicated as Detail C in FIG. 245;

FIG. 251 shows a partial top plan view of a portion of the body indicated as Detail D in FIG. 244;

FIG. 252 shows a cross-sectional view of the body of FIG. 245 taken along line C-C;

FIG. 253 shows a cross-sectional view of the body of FIG. 245 taken along line D-D;

FIG. 254 shows a perspective view of the coupling member of FIG. 240 according to some embodiments discussed herein;

FIG. 255 shows a side elevation view of the coupling member of FIG. 254;

FIG. 256 shows a cross-sectional view of the coupling member of FIG. 255 taken along a plane that vertically bisects the coupling member;

FIG. 257 shows a bottom plan view of the coupling member of FIG. 240;

FIG. 258 shows a partial side view of a portion of the coupling member indicated as Detail A in FIG. 255;

FIG. 259 shows a side elevation view of a plunger of the separation container of FIG. 224 according to some embodiments discussed herein;

FIG. 260 shows a partial side elevation view of a portion of the plunger indicated as Detail A in FIG. 259;

FIG. 261 shows a perspective view of a plunger seal of the plunger of FIG. 259;

FIG. 262 shows a perspective view of the plunger of FIG. 259 without the plunger seal according to some embodiments discussed herein;

FIG. 263 shows a bottom plan view of the plunger of FIG. 262;

FIG. 264 shows a top plan view of the plunger of FIG. 262;

FIG. 265 shows a side elevation view of the plunger of FIG. 262;

FIG. 266 shows a partial side elevation view of a portion of the plunger indicated as Detail A in FIG. 265;

FIG. 267 shows a side perspective view of the plunger of FIG. 265 rotated ninety degrees;

FIG. 268 shows a partial side elevation view of a portion of the plunger indicated as Detail B in FIG. 265;

FIG. 269 shows a perspective view of a flexible sealing member of the separation container of FIG. 224;

FIG. 270 shows a side elevation view of the flexible sealing member of FIG. 269;

FIG. 271 shows a cross-sectional view of the flexible sealing member of FIG. 270 taken along a plane that vertically bisects the flexible sealing member;

FIG. 272 shows a top plan view of the flexible sealing member of FIG. 269;

FIG. 273 shows a side elevation view of the flexible sealing member of FIG. 269 being actuated;

FIG. 274 shows a cross-sectional view of the flexible sealing member of FIG. 273;

FIG. 275 shows a side elevation view of the separation container of FIGS. 224-239 having its flexible sealing member and plunger actuated according to some embodiments discussed herein;

FIG. 276 shows a cross-sectional view of the separation container of FIG. 275;

FIG. 277 shows an exploded perspective view of another separation container with an end cap according to some embodiments discussed herein;

FIG. 278 shows a side elevation view of the separation container of FIG. 277;

FIG. 279 shows a cross-sectional view of the separation container of FIG. 277;

FIG. 280 shows a partial cross-sectional view of the separation container indicated as Detail B in FIG. 279;

FIG. 281 shows a partial cross-sectional view of the separation container indicated as Detail B in FIG. 280;

FIG. 282 shows a top plan view of the flexible sealing member of FIG. 277;

FIG. 283 shows a side elevation view of the separation container of FIG. 277 without an end cap according to some embodiments;

FIG. 284 shows a cross-sectional view of the separation container of FIG. 283;

FIG. 285 shows a partial cross-sectional view of the separation container indicated as Detail C in FIG. 284;

FIG. 286 shows a side elevation view of the separation container of FIG. 277 having a plunger actuated according to some embodiments;

FIG. 287 shows a cross-sectional view of the separation container of FIG. 286;

FIG. 288 shows a partial cross-sectional view of the separation container indicated as Detail A in FIG. 287;

FIG. 289 shows a side elevation view of a flexible sealing member according to some embodiments;

FIG. 290 shows a cross-sectional view of the flexible sealing member of FIG. 289;

FIG. 291 shows a perspective view of the flexible sealing member of FIG. 289;

FIG. 292 shows a top plan view of the flexible sealing member of FIG. 289;

FIG. 293 shows a partial cross-sectional view of the separation container indicated as Detail A in FIG. 290;

FIG. 294 shows a partial cross-sectional view of the separation container indicated as Detail B in FIG. 290;

FIG. 295 shows a partial cross-sectional view of the separation container indicated as Detail C in FIG. 290;

FIG. 296 shows a side elevation view of a plunger according to some embodiments;

FIG. 297 shows a perspective view of a plunger seal of the plunger of FIG. 296 according to some embodiments;

FIG. 298 shows a partial side elevation view of the plunger indicated as Detail A in FIG. 296;

FIG. 299 shows another side elevation view of the plunger of FIG. 296;

FIG. 300 shows yet another side elevation view of the plunger of FIG. 296;

FIG. 301 shows a perspective view of the plunger of FIG. 296;

FIG. 302 shows a partial side elevation view of the plunger indicated as Detail A in FIG. 299;

FIG. 303 shows a partial side elevation view of the plunger indicated as Detail B in FIG. 299;

FIG. 304 shows a partial side elevation view of the plunger indicated as Detail C in FIG. 299;

FIG. 305 shows a top plan view of the plunger of FIG. 296;

FIG. 306 shows a bottom plan view of the plunger of FIG. 296;

FIG. 307 shows a perspective view of an end cap according to some embodiments;

FIG. 308 shows another perspective view of the end cap of FIG. 307;

FIG. 309 shows a side elevation view of the end cap of FIG. 307;

FIG. 310 shows another side elevation view of the end cap of FIG. 307;

FIG. 311 shows a cross-sectional view of the end cap in FIG. 309 taken along the line A-A;

FIG. 312 shows a cross-sectional view of the end cap in FIG. 310 taken along the line B-B;

FIG. 313 shows a top plan view of the end cap of FIG. 307;

FIG. 314 shows a bottom plan of the end cap of FIG. 307;

FIG. 315 shows a cross-sectional view of the end cap in FIG. 310 taken along the line C-C;

FIG. 316 shows a cross-sectional view of the end cap in FIG. 309 taken along the line D-D;

FIG. 317 shows a side elevation view of a body of a separation container with a coupling member according to some embodiments;

FIG. 318 shows a partial side elevation view of the body and coupling member of FIG. 317;

FIG. 319 shows an exploded perspective view of the body and coupling member of FIG. 317;

FIG. 320 shows a perspective view of the body of FIG. 317 according to some embodiments;

FIG. 321 shows a side elevation view of the body of FIG. 320;

FIG. 322 shows a cross-sectional view of the body of FIG. 321 taken along line A-A;

FIG. 323 shows a partial cross-sectional view of the body indicated as Detail B in FIG. 322;

FIG. 324 shows a partial cross-sectional view of the body indicated as Detail A in FIG. 322;

FIG. 325 shows a partial cross-sectional view of the body indicated as Detail C in FIG. 321;

FIG. 326 shows a bottom plan view of the body of FIG. 320;

FIG. 327 shows a top plan view of the body of FIG. 320;

FIG. 328 shows a cross-sectional view of the body of FIG. 321 taken along line D-D;

FIG. 329 shows a cross-sectional view of the body of FIG. 321 taken along line C-C;

FIG. 330 shows a perspective view of the coupling member of FIG. 317 according to some embodiments;

FIG. 331 shows a side elevation view of the coupling member of FIG. 330;

FIG. 332 shows a cross-sectional view of the coupling member of FIG. 330;

FIG. 333 shows a partial side elevation view of the coupling member indicated as Detail A in FIG. 331;

FIG. 334 shows a top elevation view of the coupling member of FIG. 330;

FIG. 335 shows a perspective view of a rheological control member according to some embodiments;

FIG. 336 shows another perspective view of the rheological control member of FIG. 335;

FIG. 337 shows a bottom plan view of the rheological control member of FIG. 335;

FIG. 338 shows a cross sectional view of the rheological control member of FIG. 337 taken along line B-B;

FIG. 339 shows a perspective view of a retainer according to some embodiments;

FIG. 340 shows another perspective view of the retainer of FIG. 339;

FIG. 341 shows a side elevation view of the retainer of FIG. 339;

FIG. 342 shows a top plan view of the retainer of FIG. 339;

FIG. 343 shows a bottom plan view of the retainer of FIG. 339; and

FIG. 344 shows a cross-sectional view of the retainer of FIG. 342 taken along line A-A.

DETAILED DESCRIPTION

The present invention will now be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Biological testing of microorganisms is a delicate, time-sensitive, and often dangerous process that requires accuracy, precision, and preferably speed. The testing and analysis is carefully controlled, particularly when working with pathogenic microorganisms, using a repeatable, robust process and apparatus that allows the operator to easily, safely, sterilely, and quickly manipulate the sample. Accordingly, there is a technical problem of providing a controlled, repeatable process and apparatus that allows an operator to easily, safely, sterilely, and quickly prepare a sample for further testing.

Disclosed herein are methods and apparatuses for recovering microorganisms from a test sample. Some methods of characterizing and/or identifying microorganisms within a sample may require initially separating (e.g., separating, isolating, or pelleting) the microorganism, followed by recovery for subsequent downstream testing. The methods discussed herein may include separating, recovering, characterizing, and/or identifying a sample using a separation container. The separation container may be configured to separate a microorganism from a sample via centrifugation and to recover a portion of the sample for use or testing. The sample may include a liquid culture (e.g., a blood culture) from which the microorganism may be separated. Embodiments of the present invention also allow whole blood to be used as the sample without culturing beforehand. In some further embodiments, a culture medium may be used in a sample collecting vessel to culture any organisms present after the separating and recovery steps. In some embodiments, the resulting separated microorganism may be tested, either in its isolated form or resuspended in solution, in one or more downstream tests, and the downstream testing may occur within a sample collecting vessel attached to the body of the separation container or may occur separately (e.g., the sample may be separately deposited onto a downstream testing apparatus).

As used herein, the term "pellet" is intended to encompass any sample of microorganisms that has been compressed or deposited into a mass of microorganisms. For example, microorganisms from a sample can be compressed or deposited into a mass at the bottom of a tube by centrifugation. In one embodiment, the term includes a collection of microorganisms (and/or components thereof) on the bottom and/or sides of a container following centrifugation. In accordance with this invention, microorganisms may be pelleted away (e.g., as a substantially purified microorganism pellet) from non-microorganism components that may otherwise interfere with characterization and/or identification. Non-microorganism components that are separated away from the microorganisms may include non-microorganism cells (e.g., blood cells or other tissue cells, and/or their soluble fractions) and/or any components thereof.

Prior separation devices and techniques suffer from many deficiencies that hinder the testing process. For example, microorganisms may be separated by lysing the sample and then repeatedly washing, decanting, and spinning the sample until the microorganism is substantially separated. These processes often require multiple devices, additional user handling, and a high-degree of expertise and training, while producing less-than-optimal results. For example, when exposed to centrifugal force, different species of microorganism may produce varying consistencies of pellet. Prior devices may fail to recover the pellet consistently depending on the consistency of the pellet. Further, substantial training is required to successfully recover a pellet without contaminating the sample, losing the sample, or exposing the user to the microorganism. Moreover, prior separation and recovery techniques were very harsh on the microorganisms, making it difficult to obtain the highly viable microbial cells needed for certain downstream tests such as antibiotic susceptibility testing (AST), growth-based identification methods, or the culture of microorganisms recovered from whole blood. Prior separation devices also frequently damage the microorganism such that downstream testing with viable samples is imprecise or impossible. The present separation container (e.g., separation container 100) may allow an untrained user to recover a pellet with minimal training and effort and with greater consistency than prior devices.

The inventors have developed a separation container and associated apparatus, systems, and methods that solve these deficiencies. Namely, the separation container and associated apparatus, systems, and methods described herein enable a user to separate a microorganism from a sample in fewer operations with only a single centrifugation step. The separation container and associated apparatus, systems, and methods described herein also enable a user to separate and test the sample without handling the microorganism and without destroying the microorganism so that viable samples may be grown and tested downstream.

Test samples that may be separated (e.g., separated, isolated, or pelleted) using the separation containers of the present invention include both clinical and non-clinical samples in which microorganism presence and/or growth is, or may be suspected, as well as samples of materials that are routinely or occasionally tested for the presence of microorganisms. For example, the test sample can be the culture broth from a culture of a clinical or non-clinical specimen sample. In some embodiments, the test sample is a sample taken from a patient without further culturing, e.g., a whole blood sample, a urine sample, a nasal sample, a buccal swab sample, or the like. The present invention finds use in both medical and veterinary applications. Typical specimen samples that may be cultured and subsequently subjected to a separation technique for separation, isolation, or pelleting of microorganisms contained therein, may include, blood, serum, plasma, platelets, red blood cells, white blood cells, blood fractions, joint fluid, urine, nasal samples, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. Examples of non-clinical samples include foodstuffs (e.g., milk, meat products, vegetables, fruits, beverages, and puddings), cell cultures, biopharmaceuticals, cosmetics, water, parenterally-administered fluids, and the like. The above specimen types may also be used as samples for the present invention without culturing beforehand. As described further herein, the separation container may produce viable samples suitable for direct downstream testing without further culturing and without requiring washing steps.

In one embodiment, as described further herein, the separation device or container may employ a density cushion (e.g., density cushion 101 shown in FIG. 3) for the separation of microorganisms from a test sample. For example, the density cushion may have a density that is less than the microorganisms being separated but greater than the remainder of the sample. For example, a test sample known to contain or that may contain microorganisms can be loaded over a density cushion contained within the device or container, and the container or device centrifuged to separate (e.g., separate, isolate, or pellet) the microorganisms from other elements of the test sample. In accordance with this embodiment, the separation device or container will have sufficient volume to hold a density cushion and a test sample. In one embodiment, the container fits or can be fitted into a centrifuge rotor.

The volume of the container can be from about 0.1 ml to about 50 ml, e.g., from about 0.5 ml to about 25 ml, from about 1 ml to about 15 ml, e.g., from about 1.5 ml to about 8 ml. If the separation is done on a microscale, the volume of the container can be from about 2 µl to about 100 µl, e.g., from about 5 µl to about 50 µl. In some embodiments using a deformable or squeezable container, described below, the volume of the container may be less than 2 ml. In some embodiments using a plunger, the volume of the container may be from 10 ml to 15 ml, from 10 ml to 50 ml, from 15 ml to 50 ml, greater than or equal to 10 ml, or less than or equal to 50 ml.

In some embodiments, as discussed in more detail herein, the separation device or container can be preloaded with the density cushion. In some embodiments, a rheological control member (liquid or solid) can be placed on top of the density cushion before the sample is laid or layered on top in order to prevent any mixing of the density cushion and the sample. For example, an annular barrier (e.g., rheological control member 200 described below) can be placed over the prepackaged density cushion to prevent mixing of the density cushion with a test sample added at a later time. In yet another embodiment, the separation device or container can be preloaded with a density cushion and subsequently preloaded with a lysis solution. In some embodiments, the separation container may be hermetically sealed to prevent contamination.

The separation of the microorganism may be carried out by a centrifugation step in which a test sample (e.g., a lysed sample) is placed on top of the density cushion in the separation container and the container centrifuged under conditions which allow the microorganisms to be isolated (e.g., the microorganisms can form a pellet at the bottom and/or sides of the container). The separation container is centrifuged at a sufficient acceleration and for a sufficient time for the microorganisms to pass through the density cushion and be separated (e.g., a pellet formed) from other components of the test sample. The centrifugation acceleration can be about 1,000×g to about 20,000×g, e.g., about 2,000×g to about 15,000×g, e.g., about 3,000×g to about 10,000×g, etc. The centrifugation time can be about 30 seconds to about 60 minutes, e.g., about 1 minute to about 30 minutes, e.g., about 2 minute to about 10 minutes. The centrifugation can be carried out at a temperature of about 2° C. to about 45° C., e.g., about 15° C. to about 40° C., e.g., about 20° C. to about 30° C. In accordance with this embodiment, other components of the sample (e.g., non-microorganisms or components thereof that may be present in the sample) stay on top of the density cushion or within the top portion of the density cushion. This separation step isolates the microorganisms from the remaining materials in the sample, such as plasma, culture media, cell debris, and/or other components such as enzymes, sugars and nucleic acids that might interfere with testing of the recovered microorganisms. In one embodiment, the density cushion also serves to separate live microorganisms from dead microorganisms (which do not pass through the density cushion). In another embodiment the density cushion does not comprise a density gradient, either before or after the centrifugation. In other words, the separation container is not centrifuged for a sufficient amount of time and/or acceleration for the material making up the density cushion to form a density gradient.

First Embodiment

Figure 89:
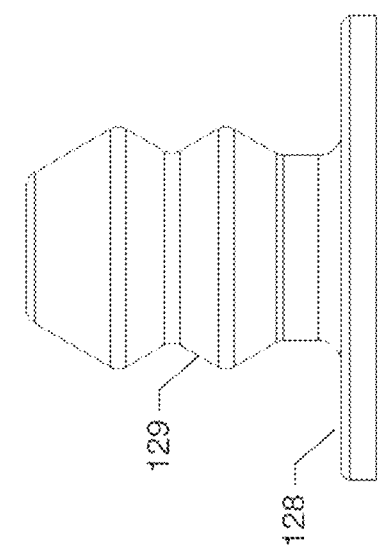
Figure 86:
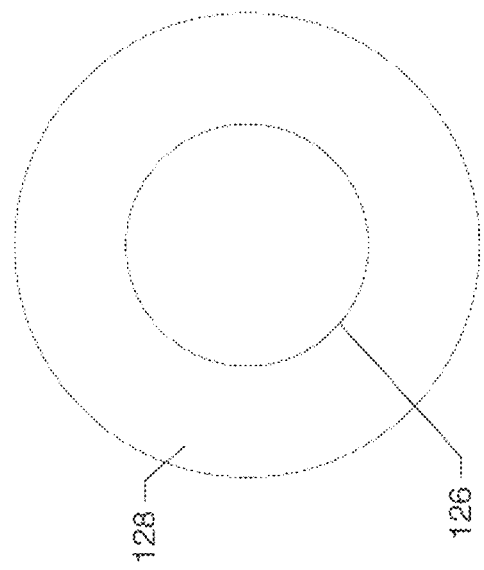
Figure 88:
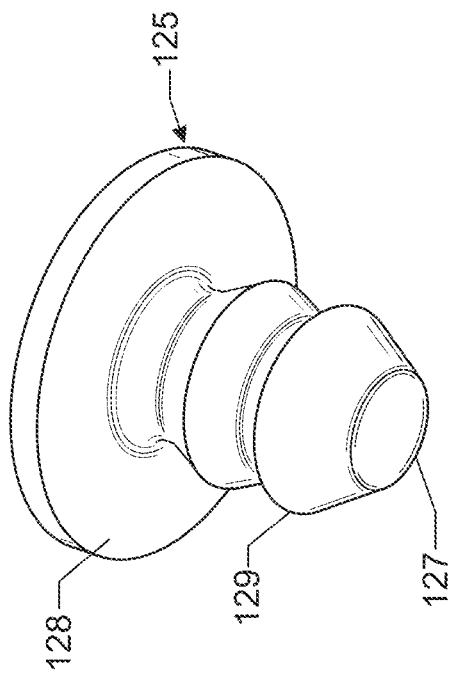

Turning to the figures, embodiments of the separation container described herein are shown. With reference to FIGS. 1-89, a first embodiment of the separation container 100 is shown. As discussed herein, the entire separation container 100 or separable portions thereof may be placed in a centrifugation assembly to separate a microorganism from a sample disposed in the container. In some embodiments, the separation container 100 may include a body 105 in which the sample may be disposed and a plunger 110, 115 in the body for extracting the separated microorganism after centrifugation. The separation container 100 may further include a seal 120 for sealing a first end 106 of the body 105 and holding the sample in the body 105 until the user actuates the plunger 110, 115. The separation container 100 may also include a flexible sealing member 125 and cap 130 assembly closing a second end 107 of the body 105 while allowing the user to actuate the plunger 110, 115. In some embodiments, the separation container 100 may include a sample collecting vessel 135 into which the separated microorganism may be extracted, and the vessel 135 may be attached to the body 105 via an adaptor 140 and threaded connector 145. After a pellet of microorganism is expressed into the sample collecting vessel 135, the vessel 135 may be vortexed to dissolve the pellet in a media (e.g., saline) in the vessel. Further views of the sample collecting vessel 135 are shown in FIGS. 154-157. In some further embodiments, the body 105 may include one or more brackets (e.g., hexagonal bracket 150 shown in FIG. 1) for engaging the centrifugation assembly and providing support for the separation container. The hexagonal bracket 150 may allow the user to grip the separation container and may support the separation container in the centrifuge holder. In some embodiments, the hexagonal bracket 150 may adapt the separation container to one or more different centrifuge holders, and in some embodiments, the hexagonal bracket 150 may suspend the base of the separation container above the base of the centrifuge. The projections may also aid in manufacturing the separation container. For example, the projections may be an alignment aid. In some embodiments, the projections are designed with one or more flat surfaces. For example, two opposing flat surfaces may be used instead of the hexagonal orientation. The one or more flat surfaces engage a socket that is configured to apply consistent torque when securing the seal (e.g., a nut) to the bottom of the separation container.

With reference to FIGS. 1-13, the separation container 100 is shown having a body 105 with a plunger 110 disposed therein. The body 105 includes a first end 106, which defines an opening in the body, and a second end 107, which defines a second opening. The body 105 may include an internal chamber 108 that is sealed at the first end 106 with a seal 120. The internal chamber 108 of the body 105 may be sealed at the second end 107 with a cap 130 and/or a flexible sealing member. In some embodiments, the body (e.g., bodies 105, 505, 705, 905) of the separation container can be molded, blow-molded, or formed using other well-known techniques in the art. In general, any known plastic, glass, or transparent material, or the like, can be used for the separation device. In some embodiments, the body 105 may be made of a stiff material, such as polypropylene or a flexible material such as low density polyethylene. In embodiments using a plunger 110, 115 as described herein, the body 105 may be rigid or substantially rigid.

The internal chamber 108 of the body 105 may define a diameter radial to longitudinal axis 155 (shown in FIGS. 2, 8, and 11). In some embodiments, the diameter of the internal chamber 108 may narrow from a collection diameter at the second end 107 to a pellet diameter at the first end 106. In some embodiments, the collection diameter may be defined in a collection region 102 of the internal chamber 108, the pellet diameter may be defined in a pellet region 104 of the internal chamber 108, and a tapered region 103 may connect the pellet region with the collection region. In some embodiments, the diameter of the internal chamber 108 at the collection region 102 is greater than the diameter of the internal chamber 108 at the pellet region 104. The wall 109 of the body 105 at the tapered region 103 can have an included angle of about 20 to about 70 degrees, e.g., about 30 to about 60 degrees. In some embodiments, the included angle of the wall 109 of the body 105 at the tapered region 103 is preferably 40 degrees or less. In some embodiments, the angle between the wall 109 of the body 105 and a longitudinal axis of the body 105 at the tapered region is preferably 20 degrees or less. In some embodiments, included angle of the wall 109 of the body 105 at the tapered region 103 is preferably from 10 degrees to 40 degrees. In some embodiments, the angle between the wall 109 of the body 105 and a longitudinal axis of the body 105 at the tapered region is preferably 5 degrees to 20 degrees. In one embodiment, the lower narrow portion is less than half of the total height of the container, e.g., less than about 40%, 30%, 20%, or 10% of the total height of the container. The pellet region 104 may be a "capillary" section at the first end 106 of the body, and the pellet region 104 may be the narrowest portion of the body 105 in which the microorganism is configured to collect during centrifugation.

In each of the embodiments discussed herein the seal 120 may be disposed across the opening defined at the first end 106 of the body 105, and the seal 120 may be configured to seal the opening and prevent the sample from escaping prior to actuating the plunger 110, 115. In some embodiments, the seal 120 may be an openable membrane (e.g., as shown in the embodiments of FIGS. 1-89) that may be punctured by the plunger 110, 115 or torn off by other mechanical means. For example, the membrane may include a foil seal or other puncturable membrane (e.g., foil, paper, wax, etc.) or a thin plastic wall molded with the rest of the body 105. In some embodiments, the membrane is a film, tape, or frangible seal configured to cover the opening at the first end 106 of the body 105. The membrane may be adhered or otherwise attached to the end surface (e.g., the annular surface surrounding the opening at the first end 106) of the body 105. In one embodiment, the first end 106 comprises a textured surface to strengthen the adherence of the seal 120 to annular surface surround the opening at the first end 106. In some embodiments, the seal 120 may be a thin layer of molded material that is formed at the first end 106 of the body 105 during molding of the body. The molded material may be integral with or formed secondarily to the body 105. In one embodiment, force multipliers are associated with the seal 120, e.g., formed in the molded material, to direct the opening of the seal 120 when punctured by the plunger 110, 115.

In some other embodiments, the seal may include a nut 510 and gasket 520 (e.g., as shown in the embodiments of FIGS. 90-136). In some further embodiments, the seal may include a removable portion 720 that may be permanently cut or removed (e.g., as shown in the embodiment of FIGS. 137-144). In yet some other embodiments, the seal may include a molded breakaway section or pull tab 920 that is torn off by the user to open the internal chamber 108 (e.g., as shown in the embodiments of FIGS. 142-153).

The flexible sealing member 125 may be disposed at the second end 107 of the body 105 and may be configured to seal the opening in the body while also allowing a user to actuate the plunger 110 therethrough. The flexible sealing member 125 may seal against the body 105, such as by contacting the annular surface of the second end 107 surrounding the opening. With reference to FIGS. 86-89, detailed views of an example flexible sealing member 125 are shown in accordance with the embodiments discussed herein. In some embodiments, the flexible sealing member 125 may include an open end 126 and a closed end 127. The plunger (e.g., plungers 110, 115 shown in FIGS. 1-22, 32-38, 49-85) may have a second end (e.g., second distal end 114 shown in FIG. 3) inserted into the open end 126 of the flexible sealing member 125 to allow the user to depress the flexible sealing member and actuate the plunger. In any embodiment described herein, the plunger 110, 115 may further be attached or adhered to the flexible sealing member 125.

In some embodiments, the flexible sealing member 125 may define a bellows gasket having a cylindrical body 129 with corrugated side walls (e.g., conertinaed wall segments). The depicted body 129 may terminate at a flange 128 which may be disposed across the second end 107 of the body 105 (shown in FIG. 3) to seal the opening in the second end. In operation, the cylindrical body 129 of the flexible sealing member 125 may crush by bending at the corrugations upon application of force by the user on the closed end 127. During actuation, the closed end 127 moving downwardly may cause the flexible sealing member 125 to press the plunger 110, 115 downwardly (e.g., as shown in FIGS. 8-13 and 73-76).

Turning back to FIGS. 1-13, the flexible sealing member 125 may be held onto the body 105 using a cap 130. The cap 130 may include an opening 131 through which a second portion of the flexible sealing member 125, including a portion of cylindrical body 129 and the closed end 127 may extend. The cap 130 may then be threaded or otherwise attached to the body 105 and may leave the closed end 127 of the flexible sealing member 125 actuatable to the user. In such embodiments, the second distal end 114 of the plunger 110 may also extend through the opening 131 while being disposed within the cylindrical body 129 of the flexible sealing member 125.

The separation container 100 may further include a sample collecting vessel 135 for receiving a discharged pellet for downstream testing. In this manner, the separation container 100 may collect and hold the separated microorganism without requiring expression of the sample pellet into a different container, risking spillage or contamination. The sample collecting vessel 135 may be attached to the body 105 and may surround the opening at the first end 106, such that the seal 120 may be inside the sample collecting vessel 135 and the vessel is configured to collect any discharge from the internal chamber 108 through the first end 106 of the body. As discussed below, the sample collecting vessel 135 may be pre-loaded with saline or another diluent for preparing a suspension of the isolated sample.

With continued reference to FIGS. 1-13, an adaptor 140 may be connected to the body 105, either by being adhered, welded, or otherwise fastened thereto, or by being integrally molded therewith. The adaptor 140 may engage a conical portion of the body 105. In some embodiments, the adaptor 140 may engage a threaded connector 145, either by being adhered, welded, or otherwise fastened thereto, or by being integrally molded therewith. The sample collecting vessel 135 in the depicted embodiment is threaded to the threaded connector 145 for securing the vessel to the body 105. With reference to FIGS. 27-31, detailed views of an adaptor 140 are shown. The adaptor 140 may include a lower flange 146 portion into which the threaded connector 145 (e.g., shown in FIG. 3) may be inserted. The adaptor 140 may further include a ridge 147 (e.g., as shown in FIG. 31) within the lower flange 146 that is configured to engage the threaded connector 145. The v-shaped ridge 147 may define an energy director for ultrasonic welding, which may allow for a better seal between the ridge 147 and threaded connector 145. As discussed herein, the adaptor 140, body 105, and threaded connector 145 may be welded (e.g., by induction, heat, or sonic welding), adhered, or otherwise fused or attached to one another, or they may be integrally molded. In such embodiments, the end cap 1250 may be used to apply an upward force on the body 1205 during welding.

In some embodiments, the adaptor 140 and threaded connector 145 may terminate above (e.g., vertically above in the orientation of FIGS. 2-3) the seal 120 and the first end 106 of the body 105. Said differently, the adaptor 140 and the threaded connector 145 may be disposed axially between the first end 106 and the second end 107, which may allow the first end 106 and the seal 120 to rest on a surface of the centrifuge apparatus during centrifugation to prevent premature breach of the seal. In embodiments of the separation container shown herein without adaptors, one of ordinary skill in the art will appreciate that an adaptor according to any of the embodiments described herein may be attached or molded with any of the disclosed separation containers. The body 105 may further comprise the hexagonal bracket 150 for supporting the separation container 100 in the centrifugation apparatus or during downstream (e.g., post-separation) testing.

Turning to FIGS. 14-26, the embodiment of FIGS. 1-13 is shown having a rheological control member 200 defined about the longitudinal member 112 of the plunger 110 and within the internal chamber 108 of the body 105. Unless otherwise described herein, the features of the embodiment of FIGS. 14-26 may be identical to the embodiment of FIGS. 1-13. The rheological control member 200 may define a barrier 205 that partially restricts flow through the internal chamber 108. The barrier 205 may be an annular structure disposed about the longitudinal member 112 of the plunger 110. With reference to FIGS. 23-26, detailed views of an example barrier 205 of the rheological control member 200 are shown. In particular, the barrier 205 may include an inner annular ring 206 and an outer annular ring 207 connected by one or more vanes 208 to restrict flow in the internal chamber 108 while still allowing some of the sample to pass therethrough.

The rheological control member 200 may further include a filter 210 for restricting the flow further. The filter 210 may seat in an annular space 209 of the barrier 205 to form a single unit. The rheological control member 200 may define an outer radius of the outer annular ring 207 that is less than the radius of the collection region 102 of the internal chamber 108 to allow the rheological control member to move freely within the body 105. The rheological control member 200 may further define an inner radius of the inner annular ring 206 that is greater than a diameter of the plunger 110 above a shelf 175. The rheological control member 200 may thereby move freely with respect to both the body 105 and the plunger 110.

In some embodiments, the rheological control member 200 may prevent mixing of the sample with the density cushion, described herein, to maintain the dual separating and purifying properties of the density cushion. For example, when a user pours the sample into the collection region 102 and a liquid density cushion is present in the internal chamber 108, the sample may mix with the density cushion and impair the separation of the microorganism from non-microbial components during centrifugation. The rheological control member 200 allows the sample to settle on the density cushion with little to no mixing. An example density cushion 101 is shown in FIG. 3, and one of ordinary skill in the art will appreciate that any embodiment disclosed herein may include the density cushion in the same manner as depicted in FIG. 3.

In some embodiments, the rheological control member 200 may be buoyant in water and/or in a density cushion material. This may enable the rheological control member 200 to float upwards (e.g., away from the seal 120) during centrifugation. In some embodiments, the rheological control member 200 may define a specific density of 0.95 or less relative to water. In some embodiments, the rheological control member 200 may define a specific density of 0.95 or less relative to the density cushion material. In some embodiments, the rheological control member 200 may define a specific density of 0.90 or less relative to water. In some embodiments, the rheological control member 200 may define a specific density of 0.90 or less relative to the density cushion material. In some embodiments, the rheological control member 200 may define a specific density of 0.85 or less relative to water. In some embodiments, the rheological control member 200 may define a specific density of 0.85 or less relative to the density cushion material. In some further embodiments, the rheological control member 200 may be buoyant in a mixture of water and density cushion material.

Turning to FIGS. 32-49, the embodiment of FIGS. 1-13 is shown having another embodiment of the rheological control member 300. Unless otherwise described herein, the features of the embodiment of FIGS. 32-49 may be identical to the embodiment of FIGS. 1-13. Although not depicted in FIGS. 32-49, the embodiment of FIGS. 32-49 may also include a seal 120, adaptor 140, threaded connector 145, and/or sample collecting vessel 135 according to any of the embodiments described herein.

With reference to FIGS. 45-49, detailed views of the rheological control member 300 are shown. The rheological control member 300 may define a barrier 305 that partially restricts flow through the internal chamber 108. The barrier 305 may be an annular structure disposed about the longitudinal member 112 of the plunger 110. In particular, the barrier 305 may include an inner annular ring 306 (shown in FIG. 49) and an outer annular ring 307 (shown in FIG. 49) connected by one or more vanes 308 to restrict flow in the internal chamber 108 while still allowing some of the sample to pass therethrough during centrifugation. In some embodiments, the inner annular ring 306 may seal against the plunger 110, and the outer annular ring 307 may seal against the wall 109 of the body 105 such that fluid must flow between the rings.

The rheological control member 300 may further include a frustoconical section 310 configured to snap a flange 311 into the barrier 305 and engage the inner annular ring 306 of the barrier. The frustoconical section 310 may further include a first annular seat 317 beneath the flange 311 for holding the barrier 305. In some embodiments the frustoconical section 310 may include a conical body 313 that diverts fluid flow radially outward to further reduce mixing of the sample and the density cushion. The rheological control member 300 may further include a lower annular member 315 that engages a second annular seat 318 and a lower abutment 316 of the frustoconical section 310. The lower annular member 315 may allow fluid to flow radially outward of itself, while reducing the turbulence of the sample flow.

In some embodiments, the frustoconical section 310 of the rheological control member 300 may include an annular bore 312 extending therethrough. The bore 312 may receive the plunger 110, 115 therein, and may allow the rheological control member 300 to slide relative to the plunger and may also form a seal between the rheological control member and the plunger. With reference to FIGS. 45-47, the frustoconical section 310 may include an outwardly angled flange 314, such that fluid flow is configured to pass through the barrier 305, between the outer annular ring 307 and the inner annular ring 306, past the vanes 308, and the fluid may then be deflected outwardly by the flange 314, lengthening the fluid flow path and reducing the risk of direct contact between the sample and the density cushion as the sample is loaded into the body.

In some embodiments, the frustoconical section 310 may be a flexible valve made of silicone or other elastomeric material. The frustoconical section 310 may be sealed against the barrier 305 during loading (e.g., in the unstretched, normally-closed position of FIG. 47, fluid may not pass between the barrier 305 and the frustoconical section 310), and the barrier 305 may be press fit within the separation container. This allows the separation container to be loaded without any concern of disturbing the density cushion. During centrifugation, however, the frustoconical section 310 may stretch downwardly (e.g., to the open position shown in FIG. 45) under the weight of the lower annular member 315 during centrifugation to allow fluid to flow over the flange 314 and past the frustoconical section 310. The lower annular member 315 may be a retainer positioned over the flexible frustoconical section 310, and the lower annular member 315 may weigh the frustoconical section 310 so that the frustoconical section distends during centrifugation. In this configuration, the rheological control member 300 prevents fluid communication between the sample and the density cushion until centrifugation.

As detailed above, in some embodiments, the rheological control member 300 may prevent mixing of the sample with the density cushion, described herein, to maintain the filtering properties of the density cushion. For example, when a user pours the sample into the collection region 102 and a liquid density cushion is present in the internal chamber 108, the sample may mix with the density cushion and prevent separation of the microorganism during centrifugation. The rheological control member 300 allows the sample to settle in the internal chamber 108 with little to no mixing. In the embodiment shown in FIGS. 45-49, the barrier 305, frustoconical section 310, and lower annular member 315 may combine to reduce mixing of the sample with the density cushion.

Turning to FIGS. 50-56, the embodiment of FIGS. 1-13 is shown having another embodiment of the rheological control member 400. Unless otherwise described herein, the features of the embodiment of FIGS. 32-49 may be identical to the embodiment of FIGS. 1-13. In the embodiment shown in FIGS. 50-56, the rheological control member 400 includes a substantially annular ring that serves the rheological control functions described herein. In the embodiments described herein, the rheological control member may be any flow restriction that prevents the density cushion and sample from mixing, which would destroy the efficacy of the density cushion, while still allowing microorganisms to pass thereby during centrifugation. For example, the rheological control member may also include a plurality of polypropylene beads disposed in the internal chamber 108. Although not necessarily required in the hands of a skilled user, the rheological control member may improve the robustness and precision of the devices, systems, and methods described herein.

In particular, in some embodiments, the rheological control member 400 may prevent mixing of the sample with the density cushion, described herein, to maintain the filtering properties of the density cushion. For example, when a user pours the sample into the collection region 102 and a liquid density cushion is present in the internal chamber 108, the sample may mix with the density cushion and prevent separation of the microorganism during centrifugation. The rheological control members described herein (e.g., rheological control members 200, 300, 400) allow the sample to settle on the density cushion with little to no mixing.

In some embodiments the rheological control member 400 may be coupled with the plunger 110, for example, by producing an annular ring that has an inner diameter less than the outer diameter of the plunger 110. In such embodiments, the ring may be buoyant and may assist with flotation of the plunger 110 during centrifugation. In some other embodiments, the annular ring may be loosely retained about the plunger 110 and freely movable along the axis 155 (shown in FIG. 3) of the plunger 110 during operation.

In some embodiments, the rheological control member 400 may be buoyant in water and/or in a density cushion material. This may enable the rheological control member 400 to float upwards (e.g., away from the seal 120) during centrifugation and may cause the rheological control member to sit atop the density cushion. In some embodiments, the rheological control member 400 may define a specific density of 0.95 or less relative to water. In some embodiments, the rheological control member 400 may define a specific density of 0.95 or less relative to the density cushion material. In some embodiments, the rheological control member 400 may define a specific density of 0.90 or less relative to water. In some embodiments, the rheological control member 400 may define a specific density of 0.90 or less relative to the density cushion material. In some embodiments, the rheological control member 400 may define a specific density of 0.85 or less relative to water. In some embodiments, the rheological control member 400 may define a specific density of 0.85 or less relative to the density cushion material. In some further embodiments, the rheological control member 400 may be buoyant in a mixture of water and density cushion material.

With reference to FIGS. 163, 165, 170, 174, 176, 178-180, 195, 213-214, 216-217, and 219-222, another rheological control member 1042 is shown. The depicted rheological control member 1042 may include a central bore 1080 for receiving a plunger 1010 therethrough. An outer surface of the rheological control member 1042 may be configured to engage the wall 1009 of the body 1005 of the separation container 1000. Between the central bore 1080 and the outer surface, the rheological control member 1042 may be a substantially solid body, through which fluid may not pass.

In operation, the rheological control member 1042 may be interference fit within the body 1005 prior to centrifugation. Said differently, an outermost diameter of the rheological control member 1042 may be greater than the diameter of the body 1005. The interference fit may prevent fluid from passing around the exterior of the rheological control member 1042, between the rheological control member and the wall 1009. In a static state (e.g., when the separation container 1000 is not being centrifuged), the internal chamber 1011 of the body 1005 may define a first diameter radial to an axis extending in the longitudinal direction of the plunger 1010. The outermost diameter of the rheological control member 1042 may be greater than the first diameter.

During centrifugation, the body 1005 of the separation container may flex slightly (e.g., as shown in the displacement diagram of FIG. 223) in a radially outward direction under the pressure of the liquid inside the separation container 1000, increasing the diameter of the internal chamber 1011 and wall 1009 of the body 1005 to a second diameter. In such embodiments, the body 1005 may be made of an at least partially flexible material (e.g., low density polyethylene). With reference to FIG. 223, the displacement visualization shows a 0.66 mm displacement in the x (radial) direction. The finite element analysis in FIG. 223 is of a low density polyethylene body 1005 having a 15 mL volume. The applied pressure during the FEA was 3.2 MPa at the base of the body 1005. The second diameter may be greater than the outermost diameter of the rheological control member 1042 such that the deformation of the wall 1009 may release the interference fit between the rheological control member 1042 and the wall 1009 and allow fluid to flow therebetween.

In some embodiments, the rheological control member 1042 may be buoyant in water and/or the density cushion (e.g., having the same buoyant properties described herein with respect to some plungers 110, 115, and/or may include a hollow space in its interior). In such embodiments, the rheological control member 1042 may float towards the second distal end 1007 of the body 1005 and out of the way. In some further embodiments, the rheological control member 1042 may be retained in a widened region 1008 of the body 1005 near the second distal end 1007 once the diameter of the body 1005 narrows sufficiently to prevent the rheological from moving freely in its original location. In some embodiments, a retaining notch or other frictional mechanism may be used to retain the rheological control member 1042 at or near the second distal end 1007. In some embodiments, the rheological control member 1042 may be disposed adjacent to the retainer 1032 after centrifugation.

In some embodiments, an annular shoulder 1061 may be formed in the wall 1009 to ensure that the rheological control member 1042 is retained at a particular axial position in the body 1005. For example, the rheological control member 1042 may be retained at a position that allows the complete density cushion to be filled below the rheological control member, in the quantities described in the various embodiments herein, while leaving space above the rheological control member 1042 for the sample to be poured to allow the most usable volume in the separation container while preventing mixing of the density cushion and sample before centrifugation. The diameter of the internal chamber of the body, radial to an axis of the body that is collinear with the length of the longitudinal member 1012 of the plunger 1010, may change across the annular shoulder 1061. In some embodiments, the annular shoulder 1061 may include a narrow side and a wide side relative to the axial direction, such that the diameter of the internal chamber of the body 1005 narrows when travelling in a direction from the second distal end 1007 to the first distal end. In some embodiments, the annular shoulder 1061 may serve as an axial limitation on the movement of the rheological control member 1042, such that the rheological control member 1042 can move freely upward, but may not fill the space of the density cushion.

The rheological control member 1042 may additionally have an annular shoulder 1062 that further improves the interference fit at the axial location where the two shoulders 1061, 1062 meet (e.g., as shown in FIG. 217). The outermost diameter of the rheological control member 1042 may be defined at the wide side of the annular shoulder 1062.

The central bore 1080 of the rheological control member 1042 may be slip fit with the outer diameter of the plunger 1010 such that the plunger may move relative to the rheological control member. In some embodiments, as shown in FIGS. 213, 214, 216, 219, and 220-222, a gasket 1043 may be provided that seals the gap between the rheological control member 1042 and the plunger 1010 before centrifugation. The gasket 1043 may be a flexible, circumferential component that extends about the plunger 1010. A protrusion 1053 of the gasket 1043 may engage a corresponding circumferential groove 1054 to prevent slipping. In some embodiments, the gasket 1043 may include an angled engagement surface 1051 oriented downward (e.g., axially toward the first distal end 1006) and radially outward from the plunger. The rheological control member 1042 may have a corresponding angled engagement surface 1052 at its distal end. During operation, the weight of the sample on the rheological control member 1042 may compress the angled engagement surface 1052 of the rheological control member 1042 onto the angled engagement surface 1051 of the gasket 1043, which may compress the gasket and increase the strength of the seal between the two. Once centrifugation begins, the rheological control member 1042 may be lifted off of the gasket 1043 towards the second distal end 1007 as described above.

Due to the limited or no fluid flow being permitted between the space above the rheological control member 1042 and the space below the rheological control member 1042 when the rheological control member 1042 is in its centrifugation position (e.g., the position shown in FIG. 213), the density cushion may not mix with the sample prior to centrifugation. In some embodiments, the separation container 1000 may be packaged, stored and/or shipped with the density cushion, rheological control member 1042, and plunger 1010 in position without leaking. In some embodiments, the separation container may be pre-spun prior to loading a sample to settle the density cushion in the internal chamber 1011. As detailed above, the rheological control member 1042 may be substituted for any of the rheological control members described herein, and may be fitted to any of the plungers 110, 115, 1010 described herein. Similarly, the other rheological control members described herein may be applied to the plunger 1010 shown in FIGS. 166-223.

Referring back to FIGS. 1-67, in some embodiments, the plunger 110 may include a longitudinal member 112 extending along an axis 155 (shown in FIG. 2) of the body 105. The plunger 110 may have a point 113 at a first distal end of the longitudinal member 112 configured to puncture the seal 120. The plunger 110 may further have a second distal end 114 that is actuatable by a user to puncture the seal 120 and express the pellet as discussed herein. In a centrifugation configuration (e.g., as shown in FIGS. 2-7), the seal 120 is intact, and the plunger 110 may be sealed within the body 105. The plunger 110 may be actuated by depressing the flexible sealing member 125, which contacts and depresses the second distal end 114 of the plunger, to break the seal 120 and express the pellet from the first end 106 of the body 105 (e.g., as shown in FIGS. 8-13) as described herein.

With reference to FIGS. 57-67, detailed views of the plunger 110 of the embodiment of FIGS. 1-56 are shown. The plunger 110 may include the longitudinal member 112, which generally extends from the point 113 at the first distal end to the second distal end 114. The point 113 may be defined on a blade 160 at the first distal end of the longitudinal member 112. By comparison between FIGS. 59 and 67, the blade 160 may define a first, wider diameter in a first radial direction (e.g., radial to the longitudinal axis 155 shown in FIG. 2), and a second, narrower diameter (e.g., the width of the blade in FIG. 59) in a second radial direction perpendicular to the first radial direction and the axis. For example, each of FIGS. 3, 9, 16, 34, 49, 52, 57, 58, and 59 illustrates an edge-on view of the blade 160 with the second, narrower diameter shown, and each of FIGS. 6, 7, 12, 13, 19, 20, 22, 37, 38, 55, 56, 64, and 67 illustrates the wider diameter of the blade.

In some embodiments, the point 113 is shaped to rupture the seal 120 efficiently when the plunger 110 is activated. For example, the point 113 may be conical-shaped and have a range of bevel angles relative to the elasticity of the seal 120. In some embodiments, the point 113 is knife-shaped, chisel-shaped, hypodermic needle-shaped, or has multiple planes, e.g., an X-shaped cross section, or the like. In one embodiment, the point 113 is shaped to create a void around the edge of the opening when the seal is punctured. In this embodiment, the void reduces capture of microorganism between the punctured seal 120 and the body 105. In further embodiments, the point 113 is designed to puncture the seal 120 but not to tear away parts of the seal 120 that would then contaminate the recovered sample. For example, the point 113 may be shaped to mirror or enhance force multipliers in the seal 120 to puncture the seal 120 without breaking away any part of the seal after rupture.

The plunger 110 may further include one or more ribs 165, 170 for engaging the wall 109 of the body 105 defining the internal chamber 108. In particular, the ribs 165, 170 may be configured to engage the pellet region 104 (shown in FIG. 3) of the body 105 to facilitate expression of the pellet (e.g., the separated microorganism). At least one of the ribs (e.g., stabilizing rib 165) may only extend partially about the circumference of the plunger 110 and in some embodiments, may be disposed to either side of the first, wider diameter of the blade 160 (e.g., as shown in FIGS. 7, 22, 38, and 56). At least one of the ribs (e.g., upper sealing rib 170) may be defined above the blade 160 and may extend circumferentially around the longitudinal member 112 of the plunger 110. In such embodiments, the sealing rib 170 may be on the opposite side of the blade 160 from the point 113. This sealing rib 170 may define a plunger diameter d, and the sealing rib may be a generally circular sealing surface that seals uniformly about the plunger regardless of the angular position of the blade 160. The sealing rib 170 may be configured to engage the wall 109 of the body 105 and seal a portion of the internal chamber 108 below the rib 170 from a portion of the internal chamber above the rib. In particular, the plunger diameter d of the sealing rib 170 may be interference fit to the pellet diameter (e.g., slightly greater than the diameter of the body 105 at the pellet region 104), such that the plunger 110, via rib 170, engages the pellet region 104 during actuation of the plunger. In this manner, the plunger 110 may fluidically isolate the pellet region 104 from the tapered region 103 and the collection region 102 when actuating the plunger.

For example, FIGS. 7, 22, 38, and 56 show detail views of the plunger 110 at the first end 106 of the body 105. In each depiction, the sealing rib 170 is configured to engage the wall 109 of the body 105 where it narrows to the pellet diameter (e.g., at the start of the pellet region 104). In such embodiments, the distance between the sealing rib 170 and the point 113 may be less than or equal to the length of the pellet region 104, such that the pellet region is fluidically isolated from the remainder of the internal chamber 108 prior to opening the seal 120.

In some further embodiments, the plunger 110 may further include a shelf 175 at which point the diameter of the plunger 110 increases to substantially greater than the pellet diameter and greater than the plunger diameter d. This shelf 175, shown in FIGS. 3, 6-7, 9, 12, 16, 19, 20, 22, 34, 37, 38, 49, 52, 55-58, and 64, may engage the transition between the tapered region 103 and the pellet region 104 of the body 105 to retain the plunger 110 within the separation container 100 and limit the downward stroke of the plunger to only the travel distance necessary to express the separated microorganism from the body 105.

The axial distance from the tip of the point 117 to the shelf 175 of the plunger 110 may be greater than the axial length of the pellet region 104 to enable the plunger 110 to open the seal 120 without falling entirely out of the body 105 or contaminating the separated sample in the sample collecting vessel 135. Moreover, the axial distance from the tip of the point 117 to the sealing rib 170 may be less than or equal to the axial length of the pellet region 104 to enable the plunger 110 to seal the pellet region 104 from the remainder of the internal chamber 108 prior to opening the seal 120. In addition, the distance between the shelf 175 and the sealing rib 170 may be less than the axial length of the pellet region 104, such that the seal between the sealing rib 170 and the wall 109 is not broken when the plunger 115 reaches its stopping point.

With reference to FIGS. 68-89, an embodiment of the separation container 100 is shown having a second plunger 115 and having a threaded adaptor 240 integral with the body 105. Unless otherwise described herein, the embodiment of FIGS. 68-89 is identical to the embodiment of FIGS. 1-13 As shown in FIGS. 70, 72, 74, 76-79, 81, and 84, the plunger 115 may include a tapered conical first distal end 118 having a conical point 117 rather than a flat blade (e.g., blade 160 shown in the embodiment of FIGS. 1-67). The plunger 115 may define a sealing rib 270 and shelf 275 that operate in substantially the same way as the sealing rib 170 and shelf 175 of the plunger 110 of FIGS. 1-67 shown and described herein. In particular, the pellet region 104 of the body 105 may be defined by a substantially cylindrical portion of the body 105 against which the sealing rib 270 may move during actuation of the plunger 115. As discussed above, the pellet region 104 may be a "capillary" section at the first end 106 of the body, and the pellet region 104 may be the narrowest portion of the body 105.

In some embodiments, when the sealing rib 270 is engaged with the cylindrical wall 109 of the body 105 at the pellet region 104, the portion of the internal chamber 108 on the side of the first end 106 of the body 105 may be fluidically separated from the remaining portion of the internal chamber 108 by the sealing action of the sealing rib 270. With reference to FIG. 79, the sealing rib 270 may define the plunger diameter $d_2$. As also discussed above, the plunger diameter $d_2$ may be greater than the pellet diameter of the pellet region 104. In one embodiment, the plunger diameter may be interference fit within the cylindrical wall 109 at the pellet region to form the seal thereagainst.

As also shown above, the plunger 115 may include a shelf 275, which constrains the downward movement of the plunger 115 in the body 105. For example, with reference to FIG. 76, the shelf 275 may define a wider portion of the longitudinal member 116 of the plunger 115. In particular, the shelf 275 may define a diameter that is greater than the diameter of the body 105 in the pellet region and less than the diameter of the body in the collection region 102. In such embodiments, the shelf 275 may engage the wall 109 of the body 105 at the tapered region 103 proximate the start of the pellet region 104 to prevent the point 117 of the plunger 115 from continuing further out of the body 105.

As discussed above with respect to the plunger 110 shown in the embodiments of FIGS. 1-67, the axial distance from the tip of the point 117 to the shelf 275 may be greater than the axial length of the pellet region 104 to enable the plunger 115 to open the seal 120 without falling entirely out of the body 105 or contaminating the separated sample in the sample collecting vessel 135. As also discussed above, the axial distance from the tip of the point 117 to the sealing rib 270 may be less than or equal to the axial length of the pellet region 104 to enable the plunger 115 to seal the pellet region 104 from the remainder of the internal chamber 108 prior to opening the seal 120. Moreover, the distance between the shelf 275 and the sealing rib 270 may be less than the axial length of the pellet region 104, such that the seal between the sealing rib 270 and the wall 109 is not broken when the plunger 115 reaches its stopping point.

With reference to FIGS. 1, 3, 6, 7, 9, 12, 13, 14, 16, 19-22, 32, 34, 37, 38, 49, 50, 52, 55, 56, 57-68, 70, 72, 74, and 76-85, in some embodiments, the plunger 110, 115 may include one or more stabilizers 180, 280 that align and center the longitudinal member 112, 116 of the plunger 110, 115 within the body 105. In some embodiments, the plunger 110, 115 may include two or more stabilizers 180, 280. In some embodiments, the plunger 110, 115 may include three or more stabilizers 180, 280. In some embodiments, the plunger 110, 115 may include four or more stabilizers 180, 280. Two of the stabilizers 180, 280 in the aforementioned embodiments may be positioned opposite one another relative to the longitudinal member 112, 116 of the plunger. In some embodiments, each stabilizer 180, 280 may extend perpendicular to the axis 155 of the longitudinal member and perpendicular to the stabilizers on either side of each respective stabilizer. The stabilizers 180, 280 may extend perpendicular to the axis 155 (e.g., as shown in FIGS. 2, 69), and may extend from the longitudinal member 112, 116 to a position proximate the body 105. The stabilizers 180, 280 may thereby include a clearance (e.g., a slip fit or greater clearance) between the stabilizers and the wall 109 of the body 105 to prevent misalignment of the plunger 110, 115 without hindering the plunger's actuation or preventing fluid from flowing through the internal chamber 108. In some embodiments, the stabilizers 180, 280 may be positioned on the longitudinal member 112, 116 at the axial position of the collection region 102, which may define the widest portion of the internal chamber 108 relative to the axis 155.

In some further embodiments, the plunger 110, 115 may be buoyant in water and/or in a density cushion material.

This may enable the plunger 110, 115 to float upwards (e.g., away from the seal 120) during centrifugation. In some embodiments, the plunger may define a specific density of 0.95 or less relative to water. In some embodiments, the plunger may define a specific density of 0.95 or less relative to the density cushion material. In some embodiments, the plunger may define a specific density of 0.90 or less relative to water. In some embodiments, the plunger may define a specific density of 0.90 or less relative to the density cushion material. In some embodiments, the plunger may define a specific density of 0.85 or less relative to water. In some embodiments, the plunger may define a specific density of 0.85 or less relative to the density cushion material. In some further embodiments, the plunger 110, 115 may be buoyant in a mixture of water and density cushion material. In some embodiments, the plunger 110, 115 may be sufficiently stiff to not overly deform when engaging the pellet region 104.

In some embodiments, the depicted plungers need not be buoyant. For example, with reference to the plunger 1010 shown in FIGS. 161-223, the plunger 1010 may be supported by a retainer 1032 that is secured within the body 1005 of the separation container 1000. In the depicted embodiment, the retainer 1032 is press fit into the second distal end 1007 of the body 1005 of the separation container 1000. The body 1005 may additionally or alternatively include a widened region 1008 at the second distal end 1007 that prevents the retainer 1032 from slipping further into the body. In operation, the retainer 1032 may retain and support the plunger 1010 such that the plunger does not puncture the seal 1020 during centrifugation. For example, during centrifugation, the fluid in the separation container may place 350 psi of pressure on the seal 1020 when 3000 rcf (relative centrifugal force, 3000×gravitational force). In some embodiments, the body 1005 may include a bracket 1050 for supporting the separation container as described with respect to the hexagonal bracket 150 herein.

The retainer 1032 and plunger 1010 may have a retention mechanism that allows the plunger to be supported by the retainer during centrifugation but also actuatable by a user after separation. With reference to FIGS. 182-192, detailed illustrations of the retainer 1032 and plunger 1010 are shown. In particular, the retainer 1032 includes one or more retaining members 1033 that engage corresponding support member 1015 on the plunger 1010. The support member 1015 may include one or more locking projections 1016 that engage the respective retaining members 1033 of the retainer 1032. In the depicted embodiment, the retainer 1032 includes two retaining members 1033 and the plunger 1010 includes two locking projections 1016 each separated from the other by 180 degrees about the longitudinal axis of the plunger 1010.

Figure 184:
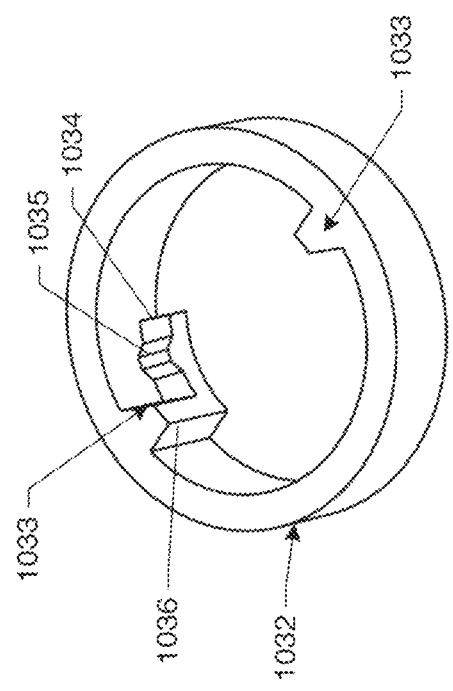
Figure 185:
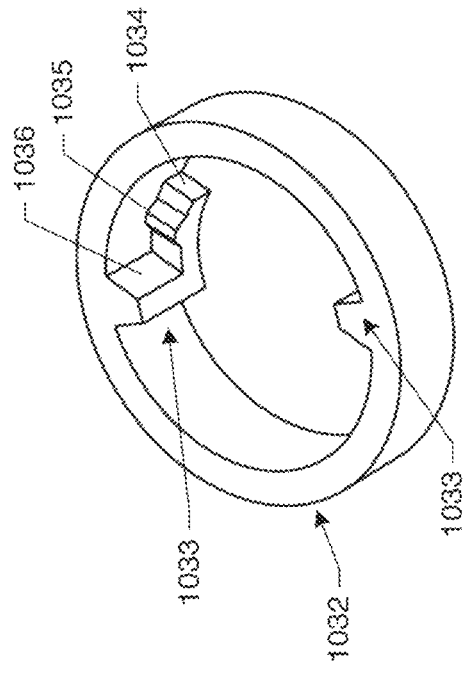

With reference to FIGS. 184-185, the retaining members 1033 may include a support projection 1034 extending from the inner wall of the retainer 1032 with a stop wall 1036 at one end of the support projection. The support projection 1034 may further include one or more locking tabs 1035. With reference to FIG. 193, the locking projections 1016 may include a substantially C-shaped receiving area defined by a lower wall 1017, a lateral wall 1018, an upper wall 1019, and a lip 1021. These features may combine to receive and engage the corresponding retaining member 1033 of the retainer 1032. For example, the support projection 1034 (shown in FIGS. 184-185) of the retaining member 1033 may be received in the locking projection 1016 (shown in FIG. 193) with an upper surface of the lower wall 1017 engaging a lower surface of the support projection 1034. The locking tab 1035 (shown in FIGS. 184-185) and/or the lip 1021 may deflect when the retaining member 1033 is engaged with the locking projection 1016 such that the locking tab 1035 may be disposed in a space between the lateral wall 1018, the upper wall 1019, and the lip 1021 to retain the plunger 1010.

During operation, the plunger may be inserted into the central opening of the retainer 1032 with the locking projections 1016 out of rotational alignment with the retaining members 1033. When the locking projections 1016 and retaining members 1033 are axially aligned, the plunger 1010 may be rotated about its longitudinal axis to cause the support projection 1034 of the retainer 1032 to engage the locking projections 1016 of the support member 1015. When engaged, the support member 1015 is held axially in place such that the plunger 1010 cannot move up or down the separation container relative to the retainer 1032, and the stop wall 1036 of the retaining members 1033 prevents the plunger 1010 from rotating in one of two rotational directions. Gaps between the plunger 1010 and retainer 1032 may allow sample material and/or density cushion to be added while the plunger 1010 and retainer 1032 are engaged. The retainer 1032 may also radially center the longitudinal member 1012 of the plunger 1010 within the body 1005 while the plunger is engaged with the retainer. The plunger 1010 may be subsequently disengaged by rotating the plunger about its longitudinal axis in an opposite rotational direction, and the plunger may be free to move axially through the retainer 1032 when the locking projections 1016 are not aligned with the retaining members 1033.

The plunger 1010 may include a tab 1022 at its second distal end 1014. The tab 1022 may give the second distal end 1014 of the plunger 1010 a non-cylindrical shape, which shape allows the user to grasp and turn the plunger through the sealing member 1025. For example, a radial pressure applied to the tab 1022 at an angular position between the widest and narrowest points of the second distal end 1014 may cause rotation in the plunger 1010. Thus, during centrifugation, the plunger 1010 may be supported by the retainer 1032 after which the user may release the plunger 1010 to express the pellet as described herein. Although shown in the embodiment of FIGS. 161-223, the retainer 1032 and support member 1015 may be applied to any of the plungers 110, 115, 1010 in any of the embodiments shown and described herein.

As described below, the plunger 1010 shown in FIGS. 161-223 may express the pellet in substantially the same manner as the plungers 110, 115 described in connection with one or more other embodiments herein. In some embodiments, the plunger may include one or more ribs 1065, 1070, and 1072 as described herein. In some further embodiments, the plunger may include two sealing ribs 1070, 1072 that are vertically separated from one another and extend circumferentially around the plunger 1010 at a location where each rib 1070, 1072 contacts the wall 1009 about its circumference to seal the area above the respective rib from the area below the respective rib. In embodiments having two or more sealing ribs 1070, 1072, one of the sealing ribs (e.g., the most distal rib 1070) may protrude through the body 1005 and out the central aperture 1044 of the coupling cap 1040 (if used) as shown in FIG. 177 to ensure that the pellet is completely expressed, while also ensuring that the density cushion and other remaining sample above the uppermost sealing rib 1072 is prevented from leaving the body 1005 and contaminating the sample collecting vessel 1038.

In some embodiments, the separation container 100 may use a density cushion to facilitate separation and purification of the microorganism from the sample under centrifugation. The separation container 100 may either be loaded with a density cushion or may come pre-packaged with a density cushion in the internal chamber 108 of the body 105. The volume/height of the density cushion in the internal chamber 108 should be sufficient to achieve separation of the microorganisms, which pass through the density cushion and are physically separated from other sample components. The volume will depend on the size and shape of the separation container. In general, a volume of about 0.1 to about 25 ml can be used. In some embodiments, a volume of about 0.2 to about 3 ml can be used. In some embodiments, a volume of about 0.2 ml to about 0.5 ml can be used. If the separation is performed on a microscale, the volume of the density cushion can be about 1 μl to about 100 μl, and in some embodiments, about 5 μl to about 50 μl. The volume of sample laid or layered on top of the density cushion should be sufficient to provide enough microorganisms to produce a pellet suitable for testing. In general, any volume that fits into the container can be used. For example, a volume of about 0.1 ml to about 50 ml can be used. In some embodiments, a volume of about 0.2 ml to about 15 ml can be used. In some embodiments, a volume of about 0.2 ml to about 1.5 ml can be used. If the separation is performed on a microscale, the volume of sample can be about 1 μl to about 100 μl, and in some embodiments about 5 μl to about 50 μl. The available space in the container for sample will depend on the size and shape of the container. In some embodiments, an intermediate layer (liquid or solid) can be placed on top of the density cushion before the sample is laid or layered on top in order to prevent any mixing of the density cushion and the sample. In one embodiment, the intermediate layer can be polyethylene beads. In another embodiment, a small air bubble can be positioned between the density cushion and the sample to prevent mixing. In a further embodiment, the density cushion can be layered on top of a high density material (e.g., a perfluorocarbon fluid) such that the microorganisms pass through the density cushion during the separation and collect at the interface between the density cushion and the high density material.

The density of the cushion is selected such that the microorganisms in the sample pass through the cushion while other components of the sample (e.g., plasma, blood culture broth, enzymes, sugars, nucleic acids) remain on top of the cushion or do not pass all of the way through the density cushion. Said differently, the density cushion may have a density that is less than the microorganisms being separated and greater than the remaining sample material. The density cushion may also be selected to separate live microorganisms (which pass through the cushion) from dead microorganisms (which do not pass through the cushion). Suitable densities will depend on the material used in the density cushion and on the sample to be separated. In one embodiment, the density of the cushion is in the range of about 1.025 to about 1.220 g/ml, e.g., about 1.030 to about 1.070 g/ml, about 1.040 to about 1.060 g/ml or any range between about 1.025 to about 1.220 g/ml. In another embodiment, the density of the cushion is about 1.025, 1.030, 1.035, 1.040, 1.045, 1.050, 1.055, 1.060, 1.065, 1.070, 1.075, 1.080, 1.085, 1.090, 1.095, 1.100, 1.105, 1.110, 1.115, 1.120, 1.130, 1.140, 1.150, 1.160, 1.170, 1.180, 1.190, 1.200, 1.210, or 1.220 g/ml.

The material for the density cushion can be any material that has the appropriate density range for the methods of this invention. In one embodiment, the material is colloidal silica. The colloidal silica may be uncoated (e.g., Ludox® (W. R. Grace, CT)) or coated, e.g., with silane (e.g., Pure-Sperm® (Nidacon Intl, Sweden) or Isolate® (Irvine Scientific, Santa Ana, Calif.)) or polyvinylpyrrolidone (e.g., Percoll™, Percoll™ Plus (Sigma-Aldrich, St. Louis, Mo.)). In one embodiment, the colloidal silica exhibiting the least interference with spectroscopic interrogation is selected. The colloidal silica may be diluted in any suitable medium to form the proper density, e.g., balanced salt solutions, physiological saline, and/or 0.25 M sucrose. Suitable densities can be obtained with colloidal silica at a concentration of about 15% to about 80% v/v, e.g., about 20% to about 65% v/v. Another suitable material for density cushions is an iodinated contrast agent, e.g., iohexol (Omnipaque™ Nyco-Prep™, or Nycodenz®) and iodixanol (Visipaque™ or OptiPrep™). Suitable densities can be obtained with iohexol or iodixanol at a concentration of about 10% to about 25% w/v, e.g., about 14% to about 18% w/v, for blood culture samples. Sucrose can be used as a density cushion at a concentration of about 10% to about 30% w/v e.g., about 15% to about 20% w/v, for blood culture samples. Other suitable materials that can be used to prepare the density cushion include low viscosity, high density oils, such as microscope immersion oil (e.g., Type DF; Cargille Labs, New York), mineral oil (e.g., Drakeol® 5, Draketex 50, Peneteck®; Penreco Co., Pennsylvania), silicone oil (polydimethylsiloxane), fluorosilicone oil, silicone gel, metrizoate-Ficoll® (LymphoPrep™), e.g., at a concentration of about 75% to about 100% for blood culture samples, diatrizoate-dextran (PolymorphoPrep™), e.g., at a concentration of about 25% to about 50% for blood culture samples, carboxymethyl cellulose, hydroxypropylmethyl cellulose, polyethylene oxide (high molecular weight), Pluronic® F127, Pluronic® F68, mixtures of Pluronic® compounds, polyacrylic acid, cross-linked polyvinyl alcohol, cross-linked polyvinyl pyrrolidine, PEG methyl ether methacrylate, pectin, agarose, xanthan, gellan, Phytagel®, sorbitol, Ficoll® (e.g., Ficoll® 400 at a concentration of about 10% to about 15% for blood culture samples), glycerol, dextran (e.g., at a concentration of about 10% to about 15% for blood culture samples), glycogen, cesium chloride (e.g., at a concentration of about 15% to about 25% for blood culture samples), perfluorocarbon fluids (e.g., perfluoro-n-octane), hydrofluorocarbon fluids (e.g., Vertrel XF), and the like as are well known in the art. In one embodiment, the density cushion is selected from one or more of colloidal silica, iodixanol, iohexol, cesium chloride, metrizoate-Ficoll®, diatrizoate-dextran, sucrose, Ficoll® 400, and/or dextran in any combination. The density cushion can also be made up of a combination of materials, e.g., a combination of colloidal silica and oil. Certain combinations of the above compounds may be beneficial for the separation and downstream testing steps of the present invention. For example, combinations of compounds with different UV-quenching properties, such as cesium chloride and Iohexol.

During operation, the separation container 100 containing the density cushion may be loaded with a sample comprising one or more microorganism for separation. As discussed herein, the sample may be lysed prior to loading the sample into the body. To load the sample, a user may remove the cap 130 and flexible sealing member 125 and pour the sample into the second end 107 of the body along the plunger 110, 115.

During loading, the rheological control member 200, 300, 400, if any, may prevent mixing of the density cushion and the sample and allow the sample to settle on top of the density cushion. The separation container 100 may then be centrifuged to separate the microorganism from the sample and concentrate the microorganism. In particular, the separation step can be carried out to separate the microorganisms from other components of the sample (e.g., non-microorganisms or components thereof) and to concentrate the microorganisms into a separated (e.g., isolated or pelleted) sample that can be recovered for culture and/or identification and characterization purposes. The separation or pelleting step does not have to be complete, i.e., it is not required that 100% separation occur. All that is required is that the separation of the microorganisms from other components of the sample be sufficient to permit downstream testing of the microorganisms without substantial interference from the other components. For example, the separation can result in a microorganism pellet that is at least about 10, 20, 30, 40, 50, 60, 70, 80, 90, 95, 96, 97, 98, or 99% pure or higher.

The separation container 100 may be centrifuged without the sample collecting vessel 135 attached to the threaded connector 145 or threaded adaptor 240 respectively. In such embodiments, the seal 120 may be disposed against a flat internal bottom of a centrifuge cup (e.g., similar to centrifuge cup 540 shown in FIG. 90) and held in place by the flat surface of the centrifuge cup.

In some embodiments, the seal 120 need not be disposed against a centrifuge cap. For example, with reference to FIGS. 166-223, an embodiment of the seal 1020 is shown with a coupling cap 1040, 1140 connecting and holding the seal to the first distal end 1006 of the separation container 1000. Additionally or alternatively, the seal 1020 may be sonic welded, heat or thermally welded, induction welded, or otherwise fused to the first distal end 1006. In some embodiments, the seal 1020 may be made of the same material as the body 1005 (e.g., polypropylene). The coupling cap 1040, 1140 and/or sonic welding may prevent the weight of the sample in the separation container 1000 from prematurely opening the seal 1020 during centrifugation.

With reference to FIGS. 161-177, 194-197, and 212-220, a coupling cap 1040 may be disposed on the first distal end 1006 of the body 1005 of the separation container 1000 about the pellet region 1004. The coupling cap 1040 may secure the seal 1020 to the body 1005 via compression between a lower flange 1041 (shown in FIGS. 166, 171, 177, 197, and 200) of the coupling cap 1040 and the first distal end 1006 of the body 1005. In such embodiments, the coupling cap 1040 may apply even pressure about the perimeter of the seal 1020 to prevent premature opening. In some embodiments the coupling cap 1040 may be sonic welded or otherwise fused to the body 1005.

The coupling cap 1040 may further include a central aperture 1044 through which the plunger 1010 may express the pellet during operation. In some embodiments, the central aperture 1044 may define a diameter that is greater than or equal to the diameter of the pellet region 1004. The coupling cap 1040 may further include a circumferential v-shaped ridge 1047 on the flange 1041. The v-shaped ridge 1047 may focus the sonic energy during attachment to the body 1005 for a better bond. In practice, the v-shaped ridge 1047 may flatten during the bonding process between the coupling cap 1040 and the body 1005.

In some embodiments, with reference to FIGS. 194-197, the coupling cap 1040 may include one or more projections 1046 (e.g., circumferential rings) extending from an outer surface of the coupling cap 1040. The projections 1046 may engage the sample collecting vessel 1038 and frictionally retain the sample collecting vessel 1038 to the remainder of the separation container 1000. The coupling cap 1040, including the projections 1046, may define an outer diameter that is greater than an internal diameter of the sample collecting vessel 1038 so that the coupling cap 1040 and sample collecting vessel are held together by an interference fit.

With reference to FIGS. 180-181 and 198-200, the coupling cap 1040 is shown being formed in two pieces. In some embodiments, the coupling cap 1040 may include an outer sealing member 1049 that includes the projections 1046 and an inner cap 1048 that includes the flange 1041 and that engages the first distal end 1006 of the body 1005. The inner cap 1048 may include one or more cap projections 1039 that engage corresponding recesses in the outer sealing member 1049 to hold the two together. In some embodiments, the outer sealing member 1049 may be made of a softer, more flexible material (e.g., an elastomeric material) than the inner cap 1048, such that the inner cap 1048 may fuse with the body 1005 (e.g., the inner cap 1048 may be made of the same material as the body 1005) while the outer sealing member deforms against the inner cap 1048 and sample collecting vessel 1038 to provide a better seal. The outer sealing member 1049 may be overmolded onto the inner cap 1048 and/or the body 1005. The coupling cap 1040 may otherwise operate in substantially the same manner as detailed above with respect to FIGS. 161-177, 194-197, and 212-220.

Turning to FIGS. 201-205, an embodiment of the coupling cap 1140 is shown having an enlarged inner cap 1148. In the depicted embodiment, the inner cap 1148 includes a frustoconical portion 1146 that abuts the tapered region 1003 of the body 1005. The frustoconical portion 1146 may include a flange 1143 for resting or supporting the separation container 1000, and the frustoconical portion 1146 may include a gripping section 1142 that may be a circumferential portion of the inner cap 1148 that angles toward and engages the body 1005. The operation of the coupling cap 1140 may otherwise be the same as disclosed with respect to the coupling cap 1040 above. Each of the coupling caps 1040, 1140 herein above may be applied in connection with any of the separation containers detailed herein, and coupling caps 1040, 1140 may be interchanged with or added to the foil securing methods described in connection with any of the embodiments disclosed herein.

In some embodiments, with reference to FIGS. 206-211, the seal 1020 may be attached directly to the first distal end 1006 of the body 1005. For example, in some embodiments, the seal 1020 may be sonic welded to the first distal end 1006. Fusing the seal 1020 directly to the body 1005 may simplify manufacturing and increase the contact area between the seal 1020 and the body 1005 since no contact area is required for a coupling cap 1040, 1140. In such embodiments, the seal 1020 may be made from, or coated with, the same material as the body 1005. With continued reference to FIGS. 206-211, an outer sealing member 1049 may be used without an inner cap to seal the pellet region 1004 against the sample collecting vessel 1038. In such embodiments, the body 105 may include one or more cap projections 1039 to secure the outer sealing member 1049 in substantially the same manner described above with respect to the inner cap 1048.

The container 100 may be centrifuged with the second end 107 of the body disposed radially inward with respect to the rotational axis of the centrifuge and the first end 106 disposed radially outward, such that the apparent centrifugal force causes heavier portions of the sample (e.g., the microorganism) to collect at the first end 106.

As the sample is centrifuged, the microorganism may pass through the density cushion and collect at the first end 106 of the body 105, first accumulating in the pellet region 104 and, in some embodiments, subsequently at least partially filling the tapered region 103 with microorganism. The wall 109 of the body 105 at the tapered region 103 may direct the microorganism radially inward towards the pellet region 104. The centrifugation process may separate the microorganism into a concentrated pellet resting against the seal 120 at the first end 106. As the sample is being centrifuged, the plunger 110, 115 may float with an upward buoyant force towards the second end 107 of the body 105. The buoyant force may be provided by the density of the plunger relative to the density of the sample and density cushion as detailed above. In some embodiments, the plunger 110, 115 may include one or more flotation attachments to assist with lifting the plunger. In any of the above-described embodiments, the buoyancy of the plunger 110, 115 may prevent the plunger from prematurely piercing the seal 120 and prevent the plunger from prematurely separating the pellet region from the rest of the internal chamber 108 (e.g., preventing the sealing rib 170, 270 from prematurely engaging the wall 109 to prevent fluid flow into the pellet region 104).

In some embodiments, after centrifugation is complete, a concentrated pellet of microorganism, having the purity described above, will be disposed in at least the pellet region 104 of the body 105, and no washing or further centrifuging steps may be required. The user may remove the separation container 100 from the centrifuge and conduct downstream analysis of the microorganism through any of the methods and techniques described herein.

In some embodiments, the pellet may be removed from the body 105 of the separation container 100, by actuating the plunger 110, 115, and the plunger 110, 115 may extract the pellet without compromising the purity or viability of the microorganism. In particular, the plunger 110, 115 may be depressed to express the separated pellet of microorganism from the body 105. The user may press downwardly on the flexible sealing member 125 in which the second distal end 114, 119 of the plunger 110, 115 is disposed to actuate the plunger axially downwardly towards the first end 106.

As the plunger 110, 115 is depressed, the plunger may first seal against the wall 109 of the pellet region 104 to prevent fluid communication between the pellet and the remaining sample and density cushion above. For example, in the embodiments shown in FIGS. 1-89, the sealing rib 170, 270 may be lowered into contact with the cylindrical wall 109 at the pellet region 104, which thereby seals the fluid below the rib from the fluid above the rib as two separate sub-compartments.

Continued downward movement of the plunger 110, 115 after sealing may cause pressure to build within the pellet region 104 between the sealing surface of the plunger (e.g., sealing rib 170, 270) and the seal 120 at the first end 106 of the body 105. As pressure builds and the plunger 110, 115 continues to move downwardly, the point 113, 117 of the plunger contacts and opens the seal 120 by piercing through the seal or separating the seal from the body 105. In some embodiments, the plunger 110, 115 may require ca. 2 lbf of force to express the pellet. Opening the seal 120 allows the pellet to be expressed from the internal chamber 108 under the pressure created by the plunger 110, 115 being sealed against the wall 109 of the body 105. This back pressure may ensure that the pellet is cleanly and efficiently driven from the body 105.

In some embodiments, the pressure generated by the plunger 110, 115 is optimized by controlling the volume of the internal chamber 108, the distance between the point 113 of the plunger 110, 115 and the seal 120, and the position of the sealing surface on the plunger (e.g., sealing rib 170, 270). For example, the aforementioned distance, and thus the stroke of the plunger 110, 115, may be from 5 to 15 mm from initial movement of the plunger to final contact between the shelf 175, 275 and the wall 109. In one embodiment, the pressure is optimized to express the microorganism from the opening at a pressure appropriate for capturing the microorganism in a tube. For example, the pressure may be enough to ensure that a majority of the microorganism is expressed from the tip without remaining on the edges of the opening (e.g., without remaining on the punctured seal remnants). The pressure may also be low enough that the microorganism is released in a controlled spray instead of an explosion that has the potential to aerosolize the microorganism. In one embodiment, the proportions of the plunger, the internal chamber, and the sealing surface are configured to generate a pressure that expresses the microorganism and disperses the microorganism in a spray into a downstream sample collection device without causing spray outside of the downstream sample collection device.

After the seal 120 is opened, a portion of the seal may continue to restrict or prevent flow out the opening in the first end 106 (e.g., the remaining seal 120 narrows and restricts the annular opening between the plunger 110, 115 and the body 105). In some embodiments, additional flow resistance provided by the portions of the seal 120 that remain intact may add even further back pressure against the pellet. This resistance causes the internal pressure within the pellet region 104 to increase, which may cause the microorganism pellet to be expelled from the pellet region 104 cleanly and under pressure without leaving substantial amounts of microorganism in the body. The recovered microorganism may also be viable, which may be needed for AST and/or further culturing. Moreover, the back pressure provided by the plunger 110, 115 is substantially consistent between operations, due to the known distances of travel of the plunger after sealing the wall 109 of the body 105 but before opening the seal 102. Because the back pressure provided by the plunger 110, 115 and/or seal 120 may be substantially predictable between uses, the user may more readily predict the force and timing of the expression of the pellet and avoid dangerous spillage or splatter of the microorganism.

Viability of the expelled, recovered microorganisms is dependent upon a variety of parameters such as age of the positive culture, and the chemical makeup of the selective lysis buffers and density cushion reagents. These reagents and their methods of use can be tailored to deliver microbial suspensions of high viability and vitality, as required for sensitive growth-based technologies such as antibiotic susceptibility testing (AST), or may be formulated to deliver cell suspensions of higher purity, but potentially compromised viability, if required for other downstream technologies such as MALDI-TOF and some molecular, immunological, and immunochemical methods. Viability of the recovered microbial suspensions may be determined using culture of known dilutions of the recovered suspension on agar plates, a technique common to those skilled in the art, or the like. In some embodiments, the recovered microorganism may be viable, and in some embodiments, the recovered microorganism may not be viable.

In some embodiments, after the pellet has been expressed from the body 105 but before the sealing portion of the plunger 110, 115 (e.g., the sealing rib 170, 270 in the embodiments detailed above) breaks through the opening at the first end 106, the shelf 175, 275 may engage the wall 109 of the body 105 to stop further downward movement of the plunger. In embodiments where the seal of the plunger 110, 115 (e.g., the sealing rib 170, 270 in the embodiments detailed above) is not broken, the remaining contents of the internal chamber 108 may not empty into the sample collecting vessel 135 or other receiving apparatus. In this manner, the pellet may be expressed without risk of contaminating the sample due to inadvertent leakage or improper operation. In addition, maintaining the pellet under pressure from the plunger 110, 115 creates a positive pressure system that ensures that any leakage will flow from the pellet region 104 into the remainder of the internal chamber 108. Thus, any flaw in the seal between the plunger 110, 115 and the wall 109 during expression of the pellet may result in microorganism being lost back into the internal chamber 108 but not contamination of the microorganism in the pellet region 104 for downstream testing.

Further avoiding the risk of contamination or exposure to the microorganism, the sample collecting vessel 135 may surround the opening at the first end 106 of the body 105 to receive the pellet without any risk of exposure to the user. In some embodiments, the sample collecting vessel 135 may be threaded onto the body 105 (e.g., via adaptor 140/threaded connection 145 or threaded adaptor 240). Upon actuation of the plunger 110, 115 and expression of the pellet, the pellet may be collected in the sample collecting vessel 135 for downstream testing, including in situ culture. In some embodiments, the sample collecting vessel 135 may be glass, transparent plastic, or any other material suitable for the downstream testing needs of the user. In one embodiment, for example, the sample collecting vessel 135 may be made of any optically transparent material for later optical density interrogation of the microorganism through the wall of the sample collecting vessel 135. In some other embodiments, the pellet may be expressed directly into any other microorganism containment or storage vessel or any other testing apparatus as would be understood by a person of ordinary skill in the art in light of the present disclosure.

In some embodiments, the pellet collected in the sample collecting vessel 135 may be analyzed and/or tested in its concentrated form. In some other embodiments, the sample collecting vessel 135 may include a diluent (e.g., saline or microbiological culture medium) for diluting and resuspending the microorganism for downstream analysis and/or testing. The diluent may be pre-packaged in the sample collecting vessel 135 or may be loaded into the sample collecting vessel by the user in a predefined ratio of diluent to microorganism. The volume of the pellet 104 may be known and may be predictable between samples. In particular, the volume of the pellet may be substantially the same as the volume of the pellet region 104, minus the volume of the first distal end 118, 160 of the plunger 110, 115 below the sealing portion (e.g., below the sealing rib 170, 270) and minus certain, predictable losses due to leakage back into the internal chamber 108 and microorganism remaining in the pellet region 104 after the pellet is expressed. Because the volume of the pellet may be anticipated and the downstream testing is known, it may be possible to prepare the quantity of diluent in advance and prepackage the sample collecting vessels 135 specific to the separation container 100 and downstream test used. For example, antibiotic susceptibility testing (AST) may require a relatively dilute sample compared to other tests, and a sample collecting vessel that is paired with AST may be given a precise quantity of diluent to produce the desired concentration of microorganism for testing.

In some embodiments, the axial location at which the plunger 110, 115 seals against the wall 109 of the body 105 is dependent on the axial length of the pellet region 104 (e.g., the sealing ribs 170, 270 may engage the wall 109 at the start of the pellet region 104). Thus, as discussed above, in some embodiments, the volume expressed from the pellet region 104 may also be known and fixed, and may be dependent on the volume of the pellet region. In the aforementioned embodiments, it is preferable that sufficient sample be loaded into the separation container 100 to fill the pellet region 104 with separated microorganism. For example, if a portion of the density cushion is left in the pellet region, below the sealing ribs 170, 270, after centrifugation, this additional fluid may be expressed with the concentrated pellet of microorganism. Thus, for some embodiments, to better predict the concentration of the recovered microorganism, sufficient sample material containing sufficient quantities or concentration of microorganism should be used with a given sized separation container 100 to result in a separated microorganism pellet that is at least large enough to fill the pellet region 104.

Second Embodiment

Turning now to FIGS. 90-136, a second embodiment of the separation container 500 is shown without a plunger assembly. The separation container 500 may include a body 505 with a deformable wall 509 that allows a user to squeeze the body to extract the microorganism after centrifugation. In such embodiments, the separation body 505 may be made of a flexible plastic such as low density polyethylene (LDPE) or other flexible materials. Similar to the body 105 described above in connection with the embodiment of FIGS. 1-89, the body 505 shown in FIGS. 90-136 may include a first end 506 at which the body may include an opening for extracting the microorganism pellet. Similarly, the body 505 may include a second end 507 at which the body may include an opening for receiving the sample for centrifugation. The body 505 may define a collection region 502 and a pellet region 504 with a tapered region 503 connecting the two. The collection region 502 may define a wider radial diameter with respect to an axis 555 than the pellet region 504, and the wall 509 at the tapered region 503 may angle radially inward from the collection region 502 to the pellet region 504 to direct the microorganisms into the pellet region during centrifugation. The body 505 may further define one or more projections (e.g., round projection 550) that operate in substantially the same manner as the hexagonal bracket 150 described herein for facilitating centrifugation, and one or more support struts 560 for stabilization and strength.

In some embodiments (e.g., as shown in FIGS. 92, 95, 98, 100, 102, 104, 108, 110, 112, 115, 117, 119, 122, 125, 129, 132, and 135) the wall 509 may taper inwardly for some or all of the wall's axial length in the pellet region 504. Said differently, in some embodiments, the radial diameter of the pellet region 504 may be smaller at the first end 506 than at the transition between the tapered region 503 and the pellet region 504. In some embodiments, the wall 509 may taper uniformly from the transition between the tapered region 503 and the pellet region 504 to the first end 506, as shown in FIGS. 117, 119, 122, 125, 129, 132, and 135. In some embodiments, the diameter of the pellet region may rapidly narrow proximate the first end 506, as shown in FIGS. 92, 95, 98, 100, 102, 104, 108, 110, 112, 115. In yet some further embodiments, the rapidly narrowing section may include a less tapered section immediately adjacent the first end 506 as shown in FIGS. 92, 95, 98, 100, 110, 112, and 115. In each of the aforementioned embodiments, the wall 509 may taper gradually in the remaining portion of the pellet region 504 or may define a constant radius in the remaining portion.

With reference to FIGS. 90 and 99-100, the body 505 may include threads 512 or other attachment mechanisms on its outer surface. The threads 512 may engage a nut 510 to cover and seal the opening to the pellet region 504 at the first end 506 of the body 505. The nut 510 may include a gasket 520 or other sealing surface in its interior to prevent leakage from the internal chamber 508 of the body 505. As shown in FIG. 100, threading the nut 510 onto the body 505 may compress the gasket 520 with the first end 506 to form a tight seal. The gasket 520 may be an RTV silicone gasket, an expanded PTFE gasket, or other sealing gasket material.

The separation container 500 may be inserted into an open end of a centrifuge cup 540 and the nut 510 may rest within a cavity 541 of the cup and against a closed end of the cup. In particular, the cup 540 may define a bottom wall 543 and a side wall 544 for supporting and stabilizing the separation container 500. As shown in FIG. 100, the nut 510 may rest on the bottom wall 543 of the centrifuge cup 540. During centrifugation, the centrifuge cup 540 may hang from one or more pivots 542 such that the first end 506 of the body 505 is rotated radially outward and the second end 507 of the body 505 is rotated radially inward during centrifugation.

With continued reference to FIG. 100, a rheological control member, shown here as a sphere 600, may be used in the internal chamber 508 for the same purpose as the above-described embodiments. In particular, the sphere 600 may prevent mixing of the density cushion and the sample during loading of the sample into the body 505. As with the above-described embodiments, in some embodiments, the sphere 600 may be replaced with an annular structure, a plurality of smaller spheres, or any other rheological control member. The sphere 600 may be buoyant in the density cushion and sample in accordance with the other embodiments of the rheological control member described herein.

During operation, the loading and centrifuging processes occur in substantially the same manner as described in the above embodiments. In some embodiments, the sample may be lysed and loaded into the internal chamber 508, while the rheological control member (e.g., sphere 600) may prevent mixing of the density cushion and the sample. The density cushion may include substantially the same properties as discussed above in connection with the embodiment of FIGS. 1-89. The separation container 500 may then be centrifuged in the cup 540 with the nut 510 and gasket 520 sealing the opening in the first end 506. During centrifugation, the heavier microorganisms may pass through the density cushion and settle in the pellet region 504, in which the microorganisms may form a microorganism pellet.

After centrifugation the separation container 500 may be removed from the cup 540, and the nut 510 and gasket 520 may be removed by the user. To express the pellet, the user may then squeeze the deformable wall 509 of the body 505 to expel the pellet into a container or testing apparatus. In some embodiments, the user may squeeze the deformable wall 509 at any point above the pellet region 504. In such embodiments, the wall 509 may be made of a flexible material capable of being deformed by a user's hand.

As in the embodiments described above, the body 905 may be configured to engage a sample collecting vessel 135 for receiving the pellet after centrifugation. For example, the body 905 shown in connection with the embodiment of FIGS. 142-153 may include an adaptor (e.g., adaptor 140 and threaded connector 145 shown in FIG. 1 or threaded adaptor 240 shown in FIG. 68) for engaging the vessel 135, or the body 905 may otherwise be structured to engage a collection device. One of ordinary skill in the art will appreciate in light of this disclosure that the properties of the separation container 500 and associated methods and apparatus may include substantially the same features and steps as the other embodiments described herein unless noted otherwise.

Third Embodiment

Turning now to FIGS. 137-141, a third embodiment of the separation container 700 is shown having substantially the same features as the separation container 500 shown in connection with FIGS. 90-136 except that the first distal end 706 of the body 705 is removable and does not otherwise include any fluid flow paths through the first distal end.

The sealed first distal end 706 of the body 705 may ensure that fluid does not leak from the body 705 during centrifugation, and the first distal end 706 may include a removable portion 720. The removable portion 720 may be removed, for example, by cutting the end off at the entrance to the pellet region 704, to then squeeze or otherwise express the pellet from the body 705. As with the above-described embodiments, the wall 709 at the pellet region 704 may taper inwardly at any or all points between the transition from the tapered region 703 to the pellet region 704 and the first distal end 706.

As in the embodiments described above, the body 705 may be configured to engage a sample collecting vessel 135 for receiving the pellet after centrifugation. For example, the body 705 shown in connection with the embodiment of FIGS. 142-153 may include an adaptor (e.g., adaptor 140 and threaded connector 145 shown in FIG. 1 or threaded adaptor 240 shown in FIG. 68) for engaging the vessel 135, or the body 705 may otherwise be structured to engage a collection device.

Fourth Embodiment

Turning to FIGS. 142-153, a fourth embodiment of the separation container 900 is shown having substantially the same features as the separation containers 500, 700 shown in connection with FIGS. 90-141 except that the first distal end 906 of the body 905 includes a pull tab 920 (shown in FIGS. 149-153) and does not otherwise include any fluid flow paths through the first distal end.

The sealed first distal end 906 of the body 905 may ensure that fluid does not leak from the body 905 during centrifugation, and the pull tab 920 may be torn off to expose the entrance to the pellet region 904 and to then allow the user to squeeze or otherwise express the pellet from the body 905. FIGS. 142-148 show an example of the separation container 900 after the pull tab 920 has been removed. As with the above-described embodiments, the wall 909 at the pellet region 904 may taper inwardly at any or all points between the transition from the tapered region 903 to the pellet region 904 and the first distal end 906.

As in the embodiments described above, the body 905 may be configured to engage a sample collecting vessel 135 for receiving the pellet after centrifugation. For example, the body 905 shown in connection with the embodiment of FIGS. 142-153 may include an adaptor (e.g., adaptor 140 and threaded connector 145 shown in FIG. 1 or threaded adaptor 240 shown in FIG. 68) for engaging the vessel 135, or the body 905 may otherwise be structured to engage a collection device.

Fifth Embodiment

Turning to FIGS. 166-223, a fifth embodiment of the separation container 1000 is shown having a body 1005 including a first distal end 1006 and a second distal end 1007. The body 1005 may include a wall 1009 defining an internal chamber 1011 divided into several regions, including a collection region 1002 (shown in FIG. 165), a widened region 1008 between the collection region and the second distal end 1007, a tapered region 1003, and a pellet region 1004. The plunger 1010 may include distal ends 1013, 1014 and a shelf 1075 for preventing the plunger from falling out of the pellet region. In some embodiments, the portions of the wall 1009 in the pellet region 1004 may be reinforced with one or more ribs 1045 extending in a longitudinal, axial direction of the body 1005 for structural support. Each of the areas and features of the body 1005 may be formed and operate according to any of the embodiments described herein.

Unless otherwise stated, the separation container 1000 may operate in the same manner, may have the same properties, and may be made with the materials and configurations of any embodiment described herein. The separation container 1000 of the fifth embodiment depicts a non-buoyant plunger 1010 that is retained by a retainer 1032 as described above. The depicted separation container 1000 also includes a rheological control member 1042 and gasket 1043 as described herein. In addition, the depicted separation container 1000 may include a coupling cap 1040, 1140 for securing the seal 1020 (e.g., a foil or other sealing membrane) to the body 1005, and for coupling the body 1005 with a sample collecting vessel 1038, which may operate in the same manner as the sample collecting vessels 135, 1038 described herein.

During assembly, the separation container 1000 may be assembled in the following ordered steps: (1) add the density cushion to the internal chamber 1011; (2) connect the plunger 1010 with a retainer 1032; (3) insert the rheological control member 1042 onto the plunger 1010; (4) slide the gasket 1043 onto the plunger 1010 beneath the rheological control member 1042; and (5) press fit the retainer 1032 into the tube, while also forming the interference fit between the rheological control member 1042 and the body 1005. In some embodiments the seal 1020 may be attached to the body 1005 prior to adding the density cushion. The interference fit may be created by inserting rods into the gaps between the retainer 1032 and the plunger 1010 to press the rheological control member 1042 downwardly.

During testing, the separation container 1000 may be operated in the following ordered steps: (1) To add the lysed sample to the tube, the cap 1030 and flexible sealing member 1025 may be removed; (2) the sample may then be transferred to the tube, with the rheological control member 1042 preventing bulk mixing of the sample with the density cushion since it is positioned between the two fluids; (3) the separation container may be optionally pre-spun before adding the sample to move any density cushion that may have migrated to the top chamber during shipping or storage. The rheological control member 1042 may be constructed for a small clearance between it and the wall 1009 of the body 1005 and may include an interference fit when not being centrifuged as discussed above. The rheological control member 1042 may also be constructed so that it does not jam into the tube by bottoming out on the tapered region 1003 of the body 1005. The testing may further include: (4) during addition of the sample the rheological control member 1042 may float if optionally not interference fit, while still providing mixing protection. The rheological control member 1042 may also have a recessed ring in the top portion, which can trap any settling components such as resin or other particulates. These particles may stay in the recessed area as the layering aid floats up the tube either during sample addition or centrifugation. The testing may further include: (5) after the sample is added, the cap 1030 and flexible sealing member 1025 may be placed back on the tube; and (6) the entire separation container 1000 may be placed in the centrifuge and spun. In embodiments where the rheological control member 1042 is sealed against the body 1005 and plunger 1010, the sample may be added directly to the internal chamber 1011 with a lytic agent and the entire separation container 1000 can be vortexed to lyse the sample before the centrifugation step.

In operation, the process for expressing the pellet is the same actuation and foil piercing process described herein with respect to each other embodiment, and in embodiments using a retainer 1032, an additional step of applying horizontal pressure to the tab 1022 of the plunger 1010 may be used to disconnect the plunger from the retainer. Unless otherwise stated, features having the same reference numeral, name, or purpose in the assembly may be interchanged with one another in any of the embodiments described herein.

Sixth Embodiment

With reference to FIGS. 224-276 a sixth embodiment of the separation container 1200 is shown. With reference to FIG. 224, an exploded view of the separation container 1200 is shown depicting a body 1205 having a seal 1220 to close an opening in one end and a cap 1230 and flexible sealing member 1225 at the other. The separation container 1200 may include a plunger 1210 having a plunger seal 1290, a rheological control member 1242, and a retainer 1232 attached thereto for ensuring smooth operation and reducing contamination of the sample pellet as described below. The separation container 1200 may further engage an end cap 1250 for supporting the body 1205 and seal 1220 during centrifugation, and the separation container may include a coupling member 1240 for coupling and sealing the body to a sample collecting vessel (e.g., the sample collecting vessels 135, 1038 described herein).

With reference to FIGS. 225-230, assembled views of the separation container 1200 are shown. In some embodiments, the separation container 1200 may engage the end cap 1250 to support the seal 1220 and body 1205 during centrifugation to allow the separation container to be adaptable to many different centrifuge cups while also improving manufacturability and quality. The end cap 1250 may hold the seal 1220 in place during induction welding in instances in which the seal is induction welded to the tube. If the seal 1220 is heat sealed, the seal may be attached before the end cap 1250 is applied. In each of the embodiments discussed herein, the end cap 1250 may support the seal 1220 from distending and rupturing during centrifugation.

The end cap 1250 may include a tapered portion 1251, which may be solid or include one or more ribs 1252 with gaps therebetween. The end cap 1250 may include a substantially flat distal end 1253 and may include a flat flange 1254 at an opposite end. The flat distal end 1253 may be configured to engage the flat or rounded bottoms of various types and models of centrifuge cup, and the distal end 1253 may be narrower than the flange 1254 at the opposite end with the tapered portion 1251 narrowing the diameter of the end cap between the two ends. In some embodiments, the tapered portion 1251 may be configured to engage the walls of conical-shaped centrifuge cups. Thus, the end cap 1250 may be structured to engage different models and structures of centrifuge without needing different adaptors or sacrificing stability.

In some embodiments, the body 1205 may include a flange 1255 that is configured to engage the flange 1254 of the end cap. In some embodiments, the flange 1255 may be disposed circumferentially about the tapered region 1203 of the body 1205 and oriented towards the flange 1254 of the end cap 1250, as shown in the embodiment of FIGS. 225, 226, 228-234, and 236-238. In some embodiments, the flanges 1254, 1255 may be removably or semi-permanently attached to each other. For example, in some embodiments, a threaded connection (not shown), snap connection (not shown), or other removable engagement may be formed between the body flange 1255 and the end cap flange 1254. In some embodiments, the flanges 1254, 1255 may be adhered, welded, molded, or otherwise semi-permanently fused to each other, such that the bond between the flanges must be mechanically broken to remove the end cap 1250. In some embodiments, the end cap 1250 may be press fit over the coupling member 1240, such that the end cap does not need to be welded to the body 1205. In each instance, the end cap 1250 may be optionally welded to the body 1205.

In some embodiments, the end cap 1250 may include a hex-shaped recess 1257 in the distal end 1253. The recess 1257 may be used to hold the separation container 1200 (e.g., by standing the separation container and end cap 1250 on a vertical post (not shown)) when not in use, when filling the container, or during centrifugation. In some embodiments, a post or other rigid object (not shown) may be inserted into the recess 1257 to assist with removal of the end cap 1250 after centrifugation. For example, in embodiments in which the end cap 1250 has its flange 1254 semi-permanently attached to the flange 1255 of the body, the post or other rigid object may be a corresponding hex shape, such that the post or other rigid object may be inserted into the recess 1257 and may be used to twist or torque the semi-permanent connection apart. The mechanical separation of the end cap 1250 with a tool (e.g., the post or other rigid object referenced above) may reduce agitation of the sample and prevent inadvertent contamination.

In some embodiments, the end cap 1250 may further include an internal platform 1256 against which the first distal end 1206 of the pellet region 1204 may rest, either with the body 1205 touching the platform 1256 or with the seal 1220 sandwiched therebetween. The platform 1256 may support the seal and prevent inadvertent rupture before the user is ready to express the final concentrated pellet, including during manufacturing, assembly, packaging, loading, and centrifugation. In addition, the platform 1256 of the end cap 1250 allows a full sized seal 1220 to be attached to the entire surface area of the distal end of the pellet region 1204 providing for improved manufacturability and an improved seal between the seal 1220 and body 1205.

With reference to FIGS. 224, 226, 229, 230, 232-242, and 254-258, a coupling member 1240 may be disposed on the body 1205 at or near the pellet region 1204 to facilitate coupling of the separation container 1200 to a sample collecting vessel (e.g., the sample collecting vessels 135, 1038 detailed herein) and/or to provide a further seal within the end cap 1250 to prevent leakage of the contents of the body 1205. The coupling member 1240 may include one or more circumferential ridges 1241 to provide a seal against the sample collecting vessel. The coupling member 1240 may further include a first, distal sealing surface 1243 and a second, upper sealing surface 1244, which may be pointed (e.g., like ridges 1241) or flat. The sealing surfaces 1243, 1244 and the ridges 1241 may progressively decrease in their diameter when travelling towards the first distal end 1206 of the pellet region 1204. For example, the first sealing surface 1243 may be the narrowest sealing surface of the coupling member 1240 and the second sealing surface 1244 may be the widest sealing surface of the coupling member with each ridge 1241 therebetween progressively increasing in diameter, which may facilitate insertion of the separation container into the sample collecting vessel while providing a strong seal.

With reference to FIG. 230, in some embodiments, the second sealing surface 1244 may be wider than the inner diameter of a sample collecting vessel (not shown) (e.g., the sample collecting vessels 135, 1038 shown herein) and the second sealing surface 1244 may include a chamfer 1245 for engaging the upper edge of the sample collecting vessel. The chamfer 1245 may either create a seal against the upper rim of the sample collecting vessel or may compress the second sealing surface 1244 inward to fit the second sealing surface within the sample collecting vessel, while reducing the force required for engagement. In some embodiments, any other connector or coupling may be used to engage the body 1205 with a sample collecting vessel. The other connector or coupling may be attached to either the body 1205 or the sample collecting vessel or may be a separate device.

The end cap 1250 may include a narrow, first wall 1246 near or adjacent to the platform 1256 and may include a wider, second wall 1247 above the first wall opposite the platform. The first wall 1246 and the second wall 1247 (the inner and/or outer surfaces) may be parallel to the wall of the pellet region 1204 or may be tapered inwardly slightly such that the distal end closest to the platform 1256 is narrower than the opposite end for either wall segment 1246, 1247. The first wall 1246 and second wall 1247 may define diameters that are less than or equal to the diameters of the respective first sealing surface 1243 and second sealing surface 1244 at least at the same respective axial positions above the platform 1256.

With continued reference to FIG. 230, the body 1205 may include one or more circumferential ribs 1248, 1249 that provide structural rigidity to the connection between the body and the coupling member 1240. For example, in the embodiment shown in FIG. 230, the body includes two circumferential ribs 1248, 1249, one disposed proximate the tapered region 1203 of the body and one disposed proximate the first distal end 1206 of the pellet region 1204. In the embodiment shown in FIG. 230, a first circumferential rib 1248 is embedded in a corresponding recess in the first sealing surface 1243 of the coupling member 1240. Similarly, in the embodiment shown in FIG. 230, a second circumferential rib 1249 is embedded in a corresponding recess 1260, 1261 in the second sealing surface 1244 of the coupling member 1240. The coupling member 1240 and the body 1205 may be attached via overmolding, elastically stretching the coupling member 1240 over the body 1205, or fusing multiple pieces of the coupling member 1240 together around the body 1205. In some embodiments, the coupling member 1240 may be made of a compliant material such as elastomer. The coupling member 1240 may be overmolded onto the body 1205. In some embodiments, the coupling member 1240 may be made from silicone or thermoplastic elastomers such as Medalist® MD-12140.

With reference to FIGS. 241, 243, 245, 248, 250, 252, 256, and 257, the body 1205 may also include one or more vertical ribs 1262, and the coupling member 1240 may include one or more corresponding recesses 1263 for receiving and engaging the vertical ribs 1262. In some embodiments, the body 1205 may include a base flange 1264 at the distal end of the pellet region 1204 for retaining the coupling member 1240 with its upper surface and engaging the seal 1220 with its lower surface (e.g., via sonic welding).

An end of the coupling member 1240 opposite the base flange 1264 may further abut a portion of the outer surface of the tapered region 1203, such that the combined upward retention from the base flange and the downward retention from the tapered region encourage the coupling member 1240 to a stable position (e.g., the position shown in FIG. 242). In some embodiments, the coupling member 1240 may be disposed between the flange 1255 on the body 1205 in the tapered region 1203 and the base flange 1264 such that the coupling member 1240 fits within the end cap 1250. The coupling member 1240 may include bi-directional (e.g., perpendicular) recesses (e.g., recesses 1260, 1261, 1263) to engage the corresponding bi-directional ribs (e.g., ribs 1248, 1249, 1262) of the body and prevent both axial and rotational movement of the coupling member.

As discussed in connection with other embodiments herein, the body 1205 may include a first distal end 1206, a second distal end 1207, a tapered region 1203, a pellet region 1204, a collection region 1202, a widened region 1208, and a wall 1209, each of which may operate and may be structured as described in each embodiment herein. The separation container 1200 may further include a retainer 1232 attached to the body 1205 in the widened region 1208. In some embodiments, with reference to FIGS. 243, 244, 249, and 251, the widened region 1208 of the body 1205 may include one or more slots 1265 which may receive and secure the retainer 1232 therein. The retainer 1232 may be otherwise structured and operable as described above with respect to the retainer 1032 to secure the plunger 1210 in a predetermined vertical position (e.g., a position in which the upper edge of the retainer 1232 is coplanar with the second distal end 1207 of the body 1205). For example, with reference to FIG. 259, the plunger 1210 may include a support member 1215 having the features and structure shown and described in connection with the support member 1015 of the plunger 1010, and the retainer 1232 may include retaining members 1233 and corresponding features having the features and structure shown and described in connection with the retainer 1032 of the plunger 1010.

With reference to FIGS. 259-268, the plunger 1210 is shown in accordance with some embodiments discussed herein. The plunger 1210 may include a longitudinal member 1216 coming to a conical point 1217 at a first distal end 1218. The plunger may include a piercing section 1270 defining a cylindrical portion of the longitudinal member 1216 which terminates with a taper at the point 1217. The piercing section 1270 may operate in substantially the same manner as the blade 160 or point 117 discussed herein, and the piercing section 1270 and point 1217 may be narrower than the longitudinal member 1216 or the remaining portions of the plunger 1210 to allow for collection of additional sample in the pellet region 1204. In this manner, the relative diameters and sizes of the components shown in the figures are intended to be accurate as example embodiments (e.g., the piercing section 1270 is depicted narrower than the remainder of the longitudinal member 1216).

In some embodiments, the plunger 1210 may include at least one sealing rib 1272 formed circumferentially about the longitudinal member 1216, and may include a tapered region 1271 between the sealing rib 1272 and the piercing section 1270. This sealing rib 1272 may define the plunger diameter d, and the sealing rib may be a generally circular sealing surface that seals uniformly about the plunger. The sealing rib 1272 may be configured to engage the wall 1209 of the body 1205 and seal a portion of the internal chamber 1211 below the rib 1272 from a portion of the internal chamber above the rib. In particular, the plunger diameter d of the sealing rib 1272 may be interference fit to the pellet diameter (e.g., slightly greater than the diameter of the body 1205 at the pellet region 1204), such that the plunger 1210, via rib 1272, engages the pellet region 1204 during actuation of the plunger. In this manner, the plunger 1210 may fluidically isolate the pellet region 1204 from the tapered region 1203 and the collection region 1202 when actuating the plunger. The sealing rib 1272 may be molded with and made from the same, generally-rigid material as the plunger.

In some embodiments, the plunger 1210 may further include a plunger seal 1290 attached to the plunger above the sealing rib 1272 (e.g., the sealing rib 1272 may be disposed between the plunger seal 1290 and the point 1217. The plunger seal 1290 may define a diameter that is greater than or equal to the diameter of the sealing rib 1272 and the diameter of the pellet region 1204. As described herein, the plunger seal 1290 may seal the internal chamber 1211 of the body at the pellet region 1204 to prevent leakage of the density cushion when the sealing rib 1272 emerges from the first distal end 1206 of the body 1205 when the plunger 1210 is fully depressed.

In some embodiments, the plunger 1210 may define a recess 1273 in the longitudinal member 1216 in which a portion of the plunger seal 1290 is disposed. The recess 1273 may include a first shoulder 1274 and a second shoulder 1275 which may abut either side of the plunger seal 1290 to retain the plunger seal within the recess and may extend radially from the inner diameter of the recess to a diameter of the longitudinal member 1216. In some embodiments, further ridges (also referenced herein as chamfers) (shown in FIG. 260) or changes in diameter may be used to retain the plunger seal 1290.

In some embodiments, the plunger 1210 may further define a through passage 1276 in the recess 1273 through which a corresponding locking arm 1277 of the plunger seal 1290 may extend to prevent rotational or axial movement of the plunger seal. In some embodiments, the plunger seal 1290 may be overmolded onto the plunger 1210 such that the locking arm 1277 is fixedly and permanently formed within the through passage 1276. In some embodiments, the plunger seal 1290 may be formed from a softer material (e.g., an elastomeric material) than the plunger 1210 to provide a further seal against the wall 1209 when the plunger is depressed. The plunger seal 1290 may be made from an elastomer such silicone or thermoplastic elastomers just as with coupling member 1240. In some embodiments, the material of the plunger seal 1290 should be compliant (e.g., TPE with a 50 Shore A durometer). The plunger seal 1290 may mitigate molding defects in the more rigid plunger 1210 (e.g., imperfections in the seal of the sealing rib 1272. In some embodiments, the plunger seal 1290 may deform more easily than the rib 1272 and require less force to move along the wall 1209. The plunger seal 1290 may include chamfered edges near the shoulders 1274, 1275 for easier actuation.

In some embodiments, the longitudinal member 1216 of the plunger may include a further tapered region 1278 above the recess 1273 (e.g., the recess 1273 is disposed between the point 1217 and the further tapered region 1278) such that the portion of the longitudinal member 1216 above the further tapered region 1278 is wider. The further tapered region 1278 and the longitudinal member 1216 on the larger side of the further taper may define a diameter that is substantially greater than the pellet region 1204.

In some embodiments, the longitudinal member 1216 may include a step 1279 which may help to reduce the required actuation force of the plunger 1210 because of the relatively narrower diameter of the step compared to the surrounding body of the plunger.

With reference to FIGS. 259, 262-265, and 267, a second distal end 1219 of the plunger, opposite the point 1217, may include a gripping portion 1280 for allowing the user to depress (e.g., move the plunger axially in the longitudinal direction) and/or twist (e.g., rotate the plunger about the longitudinal axis, for example, to release the support member 1215 and retainer 1232) the plunger 1210. The gripping portion 1280 may be generally cylindrical (e.g., as shown in FIG. 1210, such that the user can rotate the plunger 1210 by rolling the gripping portion 1280 between their fingers. In some embodiments, the gripping portion 1280 may be asymmetrical (e.g., oblong like the tab 1022 detailed above).

With reference to FIGS. 224-239 and 269-272, the gripping portion 1280 of the plunger 1210, which may be sealed within the separation container 1200, may be manipulated through the flexible sealing member 1225 to prevent leakage or contamination. The flexible sealing member 1225 may be made of an elastomeric material, and in some embodiments, the flexible sealing member 1225 may be made of an at least partially transparent material. In some embodiments, the flexible sealing member 1225 may be retained by a cap 1230 that is structured and functions substantially the same as the caps (e.g., caps 130, 1030) described herein, with an opening 1231 (shown in FIG. 224) through which the flexible sealing member 1225 may extend. The cap 1230 may then thread onto the body 1205 to secure a flange 1281 of the flexible sealing member therebetween. In some embodiments depicted herein (e.g., as shown in FIG. 225, 228, 231-233, 236-237), the flexible sealing member 1225 is depicted as being transparent to allow visibility of the plunger 1210 therein. However, in some embodiments, the flexible sealing member 1225 may be transparent, opaque, or partly transparent or opaque.

With reference to FIGS. 269-271, the flexible sealing member 1225 may include a top 1282, which the user may depress to also depress the plunger 1210 (shown in FIG. 224). The top 1282 and flange 1281 may be connected by a wall 1283 of the flexible sealing member 1225. Turning to FIGS. 273-276, upon actuation by the user, the top 1282 may translate downwardly towards the flange 1281 and remainder of the separation container to cause the axial movement of the plunger 1210. In some embodiments, the top 1282 may collapse slightly around the user's finger. As the top 1282 and flange 1281 move closer to each other the wall 1283 collapses and hinges to allow the top 1282 to remain in contact with the plunger. In some embodiments, the wall 1283 deforms at least partially outward to allow the top 1282 to depress the plunger 1210 to a position completely flush with the cap 1230.

Referring to FIGS. 269-274, in some embodiments, wall 1283 comprises a plurality of segments 1284, 1285, 1286, 1287, which may be vertical (e.g., the vertical segments 1285, 1287) or non-vertical (e.g., the non-vertical segments 1284, 1286). In some embodiments, the wall 1283 may define an at least partially inwardly concave shape (e.g., the semi-rounded shape shown in FIG. 271) to cause the wall to deflect out of the path of the plunger. For example, in some embodiments, the wall may include a vertical segment 1285 adjacent two non-vertical segments 1284, 1286. The vertical wall segment 1285 may be generally concentric about the longitudinal axis of the plunger 1210 with the surface of the vertical wall segment 1285 defining an at least partial cylinder sharing a common axis with the plunger. The two non-vertical segments 1284, 1286 may each be angled radially inwardly from their respective circumferential junctions with the vertical segments 1285. In such embodiments, the travel distance of the plunger 1210 and the deformation range of the flexible sealing member 1225 may be greater than an equivalently tall bellows design.

In the embodiment shown in FIG. 271, the top 1282 is connected to a first non-vertical wall segment 1284 that is angled downwardly and outwardly from the top. The first non-vertical wall segment 1284 is then connected to a first vertical wall segment 1285. The first vertical wall segment 1285 is then connected to a second non-vertical wall segment 1286 that is angled downwardly and inwardly from the first vertical wall segment. The second non-vertical wall segment 1286 is then connected to a second vertical wall segment 1287, which abuts the flange 1281. In some embodiments, the wall segments may smoothly transition between each other. In some embodiments, the flexible sealing member (e.g., flexible sealing members 125, 1025) of any other embodiment may be used in place of the flexible sealing member 1225.

In some embodiments, the wall 1283 may hinge about the non-vertical wall segments 1284, 1286 with the vertical wall segments 1285, 1287 remaining substantially vertical, such that the first vertical wall segment 1285 moves outwardly, while the non-vertical wall segments 1284, 1286 hinge and the top 1282 moves downwardly during operation. For example, FIGS. 273-276 illustrate an embodiment of the flexible sealing member 1225 in an actuated position. In the depicted embodiment, the top 1282 of the flexible sealing member 1225 has been pressed downwardly with the wall 1283 hinging about the junction between the first non-vertical wall segment 1284 and the first vertical wall segment 1285, with portions of the top 1282 and/or wall 1283 optionally elongating with the force of the actuation. In some embodiments, as discussed herein, the flexible sealing member 1225 may deform sufficiently far to press the top of the plunger 1210 to a position parallel to, above, below, parallel or below, or parallel or above, a plane of the cap 1230, a plane of the top of the body 1205, and/or a plane of the flange 1281.

Referring back to FIGS. 224-239, the separation container 1200 may include a rheological control member 1242, which may be structured and operate according to any of the embodiments discussed herein. For example, in some embodiments, the rheological control member 1242, body 1205, and plunger 1210 may be structured and cooperate in substantially the same manner as the rheological control member 1042, body 1005, and plunger 1010 of FIG. 165 or FIG. 213, and may include the gasket 1043 and corresponding structure and operation described therewith. In some other embodiments, the rheological control member 1242 may be structured and operate as shown and described with respect to the embodiments of FIGS. 14-31, FIGS. 32-49, or FIGS. 50-67.

Unless otherwise stated, the separation container 1200 may operate in the same manner, may have the same properties, and may be made with the materials and configurations of any embodiment described herein. The separation container 1200 of the sixth embodiment depicts a non-buoyant plunger 1210 that is retained by a retainer 1232 as described above. The depicted separation container 1200 also includes a rheological control member 1242 as described herein. In addition, the depicted separation container 1200 may engage an end cap 1250 for securing the seal 1220 (e.g., a foil or other sealing membrane) to the body 1205 and supporting the separation container during centrifugation. The separation container 1200 may further include a coupling member 1240 for coupling the body 1205 with a sample collecting vessel 135, 1038, which may be used in a similar manner to the sample collecting vessels 135, 1038 described herein.

During assembly, the separation container 1200 may be assembled in the following ordered steps: (1) add the density cushion to the internal chamber 1211; (2) connect the plunger 1210 with a retainer 1232; (3) insert the rheological control member 1242 onto the plunger 1210; (4) slide the gasket 1043 onto the plunger 1210 beneath the rheological control member 1242 (for embodiments using a gasket); (5) engage the retainer 1232 with the slots 1265 in the body 1205, while also forming an interference or slip fit between the rheological control member 1242 and the body 1205; (6) insert the flexible sealing member 1225 into the opening 1231 in the cap 1230; and (7) secure the flexible sealing member 1225 and cap 1230 onto the body 1205 while encapsulating the plunger within the separation container (e.g., seal the separation container either before or after inserting a sample for testing). An interference fit may be created by inserting rods into the gaps between the retainer 1232 and the plunger 1210 to press the rheological control member 1242 downwardly. In some embodiments the seal 1220 may be attached to the body 1205 prior to adding the density cushion. In accordance with some embodiments discussed herein, the rheological control member may be initially inserted with an interference fit before being released during centrifugation by the outward deformation of the wall 1209 of the body 1205.

During testing, the separation container 1200 may be operated in the following ordered steps: (1) To add the lysed sample to the tube, the cap 1230 and flexible sealing member 1225 may be removed; (2) the sample may then be transferred to the body 1205, with the rheological control member 1242 preventing bulk mixing of the sample with the density cushion by being positioned between the two fluids; (3) the separation container may be optionally pre-spun before adding the sample to move any density cushion that may have migrated to the top chamber during shipping or storage. The rheological control member 1242 may be constructed for a small clearance between it and the wall 1209 of the body 1205 and may include annular shoulders (e.g., shoulders 1061, 1062) when not being centrifuged as discussed above (e.g., to limit the downward movement of the rheological control member). In some embodiments, the rheological control member 1242 may also be constructed so that it does not interact with or reach the tapered region 1203 of the body 1205.

The testing may further include: (4) during addition of the sample the rheological control member 1242 may float if optionally not interference fit, while still providing mixing protection. The rheological control member 1242 may also have a recessed ring in the top portion, which can trap any settling components such as resin or other particulates. These particles may stay in the recessed area as the layering aid floats up the tube either during sample addition or centrifugation. The testing may further include: (5) after the sample is added, the cap 1230 and flexible sealing member 1225 may be placed back on the tube; and (6) the entire separation container 1200 may be placed in the centrifuge and spun. In embodiments where the rheological control member 1242 is sealed against the body 1205 and plunger 1210, the sample may be added directly to an internal chamber 1211 with a lytic agent and the entire separation container 1200 can be vortexed to lyse the sample before the centrifugation step.

In operation, the process for expressing the pellet is the same actuation and foil piercing process described herein with respect to each other plunger embodiment, and in embodiments using a retainer 1232, an additional step of applying horizontal, rotational pressure to the gripping portion 1280 of the plunger 1210 may be used to disconnect the plunger from the retainer. With reference to FIGS. 225-230, the separation container 1200 is shown in a storage or loaded position (depending on whether sample has been introduced to the body 1205) in which the plunger 1210 is attached to and retained by the retainer 1232. FIGS. 231-235 show the separation container 1200 whose plunger 1210 has been released from the retainer 1232, but the plunger has not yet pierced the seal 1220. In the position shown in FIGS. 231-235, the sealing rib 1272 has abutted the wall 1209 of the body 1205 at the junction between the tapered region 1203 and the pellet region 1204 when the point 1217 contacts the foil. Turning to FIGS. 236-239 and 275-276, the plunger 1210 is shown fully depressed with the rib 1272 having passed through the first distal end 1206 of the body 1205, the pellet having been fully expressed, and the plunger seal 1290 preventing leakage of the fluid (e.g., density cushion) thereabove. For example, in some embodiments, the distance between the sealing surfaces of the rib 1272 and the plunger seal 1290 may be less than the length of the pellet region 1204 to prevent leakage of the density cushion or contamination of the sample. Unless otherwise stated, features having the same reference numeral, name, structure, or purpose in the assembly may be interchanged with one another in any of the embodiments described herein and the present inventors specifically contemplate each possible permutation of structures and features.

Seventh Embodiment

With reference to FIGS. 277-344, a seventh embodiment of the separation container 1300 is shown. With reference to FIG. 277, an exploded view of the separation container 1300 is shown depicting a body 1305 having a seal 1320 to close an opening 1312 (shown in FIG. 280) in one end and a cap 1330 and flexible sealing member 1325 at the other. The separation container 1300 may include a plunger 1310 having a plunger seal 1390, a rheological control member 1342, and a retainer 1332 attached thereto for ensuring smooth operation and reducing contamination of the sample pellet as described below. The separation container 1300 may further engage an end cap 1350 for supporting the body 1305 and seal 1320 during centrifugation, and the separation container may include a coupling member 1340 for coupling and sealing the body to a sample collecting vessel (e.g., the sample collecting vessels 135, 1038 described herein).

With reference to FIGS. 278-282, assembled views of the separation container 1300 are shown with an end cap 1350. In some embodiments, the separation container 1300 may engage the end cap 1350 to support the seal 1320 and body 1305 during centrifugation to allow the separation container to be adaptable to many different centrifuge cups while also improving manufacturability and quality. The end cap 1350 may hold the seal 1320 in place during induction welding in instances in which the seal is induction welded to the tube. If the seal 1320 is heat sealed, the seal may be attached before the end cap 1350 is applied. In each of the embodiments discussed herein, the end cap 1350 may support the seal 1320 from distending and rupturing during centrifugation. In some embodiments, the seal 1320 may be connected to the body 1305 with sufficient strength to prevent the seal from opening under the force of centrifugation without an end cap 1350.

In some embodiments, the end cap 1350 may be a centrifuge adaptor configured to stably support the separation container 1300 in a centrifuge. The end cap 1350 may include a tapered portion 1351, which may be solid or include one or more ribs 1352 with gaps therebetween. In some embodiments, a portion of the ribs 1352 may define the tapered portion 1351. The end cap 1350 may include a substantially flat distal end 1353 and may include a flange 1354 and/or a concentric wall 1358 at an opposite end to assist with alignment of the end cap 1350 in the respective axial and radial directions. The flat distal end 1353 may be configured to engage the flat or rounded bottoms of various types and models of centrifuge cup, and the distal end 1353 may be narrower than the flange 1354 and/or concentric wall 1358 at the opposite end with the tapered portion 1351 narrowing the diameter of the end cap between the two ends. In some embodiments, the tapered portion 1351 may be configured to engage the walls of conical-shaped centrifuge cups. Thus, the end cap 1350 may be structured to engage different models and structures of centrifuge without needing different adaptors or sacrificing stability.

In some embodiments, the body 1305 may include a flange 1355 that is configured to engage the flange 1354 and/or concentric wall 358 of the end cap 1350. In some embodiments, the flange 1355 may be disposed circumferentially about the tapered region 1303 of the body 1305 and oriented towards the flange 1354 of the end cap 1350, as shown in the embodiment of FIGS. 277-280. In some embodiments, the flanges 1354, 1355 may be removably or semi-permanently attached to each other. For example, in some embodiments, a frictionally-retained interference fit, a threaded connection (not shown), snap connection (not shown), or other removable engagement may be formed between the body flange 1355 and the end cap flange 1354. In some embodiments, the flanges 1354, 1355 may be adhered, welded, molded, or otherwise semi-permanently fused to each other, such that the bond between the flanges must be mechanically broken to remove the end cap 1350. In some embodiments, the end cap 1350 may be press fit over the coupling member 1340, such that the end cap is frictionally retained and does not need to be welded or threaded to the body 1305. In each instance, the end cap 1350 may be optionally welded to the body 1305.

In some embodiments, the end cap 1350 may include a hex-shaped recess 1357 in the distal end 1353. The recess 1357 may be used to hold the separation container 1300 (e.g., by standing the separation container and end cap 1350 on a vertical post (not shown)) when not in use, when filling the container, or during centrifugation. In some embodiments, a post or other rigid object (not shown) may be inserted into the recess 1357 to assist with removal of the end cap 1350 after centrifugation. For example, in embodiments in which the end cap 1350 has its flange 1354 semi-permanently attached to the flange 1355 of the body, the post or other rigid object may be a corresponding hex shape, such that the post or other rigid object may be inserted into the recess 1357 and may be used to twist or torque the semi-permanent connection apart. The mechanical separation of the end cap 1350 with a tool (e.g., the post or other rigid object referenced above) may reduce agitation of the sample and prevent inadvertent contamination.

In some embodiments, the end cap 1350 may further include an internal platform 1356 (also referred to herein as a "support surface") against which the first distal end 1306 of the pellet region 1304 may rest, either with the body 1305 touching the platform 1356 or with the seal 1320 sandwiched therebetween. The platform 1356 may support the seal and prevent inadvertent rupture before the user is ready to express the final concentrated pellet, including during manufacturing, assembly, packaging, loading, and centrifugation. The internal platform 1356 may define a substantially flat, planar surface in the internal cavity of the end cap 1350 against which the seal 1320 during centrifugation. In addition, the platform 1356 of the end cap 1350 allows a full sized seal 1320 to be attached to the entire surface area of the distal end of the pellet region 1304 providing for improved manufacturability and an improved seal between the seal 1320 and body 1305.

With reference to FIGS. 307-316, an embodiment of the end cap 1350 is shown. In the depicted embodiment, the end cap 1350 further comprises projecting ribs 1359 extending into the interior cavity of the end cap. The projecting ribs 1359 may include one or more ribs, and in some embodiments, a plurality of projecting ribs 1359 are spaced circumferentially about the end cap relative to an axis A (shown in FIG. 311) of the end cap. With reference to FIGS. 280-281, in some embodiments, the projecting ribs 1359 are configured to deform the coupling member 1340 to allow air trapped at the end of the internal cavity of the end cap 1350 adjacent the platform 1356 to escape when the distal end 1306 of the body 1305 is inserted into the end cap 1350. In such embodiments, the ribs 1359 deform the coupling member 1340 to allow air to escape between ribs and/or between the ribs and the deformed surface of the coupling member (e.g., the first distal sealing surface 1343 of the coupling member). In some embodiments, the projecting ribs 1359 are disposed at a shelf joining the first wall 1346 and the second wall 1347 of the end cap 1350. Once the first distal end 1306 of the body is inserted completely into the end cap 1350, the coupling member 1340 may seal against the end cap 1350 and prohibit further communication between the seal 1320 and the external environment.

With reference to FIGS. 277, 279, 283-288, 317-319, and 330-334, a coupling member 1340 may be disposed on the body 1305 at or near the pellet region 1304 to facilitate coupling of the separation container 1300 to a sample collecting vessel (e.g., the sample collecting vessels 135, 1038 detailed herein) and/or to provide a further seal within the end cap 1350 to prevent leakage of the contents of the body 1305. The coupling member 1340 may include one or more circumferential ridges 1341 to provide a seal against the sample collecting vessel. The coupling member 1340 may further include a first, distal sealing surface 1343 and a second, upper sealing surface 1344, which may be pointed (e.g., like ridges 1341) or flat. The sealing surfaces 1343, 1344 and the ridges 1341 may progressively decrease in their diameter when travelling towards the first distal end 1306 of the pellet region 1304. For example, the first sealing surface 1343 may be the narrowest sealing surface of the coupling member 1340 and the second sealing surface 1344 may be the widest sealing surface of the coupling member with each ridge 1341 therebetween progressively increasing in diameter, which may facilitate insertion of the separation container into the sample collecting vessel while providing a strong seal.

With reference to FIG. 280, in some embodiments, the second sealing surface 1344 may be wider than the inner diameter of a sample collecting vessel (not shown) (e.g., the sample collecting vessels 135, 1038 shown herein) and the second sealing surface 1344 may include a chamfer 1345 for engaging the upper edge of the sample collecting vessel. The chamfer 1345 may either create a seal against the upper rim of the sample collecting vessel or may compress the second sealing surface 1344 inward to fit the second sealing surface within the sample collecting vessel, while reducing the force required for engagement. In some embodiments, any other connector or coupling may be used to engage the body 1305 with a sample collecting vessel. The other connector or coupling may be attached to either the body 1305 or the sample collecting vessel or may be a separate device.

The end cap 1350 may include a narrow, first wall 1346 near or adjacent to the platform 1356 and may include a wider, second wall 1347 above the first wall opposite the platform. The first wall 1346 and the second wall 1347 (the inner and/or outer surfaces) may be parallel to the wall of the pellet region 1304 or may be tapered inwardly slightly such that the distal end closest to the platform 1356 is narrower than the opposite end for either wall segment 1346, 1347. The first wall 1346 and second wall 1347 may define diameters that are less than or equal to the diameters of the respective first sealing surface 1343 and second sealing surface 1344 at least at the same respective axial positions above the platform 1356. In the embodiment of FIGS. 280-281, the first sealing surface 1343 is shown overlapping with the first wall 1346 of the end cap 1350 because the depicted coupling member 1340 has a wider diameter than the depicted end cap 1350 at this axial location. In reality, the first sealing surface 1343 deforms to fit within the distal end of the end cap 1350 in such an embodiment, and no overlap will occur in the depicted embodiment.

With continued reference to FIG. 280, the body 1305 may include one or more circumferential ribs 1348, 1349 that provide structural rigidity to the connection between the body and the coupling member 1340. For example, in the embodiment shown in FIG. 280, the body includes two circumferential ribs 1348, 1349, one disposed proximate the tapered region 1303 of the body and one disposed proximate the first distal end 1306 of the pellet region 1304. In the embodiment shown in FIGS. 280 and 332, a first circumferential rib 1348 is embedded in a corresponding recess 1360 in the first sealing surface 1343 of the coupling member 1340. Similarly, in the embodiment shown in FIGS. 280 and 332, a second circumferential rib 1349 is embedded in a corresponding recess 1361 in the second sealing surface 1344 of the coupling member 1340.

The coupling member 1340 and the body 1305 may be attached via overmolding, elastically stretching the coupling member 1340 over the body 1305, or fusing multiple pieces of the coupling member 1340 together around the body 1305. In some embodiments, the coupling member 1340 may be made of a compliant material such as elastomer. The coupling member 1340 may be overmolded onto the body 1305. In some embodiments, the coupling member 1340 may be made from silicone or thermoplastic elastomers such as Medalist® MD-12140. In some embodiments, the separation container opening 1312 may be sealed by the seal 1320, by the end cap 1350 pressing on the seal, and by the engagement of the end cap 1350 and the coupling member 1340.

With reference to FIGS. 319-334, the body 1305 may also include one or more vertical ribs 1362, and the coupling member 1340 may include one or more corresponding recesses 1363 for receiving and engaging the vertical ribs 1262. In some embodiments, the body 1305 may include a base flange 1364 at the distal end of the pellet region 1304 for retaining the coupling member 1340 with its upper surface and engaging the seal 1320 with its lower annular surface (e.g., via sonic welding), with the annular surface surrounding the opening 1312 (shown in FIG. 280).

An end of the coupling member 1340 opposite the base flange 1364 may further abut a portion of the outer surface of the tapered region 1303, such that the combined upward retention from the base flange and the downward retention from the tapered region may retain the coupling member 1340 in a stable position (e.g., the position shown in FIG. 318). In some embodiments, the coupling member 1340 may be disposed between the flange 1355 on the body 1305 in the tapered region 1303 and the base flange 1364 such that the coupling member 1340 fits within the end cap 1350 and sample collection vessels described herein to prevent fluid (including the sample) from leaking out of the separation container. The coupling member 1340 may include bi-directional (e.g., perpendicular) recesses (e.g., recesses 1360, 1361, 1363) to engage the corresponding bi-directional ribs (e.g., ribs 1348, 1349, 1362) of the body and prevent both axial and rotational movement of the coupling member.

As discussed in connection with other embodiments herein, the body 1305 may include a first distal end 1306, a second distal end 1307, a tapered region 1303, a pellet region 1304, a collection region 1302, a widened region 1308, and a wall 1309, each of which may operate and may be structured as described in each embodiment herein. The separation container 1300 may further include a retainer 1332 attached to the body 1305 in the widened region 1308. In some embodiments, with reference to FIGS. 319, 320, 322, 323, 327, the widened region 1308 of the body 1305 may include one or more supporting projections 1365 which may receive and secure the retainer 1332 on a distal end thereof. In some embodiments, the inner diameter of the body 1305 with the projection 1365 in the widened region 1308 is the same as the diameter of the collection region 1302. The retainer 1332 may be otherwise structured and operable as described above with respect to the retainers 1032, 1232 to secure the plunger 1310 in a predetermined vertical position (e.g., a position in which the upper edge of the retainer 1332 is coplanar with the second distal end 1307 of the body 1305). For example, with reference to FIG. 259, the plunger 1310 may include a support member 1315 having the features and structure shown and described in connection with the support member 1015, 1215 of the plunger 1010, 1210 above, and the retainer 1332 may include retaining members 1333 and corresponding features having the features and structure shown and described in connection with the retainer 1032, 1232 of the plunger 1010, 1210.

With reference to FIGS. 296-306, the plunger 1310 is shown in accordance with some embodiments discussed herein. The plunger 1310 may include a longitudinal member 1316 coming to a conical point 1317 at a first distal end 1318. The plunger may include a piercing section 1370 defining a cylindrical portion of the longitudinal member 1316 which terminates with a taper at the point 1317. The piercing section 1370 may operate in substantially the same manner as the blade 160 or point 117 discussed herein, and the piercing section 1370 and point 1317 may be narrower than the longitudinal member 1316 or the remaining portions of the plunger 1310 to allow for collection of additional sample in the pellet region 1304. In this manner, the relative diameters and sizes of the components shown in the figures are intended to be accurate as example embodiments (e.g., the piercing section 1370 is depicted narrower than the remainder of the longitudinal member 1316).

In some embodiments, the plunger 1310 may include at least one sealing rib 1372 formed circumferentially about the longitudinal member 1316, and may include a tapered region 1371 between the sealing rib 1372 and the piercing section 1370. This sealing rib 1372 may be a generally circular sealing surface that seals uniformly about the plunger. The sealing rib 1372 may be configured to engage the wall 1309 of the body 1305 and seal a portion of the internal chamber 1311 below the rib 1372 from a portion of the internal chamber above the rib. In particular, the diameter d of the sealing rib 1372 may be interference fit to the pellet diameter (e.g., slightly greater than the diameter of the body 1305 at the pellet region 1304), such that the plunger 1310, via rib 1372, engages the pellet region 1304 during actuation of the plunger. In this manner, the plunger 130 may at least partially fluidically isolate the pellet region 1304 from the tapered region 1303 and the collection region 1302 when actuating the plunger. In some embodiments, the sealing rib 1372 may define a diameter that is equal to or greater than a diameter of the pellet region 1304. In some embodiments, the sealing rib 1372 may define a diameter that is equal to or less than a diameter of the pellet region 1304. The sealing rib 1372 may be molded with and made from the same, generally-rigid material as the plunger.

In some embodiments, the plunger 1310 may include a plunger seal 1390 attached to the plunger in addition to or instead of the sealing rib 1372. In some embodiments, the sealing rib 1372 may be disposed between the plunger seal 1390 and the point 1317 at the first distal end 1318. The plunger seal 1390 may define a plunger diameter that is greater than or equal to the diameter of the sealing rib 1372 and greater than or equal to the diameter of the pellet region 1304. As described herein, the plunger seal 1390 may seal the internal chamber 1311 of the body at the pellet region 1304 to prevent leakage of the density cushion when the portions of the plunger between the plunger seal and the point 1317 emerge from the opening 1312 (shown in FIG. 280) at the first distal end 1306 of the body 1305 when the plunger 1310 is fully depressed. In some embodiments, a volume of sample is configured to be retained between the plunger seal 1390, the wall of the separation container body 1305 (e.g., in the pellet region 1304 during actuation), the first distal end 1306 of the body 1305, and a portion of the longitudinal member 1316 between the point 1317 and the plunger seal 1390. The volume is retained upon actuation of the plunger 1310 when the plunger seal 1390 engages the wall 1309 at the pellet region 1304. As described herein, various diameters of the plunger 1310 may be taken radial to an axis (e.g., axis A shown in FIG. 279) extending between the first distal end 1318 and the second distal end 1319 of the plunger. In such embodiments, engagement of the plunger seal 1390 with the wall 1309 (e.g., at the pellet region 1304) may divide the internal chamber 1311 into at least two sub-chambers above and below the plunger seal.

In some embodiments, the plunger 1310 may define a recess 1373 in the longitudinal member 1316 in which a portion of the plunger seal 1390 is disposed. The recess 1373 may include a first shoulder 1374 and a second shoulder 1375 which may abut either side of the plunger seal 1390 to retain the plunger seal within the recess and may extend radially from the inner diameter of the recess to a diameter of the longitudinal member 1316. In some embodiments, further ridges (also referenced herein as chamfers) (shown in FIG. 302) or changes in diameter may be used to retain the plunger seal 1390.

In some embodiments, the plunger 1310 may further define a through passage 1376 in the recess 1373 of the longitudinal member 1316 through which a corresponding locking arm 1377 of the plunger seal 1390 may extend to prevent rotational or axial movement of the plunger seal. In some embodiments, the plunger seal 1390 may be overmolded onto the plunger 1310 such that the locking arm 1377 is fixedly and permanently formed within the through passage 1376. In some embodiments, the plunger seal 1390 may be formed from a softer material (e.g., an elastomeric material) than the plunger 1310 to provide a further seal against the wall 1309 when the plunger is depressed. In some embodiments, the plunger seal may be integral with the plunger 1310. The plunger seal 1390 may be made from an elastomer such silicone or thermoplastic elastomers as described herein with respect to the coupling member 1340. In some embodiments, the material of the plunger seal 1390 should be compliant (e.g., TPE with a 50 Shore A durometer). The plunger seal 1390 may mitigate molding defects in the more rigid plunger 1310 (e.g., imperfections in the seal of the sealing rib 1372. In some embodiments, the plunger seal 1390 may deform more easily than the rib 1372 and require less force to move along the wall 1309. The plunger seal 1390 may include chamfered edges near the shoulders 1374, 1375 for easier actuation.

In some embodiments, the longitudinal member 1316 of the plunger may include a further tapered region 1378 (also referred to as a "shoulder" herein) above the recess 1373 (e.g., the recess 1373 is disposed between the point 1317 and the further tapered region 1378) such that the portion of the longitudinal member 1316 above the further tapered region 1378 is wider. The further tapered region 1378 and the longitudinal member 1316 on the larger side of the further taper may define a diameter that is substantially greater than the pellet region 1304. In some embodiments, the distance between the further tapered region 1378 and the point 1317 of the plunger 1310 may be less than or equal to an axial length of the pellet region 1304, such that the further tapered region 1378 is configured to impinge on the wall 1309 proximate the junction between the tapered region 1303 of the body 1305 and the pellet region 1304 of the body before the plunger seal 1390 completely exits the first distal end 1306 of the body and before fluid above the plunger seal can escape. In some embodiments, the impingement of the further tapered region 1378 (also referred to as a shoulder) may define the maximum axial displacement of the plunger 1310. In some embodiments, an axial distance between the plunger seal 1390 and the tapered region 1378 and an axial length of the pellet region 1304 are configured such that the plunger seal 1390 remains at least partially within the body 1305 at the maximum displacement of the plunger 1310. In some embodiments, an axial distance between the plunger seal 1390 and the first distal end 1318 of the plunger is less than or equal to an axial length of the pellet region 1304 such the plunger seal 1390 is configured to engage the pellet region 1304 of the body 1305 before the plunger 1310 opens the seal 1320 during actuation. In some embodiments, the further tapered region 1378 may define an angle that matches the angle of the tapered region 1303 according to any of the embodiments described herein.

In some embodiments, the longitudinal member 1316 may include a step 1379 which may help to reduce the required actuation force of the plunger 1310 because of the relatively narrower diameter of the step compared to the surrounding body of the plunger.

With reference to FIGS. 296, 299-301, 304-305, a second distal end 1319 of the plunger, opposite the point 1317 at the first distal end 1318, may include a gripping portion 1380 for allowing the user to depress (e.g., move the plunger axially in the longitudinal axis extending between the first distal end 1318 and the second distal end 1319) and/or twist (e.g., rotate the plunger about the longitudinal axis, for example, to release the support member 1315 and retainer 1332) the plunger 1310. In some embodiments, the gripping portion 1380 may be spaced from the second distal end 1319 (e.g., as shown in FIG. 301). In some embodiments, the gripping portion 1380 may be substantially rectangular. For example, with reference to FIG. 305, the gripping portion 1380 may define a rectangular or square cross section in a plane perpendicular to the axis of the longitudinal member 1316. In some embodiments, the gripping portion may be generally cylindrical. In some embodiments, the gripping portion may be asymmetrical. In some embodiments, the gripping portion may include knobs or projections to facilitate rotation of the plunger about the axis of the longitudinal member.

In some embodiments, the retainer (also referred to as a "collar" herein) 1332 may be configured to engage the plunger 1310 to prevent axial displacement of the plunger. In some embodiments, the retainer 1332 may comprise an annular wall 1337 having engagement features (e.g., retaining members 1333) defined thereon. In some embodiments, the retainer may comprise features (e.g., walls, grooves, or projections) integral with the body 1305 of the separation container 1300 configured to engage one or more portions of the plunger 1310, such that the retainer and the body define a single piece. In some embodiments, the retainer 1332 may be separately engaged with the body 1305 (e.g., via press fit).

With reference to FIGS. 296, 299, 300, 301, 303, and 339-344, the retainer 1332 and plunger 1310 may have a retention mechanism that allows the plunger to be supported by the retainer during centrifugation but also actuatable by a user after separation. In particular, in some embodiments, the retainer 1332 may support the plunger 1310 under axial loads (e.g., loads along the axis A shown in FIG. 279) of at least three-thousand times the force of gravity, while the plunger 1310 may engage and disengage with the retainer 1332 by rotating the plunger 1310 about the axis A shown in FIG. 279. In particular, the retainer 1332 includes one or more retaining members 1333 that engage corresponding support member 1315 on the plunger 1310. The support member 1315 may include one or more locking members 1314 that engage the respective retaining members 1333 of the retainer 1332. In the depicted embodiment, the retainer 1332 includes two retaining members 1333 and the plunger 1310 includes two locking members 1314 each separated from the other by 180 degrees about the longitudinal axis of the plunger 1310.

In the depicted embodiment, the retaining members 1333 may include a support projection 1334 extending from the annular wall 1337 of the retainer 1332 with a stop wall 1336 at one end of the support projection. The support projection 1334 may further include one or more locking tabs 1335. With reference to FIG. 303, the locking members 1314 may include a substantially C-shaped receiving area defined by a lower wall 1396, a lateral wall 1397, an upper wall 1398, and a lip 1399. These features may combine to receive and engage the corresponding retaining member 1333 of the retainer 1332. For example, the support projection 1334 (shown in FIGS. 339-344) of the retaining member 1333 may be received in the locking member 1314 (shown in FIG. 303) with an upper surface of the lower wall engaging a lower surface of the support projection 1334. The locking tab 1335 (shown in FIGS. 339, 342, and 344) and/or the lip 1399 may deflect when the retaining member 1333 is engaged with the locking member 1314 such that the locking tab 1335 may be disposed in a space between the lateral wall 1397, the upper wall 1398, and the lip 1399 to retain the plunger 1310.

In some embodiments, the inner, annular wall 1337 of the retainer 1332 may define a circumferential direction in a plane spanning the central opening and oriented about the central opening and an axial direction oriented perpendicular to the plane (e.g., along the axis A shown in FIG. 279). In some embodiments, the at least one support projection 1334 may define a circumferential wall that is longer in the circumferential direction than in the axial direction (e.g., as shown in FIGS. 339-344). In some embodiments, the stop wall 1336 may be configured to prevent rotation of the plunger in a clockwise direction or a counterclockwise direction in an instance in which the at least one support projection 1334 is engaged with the at least one locking member 1314 of the plunger 1310. In some embodiments, the stop wall 1336 may extend from a first surface of the at least one support projection 1334 and may prevent rotation of the plunger in a clockwise direction or a counterclockwise direction about the axis A. In some embodiments, the retainer 1332 may include two retaining members 1333 disposed diametrically opposite one another relative to the annular wall 1337. In some embodiments, the support member 1315 may include two locking members 1314 disposed diametrically opposite one another relative to the longitudinal axis of the plunger 1310.

In some embodiments, the at least one retaining member 1333 may include at least one locking tab 1335 extending from a first surface of the at least one support projection 1334. The at least one locking tab 1335 may be configured to engage the at least one locking member 1314 of the plunger 1310 to releasably retain the plunger by increasing a force required to rotate the plunger about the longitudinal axis A when the at least one locking tab 1335 is engaged with the at least one locking member 1314 of the plunger 1310. In some embodiments, the at least one locking member 1314 defines a C-shaped wall configured to be disposed on both sides of the circumferential wall relative to the axial direction in an instance in which the at least one locking member and the at least one retaining member are engaged, and the C-shaped wall may comprise the lower wall 1396, lateral wall 1397, upper wall 1398, and/or the lip 1399 discussed herein. In some embodiments, the lower wall 1396 and/or upper wall 1398 may be defined as a locking wall configured to engage the at least one retaining member 1333 of the retainer 1332.

With reference to FIGS. 277-306, the gripping portion 1380 of the plunger 1310, which may be sealed within the separation container 1300, may be manipulated through the flexible sealing member 1325 to prevent leakage or contamination. In such embodiments, the gripping portion 1380 and second distal end 1319 of the plunger 1310 may extend at least partially into a cavity of the flexible sealing member 1325 via an open end at the flange 1381 of the flexible sealing member. The flexible sealing member 1325 may be made of an elastomeric material, and in some embodiments, the flexible sealing member 1325 may be made of an at least partially transparent material. In some embodiments, the flexible sealing member 1325 may be retained by a cap 1330 that is structured and functions substantially the same as the caps (e.g., caps 130, 1030, 1230) described herein, with an opening 1331 (shown in FIG. 277) through which the flexible sealing member 1325 may extend. The cap 1330 may then thread onto the body 1305 to secure a flange 1381 of the flexible sealing member therebetween such that the flange 1381 may engage the body and seal the second distal end 1307 of the body 1305 to close the internal chamber 1311 of the body 1305.

With reference to FIGS. 289-295, the flexible sealing member 1325 may include a top 1382, which the user may depress to also depress the plunger 1310 (shown in FIG. 287). The top 1382 and flange 1381 may be connected by a wall 1383 of the flexible sealing member 1325. Upon actuation by the user, the top 1382 may translate downwardly towards the flange 1381 and remainder of the separation container to cause the axial movement of the plunger 1310. The top 1382 may also be configured to rotate relative to the flange 1381 during locking and unlocking of the plunger 1310 (e.g., while rotating the plunger about its longitudinal axis) while deforming the wall 1383 therebetween such that the flange 1381 remains stationary relative to the body 1305 while the top 1382 rotates with the plunger 1310. The wall 1383 of the flexible sealing member 1325 may return to a neutral position after being rotated and released. In some embodiments, the top 1382 may collapse slightly around the user's finger during actuation. As the top 1382 and flange 1381 move closer to each other the wall 1383 collapses and hinges to allow the top 1382 to remain in contact with the plunger. In some embodiments, the wall 1383 deforms at least partially outward to allow the top 1382 to depress the plunger 1310 to a position completely flush with at least a top surface of the cap 1330. The flexible sealing member may comprise a receiving portion 1384 at the top 1382 that is configured to receive the second distal end of the plunger 1310 therein.

Referring to FIGS. 289-295, an embodiment of the flexible sealing member 1325 is shown. In the depicted embodiment, the wall 1383 expands continuously outwardly when moving from the top 1382 to the flange 1381. Said differently, the flexible sealing member 1325 may define a radius r (shown in FIG. 290) in a radial direction from an axis A (also referred to as a "sealing member axis" or "displacement axis" and shown in FIG. 290) extending between the top 1382 and a plane of the flange 1381. With reference to FIG. 279, the axis A of the flexible sealing member 1325 may be configured to be collinear with the longitudinal axis A of the plunger 1310, body 1305, and end cap 1350. In some embodiments, the radius at each point along the axis of the flexible sealing member 1325 between the open end at the flange 1381 and the closed top 1382 is greater than the radius at each point closer to the closed top 1382 and less than the radius at each point closer to the open end at the flange 1381. In some embodiments, the wall 1383 may expand outward or be vertical when moving from the top 1382 to the flange 1381. Said differently, in some embodiments, the radius at each point along the axis of the flexible sealing member 1325 between the open end at the flange 1381 and the closed top 1382 is greater than or equal to the radius at each point closer to the closed top 1382 and less than or equal to the radius at each point closer to the open end at the flange 1381. In some embodiments, the wall 1383 may have no inwardly sloped surfaces (e.g., surfaces where the radius is less at a point closer to the flange than another point farther from the flange). In some embodiments, the wall 1383 may have at least a two degree angle relative to the axis A, where the angle is oriented towards the flange between the wall and a vertical axis parallel to the axis A. In some embodiments each portion of the wall 1383 may define an angle with the flange 1381 that is greater than or equal to 90 degrees with respect to the shortest angle between the flange and wall when the flexible sealing member is in the unactuated position. Such embodiments may facilitate more efficient manufacturing and lower component costs because the flexible sealing member 1325 may slide from its mold without stretching. In the above-described embodiments, the angle of the wall 1383 may change upon actuation of the flexible sealing member either to rotate or axially depress the plunger 1310.

With continued reference to FIGS. 289-295, in some embodiments, the wall 1383 may comprise a series of wall segments extending from the top 1382 to the flange 1381, which vary in angle relative to the axis A. In some embodiments, as depicted in FIG. 290, the wall 1383 may alternate in its angle between steeper and shallower angles at each junction between segments. With reference to FIGS. 293-295, the wall 1383 may have one or more hinge points 1385 having a lesser wall thickness than the wall segments on either side. These hinge points 1385 may facilitate the flexible sealing member 1325 collapsing during actuation of the plunger such that the wall 1383 deflects out of the path of the plunger 1310. In some embodiments, the travel distance of the plunger 1310 and the deformation range of the flexible sealing member 1325 may be greater than an equivalently tall bellows design.

In the embodiment shown in FIGS. 289-291, the top 1382 is connected to a first vertical wall segment 1386. The first vertical wall segment 1386 is then connected to a first non-vertical wall segment 1387 that may be angled downwardly and outwardly from the top. The first non-vertical wall segment 1387 may then be connected to a second vertical wall segment 1386. The second vertical wall segment 1386 may then be connected to a second non-vertical wall segment 1387 that may be angled downwardly and outwardly from the second vertical wall segment 1386. The second non-vertical wall segment 1387 may then be connected to a third vertical wall segment 1386, which may abut the flange 1381. In some embodiments, a surface of the non-vertical wall segments 1387 may include a vertical portion therein to define a portion of the hinge point 1385 (e.g., portions of the outer surface or inner surface may narrow to create a portion of a narrowed hinge point in the otherwise non-vertical wall segment. In some embodiments, the wall segments may smoothly transition between each other. In some embodiments, the flexible sealing member (e.g., flexible sealing members 125, 1025, 1225) of any other embodiment may be used in place of the flexible sealing member 1325.

During downward actuation, the flexible sealing member 1325 may collapse so that the vertical wall segments 1386 translate down as the non-vertical wall segments 1387 behave as in a hinging action (e.g., via hinge points 1385) so that in the collapsed state the segments form a nested set of concentric walls. When fully compressed, the vertical wall segments 1386 may form concentric nested ridges with the angled wall segments (e.g., non-vertical wall segments 1387) changing orientation at the hinge points 1385.

Referring back to FIGS. 277, 279, 284, 287, and 335-338, the separation container 1300 may include a rheological control member 1342, which may be structured and operate according to any of the embodiments discussed herein. For example, in some embodiments, the rheological control member 1342, body 1305, and plunger 1310 may be structured and cooperate in substantially the same manner as the rheological control members 1042, 1242, bodies 1005, 1205, and plungers 1010, 1210 herein, and may include the gasket 1043 and corresponding structure and operation described therewith. In some other embodiments, the rheological control member 1342 may be structured and operate as shown and described with respect to the embodiments of FIGS. 14-31, FIGS. 32-49, or FIGS. 50-67. In some embodiments, the rheological control member 1342 may be configured to impinge the wall 1309 of the body 1305 during loading of the sample, and the wall 1309 may flex outwardly during centrifugation to release the rheological control member. Likewise, in some embodiments, the wall 1309 of the body 1305 may include a shoulder (e.g., annular shoulder 1061) that impinges the rheological control member below a certain axial position in accordance with the embodiments described herein.

With reference to FIGS. 335-338, in some embodiments, the rheological control member 1342 may include an annular wall 1391 comprising an inner surface 1392 defining a bore of the rheological control member through which the plunger 1310 is configured to pass. The rheological control member 1342 may further comprise an outer surface 1393 defining an outer diameter of the rheological control member. In some embodiments, the rheological control member 1342 may further comprise one or more ribs 1394. The ribs 1394 may be configured to engage the wall 1309 of the body 1305 (e.g., at the tapered region 1303) to allow fluid to flow past the rheological control member 1342 and prevent the rheological member from completely sealing the upper portion of the internal chamber 1311 from the lower portion of the internal chamber. In some embodiments, the rheological control member 1342 may comprise at least one annular trough 1395 extending circumferentially about a top of the rheological control member. In some embodiments, fluid passes around the outer surface 1393 of the rheological control member 1342 and/or through the center (e.g., along the inner surface 1391) between the plunger 1310 and the rheological control member 1342 during addition of the sample to layer the sample (e.g., without disturbing a density cushion). In some embodiments, the annular trough 1395 may be solid and may not allow fluid to pass therethrough. The trough 1395 may be configured to capture unwanted portions of the blood culture sample (e.g., excess resin beads). In some embodiments, the annular trough may include a hole, a plurality of holes, or a mesh screen.

Unless otherwise stated, the separation container 1300 may operate in the same manner, may have the same properties, and may be made with the materials and configurations of any embodiment described herein. The separation container 1300 of the seventh embodiment depicts a non-buoyant plunger 1310 that is retained by a retainer 1332 as described above. The depicted separation container 1300 also includes a rheological control member 1342 as described herein. In addition, the depicted separation container 1300 may engage an end cap 1350 for securing the seal 1320 (e.g., a foil sheet or other sealing membrane) to the body 1305 and supporting the separation container during centrifugation. The separation container 1300 may further include a coupling member 1340 for coupling the body 1305 with a sample collecting vessel 135, 1038, which may be used in a similar manner to the sample collecting vessels 135, 1038 described herein.

During assembly, the separation container 1300 may be assembled in the following ordered steps, some of which may be omitted depending on the final structure and contents of the separation container in accordance with the embodiments described herein: (1) add the density cushion to the internal chamber 1311; (2) connect the plunger 1310 with a retainer 1332; (3) insert the rheological control member 1342 onto the plunger 1310; (4) slide the gasket 1043 onto the plunger 1310 beneath the rheological control member 1342 (for embodiments using a gasket); (5) engage the retainer 1332 with the supporting projections 1365 in the body 1305, while also forming an interference or slip fit between the rheological control member 1342 and the body 1305; (6) insert the flexible sealing member 1325 into the opening 1331 in the cap 1330; and (7) secure the flexible sealing member 1325 and cap 1330 onto the body 1305 while encapsulating the plunger within the separation container (e.g., seal the separation container either before or after inserting a sample for testing). An interference fit may be created by inserting rods into the gaps between the retainer 1332 and the plunger 1310 to press the rheological control member 1342 downwardly. In some embodiments the seal 1320 may be attached to the body 1305 prior to adding the density cushion. In accordance with some embodiments discussed herein, the rheological control member may be initially inserted with an interference fit before being released during centrifugation by the outward deformation of the wall 1309 of the body 1305.

During testing, the separation container 1300 may be operated in the following ordered steps: (1) To add the lysed sample to the tube (e.g., lysed from a raw sample), the cap 1330 and flexible sealing member 1325 may be removed; (2) the sample may then be transferred to the body 1305, with the rheological control member 1342 preventing bulk mixing of the sample with the density cushion by being positioned between the two fluids; (3) the separation container may be optionally pre-spun before adding the sample to move any density cushion that may have migrated to the top chamber during shipping or storage. The rheological control member 1342 may be constructed for a small clearance between it and the wall 1309 of the body 1305 and may include annular shoulders (e.g., shoulders 1061, 1062) when not being centrifuged as discussed above (e.g., to limit the downward movement of the rheological control member). In some embodiments, the rheological control member 1342 may also be constructed so that it does not interact with or reach the tapered region 1303 of the body 1305. During centrifugation, the sample may run down the wall 1309 of the tapered region 1303 and collect into the pellet in the pellet region 1304.

In some embodiments, the included angle of the wall 1309 of the body 1305 at the tapered region 1303 is preferably 40 degrees or less. In some embodiments, the angle between the wall 1309 of the body 1305 and a longitudinal axis of the body 1305 at the tapered region is preferably 20 degrees or less. In some embodiments, included angle of the wall 1309 of the body 1305 at the tapered region 1303 is preferably from 10 degrees to 40 degrees. In some embodiments, the angle between the wall 1309 of the body 1305 and a longitudinal axis of the body 105 at the tapered region is preferably 5 degrees to 20 degrees. In some embodiments, the wall 1309 at the tapered region 1303 may define an included angle from about 20 to about 70 degrees. In some embodiments, the wall 1309 at the tapered region 1303 may define an included angle from 40 degrees to 60 degrees. In some embodiments, the wall 1309 at the tapered region 1303 may define an included angle from 5 degrees to 20 degrees. In some embodiments, the wall 1309 at the tapered region 1303 may define an included angle from 5 degrees to 60 degrees. In some embodiments, the wall 1309 at the tapered region 1303 may define an included angle from 5 degrees to 40 degrees. In some embodiments, the wall 1309 at the tapered region 1303 may define an included angle from 10 degrees to 40 degrees. In some embodiments, the wall 1309 at the tapered region 1303 may define an included angle from 15 degrees to 40 degrees. In some embodiments, the wall 1309 at the tapered region 1303 may define an included angle from 20 degrees to 40 degrees. In some embodiments, the wall 1309 at the tapered region 1303 may define an included angle from 20 degrees to 60 degrees. In some embodiments, the wall 1309 at the tapered region 1303 may define an included angle from 25 degrees to 60 degrees. In some embodiments, the wall 1309 at the tapered region 1303 may define an included angle from 30 degrees to 60 degrees. In some embodiments, the wall 1309 at the tapered region 1303 may define an included angle from 35 degrees to 60 degrees. In some embodiments, the wall 1309 at the tapered region 1303 may define an included angle from 35 degrees to 40 degrees.

In some embodiments, the wall 1309 at the tapered region 1303 may define a maximum included angle of 60 degrees. In some embodiments, the wall 1309 at the tapered region 1303 may define a maximum included angle of 55 degrees. In some embodiments, the wall 1309 at the tapered region 1303 may define a maximum included angle of 50 degrees. In some embodiments, the wall 1309 at the tapered region 1303 may define a maximum included angle of 45 degrees. In some embodiments, the wall 1309 at the tapered region 1303 may define a maximum included angle of 40 degrees. In some embodiments, the wall 1309 at the tapered region 1303 may define a maximum included angle of 35 degrees. In some embodiments, the wall 1309 at the tapered region 1303 may define a maximum included angle of 30 degrees. In some embodiments, the wall 1309 at the tapered region 1303 may define a maximum included angle of 25 degrees. In some embodiments, the wall 1309 at the tapered region 1303 may define a maximum included angle of 20 degrees.

In some embodiments, the wall 1309 at the tapered region 1303 may define a minimum included angle of 5 degrees. In some embodiments, the wall 1309 at the tapered region 1303 may define a minimum included angle of 10 degrees. In some embodiments, the wall 1309 at the tapered region 1303 may define a minimum included angle of 15 degrees. In some embodiments, the wall 1309 at the tapered region 1303 may define a minimum included angle of 20 degrees. In some embodiments, the wall 1309 at the tapered region 1303 may define a minimum included angle of 25 degrees. In some embodiments, the wall 1309 at the tapered region 1303 may define a minimum included angle of 30 degrees. In some embodiments, the wall 1309 at the tapered region 1303 may define a minimum included angle of 35 degrees. In some embodiments, the wall 1309 at the tapered region 1303 may define a minimum included angle of 40 degrees.

In some embodiments, exceeding a maximum angle may cause biomass to adhere to the wall 1309. For example, in some embodiments, the included angle of the wall 1309 of the tapered region being over 40 degrees may cause biomass accumulation. In some embodiments, the included angle of the wall 1309 at the tapered region 1303 may be configured to ensure biomass does not adhere to the wall during centrifugation, maximize the sample volume, and/or limit the length of the separation container 1300 to fit within a standard syringe.

The testing may further include: (4) during addition of the sample the rheological control member 1342 may float if optionally not interference fit, while still providing mixing protection. The rheological control member 1342 may also have a recessed ring in the top portion, which can trap any settling components such as resin or other particulates. These particles may stay in the recessed area as the layering aid floats up the tube either during sample addition or centrifugation. The testing may further include: (5) after the sample is added, the cap 1330 and flexible sealing member 1325 may be placed back on the tube; and (6) the entire separation container 1300 may be placed in the centrifuge and spun. In embodiments where the rheological control member 1342 is sealed against the body 1305 and plunger 1310, the sample may be added directly to an internal chamber 1311 with a lytic agent and the entire separation container 1300 can be vortexed to lyse the sample before the centrifugation step.

In operation, the process for expressing the pellet is the same actuation and foil piercing process described herein with respect to each other plunger embodiment, and in embodiments using a retainer 1332, an additional step of applying horizontal, rotational pressure to the gripping portion 1380 of the plunger 1310 may be used to disconnect the plunger from the retainer. With reference to FIGS. 278-282, the separation container 1300 is shown in a storage or loaded position (depending on whether sample has been introduced to the body 1305) in which the plunger 1310 is attached to and retained by the retainer 1332. FIGS. 283-285 show the separation container 1300 whose plunger 1310 has been released from the retainer 1332, but the plunger has not yet pierced the seal 1320. In the position shown in FIGS. 283-285, the sealing rib 1372 has abutted the wall 1309 of the body 1305 at the junction between the tapered region 1303 and the pellet region 1304 when the point 1317 contacts the seal 1320, but the plunger seal 1390 has not yet engaged the pellet region 1304. In some embodiments, the plunger seal 1390 may engage the pellet region 1304 before the seal 1320 is opened. In some embodiments, the plunger seal 1390 may engage the pellet region 1304 simultaneous with the seal 1320 is opened. In some embodiments, the plunger seal 1390 may engage the pellet region 1304 after the seal 1320 is opened, and in such embodiments, the sealing rib 1372 may engage the pellet region 1304 simultaneous with or prior to the seal 1320 opening (e.g., as shown in FIG. 285) to initially provide an at least partial seal of the pellet region prior to engagement of the plunger seal 1390 with the pellet region. In some embodiments, prior to the seal 1320 opening, any density cushion present above the pellet region 1304 may be displaced upward as the plunger 1310 moves in a downward direction along its longitudinal axis. In some instances, residual volumes of the density cushion present in the pellet region may not affect testing performance.

Turning to FIGS. 286-288, the plunger 1310 is shown fully depressed with the point 1317 and rib 1372 having passed through the opening at the distal end 1306 of the body 1305, the pellet having been fully expressed, and the plunger seal 1390 preventing leakage of the fluid (e.g., density cushion) thereabove. For example, in some embodiments, the distance between the sealing surfaces of the rib 1372 and the plunger seal 1390 may be less than the length of the pellet region 1304 to prevent leakage of the density cushion or contamination of the sample. Unless otherwise stated, features having the same reference numeral, name, structure, or purpose in the assembly may be interchanged with one another in any of the embodiments described herein and the present inventors specifically contemplate each possible permutation of structures and features.

In each of the above-described embodiments, once the separated microorganism sample has been prepared, a subsequent interrogation step can be carried out to provide measurements useful for characterization and/or identification of the microorganism. Useful interrogation means are known in the art.

Example 1: Direct ID and AST Using Large Volume Separation Containers

In some embodiments, the separation containers (e.g., separation container 100) may facilitate larger sample sizes than traditional separation equipment. To explore the potential of the aforementioned separation container and centrifuge assemblies, several devices and samples were tested in accordance with the embodiments discussed herein. In creating the instant example and the separation containers disclosed herein, the inventors noted that smaller volume devices were insufficient for certain species of microorganism, and as such, a larger volume separation container was designed that utilized the plunger 100, 115 of the present disclosure. In these instances, the recovered biomass (i.e., number of microbial cells) was not sufficient for some species, such as *A. baumannii* and *P. aeruginosa*, so a tube with a higher volume capacity was needed. The separation container used in the Example included substantially the same structure and operation as the separation container 100 described herein. In practice, the mechanical recovery of the pellet according to the instant design provided a substantial improvement in both ease of use and in user safety.

During the Example, four bacteria with differing pellet consistency were tested in accordance with TABLE 1 below:

Table 1

TABLE 1

| Species | Strain | Reason for Testing |
| --- | --- | --- |
| P. aeruginosa | 1935 | Small, firm but sticky pellet (low biomass) |
| K. pneumoniae | 79382 | Large, loose mucoid pellet (low density organism) |
| E. faecium | 50215 | Large, moderate consistency pellet |
| S. aureus | 60570 | Firmly packed pellet, difficult to dislodge |

The following testing method was utilized: (1) remove a 2 mL sample of BC broth and add to a Lysis Tube containing 4 mL LB16 buffer; (2) vortex Lysis Tube and leave for 1 min at RT; (3) add 6 mL of the resultant lysate to a large scale separation container containing 2 mL of density cushion and approx. 1 mL of polypropylene balls as a rheological control member (also referred to as a layering aid); (4) apply cap and spin tube for 10 minutes at 3,000 g at RT; (5) attach a sample collecting vessel (e.g., sample collecting vessel 135) containing 1.0 mL VITEK saline to the lower end of the body; (6) depress the plunger (e.g., plunger 110, 115) to eject the pellet into the sample collecting vessel; (7) vortex or shake the tube to create a microbial suspension; (8) read the McFarland and adjust the solution to 0.50-0.63 McFarland; (9) load the diluted suspension into appropriate VITEK AST cards; and (10) spot suspension onto MALDI slide on a 60 C heater block, dry, add matrix, dry and load into a VITEK MS MALDI-TOF system.

The testing was performed with no leakage, provided a consistent and easy mechanical transfer of the microbial pellets to the sample collecting vessel, and recovered sufficient viable bacterial cells for downstream analysis. All four bacteria were identified by MALDI-TOF (See FIG. 158). The test suspension VITEK2 AST card results were concordant with historical colony AST results, all results being within Essential Agreement, or within 1 doubling dilution of the control MIC (See FIGS. 159-160).

Example 2: General Sample Processing

In some example embodiments a sample may be processed using the following steps: (1) remove a cultured sample from a blood culture bottle; (2) dispense the blood culture into a lysis buffer; (3) vortex the mixed sample to produce lysate sample; (4) add the lysate sample to a separation container; (5) centrifuge the lysate sample to generate a pellet of the sample; (6) connect the separation container to a sample collection vessel; (7) express the pellet of the sample into the separation container; (8) resuspend the sample microorganisms in saline; and (9) dilute the resuspended sample to an appropriate concentration for downstream testing. In some embodiments, 2.5 mL of the cultured sample may be removed from the blood culture bottle. In some embodiments, the lysate sample may be centrifuged for 10 minutes at 3,000 g. In some embodiments, the separation container may be a 5 mL separation container.

Example 3: Yeast Processing

In an example embodiment, the various embodiments of the separation container described herein may be used to process yeast samples. One example yeast-processing method may include the following steps: (1) remove a cultured sample from a blood culture bottle; (2) dispense the blood culture into a lysis buffer; (3) vortex the mixed sample to produce lysate sample; (4) add the lysate sample to a separation container; (5) centrifuge the lysate sample to generate a pellet of the sample; (6) connect the separation container to a sample collection vessel; (7) express the pellet of the sample into the separation container; (8) resuspend the sample microorganisms in saline; (9) wash the resuspended sample, the washing comprising (a) centrifuging the sample, (b) removing the supernatant, (c) resuspend the sample, and (d) vortex the sample; and (10) deposit the resulting sample for downstream testing (e.g., MALDI-TOF ID). In some embodiments, the separation container may be a small volume collection tube having a volume less than 5 mL.

CONCLUSION

Many modifications and other embodiments of the inventions set forth herein will come to mind to one skilled in the art to which these embodiments of the invention pertain having the benefit of the teachings presented in the foregoing descriptions and the associated drawings. Although some figures may or may not label certain features for ease of viewing, a person of ordinary skill in the art may appreciate that any feature shown in the figures is necessarily present. Therefore, it is to be understood that the embodiments of the invention are not to be limited to the specific embodiments disclosed and that modifications and other embodiments are intended to be included within the scope of the appended claims. For example, unless otherwise noted, common features between multiple embodiments may have substantially the same operation and properties. Similarly, different components (e.g., the different rheological control members 200, 300, 400, 1042, 1242, 1342, different plungers 110, 115, 1010, 1210, 1310 or lack thereof) may be readily substituted between embodiments. Although specific terms are employed herein, they are used in a generic and descriptive sense only and not for purposes of limitation.

For the avoidance of doubt, the present disclosure includes the subject matter as defined in the following numbered paragraphs (abbreviated "para.").

Para. 1. A separation container for extracting a portion of a sample for use or testing, the separation container comprising:
a body defining an internal chamber, wherein the body defines an opening, and wherein the body is configured to receive the sample within the internal chamber;

a seal disposed across the opening, such that the seal is configured to seal the opening of the body; and a plunger movably disposed at least partially inside the internal chamber, wherein the plunger is configured to be actuated to open the seal and express the portion of the sample.

Para. 2. The separation container of Para. 1, wherein the body defines an axis extending from the opening to a second end of the body, wherein a longitudinal member of the plunger is disposed on the axis, wherein the internal chamber defines a diameter radial to the axis, and wherein the diameter narrows from a collection diameter to a pellet diameter in a direction extending axially from the second end to the opening.

Para. 3. The separation container of Para. 2, wherein at least a portion of the plunger is configured to sealingly engage the body at a portion of the body corresponding to the pellet diameter.

Para. 4. The separation container of Para. 3, wherein the at least the portion of the plunger defines a plunger diameter radial to a length of the longitudinal member, and wherein the plunger diameter is greater than or equal to the pellet diameter.

Para. 5. The separation container of any one of the preceding Paras., wherein the at least the portion of the plunger comprises a plunger seal disposed circumferentially about the longitudinal member of the plunger, wherein the plunger seal is configured to engage the body at the portion of the body corresponding to the pellet diameter.

Para. 6 The separation container of any one of the preceding Paras., wherein the plunger is configured to allow the portion of the sample to pass by the plunger from a second end towards the opening during centrifugation, and wherein the plunger is configured to prevent a remaining part of the sample from exiting the opening in an instance in which the plunger is actuated, such that the plunger is configured to divide the internal chamber into two sub-chambers.

Para. 7. The separation container of any one of the preceding Paras., wherein the plunger is buoyant in water or a density cushion material.

Para. 8. The separation container of any one of the preceding Paras., wherein the plunger defines a point at a first distal end of a longitudinal member of the plunger, and wherein the point is configured to pierce the seal to allow fluid communication between the internal chamber and an area outside the body via the opening.

Para. 9. The separation container of any one of the preceding Paras., further comprising a sample collecting vessel configured to engage the body, wherein the sample collecting vessel is configured to surround the opening, such that the sample collecting vessel is configured to collect the portion of the sample passing through the seal.

Para. 10. The separation container of any one of the preceding Paras., wherein the body comprises a wall at least partially bounding the internal chamber, and wherein the separation container further comprises:

a rheological control member disposed in the internal chamber, wherein the rheological control member is disposed between the plunger and the wall, and optionally, wherein the rheological control member defines a bore through which the plunger is disposed.

Para. 11. The separation container of Para. 10, wherein the body defines a second end and an axis extending from the opening to the second end, wherein the internal chamber defines a diameter perpendicular to the axis, wherein the wall is at least partially flexible such that the diameter of the internal chamber is a first diameter in a static state and the diameter of the internal chamber expands to a second diameter during centrifugation, wherein the rheological control member defines an outermost diameter radial to the axis of the body, wherein the outermost diameter of the rheological control member is greater than the first diameter, and wherein the second diameter is greater than the outermost diameter of the rheological control member.

Para. 12. The separation container of Para. 11, wherein the body comprises a collection region defining the diameter of the internal chamber, wherein the body comprises a widened region defining a greater diameter than the diameter of the collection region, and wherein the greater diameter of the widened region is greater than the outermost diameter of the rheological control member.

Para. 13. The separation container of Para. 11 or 12, wherein the rheological control member comprises a second annular shoulder comprising a wide side defining the outermost diameter and a narrow side defining a narrower diameter than the outermost diameter.

Para. 14. The separation container of any one of Paras. 10-13, wherein the wall comprises an annular shoulder at which the diameter of the internal chamber changes, wherein the first diameter is defined on a narrow side of the annular shoulder in the static state, and wherein the annular shoulder is configured to engage the rheological control member.

Para. 15. The separation container of any one of Paras. 10 to 14, further comprising a gasket disposed circumferentially about the plunger, and wherein the gasket is configured to seal a central opening between the bore of the rheological control member and the plunger.

Para. 16. A method for preparing samples for downstream use or testing, the method comprising:

disposing a sample into a separation container, wherein the separation container comprises:

a body defining an internal chamber, wherein the body defines an opening;

a seal disposed across the opening, such that the seal is configured to seal the opening of the body; and a plunger movably disposed at least partially inside the internal chamber, wherein the plunger is configured to be actuated to open the seal;

centrifuging the separation container to create a pellet from a portion of the sample within the internal chamber; and expressing the pellet from the opening in the body by depressing the plunger.

Para. 17. The method for preparing samples of Para. 16, wherein centrifuging the separation container to create the pellet comprises allowing the portion of the sample to collect at a first end of the body, wherein the opening is defined at the first end.

Para. 18. The method for preparing samples of Para. 16 or 17, wherein expressing the pellet comprises depressing the plunger into sealing engagement with a portion of the body to create pressure between the plunger and the seal, and expelling the pellet from the opening under the pressure by opening the seal.

Para. 19. The method for preparing samples of any one of Paras. 16-18, further comprising:
creating the sample by lysing a raw sample.

Para. 20. The method for preparing samples of any one of Paras. 16-19, further comprising:
creating the sample by culturing a raw sample.

Para. 21. The method for preparing samples of any one of Paras. 16-20, further comprising:
expressing the pellet into a sample collecting vessel.

Para. 22. The method for preparing samples of Para. 21, wherein the sample collecting vessel comprises a culture medium configured to culture organisms present in the pellet.

Para. 23. The method for preparing samples of any one of Paras. 16-22, wherein the pellet comprises viable portions of the sample suitable for antibiotic susceptibility testing (AST).

Para. 24. The method for preparing samples of any one of Paras. 16-23, wherein the pellet comprises viable portions of the sample suitable for a culture step.

Para. 25. The method for preparing samples of any one of Paras. 16-24, wherein the pellet comprises viable portions of the sample suitable for phenotypic identification methods and/or other growth-based downstream testing methods.

Para. 26. The method for preparing samples of any one of Paras. 16-25, wherein the pellet comprises portions of the sample suitable for identification by mass spectrometry.

Para. 27. The method for preparing samples of any one of Paras. 16-26, further comprising analyzing the pellet using an analytical technique selected from a group consisting of a nucleic acid amplification technique, a spectroscopy technique, an immunoassay technique, a probe-based assay, and an agglutination test.

Para. 28. A separation container comprising:
a body defining an internal chamber, wherein the body defines an opening, and wherein the body is configured to receive a sample within the internal chamber;
means for sealing the opening of the body; and
means for opening the means for sealing and expressing a portion of the sample.

Para. 29. The separation container of Para. 28, further comprising a rheological control member configured to float on the sample; and optionally, means for holding the rheological control member at a fixed position during filling and releasing the rheological control member to float during centrifugation.

Para. 30. An assembly comprising:
a retainer within a body of a separation container comprising an annular wall defining a central opening; and
a plunger comprising a longitudinal member defining a longitudinal axis; and
wherein the central opening of the retainer is configured to receive the plunger therethrough; and
wherein the retainer is configured to releasably engage the plunger to hold the plunger at a predetermined position.

Para. 31. The assembly of Para. 30, wherein the retainer further comprises at least one retaining member, wherein the plunger further comprises at least one locking member, and wherein the at least one retaining member of the retainer is configured to releasably engage the at least one locking member of the plunger.

Para. 32. The assembly of Para. 31, wherein the at least one retaining member comprises at least one support projection extending from the annular wall, wherein the at least one retaining member is configured to engage the plunger.

Para. 33. The assembly of Para. 32, wherein the annular wall defines a circumferential direction in a plane spanning the central opening and oriented about the central opening and an axial direction oriented perpendicular to the plane, and wherein the at least one support projection defines a circumferential wall that is longer in the circumferential direction than in the axial direction.

Para. 34. The assembly of Para. 33, wherein the at least one retaining member further comprises at least one stop wall configured to prevent rotation of the plunger in a clockwise direction or a counterclockwise direction in an instance in which the at least one support projection is engaged with the at least one locking member of the plunger.

Para. 35. The assembly of Para. 33 or 34, wherein the at least one retaining member further comprises at least one stop wall extending from a first surface of the at least one support projection, and wherein the at least one stop wall is configured to prevent rotation of the plunger in a clockwise direction or a counterclockwise direction.

Para. 36. The assembly of any one of Paras. 33 to 35, wherein the at least one retaining member further comprises at least one locking tab extending from a first surface of the at least one support projection, and wherein the at least one locking tab is configured to engage the at least one locking member of the plunger to releasably retain the plunger by increasing a force required to rotate the plunger about the longitudinal axis when the at least one locking tab is engaged with the at least one locking member of the plunger.

Para. 37. The assembly of any one of Paras. 33 to 36, wherein the at least one locking member defines a C-shaped wall configured to be disposed on both sides of the circumferential wall relative to the axial direction in an instance in which the at least one locking member and the at least one retaining member are engaged.

Para. 38. The assembly of Para. 37, wherein the at least one retaining member further comprises at least one locking tab extending from a first surface of the at least one support projection,
wherein the C-shaped wall comprises a lower wall configured to be disposed opposite the first surface of the at least one support projection relative to the circumferential wall,
wherein the C-shaped wall comprises a lip configured to impinge the at least one locking tab to at least partially resist rotation of the plunger about the longitudinal axis,
and wherein the at least one locking tab is configured to engage the at least one locking member of the plunger to releasably retain the plunger.

Para. 39. The assembly of any one of Paras. 31 to 36, wherein the at least one locking member comprises a locking wall extending at least partially perpendicular to the longitudinal axis, wherein the locking wall is configured to engage the at least one retaining member of the retainer.

Para. 40. The assembly of any one of Paras. 31 to 39, wherein the at least one retaining member comprises at least two retaining members, and wherein the at least one locking member comprises at least two locking members.

Para. 41. The assembly of Para. 40, wherein the at least two retaining members comprise a first retaining member and a second retaining member, wherein the first retaining member is disposed diametrically opposite the second retaining member about the annular wall, wherein the at least two locking members comprise a first locking member and a second locking member, and wherein the first locking member is disposed opposite the second locking member relative to the longitudinal member.

Para. 42. The assembly of any one of Paras. 30 to 41, wherein the plunger is configured to rotate about the longitudinal axis to engage the retainer, and wherein in an instance in which the plunger and the retainer are engaged, the plunger is prevented from moving along the longitudinal axis.

Para. 43. The assembly of any one of Paras. 30 to 42, wherein the annular wall defines a circumferential direction in a plane spanning the central opening and oriented about the central opening and an axial direction oriented perpendicular to the plane, wherein the axial direction is parallel to the axial direction, and wherein the plunger is configured to rotate within the plane to engage the retainer.

Para. 44. The assembly of any one of Paras. 30 to 43, wherein the body of the separation container defines an internal chamber, wherein the retainer is positioned within the internal chamber, wherein the plunger is configured to extend at least partially into the internal chamber, and wherein the retainer is configured to retain the plunger at the predetermined position with respect to the body.

Para. 45. The assembly of Para. 44, wherein in an instance in which the plunger and the retainer are engaged, centrifugation of the assembly is configured to apply centripetal force along the longitudinal axis.

Para. 46. The assembly of Para. 44 or 45, wherein the retainer further comprises at least one retaining member, wherein the plunger further comprises at least one locking member, wherein the at least one retaining member of the retainer is configured to engage the at least one locking member of the plunger, and wherein the at least one retaining member is configured to engage the at least one locking member only from a rotational direction about the longitudinal axis.

Para. 47. The assembly of any one of Paras. 44 to 46, wherein the retainer and the body of the separation container are integrally formed as a single piece.

Para. 48. The assembly of any one of Paras. 44 to 47, wherein the retainer is separately connected to the body of the separation container.

Para. 49. The assembly of Para. 48, wherein the retainer is press fit into the body of the separation container.

Para. 50. The assembly of any one of Paras. 44 to 49, further comprising:
a flexible sealing member disposed at a second end of the body of the separation container, wherein a second distal end of the plunger is configured to extend at least partially into the flexible sealing member; and
a cap threaded to the body at the second end, wherein a portion of the flexible sealing member is configured to be disposed between the cap and the body, and wherein the cap defines an opening through which a second portion of the flexible sealing member and the second distal end of the plunger are configured to extend; and
wherein the plunger is configured to disengage from the retainer by gripping and rotating the plunger through the flexible sealing member.

Para. 51. A method of operating a plunger and retainer assembly, the assembly comprising a retainer within a body of a separation container comprising an annular wall defining a central opening, at least one retaining member, and a plunger comprising a longitudinal member defining a longitudinal axis; the method comprising:
rotating the plunger about the longitudinal axis to disengage the plunger from the retainer; and
actuating the plunger by applying a force to the plunger along the longitudinal axis.

Para. 52. The method of Para. 51, wherein the plunger is at least partially disposed in the body of the separation container, the method further comprising:
disposing a sample in the body of the separation container;
centrifuging the assembly before the rotating and the actuating of the plunger, such that the plunger is configured to be retained at a predetermined position relative to the body of the separation container during centrifugation.

Para. 53. The method of Para. 52 further comprising lysing the sample before disposing the sample in the body of the separation container.

Para. 54. An assembly comprising:
a plunger comprising a longitudinal member defining a longitudinal axis;
a body of a separation container; and
means for releasably retaining the plunger at least partially within the body of the separation container at a predetermined position.

Para. 55. The assembly of Para. 54, wherein the means for releasably retaining the plunger define an engaged state and a disengaged state, and wherein in the engaged state, the means for releasably retaining the plunger are configured to prohibit the plunger from moving along the longitudinal axis.

Para. 56. The assembly of Para. 55, wherein the means for releasably retaining the plunger are configured to engage and disengage by rotating the plunger about the longitudinal axis.

Para. 57. A plunger for expressing a portion of a sample from a container, the plunger comprising:
a longitudinal member defining a first distal end, a second distal end, and an axis extending between the first distal end and the second distal end; and
a plunger seal positioned about the longitudinal member at a location between the first distal end of the longitudinal member and the second distal end of the longitudinal member, the plunger seal defining a plunger seal diameter perpendicular to the axis; and
wherein at least a portion of the longitudinal member between the location and the first distal end of the longitudinal member defines a plunger diameter that is less than the plunger seal diameter, such that in operation the at least the portion of the longitudinal member is configured to retain a volume of sample between a wall of the container, a distal end of the container, the plunger seal, and the at least the portion of the longitudinal member.

Para. 58. The plunger of Para. 57, wherein the first distal end of the longitudinal member defines a point configured to pierce a seal of the container.

Para. 59. The plunger of Para. 57 or 58, wherein the plunger seal is overmolded onto the longitudinal member.

Para. 60. The plunger of any one of the preceding claims, wherein the longitudinal member defines a through passage extending through the longitudinal member at least partially perpendicular to the axis, wherein the plunger seal is disposed on the longitudinal member at an axial location of the through passage, and wherein the plunger seal extends through the through passage.

Para. 61. The plunger of any one of Paras. 57 to 60, wherein the plunger seal is elastomeric.

Para. 62. The plunger of Para. 57 or 58, wherein the plunger seal is integral with the longitudinal member.

Para. 63. The plunger of any one of Paras. 57 to 62, further comprising a sealing rib disposed circumferentially about the longitudinal member of the plunger, wherein the sealing rib is disposed between the plunger seal and the first distal end relative to the axis.

Para. 64. The plunger of any one of Paras. 57 to 62, wherein the longitudinal member defines a shoulder between the second distal end and the plunger seal, wherein a diameter of the shoulder is greater than the plunger seal diameter.

Para. 65. A separation container comprising:
- a container body defining an internal chamber configured to receive a sample, wherein the container body defines an opening, a collection region having a collection diameter, and a pellet region having a pellet diameter, wherein the collection diameter is greater than the pellet diameter, and wherein the pellet region is defined between the opening and the collection region in the internal chamber;
- a seal disposed across the opening, such that the seal is configured to seal the opening of the container body; and
- a plunger configured to be disposed at least partially within the internal chamber to open the seal, the plunger comprising:
  - a longitudinal member defining a first distal end, a second distal end, and an axis extending between the first distal end and the second distal end, wherein the first distal end of the plunger is configured to open the seal; and
  - a plunger seal positioned about the longitudinal member at a location between the first distal end of the longitudinal member and the second distal end of the longitudinal member, the plunger seal defining a plunger seal diameter perpendicular to the axis;
- wherein the plunger seal diameter is greater than or equal to the pellet diameter; and
- wherein at least a portion of the longitudinal member between the location and the first distal end of the longitudinal member defines a plunger diameter that is less than the plunger seal diameter, such that in operation the at least the portion of the longitudinal member is configured to retain a volume between a wall of the container, a distal end of the container, the plunger seal, and the at least the portion of the longitudinal member.

Para. 66. The separation container of Para. 65, wherein the longitudinal member defines a shoulder between the second distal end and the plunger seal;
- wherein a diameter of the shoulder is greater than the pellet diameter, and less than the collection diameter; and
- wherein the shoulder is configured to impinge the container body to define a maximum displacement of the plunger.

Para. 67. The separation container of Para. 66, wherein an axial distance between the plunger seal and the shoulder is less than or equal to an axial length of the pellet region, such that the plunger seal remains at least partially within the container body at the maximum displacement of the plunger.

Para. 68. The separation container of Para. 66 or 67, wherein an axial distance between the plunger seal and the first distal end of the plunger is less than or equal to an axial length of the pellet region such the plunger seal is configured to engage the pellet region of the container body before the plunger opens the seal during actuation.

Para. 69. The separation container of any one of Paras. 66 to 68, wherein the first distal end of the longitudinal member defines a point configured to pierce the seal.

Para. 70. The separation container of any one of Paras. 66 to 68, wherein an axial distance between the plunger seal and the shoulder and an axial length of the pellet region are configured such that the plunger seal remains at least partially within the container body at the maximum displacement of the plunger.

Para. 71. The separation container of any one of Paras. 65 to 70, wherein the plunger seal is overmolded onto the longitudinal member.

Para. 72. The separation container of any one of Paras. 65 to 71, wherein the container body further comprises a tapered region connecting the collection region and the pellet region, and wherein a diameter of the tapered region varies relative to an axial direction from the pellet diameter at a junction between the pellet region and the tapered region to the collection diameter at a junction between the collection region and the tapered region.

Para. 73. A method of expressing a portion of a sample from the separation container, the separation container comprising a container body defining an internal chamber, an opening, a collection region having a collection diameter, and a pellet region having a pellet diameter, wherein the collection diameter is greater than the pellet diameter, and wherein the pellet region is defined between the opening and the collection region in the internal chamber; a seal disposed across the opening; and a plunger disposed at least partially within the internal chamber, the plunger comprising a longitudinal member defining a first distal end, a second distal end, and an axis extending between the first distal end and the second distal end, and a plunger seal positioned about the longitudinal member at a location between the first distal end of the longitudinal member and the second distal end of the longitudinal member, wherein the plunger seal defines a plunger seal diameter perpendicular to the axis; wherein the plunger seal diameter is greater than or equal to the pellet diameter; and wherein at least a portion of the longitudinal member between the location and the first distal end of the longitudinal member defines a plunger diameter that is less than the plunger seal diameter; the method comprising:
- displacing the plunger along the axis to cause the plunger seal to engage the container body at the pellet region, wherein engagement of the plunger seal and the container body retains the volume between a wall of the container, a distal end of the container, the plunger seal, and the at least the portion of the longitudinal member.

further displacing the plunger along the axis to open the seal with the first distal end of the plunger; and further displacing the plunger to express the volume of the sample from the opening via pressure created by the plunger seal.

Para. 74. A separation container comprising:
a container body defining an internal chamber configured to receive a sample, wherein the container body defines an opening, a collection region having a collection diameter, and a pellet region having a pellet diameter, wherein the collection diameter is greater than the pellet diameter, and wherein the pellet region is defined between the opening and the collection region in the internal chamber;
means for sealing the opening;
means for opening the means for sealing the opening and expressing a portion of the sample; and
means for fluidically separating the portion of the sample from other fluid in the internal chamber during expression of the portion of the sample.

Para. 75. The separation container of Para. 74, wherein the means for fluidically separating the portion of the sample from the other fluid in the internal chamber is attached to the means for opening the means for sealing the opening and expressing the portion of the sample.

Para. 76. The separation container of Para. 74 or 75, wherein the means for opening the means for sealing and expressing the portion of the sample is configured to express only the portion of the sample during operation.

Para. 77. An assembly comprising:
a separation container comprising:
a body, the body defining an internal chamber, wherein the body defines an opening at a first end, and wherein the body is configured to receive a sample within the internal chamber; and
a seal attached to the body and disposed across the opening, wherein the seal is configured to seal the opening of the body; and
an end cap disposed at the first end of the body and removably connected to the body, wherein the seal is positioned between the end cap and the body.

Para. 78. The assembly of Para. 77, wherein the body further defines an annular surface around the opening, and wherein the seal is attached to the annular surface.

Para. 79. The assembly of Para. 78, wherein the end cap defines a support surface configured to be positioned parallel to the annular surface of the body with the seal being disposed between the support surface and the annular surface.

Para. 80. The assembly of any one of Paras. 77 to 79, wherein the seal comprises a membrane.

Para. 81. The assembly of Para. 80, wherein the seal comprises a foil sheet.

Para. 82. The assembly of any one of Paras. 77 to 81, wherein the seal is welded to the body of the separation container.

Para. 83. The assembly of any one of Paras. 77 to 82, wherein the end cap is a centrifuge adaptor comprising at least one of a flat distal end and a tapered portion configured to engage a centrifuge cup.

Para. 84. The assembly of Para. 83, wherein the end cap comprises both a flat distal end and a tapered portion.

Para. 85. The assembly of Para. 84, wherein the flat distal end comprises a recess configured to receive a post therein.

Para. 86. The assembly of any one of Paras. 77 to 85, wherein the first end of the body is inserted into a cavity of the end cap, and wherein the end cap is removably connected to the body by friction.

Para. 87. The assembly of Para. 86, further comprising a coupling member disposed between the end cap and the container body, wherein the end cap comprises an inner surface configured to apply a radially inward pressure to the coupling member and body to retain the end cap on the body.

Para. 88. The assembly of Para. 87, wherein the coupling member comprises an elastomeric sleeve disposed over the first end of the body between the body and the end cap.

Para. 89. The assembly of Para. 88 further comprising a sample collecting vessel; wherein the end cap is configured to be removable; wherein in an instance in which the end cap is removed, the sample collecting vessel is configured to fit over and be retained by at least the elastomeric sleeve.

Para. 90. The assembly of Para. 89 further comprising a plunger comprising a longitudinal member defining a first distal end, a second distal end, and an axis extending between the first distal end and the second distal end; wherein the plunger is configured to open the seal and express at least a portion of the sample from the opening of the body of the separation container; and wherein the elastomeric sleeve is configured to seal the sample collecting vessel from an external environment.

Para. 91. The assembly of any one of Paras. 88 to 90, wherein the end cap further comprises one or more ribs configured to compress the elastomeric sleeve to release air trapped in the end cap during insertion of the end cap onto the body.

Para. 92. The assembly of any one of Paras. 88 to 91, wherein the elastomeric sleeve is disposed between the first end and the second end of the body, such that the end cap is configured to directly contact the seal.

Para. 93. A method using an assembly, the assembly comprising a separation container comprising a body, the body defining an internal chamber, wherein the body defines an opening at a first end, and wherein the body is configured to receive a sample within the internal chamber, the separation container further comprising a seal attached to the body and disposed across the opening, wherein the seal is configured to seal the opening of the body; the assembly further comprising an end cap; the method comprising:
releasably engaging the end cap with the body such that the seal is disposed between the end cap and the body, wherein the end cap is configured to prevent the seal from detaching from the body during centrifugation.

Para. 94. The method of Para. 93 further comprising:
centrifuging the assembly;
disengaging the end cap from the body; and
opening the seal.

Para. 95. The method of Para. 94, wherein the assembly further comprises a sample collecting vessel, the method further comprising:
engaging the sample collecting vessel with the body at the opening; and expressing at least a portion of the sample into the sample collecting vessel.

Para. 96. The method of Para. 95, wherein the assembly further comprises a plunger comprising a longitudinal member defining a first distal end, a second distal end, and an axis extending between the first distal end and the second distal end, wherein opening the seal comprises opening the seal with the first distal end of the plunger, wherein expressing the pellet comprises depressing the plunger into sealing engagement with a portion of the body to create pressure between the plunger and the seal and expelling the pellet from the opening under the pressure.

Para. 97. An assembly comprising:
a separation container comprising:
a body, the body defining an internal chamber, wherein the body defines an opening at a first end, and wherein the body is configured to receive a sample within the internal chamber; and
means for sealing the opening of the body; and
means for preventing the seal from separating from the body during centrifugation.

Para. 98. The assembly of Para. 97, wherein the means for sealing the opening of the body is attached to the body.

Para. 99. The assembly of Para. 97 or 98, wherein the means for preventing the seal from separating from the body during centrifugation is frictionally retained against the seal.

Para. 100. The assembly of any one of Paras. 97 to 99, wherein the means for preventing the seal from separating from the body during centrifugation is configured to apply a retaining force to the means for sealing the opening of the body during centrifugation.

Para. 101. The assembly of any one of Paras. 97 to 100, wherein the means for preventing the seal from separating from the body during centrifugation comprises means for releasing air trapped between the body and the means for preventing the seal from separating from the body during centrifugation.

Para. 102. A separation container comprising:
a body defining an internal chamber, wherein the body defines a first opening at a first end and a second opening at a second end, and wherein the body is configured to receive a sample within the internal chamber;
a seal disposed across the first opening, such that the seal is configured to seal the first opening of the body;
a plunger movably disposed at least partially inside the internal chamber, wherein the plunger is configured to be actuated to open the seal and extract a portion of the sample; and
a flexible sealing member at least partially covering the second opening, wherein at least a portion of the plunger is configured to extend at least partially into the flexible sealing member, such that compression of the flexible sealing member is configured to actuate the plunger.

Para. 103. The separation container of Para. 102, wherein the flexible sealing member comprises a flange defining an annular surface configured to engage the body.

Para. 104. The separation container of Para. 103, wherein the flexible sealing member further comprises a wall extending from the flange, and wherein an angle between the flange and the wall is greater than or equal to 90 degrees when the flexible sealing member is in an unactuated position.

Para. 105. The separation container of Para. 104, wherein the wall comprises a plurality of wall segments, and wherein an angle between the flange and each of the plurality of wall segments is greater than or equal to 90 degrees when the flexible sealing member is in the unactuated position.

Para. 106. The separation container of any one of Paras. 102 to 105, further comprising a cap secured to the body at the second end, wherein a portion of the flexible sealing member is configured to be disposed between the cap and the body, and wherein the cap defines an opening through which a second portion of the flexible sealing member and the second end of the plunger are configured to extend.

Para. 107. The separation container of any one of Paras. 102 to 106, wherein the flexible sealing member comprises a bellows-shaped gasket.

Para. 108. The separation container of any one of Paras. 102 to 107, wherein the flexible sealing member defines an open end configured to receive the portion of the plunger therein, and wherein the flexible sealing member further defines a closed end, such that the flexible sealing member is configured to engage the body at the open end to enclose the internal chamber and a cavity of the flexible sealing member.

Para. 109. The separation container of Para. 108, wherein the plunger comprises a first end, a second end, and a longitudinal axis extending between the first end and the second end,
wherein the portion of the plunger comprises the second end of the plunger,
wherein the flexible sealing member defines a sealing member axis extending between the open end and the closed end,
wherein the sealing member axis is configured to be collinear with the longitudinal axis of the plunger in an operational position,
wherein the flexible sealing member defines a radius perpendicular to the longitudinal axis, and
wherein the radius is configured to decrease from the open end to the closed end.

Para. 110. The separation container of Para. 109, wherein the radius at each point along the sealing member axis between the open end and the closed end is less than or equal to the radius at each point closer to the closed end and greater than or equal to the radius at each point closer to the open end.

Para. 111. The separation container of any one of Paras. 108 to 110, wherein when the flexible sealing member is actuated, the closed end of the flexible sealing member is configured to move toward the open end of the flexible sealing member along a displacement axis.

Para. 112. The separation container of Para. 111, wherein when the flexible sealing member is actuated, the closed end is configured to be positioned at a same axial position along the displacement axis as or closer to the first end of the body than the open end.

Para. 113. The separation container of Paras. 102 to 112, wherein the flexible sealing member defines a wall configured to at least partially surround the portion of the plunger, wherein the wall defines an inwardly concave shape, such that the wall is configured to flex outwardly from the plunger when the plunger is actuated.

Para. 114. The separation container of Paras. 102 to 112, wherein the flexible sealing member comprises a first circumferential wall segment connected to a top of the flexible sealing member, a second circumferential wall segment connected to the first circumferential wall segment, and a third circumferential wall segment connected to the second circumferential wall segment;
wherein the second circumferential wall segment is concentric about a longitudinal axis of the plunger; and
wherein the first circumferential wall segment and the second circumferential wall segment are each angled at least partially inwardly towards the plunger from their respective connections to the second circumferential wall segment.

Para. 115. A method of using a separation container, the separation container comprising a body defining an internal chamber, wherein the body defines a first opening at a first end and a second opening at a second end; the separation container further comprising a seal disposed across the first opening, such that the seal is configured to seal the first opening of the body; a plunger movably disposed at least partially inside the internal chamber; and a flexible sealing member at least partially covering the second opening, wherein at least a portion of the plunger is configured to extend at least partially into the flexible sealing member; the method further comprising:
disposing a sample in the internal chamber of the separation container;
centrifuging the separation container; and
after centrifugation, compressing the flexible sealing member to actuate the plunger and open the seal to extract a portion of the sample.

Para. 116. The method of Para. 115, wherein the plunger is held axially by a retainer during centrifugation, wherein compressing the flexible sealing member to actuate the plunger further comprises unlocking the plunger from the retainer.

Para. 117. The method of Para. 116, wherein compressing the flexible sealing member to actuate the plunger further comprises rotating a portion of the flexible sealing member and the plunger about a longitudinal axis of the plunger, wherein the longitudinal axis extends from a first end of the plunger to a second end of the plunger.

Para. 118. The method of Para. 117, wherein rotating the portion of the flexible sealing member comprises deforming the flexible sealing member such that the portion of the flexible sealing member rotates while a flange of the flexible sealing member remains fixed relative to the body.

Para. 119. The method of Paras. 117 or 118, wherein the separation container further comprises a cap secured to the body at the second end,
wherein a second portion of the flexible sealing member is configured to be disposed between the cap and the body,
wherein the cap defines an opening through which the portion of the flexible sealing member and the second end of the plunger are configured to extend.

Para. 120. A separation container comprising:
a body defining an internal chamber, wherein the body defines a first opening at a first end and a second opening at a second end, and wherein the body is configured to receive a sample within the internal chamber;
means for sealing the first opening of the body;
means for opening the means for sealing and expressing a portion of the sample; and
means for allowing manipulation of the means for opening the means for sealing and expressing the portion of the sample while also sealing the second opening of the body.

Para. 121. The separation container of Para. 120, wherein the means for allowing manipulation of the means for opening the means for sealing and expressing the portion of the sample while also sealing the second opening of the body is configured to allow both rotational and axial movement of the means for sealing and expressing the portion of the sample.

What is claimed is:

1. A centrifugable assembly for a sample, the assembly comprising:
   a plunger configured to be disposed at least partially within a separation container, the plunger defining a longitudinal axis; and
   a body of the separation container comprising a retainer configured to engage the plunger by rotating the plunger about the longitudinal axis,
   wherein in an instance in which the retainer and the plunger are engaged, the retainer is configured to maintain the plunger at a predetermined position to prohibit the plunger from moving along the longitudinal axis, and
   wherein in an instance in which the retainer and the plunger are disengaged, the plunger is configured to be movable along the longitudinal axis.

2. The assembly of claim 1, wherein the retainer is an integral portion of the body of the separation container or a separate component engaged with the body of the separation container.

3. The assembly of claim 1, wherein the retainer is press fit within the body of the separation container.

4. The assembly of claim 1, wherein the plunger is configured to rotationally engage the retainer upon receipt of a threshold radial pressure applied to the plunger in a first rotational direction.

5. The assembly of claim 4, wherein the plunger is configured to rotationally disengage the retainer upon receipt of a threshold radial pressure applied to the plunger in a second rotational direction, the second rotational direction opposite to the first rotational direction.

6. The assembly of claim 1, wherein the retainer radially centers the plunger within the body of the separation container.

7. The assembly of claim 1, wherein the retainer comprises one or more retaining members for engaging a corresponding support member of the plunger.

8. The assembly of claim 7, wherein the retainer is configured to rotationally engage with the plunger in an instance when the one or more retaining members are axially aligned with the corresponding support member of the plunger and the plunger is rotated in a first rotational direction.

9. The assembly of claim 8, wherein the corresponding support member of the plunger comprises one or more locking projections.

10. The assembly of claim 9, wherein the one or more locking projections and the one or more retaining members are configured to not contact each other in an instance when axially translating the plunger at a first rotational position, and are configured to contact each other in an instance when axially translating the plunger at a second rotational position.

11. The assembly of claim 9, wherein the corresponding support member of the plunger comprises a first locking projection and a second locking projection, wherein the second locking projection is disposed opposite the first locking projection relative to the longitudinal axis of the plunger.

12. The assembly of claim 9, wherein the one or more locking projections each define a C-shaped wall comprising a lower wall, an upper wall, and a lateral wall, the lateral wall coupling the upper wall to the lower wall.

13. The assembly of claim 12, wherein the one or more locking projections each further comprise a locking lip extending from the upper wall at an opening defined by the C-shaped wall, and wherein the C-shaped wall and locking lip are configured to receive and releasably engage the corresponding one or more retaining members of the retainer.

14. The assembly of claim 13, wherein the one or more retaining members comprise at least one support projection extending from an inner surface of the separation container, the at least one support projection comprising a locking tab extending from a first surface of the at least one support projection.

15. The assembly of claim 14, wherein the first surface of the at least one support projection is configured to be disposed opposite the upper wall of the C-shaped wall when the retainer is engaged with the plunger and wherein the one or more retaining members further comprise at least one stop wall configured to prevent rotation of the plunger in a first rotational direction in an instance in which the at least one support projection is engaged with the plunger.

\* \* \* \* \*